US008084457B2

(12) United States Patent
Choidas et al.

(10) Patent No.: US 8,084,457 B2
(45) Date of Patent: Dec. 27, 2011

(54) PHARMACEUTICALLY ACTIVE 4,6-DISUBSTITUTED AMINOPYRIMIDINE DERIVATIVES AS MODULATORS OF PROTEIN KINASES

(75) Inventors: Axel Choidas, Gauting (DE); Alexander Backes, Munich (DE); Matt Cotten, Barjul (GM); Ola Engkvist, Bjärnum (SE); Beatrice Felber, Eching (DE); Achim Freisleben, Munich (DE); Klaus Godl, Krailling (DE); Zoltán Greff, Budapest (HU); Peter Habenberger, Munich (DE); Doris Hafenbradl, Pullach (DE); Christian Hartung, Munich (DE); Thomas Herget, Darmstadt (DE); Edmund Hoppe, Krailling (DE); Bert Klebl, Oberschweinbad (DE); Andrea Missio, Sovizzo (IT); Gerhard Müller, Utting (DE); Wilfried Schwab, Neuried (DE); Birgit Zech, Gräfelfing (DE); Jose Bravo, Haverhill (GB); John Harris, Eynsford (GB); Joelle Le, London (GB); Jackie Macritchie, Walden (GB); Vladimir Savic, Belgrade (RS); Brad Sherborne, Auchterarder (GB); Don Simpson, Haverhill (GB)

(73) Assignees: Lead Discovery Center GmbH, Dortmund (DE); Bayer Pharma AG, Berlin (DE)

( * ) Notice: Subject to any disclaimer, the term of this patent is extended or adjusted under 35 U.S.C. 154(b) by 0 days.

(21) Appl. No.: 10/572,043

(22) PCT Filed: Sep. 15, 2004

(86) PCT No.: PCT/EP2004/010353
§ 371 (c)(1),
(2), (4) Date: Dec. 12, 2006

(87) PCT Pub. No.: WO2005/026129
PCT Pub. Date: Mar. 24, 2005

(65) Prior Publication Data
US 2007/0191344 A1    Aug. 16, 2007

Related U.S. Application Data

(60) Provisional application No. 60/504,527, filed on Sep. 22, 2003, provisional application No. 60/569,806, filed on May 12, 2004.

(30) Foreign Application Priority Data

Sep. 15, 2003  (EP) ..................... 03020888
Apr. 30, 2004  (EP) ..................... 04010308

(51) Int. Cl.
*A01N 43/54*   (2006.01)
*C07D 239/42*  (2006.01)
*C07D 401/04*  (2006.01)
*C07D 239/00*  (2006.01)
*C07D 239/02*  (2006.01)

(52) U.S. Cl. ..................... 514/256; 544/242
(58) Field of Classification Search .............. None
See application file for complete search history.

(56) References Cited

U.S. PATENT DOCUMENTS

| 3,908,012 A | 9/1975 | De Angelis et al. |
| 3,950,525 A * | 4/1976 | De Angelis et al. ......... 514/269 |
| 4,725,600 A * | 2/1988 | Takaya et al. ............. 514/269 |
| 2004/0204386 A1 * | 10/2004 | Bhatt et al. ............... 514/64 |

FOREIGN PATENT DOCUMENTS

| EP | 0168262 A | 1/1986 |
| WO | 02096867 A | 12/2002 |

OTHER PUBLICATIONS

Luo, et. al., Tettrahedron Letters, 43, (2002), pp. 5739-5742.*
Schmidt, et. al., Journal of Heterocyclic Chemistry, 39, (2002), pp. 949-956.*
Falch E et al: "Substituted Heteroaromatic Anthranilic Acids With Antiinflammatory Activity" Journal of Medicinal Chemistry, American Chemical Society. Washington, US, vol. 11, No. 3, May 1968, pp. 608-611, XP001069203.
El-Reedy A M et al: "Azolopyrimidines and Pyrimidoquinazolines From 4-Chloropyrimidines" Journal of Heterocyclic Chemistry, Heterocorporation. Provo, US, vol. 26, No. 2, 1989, pp. 313-316, XP000929372.
Clare, Paula M. et al: "The Cyclin-Dependent Kinases cdk2 and cdk5 Act by A Random, Anticooperative Kinetic Mechanism" Journal of Biological Chemistry, 256(51), 48292-48299, 2001, XP002312583.

* cited by examiner

*Primary Examiner* — Jeffrey Murray
(74) *Attorney, Agent, or Firm* — Meyertons, Hood, Kivlin, Kowert & Goetzel, P.C.; Eric B. Meyertons

(57) ABSTRACT

The present invention relates to 4,6-disubstituted aminopyrimidine derivatives and/or pharmaceutically acceptable salts thereof, the use of these derivatives as pharmaceutically active agents, especially for the prophylaxis and/or treatment of infectious diseases, including opportunistic diseases, prion diseases, immunological diseases, autoimmune diseases, bipolar and clinical disorders, cardiovascular diseases, cell proliferative diseases, diabetes, inflammation, transplant rejections, erectile dysfunction, neurodegenerative diseases and stroke, and pharmaceutical compositions containing at least one of said 4,6-di substituted aminopyrimidine derivatives and/or pharmaceutically acceptable salts thereof. Furthermore, the present invention relates to the use of said 4,6-disubstituted aminopyrimidine derivatives as inhibitors for a protein kinase and a medium comprising at least one of said 4,6-disubstituted aminopyrimidine derivatives in an immobilized form and the use of said medium for enriching, purifying and/or depleting nucleotide binding proteins which bind to the immobilized 4,6-disubstituted aminopyrimidine derivatives.

25 Claims, 5 Drawing Sheets

Figure 3: Effect of compounds on dependent NFκB-transcriptional activity,

Figure 4: Effect of compounds on HBV replication

PHARMACEUTICALLY ACTIVE 4,6-DISUBSTITUTED AMINOPYRIMIDINE DERIVATIVES AS MODULATORS OF PROTEIN KINASES

CROSS-REFERENCE TO RELATED APPLICATION

This application claims the benefit of U.S. provisional application Ser. Nos. 60/504,527 filed 22 Sep. 2003 and 60/569,806 filed 12 May 2004.

BACKGROUND OF THE INVENTION

1. Field of the Invention

The present invention relates to 4,6-disubstituted aminopyrimidine derivatives and/or pharmaceutically acceptable salts thereof, the use of these derivatives as pharmaceutically active agents, especially for the prophylaxis and/or treatment of infectious diseases, including opportunistic diseases, prion diseases, immunological diseases, autoimmune diseases, bipolar and clinical disorders, cardiovascular diseases, cell proliferative diseases, diabetes, inflammation, transplant rejections, erectile dysfunction, neurodegenerative diseases and stroke. Furthermore, the present invention is directed towards pharmaceutical composition containing at least one of the 4,6-disubstituted aminopyrimidine derivatives and/or pharmaceutically acceptable salts thereof.

2. Background Art

One of the most important and fundamental processes in biology is the division of cells during the cell cycle. This process ensures the controlled production of subsequent generations of cells with defined biological function. It is a highly regulated phenomenon and responds to a diverse set of cellular signals both within the cell and from external sources. Cyclin dependent kinases (CDKs) play a key role in regulating the cell cycle machinery. These complexes consist of two components: a catalytic subunit (the kinase) and a regulatory subunit (the cyclin). To date, eleven kinase subunits have been identified (S. Mani et al., Exp. Opin. Invest. Drugs 2000, 9(8), 1849-1870, J. C. Sergere et al., Biochem. Biophys. Res. Commun. 2000, 276, 271-277, D. Hu et al, J. Biochem. Chem. 2003, 278(10), 8623-8629).

It is known, that CDKs play a role in the regulation of cellular proliferation. Therefore, CDK inhibitors could be useful in the treatment of cell proliferative disorders such as cancer, neuro-fibromatosis, psoriasis, fungal infections, endotoxic shock, transplantation rejection, vascular smooth cell proliferation associated with arteriosclerosis, pulmonary fibrosis, arthritis, glomerulonephritis and post-surgical stenosis and restenosis (U.S. Pat. No. 6,114,365). CDKs are also known to play a role in apoptosis. Therefore CDK inhibitors could be useful in the treatment of cancer; autoimmune diseases, for example systemic lupus, erythematosus, autoimmune mediated glomerulonephritis, rheumatoid arthritis, psoriasis, inflammatory bowel disease, and autoimmune diabetes; neurodegenerative diseases for example Alzheimer's disease, AIDS-related dementia, Parkinson's disease, amyotrophic lateral sclerosis, retinitis pigmentosa, spinal muscular atrophy and cerebellar degeneration; myelodysplastic syndromes, aplastic anemia, ischemic injury associated with myocardial infarctions, stroke and reperfusion injury, arrhythmia, atherosclerosis, toxin-induced or alcohol related liver diseases; hematological diseases, for example, chronic anemia and aplastic anemia; degenerative diseases of the musculoskeletal system, for example, osteoporosis and arthritis, cystic fibrosis, multiple sclerosis, kidney diseases and cancer pain and for the treatment of cardiovascular diseases (U.S. Pat. No. 6,107,305 and WO 02/100401). Further it is known, that CDK inhibitors could be used for the treatment of virally induced infectious diseases, such as EBV, HBV, HCV and HIV (WO 02/100401).

Recently, it was described, that HIV-1 replication could be affected by inhibiting CDKs (C. de la Fuenta, Current HIV research, 2003, 1(2), 131-152; Y. K. Kim et al., Molecular and Cellular Biology, 2002, 22(13), 4622-4637). Especially CDK9 is reported to be essential for the HIV-1 replication (H. S. Mancebo et al, Genes Dev. 1997, 11(20): 2633-44, O. Flores et al., Proc Natl. Acad. Scd. USA. 1999, 96(13):7208-13).

Most of the known CDK inhibitors, such as olomoucine, roscovitine, CYC202, purvalanols, indolinones, paullones and 7-hydroxy-staurosporine are focusing on the inhibition of CDK1 and CDK2 with the goal of antitumor activity (Current opinion in Pharmacology, 2003, 3, 1-9). A summary of the known CDK-inhibitors is given by M. Huwe et al. (A. Huwe et al., Angew Chem Int Ed Engl. 2003; 42(19): 2122-38).

Flavopiridol is described as a low-molecular, but unselective inhibitor of CDKs, including CDK9 (W. Filgueira de Azevedo et al., Biochem. and Biophys. Res. Commun. 2002, 293(1), 566-571). Other compounds that were shown to inhibit CDKs are staurosporine, fascaplysin and hymenialdisine.

The use of 4-Aminopyrimidine derivatives as neuroprotective agents is described in WO 02/12198. These compounds generally contain as a basic residue a substituted amine in para position of the anilino part of the molecule and it is stated, that these compounds did not inhibit MEK1/2 kinase activity in P19 neurons.

U.S. Pat. No. 3,950,25 describes the use of 4-Amino-6-aryl-pyrimidines as platelet aggregation inhibitors and bronchodilators. U.S. Pat. No. 3,478,030 describes the synthesis of benzamide substituted anilino aminopyrimidine derivatives. These compounds are used as potent dilators of coronary arteries. WO 02/79197 describes the use of aryl-substituted 2-aminopyrimidine derivatives as protein kinase inhibitors, for example as inhibitor of JNK, GSK-3, Src, Lck or CDK2.

There is a high unmet medical need to develop CDK inhibitors, useful in treating various conditions associated with CDK activation, in particular concerning CDK9 kinase activity, which is associated with HIV replication.

SUMMARY OF THE INVENTION

It is object of the present invention to provide compounds and/or pharmaceutically acceptable salts thereof which can be used as pharmaceutically active agents, especially for prophylaxis and/or treatment of infectious diseases, including opportunistic diseases, prion diseases, immunological diseases, autoimmune diseases, bipolar and clinical disorders, cardiovascular diseases, cell proliferative diseases, diabetes, inflammation, transplant rejections, erectile dysfunction, neurodegenerative diseases and stroke, methods to treat said diseases, as well as compositions comprising at least one of those compounds and/or pharmaceutically acceptable salts thereof as pharmaceutically active ingredients. Another object of the present invention is to provide a medium and a method, which are capable of specifically enriching nucleotide-binding proteins such as protein kinases from a pool of proteins, such as a proteome, a cell lysate or a tissue lysate.

This object is solved by the compounds and/or their pharmaceutically acceptable salt according to independent claim 1, the compounds of the present invention for use as a pharmaceutically active agents according to independent claim 34, the use of the compounds of the present invention for the preparation of a pharmaceutical composition for the prophylaxis and/or treatment of infectious diseases, including opportunistic diseases, prion diseases, immunological diseases, autoimmune diseases, bipolar and clinical disorders, cardiovascular diseases, cell proliferative diseases, diabetes, inflammation, transplant rejections, erectile dysfunction, neurodegenerative diseases and stroke, the use of compounds according to the present invention as inhibitors for a protein kinase according to independent claim 54, the pharmaceutical compositions according to claim 57, the medium according to claim 58, and the method for enriching, purifying or depleting nucleotide binding proteins according to independent claim 66.

Further advantageous features, aspects and details of the invention are evident from the dependent claims, the description, the examples and the drawings.

DETAILED DESCRIPTION OF THE PREFERRED EMBODIMENT(S)

The novel 4,6-disubstituted aminopyrimidine compounds according to the present invention are defined by the general formula (I)

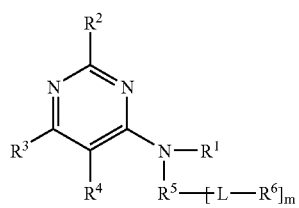

(I)

wherein $R^1$ is selected from the group comprising:
—H, linear or branched $C_1$-$C_6$ substituted or unsubstituted alkyl, linear or branched $C_2$-$C_6$ alkenyl or linear or branched $C_2$-$C_6$ alkinyl;

$R^2$ and $R^4$ are independently selected from the group consisting of:
—H, linear or branched $C_1$-$C_6$ substituted or unsubstituted alkyl, linear or branched $C_2$-$C_6$ alkenyl, linear or branched $C_2$-$C_6$ alkinyl, aryl, —F, —Cl, —Br, —I, —CN, —NH$_2$ or —NO$_2$;

$R^3$ is selected from the group comprising:
—F, —Cl, —Br, —I, substituted or unsubstituted aryl, substituted or unsubstituted —O-aryl, —NH-aryl, —S-aryl, or substituted or unsubstituted —O-heterocyclyl, —NH-heterocyclyl, —S-heterocyclyl, or substituted or unsubstituted —CH═CH-aryl, or substituted or unsubstituted heteroaryl, or substituted or unsubstituted heterocyclyl, or substituted or unsubstituted $C_3$-$C_8$ cycloalkyl, or —NH—(CH$_2$)$_n$—X, wherein n is an integer from 0 to 6 and X is selected from —OH, —NH$_2$ or substituted or unsubstituted $C_3$-$C_8$ cycloalkyl;

$R^5$ is selected from the group consisting of:
Substituted or unsubstituted aryl, substituted or unsubstituted heteroaryl, substituted or unsubstituted heterocyclyl, substituted or unsubstituted $C_3$-$C_8$ cycloalkyl, or —(CH$_2$)$_o$—Y, wherein o is an integer from 0 to 6 and Y represents substituted or unsubstituted aryl, substituted or unsubstituted heteroaryl, substituted or unsubstituted heterocyclyl or substituted or unsubstituted $C_3$-$C_8$ cycloalkyl;

$R^6$ is selected from the group consisting of:
—H, linear or branched substituted or unsubstituted $C_1$-$C_8$ alkyl, substituted or unsubstituted aryl, substituted or unsubstituted heteroaryl, substituted or unsubstituted heterocyclyl, substituted pyrrolidinyl, substituted or unsubstituted $C_3$-$C_8$ cycloalkyl, disubstituted cyclohexyl, cyclopentyl, substituted or unsubstituted $C_5$-$C_{12}$ bicycloalkyl, substituted or unsubstituted adamantyl, —(CH$_2$)$_q$-group, wherein q is an integer from 1 to 3, under the proviso, if $R^6$ is selected to be a methylene chain —(CH$_2$)$_q$-group, $R^{17}$ or $R^{19}$ are selected to be a methylene chain —(CH$_2$)$_s$-group, wherein s is an integer from 1 to 3 or a —(CH$_2$)$_t$-A-group, t is an integer from 1 to 3 and A is selected from O or N, respectively, and $R^6$ and $R^{17}$ or $R^6$ and $R^{19}$ form together a 5 to 8 membered ring system, or $R^6$ represents —(CH$_2$)$_p$—Z, wherein p is an integer from 0 to 6 and Z is selected from the group comprising:
substituted or unsubstituted aryl, substituted or unsubstituted heteroaryl, substituted or unsubstituted heterocyclyl, —N(R$^7$R$^8$), wherein $R^7$ and $R^8$ represent independently from each other —H, or linear or branched substituted or unsubstituted $C_1$-$C_6$ alkyl, or Z is selected from —(CR$^9$R$^{10}$R$^{11}$), wherein $R^9$, $R^{10}$ and $R^{11}$ are independently of each other selected from the group consisting of:
—H, linear or branched substituted or unsubstituted $C_1$-$C_8$ alkyl, substituted or unsubstituted aryl or —N(R$^{12}$R$^{13}$), wherein $R^{12}$ and $R^{13}$ represent independently of each other —H or linear or branched substituted or unsubstituted $C_1$-$C_6$ alkyl, under the proviso, if Z represents —(CR$^9$R$^{10}$R$^{11}$) as defined above, p is selected to be an integer from 0 to 6, and if Z is selected from substituted or unsubstituted aryl, substituted or unsubstituted heteroaryl, substituted or unsubstituted heterocyclyl, or —N(R$^7$R$^8$) as defined above, p is selected to be an integer from 1 to 6;

L is selected from the group comprising:

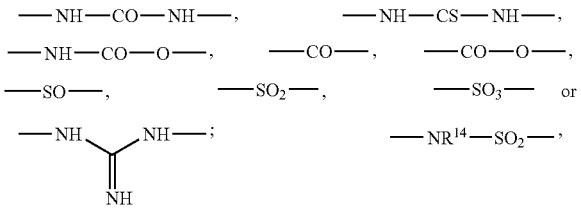

wherein $R^{14}$ is selected from —H, linear or branched substituted or unsubstituted $C_1$-$C_6$ alkyl, —SO$_2$—R$^{15}$, wherein $R^{15}$ is selected from linear or branched $C_1$-$C_6$ alkyl, or $R^{14}$ represents —(CH$_2$)$_r$—COOR$^{16}$, wherein r is an integer from 0 to 6 and $R^{16}$ is selected from —H or linear or branched substituted or unsubstituted $C_1$-$C_6$ alkyl, —NR$^{17}$—CO—,
wherein $R^{17}$ is selected from —H, linear or branched substituted or unsubstituted $C_1$-$C_6$ alkyl, or a —(CH$_2$)$_s$-group, wherein s is an integer from 1 to 3, and
wherein $R^6$ and $R^{17}$ represent both a methylene chain group, $R^6$ and $R^{17}$ may form together a 5 to 8 membered ring system:

wherein $R^{18}$ is selected from —H, or linear or branched substituted or unsubstituted $C_1$-$C_6$ alkyl,
—CO—$NR^{19}$—,
wherein $R^{19}$ is selected from —H, linear or branched substituted or unsubstituted $C_1$-$C_6$ alkyl, or a —$(CH_2)_t$-A-group, wherein t is an integer from 1 to 3 and A is selected from N or O, and wherein if $R^6$ represents a —$(CH_2)_q$-group and $R^{19}$ represents a —$(CH_2)_t$-A-group,
$R^6$ and $R^{19}$ may form together a 5 to 8 membered ring system

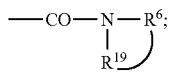

and m is selected to be 0 or 1,
and/or stereoisomeric forms and/or pharmaceutically acceptable salts thereof.

Preferred are compounds having the general formula (I):

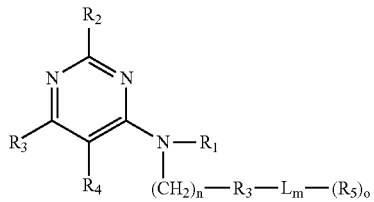

(I)

wherein
each $R_1$ represents independently $R_3$, $R_5$, —H, linear or branched substituted or unsubstituted $C_1$-$C_6$ alkyl, linear or branched $C_2$-$C_6$ alkenyl or linear or branched $C_2$-$C_6$ alkinyl or adamantyl,
$R_2$ and $R_4$ are independently selected from the group consisting of:
$R_3$, $R_5$, —H, —CN, —$NH_2$, —$NO_2$, linear or branched substituted or unsubstituted $C_1$-$C_6$ alkyl, linear or branched $C_2$-$C_6$ alkenyl or $C_2$-$C_6$ linear or branched alkinyl;
$R_3$ and $R_3'$ are independently selected from the group consisting of:
a) halogen, represented by —F, —Cl, —Br or —I,
b) $C_3$-$C_8$ cycloalkyl, which is optionally substituted by at least one of the groups $R_6$, $R_6'$, $R_7$ or $R_7'$,
c) $C_4$-$C_{12}$ bicyclo-alkyl, which is optionally substituted by at least one of the groups $R_6$, $R_6'$, $R_7$ or $R_7'$,
d) aryl, which is optionally substituted by at least one of the groups $R_6$, $R_6'$, $R_7$ or $R_7'$,
e) X-aryl, which is optionally substituted by at least one of the groups $R_6$, $R_6'$, $R_7$ or $R_7'$ and wherein X is independently selected from —O—, —NH—, —S—, linear or branched —$CH_2$—($C_2$-$C_6$ alkyl)-group, linear or branched —$CH_2$—($C_2$-$C_6$ alkenyl)-group, which is optionally substituted by at least one of the groups $R_6$, $R_6'$, $R_7$ or $R_7'$,
f) partially or fully saturated 5 or 6 membered heterocyclic ring, which is optionally substituted by at least one of the groups $R_6$, $R_6'$, $R_7$ or $R_7'$; this heterocyclic ring can be fused to another 5 or 6 membered heterocyclic ring, which is optionally substituted by at least one of the groups $R_6$, $R_6'$, $R_7$ or $R_7'$,
or a 5 or 6 membered heteroaryl ring, which is optionally substituted by at least one of the groups $R_6$, $R_6'$, $R_7$ or $R_7'$; this heteroaryl ring can be fused to another partially or fully saturated 5 or 6 membered heterocyclic group, which is optionally substituted by at least one of the groups $R_6$, $R_6'$, $R_7$ or $R_7'$ or to a 5 or 6 membered heteroaryl ring, which is optionally substituted by at least one of the groups $R_6$, $R_6'$, $R_7$ or $R_7'$;

g) guanidinyl group, optionally substituted by at least one group $R_5$ or h) —Y—$(CH_2)_p$—Z group, wherein Y represents O, S or $NR_5$ and Z represents $R_5$, —$OR_5$, —$N(R_5)_2$ or —$COOR_5$, wherein in the cases, that the group $R_3'$ represents one of the groups cited under a), g) or h) the indices m and o of the -$(L)_m$-$(R_5)_o$-group are selected to be 0, $R_5$ is independently selected from the group consisting of:
—H, $R_1$, $R_2$, $R_3$, $R_4$, —$(CH_2)_q$—$COOR_1$, —CH=CH—$COOR_1$,
—$C(R_1)_2N(R_1)_2$, —$(CH_2)_rN(R_1)_2$, —$NR_1$—$COOR_1$ or —$C(R_1)_3$, $R_6$ and $R_6'$ are independently selected from the group consisting of:
$R_1$, $R_2$, $R_4$, $R_5$, L-H, —H, —$OR_1$, —$N(R_1)_2$, —$C(R_1)_3$, —$CH(R_1)_2$, or —$CH_2R_1$;

$R_7$ and $R_7'$ represent independently from each other $R_6$ and $R_6'$;

L is selected from the group comprising:
—$NR_5$—$SO_2$—, —$NR_5$—CO—$(CH_2)_s$—, —NH—CO—NH—, —CO—$NR_5$—, —$SO_2$—$NR_5$— or —NH— under the proviso, that if m is selected to be 1, o is selected to be 1 as well, m is independently selected to be 0 or 1, n is independently selected to be an, integer from 0 to 6, o is independently selected to be 0 or 1, p, q, r and s are independently from each other an integer from 0 to 6 and/or stereoisomeric forms and/or pharmaceutically acceptable salts thereof.

In formula (I) shown above, the group $R_3'$-$L_m$-$(R_5)_o$ is to be understood in the sense, that the group denoted by $R_3'$ is optionally substituted by a group -$L_m$-$(R_5)_o$. This means that if $R_3'$ is for instance an aryl group, such as phenyl, one of the hydrogen atoms bonded to the aryl group is exchanged by a -$L_m$-$(R_5)_o$ group.

The group aryl as used in items d) and e) of the definition of the groups $R_3$ and $R_3'$, preferably describes an aryl group independently selected from the group consisting of phenyl, biphenyl or naphthyl.

In a preferred embodiment of the compounds according to the present invention the rings defined under f) of the definition of the groups $R^3$ and $R^{3'}$ are independently selected to be

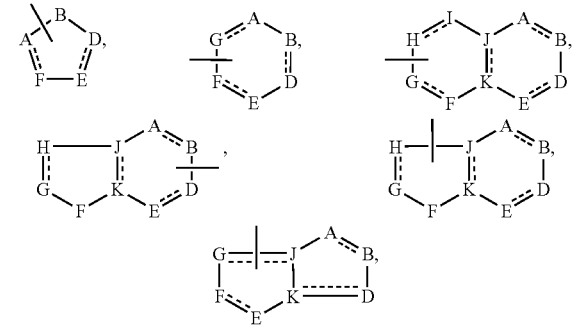

wherein

A, B, D, E, F, G, H and I represent independently of each other:

$CR_6$, $C(R_6)_2$, N, $NR_6$, O or $SR_6$

J and K are independently from each other: C or N, under the proviso that O—O and S—S bonds are excluded and that at least one of the ring atoms in the heterocycle is N, S or O, and each ═══ represent independently from each other a single or a double bond under the proviso that one of the groups $R_6$ comprised in A, B, D, E, F, G H, I, J and K is exchanged with a $-(L)_m-(R_5)_o$-group.

In a further preferred embodiment of the compounds according to the invention $R_1$, $R_2$ and $R_4$ represent independently of each other $R_3$, $R_5$, —H, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH_2$—$C(CH_3)_3$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$C_2H_4$—$CH(CH_3)_2$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$CH$=$CH_2$, —C≡CH, —$CH_2$—$CH$=$CH_2$, —$C(CH_3)$=$CH_2$, —$CH$=$CH$—$CH_3$, —C≡C—$CH_3$, —$CH_2$—C≡CH, —$C_2H_4$—$CH$=$CH_2$, —$CH$=$CH$—$C_2H_5$, —$CH$=$C(CH_3)_2$, —$CH_2$—$CH$=$CH$—$CH_3$, —$CH$=$CH$—$CH$=$CH_2$, —$C_2H_4$≡CH, —C≡C—$C_2H_5$, —$CH_2$—C≡C—$CH_3$, —C≡C—$CH$=$CH_2$, —$CH$=$CH$—C≡CH, —C≡C—C≡CH, —$C_3H_6$—$CH$=$CH_2$, —$CH$=$CH$—$C_3H_7$, —$C_2H_4$—$CH$=$CH$—$CH_3$, —$CH_2$—$CH$=$CH$—$C_2H_5$, —$CH_2$—$CH$=$CH$—$CH$=$CH_2$, —$CH$=$CH$—$CH$=$CH$—$CH_3$, —$CH$=$CH$—$CH_2$—$CH$=$CH_2$, —$C(CH_3)$=$CH$—$CH$=$CH_2$, —$CH$=$C(CH_3)CH$=$CH_2$, —$CH$=$CH$—$C(CH_3)$=$CH_2$, —$CH_2$—$CH$=$C(CH_3)_2$, —$C(CH_3)$=$C(CH_3)_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—$CH$=$CH_2$, —$CH_2$—$CH$=$CH$—C≡CH, —$CH_2$—C≡C—C≡CH, —C≡C—$CH$=$CH$—$CH_3$, —$CH$=$CH$—C≡C—$CH_3$, —C≡C—C≡C—$CH_3$, —C≡C—$CH_2$—$CH$=$CH_2$, —$CH$=$CH$—$CH_2$—C≡CH, —C≡C—$CH_2$—C≡CH, —$C(CH_3)$=$CH$—$CH$=$CH_2$, —$CH$=$C(CH_3)$—$CH$=$CH_2$, —$CH$=$CH$—$C(CH_3)$=$CH_2$, —$C(CH_3)$=$CH$—C≡CH, —$CH$=$C(CH_3)$—C≡CH, —C≡C—$C(CH_3)$=$CH_2$, —$C_4H_8$—$CH$=$CH_2$, —$CH$=$CH$—$C_4H_9$, —$C_3H_6CH$=$CH$—$CH_3$, —$CH_2$—$CH$=$CH$—$C_3H_7$, —$C_2H_4$—$CH$=$CH$—$C_2H_5$, —$CH_2$—$C(CH_3)$=$C(CH_3)_2$, —$C_2H_4$—$CH$=$C(CH_3)_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$; and $R_3$ and $R_{3'}$ represent independently of each other

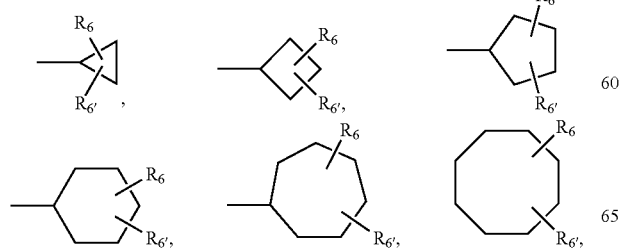

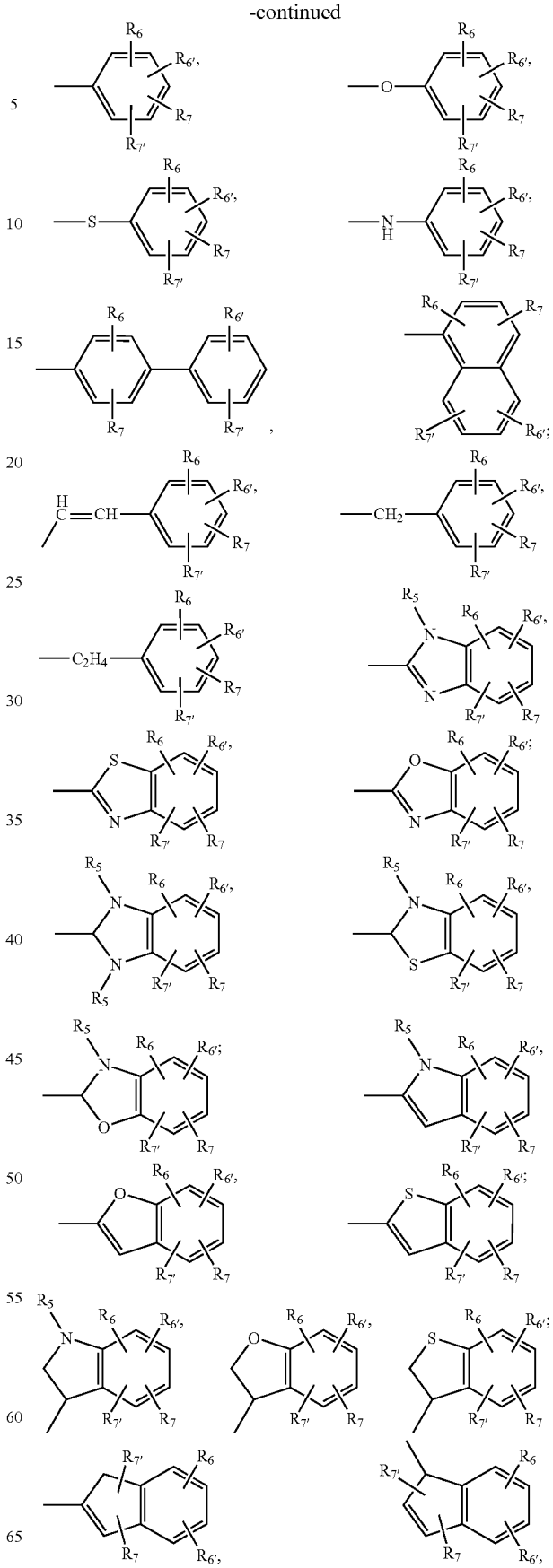

-continued
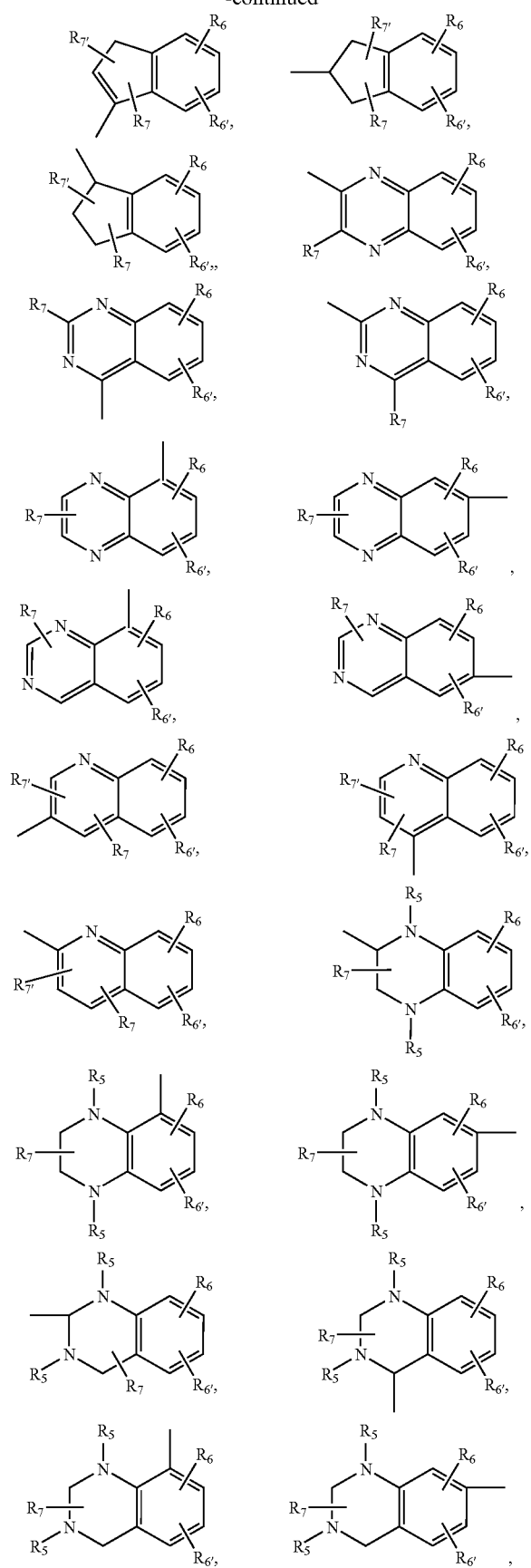
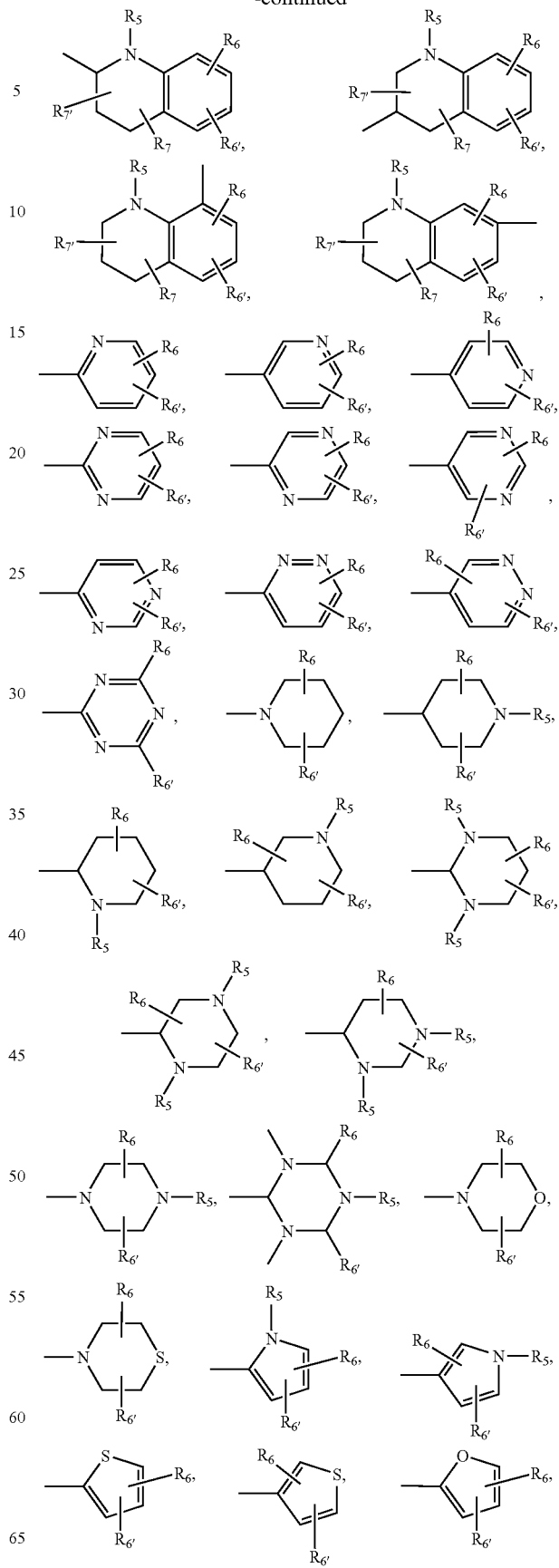

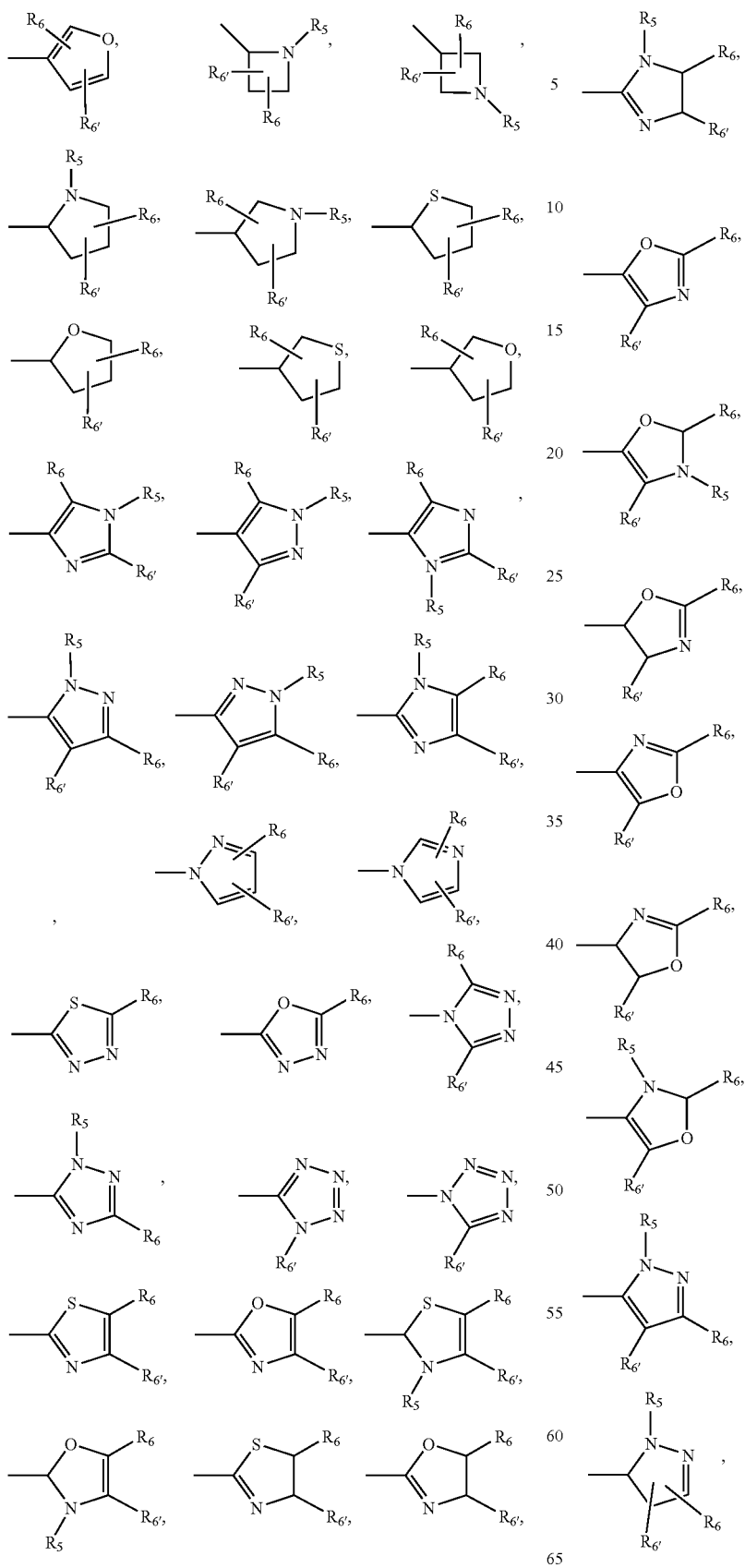

-continued
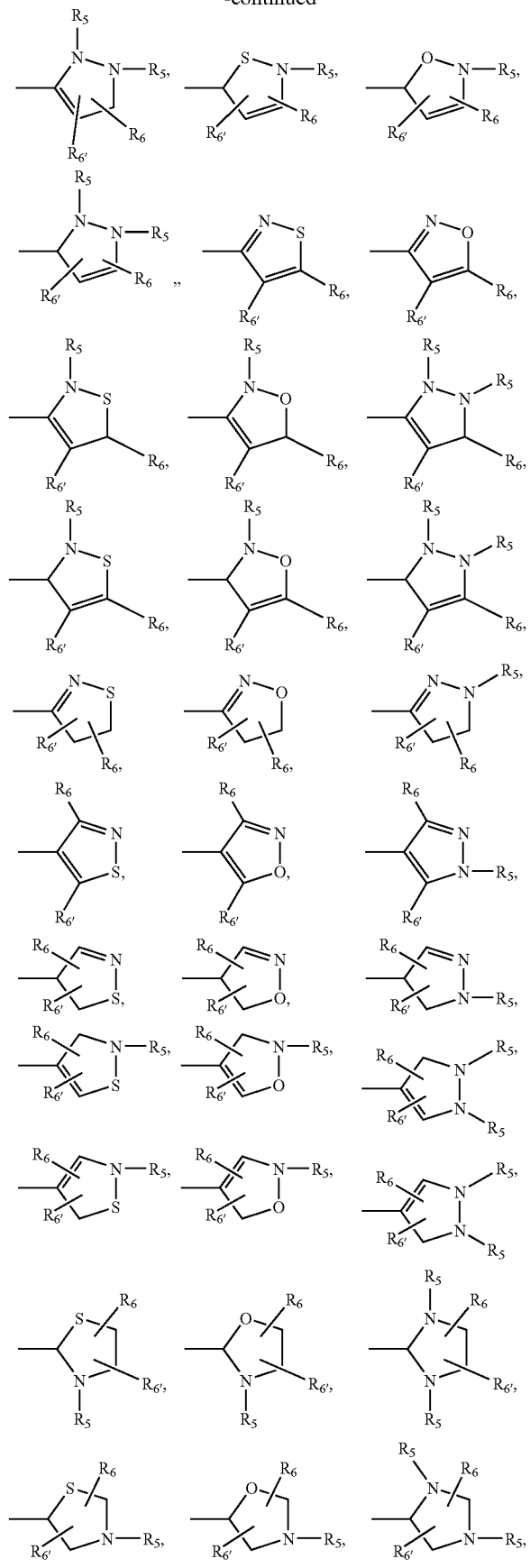
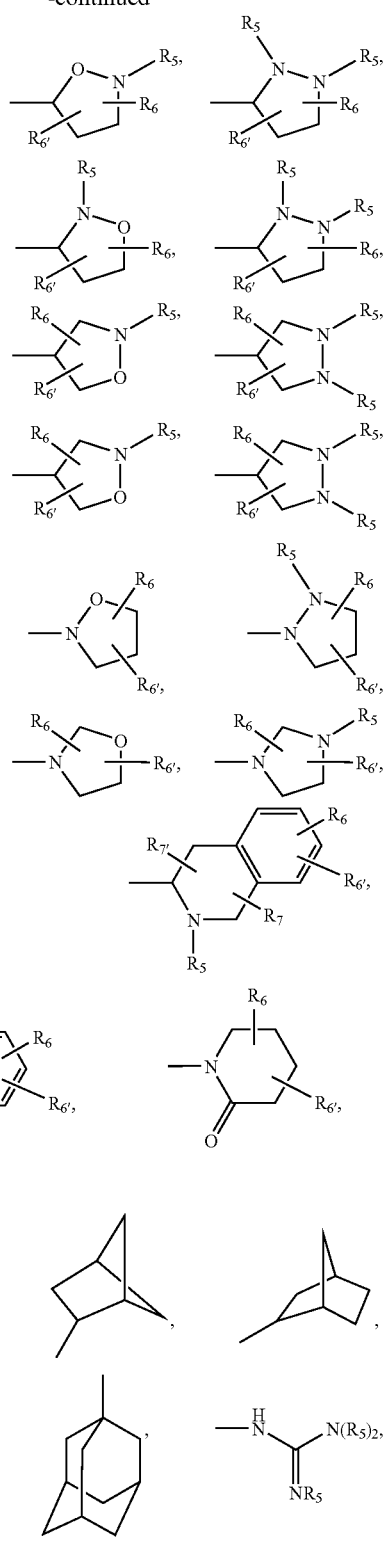
and $R_5$, $R_6$, $R_6'$, $R_7$, $R_7'$, L, X, Y, Z, n, m, o, p, q, r and s have the meanings as defined before.
In yet a further preferred embodiment of the compounds according to the present invention $R_1$ represents —H or linear or branched $C_1$-$C_6$ alkyl, linear or branched $C_2$-$C_6$ alkenyl or linear or $C_2$-$C_6$ branched alkinyl, $R_2$ and $R_4$ represent independently of each other —H or linear or branched $C_1$-$C_6$ alkyl, linear or branched $C_2$-$C_6$ alkenyl, linear or branched
$C_2$-$C_6$ alkinyl, —$NH_2$, —$NO_2$, —CN, $R_3$ or $R_5$;
$R_3$, $R_3'$, $R_5$, $R_6$, $R_6'$, $R_7$, $R_7'$, L, X, Y, Z, n, m, o, p, q, r and s have the meanings as defined above.

In a further preferred embodiment of the compounds according to the present invention $R_1$ represents —H or linear or branched $C_1$-$C_6$ alkyl,
$R_2$ and $R_4$ represent independently of each other —H, —$NH_2$, linear or branched $C_1$-$C_6$ alkyl,
$R_3$ and $R_3'$ are independently selected from the group comprising of:
Halogen, X-aryl, which is optionally substituted by at least one of the groups $R_6$, $R_6'$, $R_7$ or $R_7'$, aryl, which is optionally substituted by at least one of the groups $R_6$, $R_6'$, $R_7$ or $R_7'$;
partially or fully saturated 5 or 6 membered heterocyclic ring, which is optionally substituted by at least one of the groups $R_6$, $R_6'$, $R_7$ or $R_7'$; this heterocyclic ring can be fused to another 5 or 6 membered heterocyclic ring, which is optionally substituted by at least one of the groups $R_6$, $R_6'$, $R_7$ or $R_7'$,
5 or 6 membered heteroaryl ring, which is optionally substituted by at least one of the groups $R_6$, $R_6'$, $R_7$ or $R_7'$; this heteroaryl ring can be fused to another partially or fully saturated 5 or 6 membered heterocyclic ring, which is optionally substituted by at least one of the groups $R_6$, $R_6'$, $R_7$ or $R_7'$ or to a 5 or 6 membered heteroaryl ring, which is optionally substituted at least one of the groups $R_6$, $R_6'$, $R_7$ or $R_7'$,
guanidinyl group, optionally substituted by at least one $R_5$ group or a —Y—$(CH_2)_p$—Z group, wherein X, Y, Z and p have the meanings as defined in claim 1 and
$R_5$, $R_6$, $R_6'$, $R_7$, $R_7'$, L, n, m, o, q, r and s have the meanings as defined above.

In yet another preferred embodiment of the compounds of the present invention $R_1$ represents —H or linear or branched $C_1$-$C_6$ alkyl,
$R_2$ and $R_4$ represent independently of each other —H, —$NH_2$ or linear or branched $C_1$-$C_6$ alkyl,
$R_3$ and $R_3'$ are independently selected from the group comprising of:
Halogen, X-aryl, which is optionally substituted by at least one of the groups $R_6$, $R_6'$, $R_7$ or $R_7'$, aryl, which is optionally substituted by at least one of the groups $R_6$, $R_6'$, $R_7$ or $R_7'$;
partially or fully saturated 5 or 6 membered heterocyclic ring, which is optionally substituted by at least one of the groups $R_6$, $R_6'$, $R_7$ or $R_7'$; this heterocyclic ring can be fused to another 5 or 6 membered heterocyclic ring, which is optionally substituted by at least one of the groups $R_6$, $R_6'$, $R_7$ or $R_7'$,
5 or 6 membered heteroaryl ring, which is optionally substituted by at least one of the groups $R_6$, $R_6'$, $R_7$ or $R_7'$; this heteroaryl ring can be fused to another partially or fully saturated 5 or 6 membered heterocyclic ring, which is optionally substituted by at least one of the groups $R_6$, $R_6'$, $R_7$ or $R_7'$ or to a 5 or 6 membered heteroaryl ring, which is optionally substituted by at least one of the groups $R_6$, $R_6'$, $R_7$ or $R_7'$,
guanidinyl group, optionally substituted by at least one $R_5$ group or a —Y—$(CH_2)_p$—Z group, wherein X, Y, Z and p have the meanings as defined in claim 1;
L represents —$NR_5$—$SO_2$—, —$NR_5$—CO—$(CH_2)_s$—, —NH—CO—NH—, —CO—$NR_5$— or —$SO_2$—$NR_5$—,
$R_5$, $R_6$, $R_6'$, $R_7$, $R_7'$, n, m, o, q, r and s have the meanings as defined above.

In yet another preferred embodiment of the compounds according to the present invention $R_1$ represents —H or linear or branched $C_1$-$C_6$ alkyl;

$R_2$ and $R_4$ represent independently of each other —H or $NH_2$;
$R_3$ and $R_3'$ are independently selected from the group comprising of:
Halogen, X-aryl, which is optionally substituted by at least one of the groups $R_6$, $R_6'$, $R_7$ or $R_7'$, aryl, which is optionally substituted by at least one of the groups $R_6$, $R_6'$, $R_7$ or $R_7'$,
partially or fully saturated 5 or 6 membered heterocyclic ring which is optionally substituted by at least one of the groups $R_6$, $R_6'$, $R_7$ or $R_7'$; this ring can be fused to another 5 or 6 membered heterocyclic ring, which is optionally substituted by at least one of the groups $R_6$, $R_6'$, $R_7$ or $R_7'$,
5 or 6 membered heteroaryl ring, which is optionally substituted by at least one of the groups $R_6$, $R_6'$, $R_7$ or $R_7'$; this ring can be fused to another partially or fully saturated 5 or 6 membered heterocyclic ring, which is optionally substituted by at least one of the groups $R_6$, $R_6'$, $R_7$ or $R_7'$ or to a 5 or 6 membered heteroaryl ring, which is optionally substituted by at least one of the groups $R_6$, $R_6'$, $R_7$ or $R_7'$,
guanidinyl group, optionally substituted by at least one $R_5$ group or a —Y—$(CH_2)_p$—Z group, wherein X, Y, Z and p have the meanings as defined in claim 1;
L represents —$NR_5$—$SO_2$—, —$NR_5$—CO—$(CH_2)_s$—, —NH—CO—NH—, —CO—$NR_5$— or —$SO_2$—$NR_5$—,
$R_5$ is selected from the group consisting of:
linear or branched $C_1$-$C_6$ alkyl, $C_3$-$C_8$ cycloalkyl, which is optionally substituted by at least one of the groups $R_6$, $R_6'$, $R_7$ or $R_7'$; $C_4$-$C_{12}$ bicycloalkyl, which is optionally substituted by at least one of the groups $R_6$, $R_6'$, $R_7$ or $R_7'$,
aryl, which is optionally substituted by at least one of the groups $R_6$, $R_6'$, $R_7$ or $R_7'$, —$CH_2$-aryl, which is optionally substituted by at least one of the groups $R_6$, $R_6'$, $R_7$ or $R_7'$,
partially or fully saturated 5 or 6 membered heterocyclic ring, which is optionally substituted by $R_6$, $R_6'$, $R_7$ or $R_7'$; this ring can be fused to another 5 or 6 membered heterocyclic ring, which is optionally substituted by at least one of the groups $R_6$, $R_6'$, $R_7$ or $R_7'$, 5 or 6 membered heteroaryl ring, which is optionally substituted by at least one of the groups $R_6$, $R_6'$, $R_7$ or $R_7'$; this ring can be fused to another partially or fully saturated 5 or 6 membered heterocyclic ring, which is optionally substituted by at least one of the groups $R_6$, $R_6'$, $R_7$ and $R_7'$ or to a 5 or 6 membered heteroaryl ring, which is optionally substituted by at least one of the groups $R_6$, $R_6'$, $R_7$ or $R_7'$,
—$(CH_2)_q$—$COOR_1$, wherein $R_1$ represents —H or a linear or branched $C_1$-$C_6$ alkyl, —$(CH_2)_r$—$N(R_1)_2$, wherein $R_1$ represents independently —H or a linear or branched $C_1$-$C_6$ alkyl, —$(CR_1)_2$—$N(R_1)_2$, wherein $R_1$ represents independently —H or a linear or branched $C_1$-$C_6$ alkyl or —$C(R_1)_3$, wherein R1 represents independently —H, a linear or branched $C_1$-$C_6$ alkyl or an aryl group, which is optionally substituted by $R_6$, $R_6'$, $R_7$ and $R_7'$;
$R_6$, $R_6'$, $R_7$, $R_7'$, n, m, o, p, q, r and s have the meanings as defined above.

In yet another preferred embodiment of the compounds according to the present invention, $R_1$ represents —H or linear or branched $C_1$-$C_6$ alkyl,
$R_2$ and $R_4$ represent independently of each other —H or $NH_2$,
$R_3$ and $R_3'$ are independently selected from the group comprising of:
Halogen, X-aryl, which is optionally substituted by at least one of the groups $R_6$, $R_6'$, $R_7$ or $R_7'$, aryl, which is optionally substituted by at least one of the groups $R_6$, $R_6'$, $R_7$ or $R_7'$,
partially or fully saturated 5 or 6 membered heterocyclic ring, which is optionally substituted by at least one of the groups $R_6$, $R_6'$, $R_7$ or $R_7'$; this heterocyclic ring can be fused to another 5 or 6 membered heterocyclic ring, which is optionally substituted by at least one of the groups $R_6$, $R_6'$, $R_7$ or $R_7'$, 5 or 6 membered heteroaryl ring, which is optionally substituted by at least one of the groups $R_6$, $R_6'$, $R_7$ or $R_7'$; this heteroaryl ring can be fused to another partially or fully saturated 5 or 6 membered heterocyclic ring, which is optionally substituted by at least one of the groups $R_6$, $R_6'$, $R_7$ or $R_7'$ or to a 5 or 6 membered heteroaryl ring, which is optionally substituted by at least one of the groups $R_6$, $R_6'$, $R_7$ or $R_7'$ or a —Y—$(CH_2)_p$—Z group, wherein X, Y, Z and p have the meanings as defined in claim 1;

L represents —$NR_5$—$SO_2$—, —$NR_5$—CO—$(CH_2)_n$—, —NH—CO—NH—, —CO—$NR_5$— or —$SO_2$—$NR_5$—

$R_5$ is selected from the group comprising:

linear or branched $C_1$-$C_6$ alkyl, aryl, which is optionally substituted by at least one of the groups $R_6$, $R_6'$, $R_7$ or $R_7'$, partially or fully saturated 5 or 6 membered heterocyclic ring, which is optionally substituted by at least one of the groups $R_6$, $R_6'$, $R_7$ or $R_7'$; this heterocyclic ring can be fused to another 5 or 6 membered heterocyclic ring, which is optionally substituted by $R_6$, $R_6'$, $R_7$ or $R_7'$, 5 or 6 membered heteroaryl ring, which is optionally substituted by at least one of the groups $R_6$, $R_6'$, $R_7$ or $R_7'$; this heteroaryl ring can be fused to another partially or fully saturated 5 or 6 membered heterocyclic ring, which is optionally substituted by at least one of the groups $R_6$, $R_6'$, $R_7$ or $R_7'$ or to a 5 or 6 membered heteroaryl ring, which is optionally substituted by at least one of the groups $R_6$, $R_6'$, $R_7$ or $R_7'$, $C_3$-$C_8$ cycloalkyl, which is optionally substituted by at least one of the groups $R_6$, $R_6'$, $R_7$ or $R_7'$ or $C_4$-$C_{12}$ bicycloalkyl, which is optionally substituted by at least one of the groups $R_6$, $R_6'$, $R_7$ or $R_7'$;

$R_6$, $R_6'$, $R_7$ and $R_7'$ represent independently of each other: —H, —F, —Cl, —Br, —I, $R_1$, —$OR_1$, —$N(R_1)_2$, —CH=CH—$COOR_1$, —$(CH_2)_q COOR_1$, or a —O—$(CH_2)_t$-aryl, which is optionally substituted by at least one of the groups $R_6$, $R_6'$, $R_7$ or $R_7'$, wherein in these cases, $R_1$ is independently selected from —H or linear or branched $C_1$-$C_6$ alkyl and t is selected to be an integer from 0 to 6, n, m, o, p, q, r and s have the meanings as defined above.

In yet another preferred embodiment of the present invention $R_6$, $R_6'$, $R_7$, $R_7'$ represent independently of each other —H, linear or branched $C_1$-$C_6$ alkyl, —$OR_1$, —O—$(CH_2)_s$-aryl group, which is optionally substituted by at least one of the groups $R_6$, $R_6'$, $R_7$ or $R_7'$; —$N(R_1)_2$, —CH=CH—$COOR_1$ —$(CH_2)_q COOR_1$, wherein in these cases, $R_1$ represents independently —H or linear or branched $C_1$-$C_6$ alkyl.

In a further embodiment of the compounds according to the present invention, $R_1$ represents —H or linear or branched $C_1$-$C_6$ alkyl, $R_2$ and $R_4$ are independently selected from —H or —$NH_2$.

In yet another embodiment of the compounds of the present invention as defined by general formula (I), each $R_1$ independently represents —H, linear or branched $C_1$-$C_6$ alkyl, linear or branched $C_2$-$C_6$ alkenyl or linear or branched $C_2$-$C_6$ alkinyl or benzyl, preferably —H, or linear or branched $C_1$-$C_6$ alkyl, $R_2$ and $R_4$ are independently selected from the group consisting of:

—H, —CN, —$NH_2$, —$NO_2$, linear or branched $C_1$-$C_6$ alkyl, linear or branched $C_2$-$C_6$ alkenyl or $C_2$-$C_6$ linear or branched alkinyl, and preferably are independently selected from —H or —$NH_2$, $R_3$ is selected from the group consisting of halogen, pyridinyl, thienyl, phenyl and biphenyl, preferably phenyl, which are optionally substituted by at least one of the groups $R_6$, $R_6'$, $R_7$, $R_7'$, $R_6$, wherein $R_6$, $R_6'$, $R_7$, $R_7'$ are preferably selected from halogen, such as —F, —Cl, —Br, or I, —$OR_1$, —$N(R_1)_2$, wherein in these groups each $R_1$ is preferably independently selected from —H or linear or branched $C_1$-$C_6$ alkyl or benzyl, n is selected to be 0, m is 0 or 1, preferably 1, o is 0 or 1, preferably 1, $R_3'$ is phenyl, optionally substituted by at least one of the groups $R_6$, $R_6'$, $R_7$ or $R_7'$, wherein $R_6$, $R_6'$, $R_7$, $R_7'$ are preferably selected from halogen, such as —F, —Cl, —Br, or I, —$OR_1$, —$N(R_1)_2$, wherein in these groups each $R_1$ is preferably independently selected from —H or linear or branched $C_1$-$C_6$ alkyl, L is —NH—CO—$(CH_2)_s$—, wherein s is preferably 0 or 1, or —NH—$SO_2$—, and preferably is —NH—CO—, and $R_5$ is selected from the group consisting of:

a partially or fully saturated 5 or 6 membered heterocyclic ring, which is optionally substituted by at least one of the groups $R_6$, $R_6'$, $R_7$ or $R_7'$; this heterocyclic ring can be fused to another 5 or 6 membered heterocyclic ring, which is optionally substituted by at least one of the groups $R_6$, $R_6'$, $R_7$ or $R_7$, wherein $R_6$, $R_6'$, $R_7$, $R_7'$ in these heterocyclic rings are preferably selected from halogen, such as —F, —Cl, —Br, or I, —$OR_1$, —$N(R_1)_2$, wherein in these groups each $R_1$ is preferably independently selected from —H or linear or branched $C_1$-$C_6$ alkyl, and wherein $R_5$ is preferably selected from the group consisting of azetidinyl, pyrrolidinyl, or piperidinyl, each of these heterocycles optionally substituted in the above indicated manner, a 5 or 6 membered heteroaryl ring, which is optionally substituted by at least one of the groups $R_6$, $R_6'$, $R_7$ or $R_7'$; this heteroaryl ring can be fused to another partially or fully saturated 5 or 6 membered heterocyclic group, which is optionally substituted by at least one of the groups $R_6$, $R_6'$, $R_7$ or $R_7'$ or to a 5 or 6 membered heteroaryl ring, which is optionally substituted by at least one of the groups $R_6$, $R_6'$, $R_7$ or $R_7$; wherein $R_6$, $R_6'$, $R_7$, $R_7'$ in these rings are preferably selected from halogen, such as —F, —Cl, —Br, or I, —$OR_1$, —$N(R_1)_2$, wherein in these groups each $R_1$ is preferably independently selected from —H or linear or branched $C_1$-$C_6$ alkyl, and wherein $R_5$ is preferably selected from the group consisting of benzoxazoly, benzimidazolyl, chinolinyl, imidazoly, benzothiazolyl, 1,2,3,4,-Tetrahydro-isoquinolinyl, or pyridinyl, each of these groups optionally being substituted in the above indicated manner, phenyl, optionally substituted by at least one of the groups $R_6$, $R_6'$, $R_7$ or $R_7'$, wherein $R_6$, $R_6'$, $R_7$, $R_7'$ are preferably selected from halogen, such as —F, —Cl, —Br, or I, —$OR_1$, —$N(R_1)_2$, wherein in these groups each $R_1$ is preferably independently selected from —H or linear or branched $C_1$-$C_6$ alkyl, or $C_1$-$C_6$-alkyl or a $C_3$-$C_8$-cycloalkyl, which is optionally substituted by at least one of the groups $R_6$, $R_6'$, $R_7$ or $R_7'$, wherein $R_6$, $R_6'$, $R_7$, $R_7'$ are preferably selected from halogen, such as —F, —Cl, —Br, or I, —$OR_1$, —$N(R_1)_2$, wherein in these groups each $R_1$ is preferably independently selected from —H or linear or branched $C_1$-$C_6$ alkyl.

In a further embodiment of the present invention, the compound of the present invention defined by general formula (I) represents a chiral compound. The compound can be a racemate or a R or a S enantiomer.

As used in the present invention the terms linear or branched $C_1$-$C_8$ alkyl, linear or branched $C_2$-$C_6$ alkenyl or linear or branched $C_2$-$C_6$ alkinyl are meant to include the following alkyls, alkenyls or alkinyls:

—CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —(CH$_2$)$_6$—CH$_3$, —CH(CH$_3$)—(CH$_2$)$_4$—CH$_3$, —(CH$_2$)$_2$—CH(CH$_3$)—(CH$_2$)$_2$—CH$_3$, —(CH$_2$)$_3$—CH(CH$_3$)—C$_2$H$_5$, —(CH$_2$)$_4$—CH(CH$_3$)$_2$, —C(CH$_3$)$_2$—(CH$_2$)$_3$—CH$_3$, —CH$_2$—C(CH$_3$)$_2$—(CH$_2$)$_2$—CH$_3$, —(CH$_2$)$_2$—C(CH$_3$)$_2$—C$_2$H$_5$, —(CH$_2$)$_4$—CH(CH$_3$)$_2$, —(CH$_2$)$_3$—C(CH$_3$)$_3$, —CH(C$_2$H$_5$)—(CH$_2$)$_3$—CH$_3$, —(CH$_2$)$_3$—CH(C$_2$H$_5$)—CH$_3$, —C(C$_2$H$_5$)$_3$, —CH$_2$—C(C$_2$H$_5$)$_2$—CH$_3$, —(CH$_2$)$_2$—CH(C$_2$H$_5$)$_2$, —CH(C$_3$H$_7$)—(CH$_2$)$_2$—CH$_3$, —CH$_2$—CH(C$_3$H$_7$)—C$_2$H$_5$, —(CH$_2$)$_2$—CH(C$_3$H$_7$)—CH$_3$, —(CH$_2$)$_7$—CH$_3$, —CH(CH$_3$)—(CH$_2$)$_5$—CH$_3$, —(CH$_2$)$_2$—CH(CH$_3$)—(CH$_2$)$_3$—CH$_3$, —(CH$_2$)$_3$—CH(CH$_3$)—(CH$_2$)$_2$—CH$_3$, —(CH$_2$)$_4$—CH(CH$_3$)—C$_2$H$_5$, —(CH$_2$)$_5$—CH(CH$_3$)$_2$, —(CH$_2$)$_4$—C(CH$_3$)$_3$, —CH(C$_2$H$_5$)—(CH$_2$)$_4$—CH$_3$, —(CH$_2$)$_2$—CH(C$_2$H$_5$)—(CH$_2$)$_2$—CH$_3$, —(CH$_2$)$_3$—CH(C$_2$H$_5$)$_2$, —CH(C$_3$H$_7$)—(CH$_2$)$_3$—CH$_3$, —CH$_2$—CH(C$_3$H$_7$)—(CH$_2$)$_2$—CH$_3$, —(CH$_2$)$_2$—CH(C$_3$H$_7$)—C$_2$H$_5$, —(CH$_2$)$_3$—CH(C$_3$H$_7$)—CH$_3$, —CH═CH$_2$, —CH$_2$—CH═CH$_2$, —C(CH$_3$)═CH$_2$, —CH═CH—CH$_3$, —C$_2$H$_4$—CH═CH$_2$, —CH$_2$—CH═CH—CH$_3$, —CH═CH—C$_2$H$_5$, —CH$_2$—C(CH$_3$)═CH$_2$, —CH(CH$_3$)—CH═CH, —CH═C(CH$_3$)$_2$, —C(CH$_3$)═CH—CH$_3$, —CH═CH—CH═CH$_2$, —C$_3$H$_6$—CH═CH$_2$, —C$_2$H$_4$—CH═CH—CH$_3$, —CH$_2$—CH═CH—C$_2$H$_5$, —CH═CH—C$_3$H$_7$, —CH$_2$—CH═CH—CH═CH$_2$, —CH═CH—CH═CH—CH$_3$, —CH═CH—CH$_2$—CH═CH$_2$, —C(CH$_3$)═CH—CH═CH$_2$, —CH═C(CH$_3$)—CH═CH$_2$, —CH═CH—C(CH$_3$)═CH$_2$, —C$_2$H$_4$—C(CH$_3$)═CH$_2$, —CH$_2$—CH(CH$_3$)—CH═CH$_2$, —CH(CH$_3$)—CH$_2$—CH═CH$_2$, —CH$_2$—CH═C(CH$_3$)$_2$, —CH$_2$—C(CH$_3$)═CH—H$_3$, —CH(CH$_3$)—CH═CH—CH$_3$, —CH═CH—CH(CH$_3$)$_2$, —CH═C(CH$_3$)—C$_2$H$_5$, —C(CH$_3$)═CH—C$_2$H$_5$, —C(CH$_3$)═C(CH$_3$)$_2$, —C(CH$_3$)$_2$—CH═CH$_2$, —CH(CH$_3$)—C(CH$_3$)═CH$_2$, —C(CH$_3$)$_2$—CH═CH—CH$_2$, —CH═C(CH$_3$)—CH═CH—CH$_3$, —CH═CH—CH═CH—CH$_3$, —C$_4$H$_8$—CH═CH$_2$, —C$_3$H$_6$—CH═CH—CH$_3$, —C$_2$H$_4$—CH═CH—C$_2$H$_5$, —CH$_2$—CH═CH—C$_3$H$_7$, —CH═CH—C$_4$H$_9$, —C$_3$H$_6$—C(CH$_3$)═CH$_2$, —C$_2$H$_4$—CH(CH$_3$)—CH═CH$_2$, —CH$_2$—CH(CH$_3$)—CH$_2$—CH═CH$_2$, —CH(CH$_3$)—C$_2$H$_4$—CH═CH$_2$, —C$_2$H$_4$—CH═C(CH$_3$)$_2$, —C$_2$H$_4$—C(CH$_3$)═CH—CH$_3$, —CH$_2$—CH(CH$_3$)—CH═CH—CH$_3$, —CH(CH$_3$)—CH$_2$—CH═CH—CH$_3$, —CH$_2$—CH═CH—CH(CH$_3$)$_2$, —CH$_2$—CH═C(CH$_3$)—C$_2$H$_5$, —CH$_2$—C(CH$_3$)═CH—C$_2$H$_5$, —CH(CH$_3$)—CH═CH—C$_2$H$_5$, —CH═CH—CH$_2$—CH(CH$_3$)$_2$, —CH═CH—CH(CH$_3$)—C$_2$H$_5$, —CH═C(CH$_3$)—C$_3$H$_7$, —C(CH$_3$)═CH—C$_3$H$_7$, —CH$_2$—CH(CH$_3$)—C(CH$_3$)═CH$_2$, —CH(CH$_3$)—CH$_2$—C(CH$_3$)═CH$_2$, —CH(CH$_3$)—CH(CH$_3$)—CH═CH$_2$, —CH$_2$—C(CH$_3$)$_2$—CH═CH$_2$, —C(CH$_3$)$_2$—CH$_2$—CH═CH$_2$, —CH$_2$—C(CH$_3$)═C(CH$_3$)$_2$, —CH(CH$_3$)—CH═C(CH$_3$)$_2$, —C(CH$_3$)$_2$—CH═CH—CH$_3$, —CH═C(CH$_3$)—CH(CH$_3$)$_2$, —C(CH$_3$)$_2$—C(CH$_3$)═CH$_2$, —CH(CH$_3$)—C(CH$_3$)═CH—CH$_3$, —CH(C$_2$H$_5$)—CH═CH—CH$_3$, —CH(C$_2$H$_5$)—CH═CH—CH$_3$, —C(C$_4$H$_9$)═CH$_2$, —C(C$_3$H$_7$)═CH—CH$_3$, —C(C$_2$H$_5$)═CH—C$_2$H$_5$, —C(C$_2$H$_5$)═C(CH$_3$)$_2$, —C[C(CH$_3$)$_3$]═CH$_2$, —C[CH(CH$_3$)(C$_2$H$_5$)]═CH$_2$, —C[CH$_2$—CH(CH$_3$)$_2$]═CH$_2$, —C$_2$H$_4$—CH═CH—CH═CH$_2$, —CH$_2$—CH═CH—CH$_2$—CH═CH$_2$, —CH═CH—C$_2$H$_4$—CH═CH$_2$, —CH$_2$—CH═CH—CH═CH—CH$_3$, —CH═CH—CH$_2$—CH═CH—CH$_3$, —CH═CH—CH═CH—C$_2$H$_5$, —CH$_2$—CH═CH—C(CH$_3$)═CH$_2$, —CH$_2$—CH═C(CH$_3$)—CH═CH$_2$, —CH$_2$—C(CH$_3$)═CH—CH═CH$_2$, —CH(CH$_3$)—CH═CH—CH═CH$_2$, —CH═CH—CH$_2$—C(CH$_3$)═CH$_2$, —CH═CH—CH(CH$_3$)—CH═CH$_2$, —CH═C(CH$_3$)—CH$_2$—CH═CH$_2$, —C(CH$_3$)═CH—CH$_2$—CH═CH$_2$, —CH═CH—CH═C(CH$_3$)$_2$, —CH═CH—C(CH$_3$)═CH—CH$_3$, —CH═C(CH$_3$)—CH═CH—CH$_3$, —C(CH$_3$)═CH—CH═CH—CH$_3$, —CH═C(CH$_3$)—C(CH$_3$)═CH$_2$, —C(CH$_3$)═CH—C(CH$_3$)═CH$_2$, —C(CH$_3$)═C(CH$_3$)—CH═CH$_2$, —CH═CH—CH═CH—CH═CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C≡C—C$_4$H$_9$, —C$_2$H$_4$—CH(CH$_3$)—C≡CH, —CH$_2$—CH(CH$_3$)—CH$_2$—C≡CH, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —C≡C—C(CH$_3$)$_3$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —C(C≡CH)$_2$—CH$_3$, —CH$_2$—CH(C≡CH)$_2$, —CH(C≡CH)—C≡C—CH$_3$, —C≡C—CH═CH$_2$, —CH═CH—C≡CH, —CH$_2$—C≡C—CH═CH$_2$, —CH$_2$—CH═CH—C≡CH, —C≡C—CH$_2$—CH═CH$_2$, —CH═CH—CH$_2$—C≡CH, —C≡C—C≡C—CH$_3$, —CH$_2$—C≡C—CH═CH$_2$, —CH═CH—CH$_2$—C≡CH, —C≡C—CH$_2$—C≡CH, —C(CH$_3$)═CH—C≡CH, —CH═C(CH$_3$)—C≡CH, —C≡C—C(CH$_3$)═CH$_2$, and —C≡C—C≡C—C≡CH.

The term linear or branched $C_1$-$C_6$ substituted or unsubstituted alkyl, linear or branched $C_1$-$C_4$ substituted or unsubstituted alkyl or linear or branched $C_2$-$C_4$ alkenyl is meant to include the respective subgroup out of the above groups.

The term $C_3$-$C_8$ cycloalkyl denotes the following cycloalkyls:

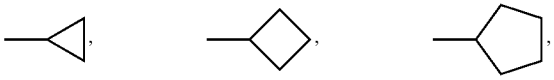

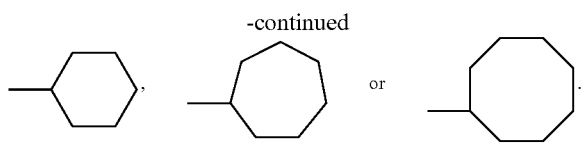

The term $C_5$-$C_{12}$ bicycloalkyl is meant to include the following bicycloalkyls:

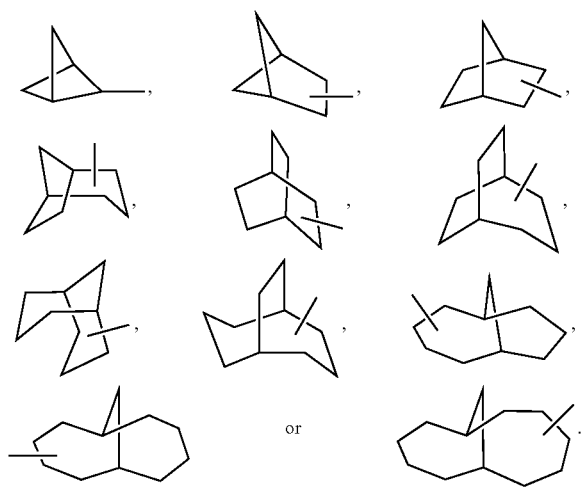

The term aryl denotes an aromatic mono- or bicyclic 6 to 10 membered ring system such as phenyl, naphthyl, 3-chlorophenyl, 2,6-dibromophenyl, 2,4,6-tribromophenyl, 4,7-dichloronaphthyl, and preferably phenyl or naphthyl.

The term heterocyclyl is meant to include a 5 to 10 membered mono- or bicyclic ringsystem, containing one to three heteroatoms independently selected from oxygen, sulfur or nitrogen and is preferably selected from the group comprising: Aziridinyl, azetidinyl, pyrrolidinyl, tetrahydrofuranyl, tetrahydrothiophenyl, piperidinyl, piperadizinyl, piperazinyl, tetrahydropyranyl, tetrahydrothiopyranyl or morpholinyl.

The term heterocyclyl further comprises all heteroaryls as defined below, wherein all double bonds of the correspondent heteroaryls are replaced by single bonds.

The term heteroaryl denotes a partially or fully unsaturated 5 to 10 membered mono- or bicyclic ringsystem, containing one to three heteroatoms independently selected from oxygen, sulfur or nitrogen and is preferably selected from the group consisting of:
Pyrrolyl, furanyl, thiophenyl, thienyl, imidazolyl, pyrazolyl, thiazolyl, oxazolyl, isothiazolyl, isoxazolyl, pyridinyl, pyridyl, pyrimidinyl, pyrimidyl, pyrazinyl, pyrazyl, pyradizinyl, pyradizyl, 3-methylpyridyl, benzothienyl, 4-ethylbenzothienyl, 3,4-diethylfuranyl, pyrrolyl, tetrahydroquinolyl, quinolyl, tetrahydroisoquinolinyl, isoquinolinyl, benzoimidazolyl, benzothiazolyl, benzooxyzolyl, benzo[1,3]dioxolyl, indolyl, benzofuranyl, benzothiophenyl, indazolyl or chrom-2-onyl.

It is to be understood, that the term heteroaryl also comprises partially unsaturated 5 to 10 membered mono- or bicyclic ringsystem, wherein one up to 4 double bonds of the ringsystem are replaced by a single bond and wherein the ringsystem contains at least one double bond.

In a preferred embodiment of the present invention, $R^1$ in the compounds according to the general formula (I) is selected from —H or linear or branched substituted or unsubstituted $C_1$-$C_6$ alkyl, preferably from —H or linear or branched substituted or unsubstituted $C_1$-$C_4$ alkyl, more preferably from —H or —$CH_3$, and is most preferably —H.

In a further preferred embodiment of the present invention, $R^2$ in the compounds according to the general formula (I) is selected from —H, —$NH_2$ or linear or branched substituted or unsubstituted $C_1$-$C_6$ alkyl, preferably from —H or linear or branched substituted or unsubstituted $C_1$-$C_4$ alkyl, and is more preferably —H.

In yet another preferred embodiment of the present invention, $R^4$ in the compounds according to the general formula (I) is selected from —H, —$NH_2$ or linear or branched substituted or unsubstituted $C_1$-$C_6$ alkyl, preferably from —H or linear or branched substituted or unsubstituted $C_1$-$C_4$ alkyl, more preferably from —H or —$CH_3$, and is most preferably —H.

In yet another preferred embodiment of the present invention, m in the compounds according to the general formula (I) is selected to be 0, $R^3$ is selected from the group comprising: Substituted or unsubstituted aryl, preferably substituted or unsubstituted phenyl, more preferably substituted phenyl, and
$R^5$ is selected from the group consisting of:
Substituted or unsubstituted aryl, preferably substituted or unsubstituted phenyl, more preferably substituted phenyl, or —$(CH_2)_o$—Y, wherein o is an integer from 0 to 4 and Y represents substituted or unsubstituted heteroaryl, preferably unsubstituted heteroaryl.

In yet another preferred embodiment of the present invention, $R^3$ and $R^5$ in the compounds according to the general formula (I) represent phenyl, wherein each phenyl is independently of each other partially or fully substituted with members selected from the group consisting of:
Linear or branched substituted or unsubstituted $C_1$-$C_6$ alkyl, preferably linear or branched substituted or unsubstituted $C_1$-$C_4$ alkyl, more preferably —$CH_3$, linear or branched $C_1$-$C_6$ alkoxy, preferably linear or branched $C_1$-$C_4$ alkoxy, more preferably —$OCH_3$, —O—$(CH_2)_u$-Phenyl, wherein u is an integer from 0 to 6, preferably from 0 to 4, more preferably from 0 to 2,
—$NR^{20}R^{21}$, wherein $R^{20}$ and $R^{21}$ are independently of each other selected from —H or linear or branched substituted or unsubstituted $C_1$-$C_6$ alkyl, more preferably from —H or linear or branched substituted or unsubstituted $C_1$-$C_4$ alkyl, and are most preferably —H, —$COOR^{22}$, wherein $R_{22}$ represents linear or branched substituted or unsubstituted $C_1$-$C_6$ alkyl, preferably linear or branched substituted or unsubstituted $C_1$-$C_4$ alkyl, more preferably —$CH_3$, or phenyl is substituted with heteroaryl selected from benzoimidazolyl, benzothiazolyl or benzoxazolyl,
and wherein each phenyl is preferably mono-, di- or trisubstituted, more preferably mono- or disubstituted.

In yet another preferred embodiment of the present invention, $R^5$ in the compounds according to the general formula (I) represents —$(CH_2)_o$—Y, wherein o is selected to be 2 and wherein Y represents unsubstituted pyridinyl, preferably unsubstituted 4-pyridinyl.

In another preferred embodiment of the present invention, m in the compounds according to the general formula (I) is selected to be 1.

In yet another preferred embodiment of the present invention, $R^3$ in the compounds according to the general formula (I) is selected from the group comprising:
—Cl, —Br, —I, preferably —Cl or —Br, more preferably —Cl, substituted or unsubstituted aryl, substituted or unsubstituted —CH=CH-aryl, preferably substituted or unsubstituted —CH=CH-phenyl, more preferably unsubstituted —CH=CH-phenyl, substituted or unsubstituted heteroaryl, substituted or unsubstituted heterocyclyl, preferably substituted heterocyclyl, substituted or unsubstituted $C_3$-$C_8$ cycloalkyl, substituted or unsubstituted W-heterocyclyl, wherein W is selected to be —NH, preferably substituted —NH-heterocyclyl or $R^3$ represents —NH—$(CH_2)_n$—X, wherein n is an integer from 0 to 4, preferably from 0 to 2, and X is selected from —OH, —$NH_2$ or substituted or unsubstituted $C_3$-$C_8$ cycloalkyl, preferably unsubstituted cycloalkyl, more preferably unsubstituted cyclohexyl.

In yet another preferred embodiment of the present invention, $R^3$ in the compounds according to the general formula (I) represents partially or fully substituted heterocyclyl, wherein the heterocyclyl is selected from the group consisting of: Pyrrolidinyl, piperidinyl, piperazinyl, morpholinyl, preferably substituted piperazinyl, wherein piperazinyl is N-substituted with linear or branched substituted or unsubstituted $C_1$-$C_4$ alkyl, preferably —$CH_3$.

In yet another preferred embodiment of the present invention, $R^3$ in the compounds according to the present invention represents substituted or unsubstituted heteroaryl, wherein the heteroaryl is selected from the group comprising: Pyridinyl, pyridyl, pyridazinyl, pyrimidinyl, imidazolyl, pyrimidyl, pyrazinyl, pyrazyl, thiophenyl, thienyl, furanyl or pyrrolyl, thiazolyl, oxazolyl, isothiazolyl, isoxazolyl, pyrazyl, pyradizinyl, pyradizyl, 3-methylpyridyl, benzothienyl, 4-ethylbenzothienyl, 3,4-diethylfuranyl, pyrrolyl, tetrahydroquinolyl, quinolyl, tetrahydroisoquinolinyl, isoquinolinyl, benzoimidazolyl, benzothiazolyl, benzooxyzolyl, benzo[1,3]dioxolyl, indolyl, benzofuranyl, benzothiophenyl, indazolyl or chrom-2-onyl and preferably pyridinyl, pyridyl, pyrimidinyl, pyrimidyl, thiophenyl or furanyl, more preferably 2-pyridinyl, 3-pyridinyl, 4-pyridinyl, pyrimidinyl, 2-thiophenyl or 2-furanyl, and wherein the substituted heteroaryl is selected from furanyl, thiophenyl or pyridinyl, preferably 3-pyridinyl or 2-thiophenyl, partially or fully substituted with linear or branched $C_1$-$C_4$ alkoxy, preferably with —$OCH_3$, or with —CO—$CH_3$, and wherein the pyridinyl or thiophenyl are preferably monosubstituted.

In another preferred embodiment of the present invention, $R^3$ in the compounds according to the present invention represents substituted or unsubstituted phenyl, preferably substituted phenyl, wherein within this embodiment phenyl is partially or fully substituted with members of the group consisting of:

—F, —Cl, —Br, —I, preferably —F or —Cl, —CN, —$NO_2$, linear or branched substituted or unsubstituted $C_1$-$C_6$ alkyl, preferably linear or branched substituted or unsubstituted $C_1$-$C_4$ alkyl, linear or branched $C_2$-$C_6$ alkenyl, preferably linear or branched $C_2$-$C_4$ alkenyl, substituted or unsubstituted phenyl, preferably unsubstituted phenyl, linear or branched $C_1$-$C_6$ alkoxy, preferably linear or branched $C_1$-$C_4$ alkoxy, —O—$(CH_2)_v$—R, wherein v is an integer from 0 to 6, preferably from 0 to 4 and R is selected from the group consisting of:

Phenyl, —O-phenyl, linear or branched substituted or unsubstituted $C_1$-$C_4$ haloalkyl, heterocyclyl, or —$NR^{23}R^{24}$, wherein $R^{23}$ and $R^{24}$ are independently of each other selected from —H or linear or branched substituted or unsubstituted $C_1$-$C_6$ alkyl, preferably from —H or linear or branched substituted or unsubstituted $C_1$-$C_4$ alkyl, linear or branched $C_1$-$C_6$ haloalkyl, preferably linear or branched $C_1$-$C_4$ haloalkyl, linear or branched $C_1$-$C_6$ thioalkyl, preferably linear or branched $C_1$-$C_4$ thioalkyl, —$(CH_2)_w$-Q wherein w is selected to be an integer from 0 to 6, preferably from 0 to 4 and Q is selected from heterocyclyl, —OH, —$NR^{25}R^{26}$, wherein $R^{25}$ and $R^{26}$ are independently of each other selected from —H, linear or branched substituted or unsubstituted $C_1$-$C_6$ alkyl, preferably —H or linear or branched substituted or unsubstituted $C_1$-$C_4$ alkyl, or —$(CH_2)_y$—O—$CH_3$, wherein y is selected to be an integer from 0 to 6, preferably from 0 to 4, or Q represents linear or branched $C_1$-$C_6$ alkoxy, preferably linear or branched $C_1$-$C_4$ alkoxy, —$(CH_2)_y$—$COR^{27}$, wherein y is an integer from 0 to 6, preferably from 0 to 4, and $R^{27}$ is selected from the group comprising:

—H, linear or branched substituted or unsubstituted $C_1$-$C_6$ alkyl, preferably linear or branched substituted or unsubstituted $C_1$-$C_4$ alkyl, —$OR^{28}$, wherein $R^{28}$ is selected from —H or linear or branched substituted or unsubstituted $C_1$-$C_6$ alkyl, preferably linear or branched substituted or unsubstituted $C_1$-$C_4$ alkyl, or $R^{28}$ is selected from —$NR^{29}R^{30}$, wherein $R^{29}$ and $R^{30}$ are independently of each other selected from —H, linear or branched substituted or unsubstituted $C_1$-$C_6$ alkyl or $C_3$-$C_8$ cycloalkyl, preferably from —H, linear or branched substituted or unsubstituted $C_1$-$C_4$ alkyl or $C_4$-$C_6$ cycloalkyl, —CH=CH—COOH, —CH=CH—$COOCH_3$ or —NH-T-$R^{31}$, wherein T is selected from —CO— or —$SO_2$— and $R_{31}$ represents linear or branched substituted or unsubstituted $C_1$-$C_6$ alkyl, preferably linear or branched $C_1$-$C_4$ alkyl, and wherein phenyl is mono—, di- or trisubstituted, preferably mono- or disubstituted, and wherein within this embodiment, it is especially preferred, that phenyl is substituted with members of the group consisting of:

—F, —Cl, —CN, —$C_2H_5$, —$CH(CH_3)_2$, —CH=$CH_2$, —$OCH_3$, —$OC_2H_5$, —$OCH(CH_3)_2$, —O-Phenyl, —O—$CH_2$-Phenyl, —O—$(CH_2)_2$—O-Phenyl, —O—$(CH_2)_2$—$N(CH_3)_2$, —O—$(CH_2)_3$—$N(CH_3)_2$, —O—$(CH_2)_3$—$NH_2$, —$OCF_3$, —OH, —$CH_2$—OH, —CH—$OCH_3$, —$SCH_3$, —$NH_2$, —$N(CH_3)_2$, —$CH_2$—$NH_2$, —$CH_2$—$N(CH_3)_2$, —CH=CH—COOH, —CH=CH—$COOCH_3$, —COOH, —$(CH_2)_2$—COOH, —$COOCH_3$, —$CF_3$, Phenyl, —C(O)—H, —C(O)—$CH_3$, —C(O)—$NH_2$, —C(O)—$NHCH(CH_3)_2$, —NH—CO—$CH_3$, —NH—$SO_2$—$CH_3$, —$CH_2$—$N(CH_3)$—$(CH_2)_2$—O—$CH_3$,

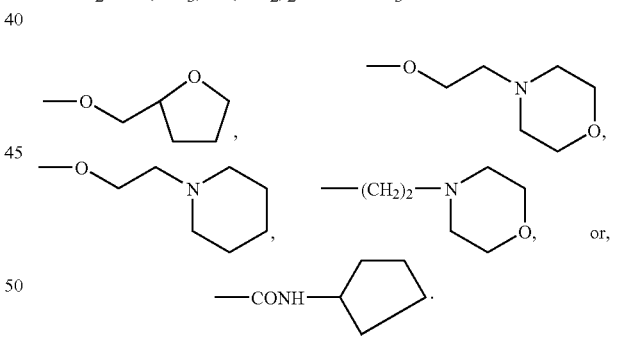

preferably phenyl is substituted with —$OCH_3$, —O—$CH_2$-Phenyl, —OH, —$OCH(CH_3)_2$ or —$NH_2$.

In a further preferred embodiment of the present invention, $R^5$ in the compounds according to the general formula (I) is selected from substituted or unsubstituted aryl, substituted or unsubstituted heteroaryl or substituted or unsubstituted heterocyclyl.

In yet another preferred embodiment of the present invention, $R^5$ in the compounds according to the general formula (I) represents substituted or unsubstituted aryl, preferably substituted or unsubstituted phenyl, more preferably unsubstituted phenyl.

It is especially preferred, if $R^5$ in the compounds according to the general formula (I) represents a substituted phenyl, that phenyl is partially or fully substituted with linear or branched substituted or unsubstituted $C_1$-$C_6$ alkyl, preferably with linear or branched substituted or unsubstituted $C_1$-$C_4$ alkyl, more preferably with —$CH_3$ or phenyl is partially or fully substituted with —O—$(CH_2)_u$-Phenyl, wherein u is an integer from 0 to 6, preferably from 0 to 4, more preferably from 0 to 2, and is most preferably 1, and wherein phenyl is preferably monosubstituted.

In a further preferred embodiment, L in the compounds according to the general formula (I) is selected from the group comprising:

—$NR^{14}$—$SO_2$—,
  wherein $R^{14}$ is selected from —H, linear or branched substituted or unsubstituted $C_1$-$C_4$ alkyl, —$SO_2$—$R^{15}$—, —$R^{15}$—$SO_2$—,
    wherein $R^{15}$ is selected from linear or branched substituted or unsubstituted $C_1$-$C_4$ alkylen,
  or $R^{14}$ represents —$(CH_2)_r$—$COOR^{16}$, wherein r is an integer from 0 to 4 and $R^{16}$ is selected from —H or linear or branched substituted or unsubstituted $C_1$-$C_4$ alkyl, —$NR^{17}$—CO—,
  wherein $R^{17}$ is selected from —H, linear or branched substituted or unsubstituted $C_1$-$C_4$ alkyl, or a —$(CH_2)_s$-group, wherein s is an integer from 1 to 3, preferably s is selected to be 1, and wherein if $R^6$ represents a —$(CH_2)_q$-group, wherein q is an integer from 1 to 3, preferably q is selected to be 2 and $R^{17}$ represents a methylene chain —$(CH_2)_s$-group, $R^6$ and $R^{17}$ may form together a 5 to 8 membered ring system, preferably $R^6$ and $R^{17}$ form together a 5 membered ring system

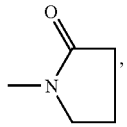 , 

wherein $R^{18}$ is selected from —H or linear or branched substituted or unsubstituted $C_1$-$C_4$ alkyl, —CO—$NR^{19}$—,
  wherein $R^{19}$ is selected from —H, linear or branched substituted or unsubstituted $C_1$-$C_4$ alkyl, or a —$(CH_2)_t$-A-group, wherein t is an integer from 1 to 3 and A is selected from N or O, and wherein if $R^6$ represents a —$(CH_2)_q$-group wherein q is an integer from 1 to 3, preferably q is selected to be 2 and $R^{19}$ represents a —$(CH_2)_t$-A- group, wherein t is selected to be 2 and A represents O, $R^6$ and $R^{19}$ may form together a 6-membered ring system

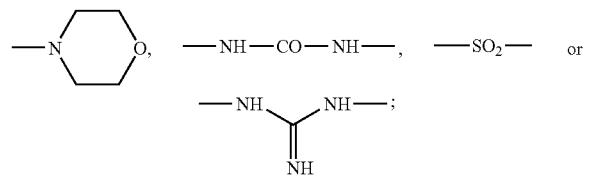

and wherein within this embodiment, it is especially preferred, that if $R^5$ represents phenyl, L is preferably in meta- or para-position of the phenyl.

In yet another preferred embodiment of the present invention, L in the compounds according to the general formula (I) is selected from the group consisting of:

—$NR^{14}$—$SO_2$—,
  wherein $R^{14}$ is selected from —H, —$(CH_2)_2$—$CH_3$, —$SO_2$—$R^{15}$ or —$R^{15}$—$SO_2$—, wherein $R^{15}$ represents linear or branched substituted or unsubstituted $C_1$-$C_4$ alkylene or —$(CH_2)_2$—$CH_3$,
  or —$(CH_2)_r$—$COOR^{16}$, wherein r is selected to be an integer from 0 to 2, and is preferably 1, and $R^{16}$ represents —$CH_3$, —$NR^{17}$—CO—, —$SO_2$—$NR^{18}$—, —CO—$NR^{19}$—,
  wherein $R^{17}$, $R^{18}$ and $R^{19}$ represent —H, —NH—CO—NH— or —$SO_2$—, wherein within this embodiment it is especially preferred, that L is selected from —NH—$SO_2$—, —NH—CO—, —CO—NH—, —$SO_2$—NH— —NH—CO—NH— or —$SO_2$—.

In yet another preferred embodiment of the present invention, $R^6$ in the compounds according to the general formula (I) is selected from the group comprising:

—H, linear or branched substituted or unsubstituted $C_1$-$C_8$ alkyl, substituted or unsubstituted aryl, substituted or unsubstituted heteroaryl, substituted or unsubstituted heterocyclyl, substituted pyrrolidinyl, substituted or unsubstituted $C_3$-$C_8$ cycloalkyl, disubstituted cyclohexyl, cyclopentyl, substituted or unsubstituted $C_5$-$C_{12}$ bicycloalkyl, substituted or unsubstituted adamantyl, or —$(CH_2)_p$—Z, wherein p is an integer from 0 to 4 and Z is selected from the group comprising: substituted or unsubstituted aryl, preferably unsubstituted aryl, substituted or unsubstituted heteroaryl, substituted or unsubstituted heterocyclyl, —$N(R_7R^8)$, wherein $R^7$ and $R^8$ represent independently from each other —H, or linear or branched $C_1$-$C_6$ alkyl, or Z represents —$(CR^9R^{10}R^{11})$, wherein $R^9$, $R^{10}$ and $R^{11}$ are independently of each other selected from the group consisting of: —H, linear or branched substituted or unsubstituted $C_1$-$C_4$ alkyl, substituted or unsubstituted aryl or —$N(R^{12}R^{13})$, wherein $R^{12}$ and $R^{13}$ represent independently of each other —H or linear or branched substituted or unsubstituted $C_1$-$C_4$ alkyl, and wherein if Z is selected from substituted or unsubstituted aryl, preferably unsubstituted aryl, substituted or unsubstituted heteroaryl, substituted or unsubstituted heterocyclyl, p can not be selected to be 0.

In yet another preferred embodiment of the present invention, $R^6$ in the compounds according to the general formula (I) is selected from the group consisting of:

—H, linear or branched substituted or unsubstituted $C_1$-$C_6$ alkyl, substituted or unsubstituted aryl, substituted or unsubstituted heteroaryl, substituted or unsubstituted heterocyclyl, substituted or unsubstituted $C_3$-$C_8$ cycloalkyl, unsubstituted $C_5$-$C_{12}$ bicycloalkyl, preferably unsubstituted bicyclo[2.2.1] heptanyl, unsubstituted adamantyl or —$(CH_2)_p$—Z, wherein p is an integer from 0 to 2 and Z is selected from the group comprising:

substituted or unsubstituted phenyl, substituted or unsubstituted heterocyclyl, —$N(R^7R^8)$, wherein $R^7$ and $R^8$ represent independently from each other —H, or linear or branched substituted or unsubstituted $C_1$-$C_4$ alkyl, or Z represents —$(CR^9R^{10}R^{11})$, wherein $R^9$, $R^{10}$ and $R^{11}$ are independently of each other selected from the group consisting of: —H, linear or branched substituted or unsubstituted $C_1$-$C_6$ alkyl, unsubstituted aryl or —$N(R^{12}R^{13})$, wherein $R^{12}$ and $R^{13}$ represent independently of each other —H or linear or branched substituted or unsubstituted $C_1$-$C_4$ alkyl.

In yet another preferred embodiment according to the present invention, $R^6$ in the compounds according to the general formula (I) represents —H or linear or branched $C_1$-$C_6$ alkyl, preferably —H, —$CH_3$, —$C_2H_5$, —$C_3H_7$, —CH$(CH_3)_2$, —$C(CH_3)_3$ or —$CH_2$—$C(CH_3)_3$, more preferably —H, —$CH_3$ or —$C(CH_3)_3$.

In yet another preferred embodiment according to the present invention, $R^6$ in the compounds according to the general formula (I) represents substituted or unsubstituted aryl, such as substituted or unsubstituted phenyl or naphtyl, wherein if $R^6$ represents substituted naphthyl, napthyl is partially or fully substituted with —OH or linear or branched $C_1$-$C_4$ alkoxy, preferably —OH and wherein napthyl is preferably monosubstituted, or wherein if $R^6$ represents substituted phenyl, phenyl is partially or fully substituted with members of the group comprising:
Phenyl, linear or branched substituted or unsubstituted $C_1$-$C_6$ alkyl, preferably linear or branched substituted or unsubstituted Cl-4 alkyl, more preferably —$CH_3$. —$C_3H_7$, —CH($CH_3$)$_2$ or —C($CH_3$)$_3$, substituted or unsubstituted heterocyclyl, preferably unsubstituted morpholinyl or N-substituted piperazinyl, wherein N-substituted piperazinyl is substituted with linear or branched $C_1$-$C_4$ alkyl, preferably with —$CH_3$, or phenyl is partially or fully substituted with —OH or —N($R^{32}R^{33}$), wherein $R^{32}$ and $R^{33}$ represent independently of each other —H or linear or branched $C_1$-$C_4$ alkyl, preferably —H or —$CH_3$, more preferably —H.

In yet another preferred embodiment according to the present invention, $R^6$ in the compounds according to the general formula (I) represents substituted or unsubstituted heteroaryl, wherein the heteroaryl is selected from the group comprising:
Pyrrolyl, thiophenyl, furanyl, imidazolyl, pyrazolyl, thiazolyl, oxazolyl, isothioazolyl, isoxazolyl, pyridinyl, pyrimidinyl, pyrazinyl, pyradizinyl, tetrahydroquinolinyl, quinolinyl, isoquinolinyl, benzoimidazolyl, benzothiazolyl, benzooxazolyl, benzo[1,3]dioxolyl, indolyl, benzofuranyl, benzothiophenyl, indazolyl or chrom-2-onyl,
preferably $R^6$ is selected from the group consisting of:
imidazolyl, wherein preferably one N-atom of the imidazolyl, is substituted with linear or branched substituted or unsubstituted $C_1$-$C_4$ alkyl, more preferably with —$CH_3$,
pyridinyl, preferably 4-pyridinyl, tetrahydroquinolinyl, quinolinyl, benzoimidazolyl, benzothiazolyl, benzo[1,3]dioxolyl, indolyl, indazolyl or chromen-2-onyl.

In yet another preferred embodiment according to the present invention, $R^6$ in the compounds according to the general formula (I) represents substituted or unsubstituted heterocyclyl, wherein heterocyclyl is selected from the group comprising:
Aziridinyl, azetidinyl, pyrrolidinyl, piperidinyl, piperazinyl, morpholinyl, preferably $R^6$ is selected from azetidinyl, pyrrolidinyl, preferably 2-pyrrolidinyl or 2-piperidinyl, 3-piperidinyl or 4-piperidinyl, preferably 2-piperidinyl.

It is especially preferred within the embodiment described above, that $R^6$ in the compounds according to the general formula (I) represents partially or fully substituted heterocyclyl, preferably partially or fully substituted piperidinyl, more preferably N-substituted piperidinyl, substituted with linear or branched substituted or unsubstituted $C_1$-$C_4$ alkyl, preferably —$CH_3$, or —N—COOR$^{34}$, wherein $R_3$ represents —H or linear or branched substituted or unsubstituted $C_1$-$C_4$ alkyl, preferably —(C$CH_3$)$_3$.

In yet another preferred embodiment of the present invention, $R^6$ in the compounds according to the general formula (I) represents substituted or unsubstituted $C_3$-$C_8$ cycloalkyl, preferably substituted or unsubstituted cyclopentyl or cyclohexyl, and wherein cyclopentyl or cyclohexyl are partially or fully substituted with linear or branched substituted or unsubstituted $C_1$-$C_6$ alkyl, —OH, —$NH_2$ or —NH—COOR$^{35}$, wherein $R^{35}$ represents —H or linear or branched substituted or unsubstituted $C_1$-$C_6$ alkyl, preferably linear or branched $C_1$-$C_4$ alkyl, more preferably —C($CH_3$)$_3$, and wherein cyclopentyl or cyclohexyl are preferably substituted with —$NH_2$, and wherein cyclopentyl or cyclohexyl are preferably mono-, di- or trisubstituted, more preferably monosubstituted.

In yet another preferred embodiment of the present invention, $R^6$ in the compounds according to the general formula (I) represents —(CH$_2$)$_p$—Z, wherein p is selected to be 1 or 2 and Z is selected from the group comprising:
Substituted or unsubstituted phenyl, wherein in case phenyl is substituted, it is substituted with linear or branched substituted or unsubstituted $C_1$-$C_4$ alkyl, preferably —$CH_3$, substituted or unsubstituted heterocyclyl, preferably substituted or unsubstituted piperidinyl, more preferably N-substituted or unsubstituted 2-piperidinyl, wherein in case 2-piperidinyl is N-substituted, it is substituted with —COOR$^{36}$, wherein $R^{36}$ represents linear or branched substituted or unsubstituted $C_1$-$C_6$ alkyl, preferably linear or branched $C_1$-$C_4$ alkyl, more preferably —C($CH_3$)$_3$, or Z represents —N($R^7R^8$), wherein $R^7$ and $R_5$ represent independently of each other —H, or linear or branched $C_1$-$C_4$ alkyl, preferably —H, —$CH_3$ or —$C_2H_5$, or $R^6$ represents —(CH$_2$)$_p$—Z, wherein p is selected to be an integer from 0 to 2 and Z is selected to be —(CR$^9R^{10}R^{11}$), wherein $R^9$, $R^{10}$ and $R^{11}$ are independently of each other selected from the group consisting of:
—H, linear or branched substituted or unsubstituted $C_1$-$C_5$ alkyl, preferably —$CH_3$, —CH($CH_3$)$_2$, or —CH($CH_3$)—$C_2H_5$, substituted or unsubstituted aryl, or —N($R^{12}R^{13}$), wherein $R^{12}$ and $R^{13}$ represent independently of each other —H or linear or branched substituted or unsubstituted $C_1$-$C_4$ alkyl, preferably —H or —$CH_3$.

In a further preferred embodiment of the present invention, m in the compounds according to the general formula (I) is selected to be 1, $R^1$, $R^2$ and $R^4$ represent —H, $R^3$ represents monosubstituted phenyl, $R^5$ represents monosubstituted or unsubstituted phenyl, L is selected from the group comprising:
—NH—CO—, —NH—SO$_2$—, —SO$_2$—NH—, —CO—NH— or —SO$_2$—, and $R^6$ is selected from the group consisting of:
—H, linear or branched substituted or unsubstituted $C_1$-$C_4$ alkyl, monosubstituted phenyl, substituted or unsubstituted heterocyclyl, wherein heterocyclyl is preferably selected from azetidinyl, pyrrolidinyl, piperidinyl, piperazinyl or morpholinyl, substituted or unsubstituted heteroaryl, wherein heteroaryl is selected from imidazolyl, pyridinyl, tetrahydroquinolinyl, quinolinyl, benzoimidazolyl, benzothiazolyl, benzo[1,3]dioxolyl, indolyl, indazolyl or chromen-2-only or $R^6$ represents substituted or unsubstituted $C_3$-$C_8$ cycloalkyl.

Especially preferred compounds of general formula (I) are represented by the following subformula

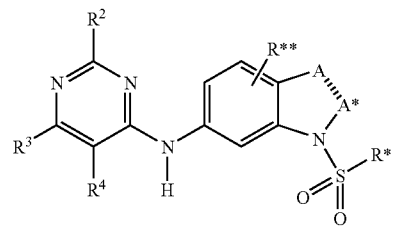

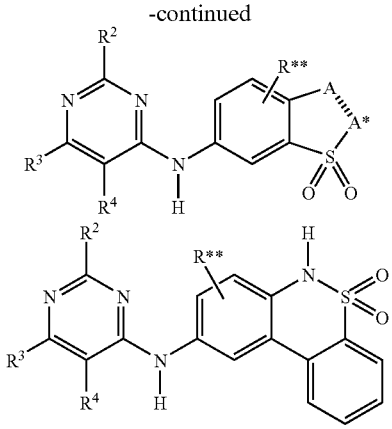

wherein A-A* represents —CH$_2$—CH$_2$—, —CH=CH—, —NH—CH$_2$—, —CH$_2$NH—, —N=CH—, —CH=N—, —N=N—, R* is a substituted or unsubstituted aryl, linear or branched substituted or unsubstituted alkyl, substituted or unsubstituted heteroaryl, substituted or unsubstituted heterocyclyl, substituted or unsubstituted cycloalkyl, C$_2$-C$_6$ alkenyl or C$_2$-C$_6$ alkinyl, R** represents hydrogen, linear or branched substituted or unsubstituted alkyl or an substitutent selected form Sub. R$^2$, R$^3$, and R$^4$ have the meanings as defined above.

Preferably R* is substituted or unsubstituted C$_1$-C$_6$ alkyl and most preferably methyl. R$^3$ represents preferably phenyl, substituted or unsubstituted aryl, or substituted or unsubstituted heteroaryl and especially an alkoxy substituted phenyl.

In yet another preferred embodiment of the present invention, compounds according to the general formula (I) are chiral compounds. It is to be understood, that chiral compounds according to the present invention represent a racemate, or a S or a R enantiomer or a mixture of isomers, respectively.

As used herein, the term "substituent", or "Sub" or the possibility that one residue may be further substituted with another group refers to the following list of substituents which may be present independently of each other:

—H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —OCF$_3$, —OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CONHC$_2$H$_5$, —NH—CO—NHC$_3$H$_7$, —NH—CO—NH-cyclo-C$_3$H$_5$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—N(C$_3$H$_7$)$_2$, —NH—CO—N(cyclo-C$_3$H$_5$)$_2$, —NH—CO—N[CH(CH$_3$)$_2$]$_2$, —NH—CO—N[C(CH$_3$)$_3$]$_2$, —NH—CS—NH$_2$, —NH—CS—NHCH$_3$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(CH$_3$)$_2$, —NH—CS—N(C$_2$H$_5$)$_2$, —NH—CS—N(C$_3$H$_7$)$_2$, —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)NHCH$_3$, —NH—C(=NH)—NHC$_2$H$_5$, —NH—C(=NH)—NHC$_3$H$_7$, —NH—C(=NH)—NH-cyclo-C$_3$H$_5$, —NH—C(=NH)—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NHC$_3$H$_7$, —O—CO—NH-cyclo-C$_3$H$_5$, —O—CO—NH[CH(CH$_3$)$_2$], —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F—CHF$_2$, —CF$_3$, —CH$_2$Cl, —CHCl$_2$, —CCl$_3$, —CH$_2$Br —CHBr$_2$, —CBr$_3$, —CH$_2$I—CHI$_2$, —Cl$_3$, —CH$_2$—CH$_2$F—CH$_2$—CHF$_2$, —CH$_2$—CF$_3$, —CH$_2$—CH$_2$Cl, —CH$_2$—CHCl$_2$, —CH$_2$—CCl$_3$, —CH$_2$—CH$_2$Br—CH$_2$—CHBr$_2$, —CH$_2$—CBr$_3$, —CH$_2$—CH$_2$I—CH$_2$—CHI$_2$, —CH$_2$—Cl$_3$, —CH$_3$, —C$_2$H$_5$, —C$_3$H$_7$, -cyclo-C$_3$H$_5$, —CH(CH$_3$)$_2$, —C(CH$_3$)$_3$, —C$_4$H$_9$, —CH$_2$—CH(CH$_3$)$_2$, —CH(CH$_3$)—C$_2$H$_5$, —C(CH$_3$)$_3$, -Ph, —CH$_2$-Ph, —CPh$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH=C(CH$_3$)$_2$, —C≡CH, —C≡C—CH$_3$, —CH$_2$—C≡CH.

In yet another preferred embodiment of the present invention, the compound according to the general formula (I) is selected from the group of compounds depicted in Table 2.

In a further aspect of the present invention, the novel compounds according to the general formula (I) are used as pharmaceutically active agent.

Further aspects of the present invention relate to the use of the compounds of general formula (I) for the preparation of a pharmaceutical composition useful for prophylaxis and/or treatment of infectious diseases including opportunistic diseases, prion diseases, immunological diseases, autoimmune diseases, bipolar and clinical disorders, cardiovascular diseases, cell proliferative diseases, diabetes, inflammation, transplant rejections, erectile dysfunction, neurodegenerative diseases, and stroke.

Infectious Diseases Including Opportunistic Infections

In yet another aspect of the present invention, the compounds according to the general formula (I) are for the preparation of a pharmaceutical composition for the prophylaxis and/or treatment of infectious diseases, including opportunistic diseases and opportunistic infections. The term infectious diseases comprises infections caused by viruses, bacteria, prions, fungi, and/or parasites.

Especially, virally induced infectious diseases, including opportunistic diseases are addressed. In a preferred embodiment of this aspect, the virally induced infectious diseases, including opportunistic diseases, are caused by retroviruses, human endogenous retroviruses (HERVs), hepadnaviruses, herpesviruses, flaviviridae, and/or adenoviruses. Preferably, the retroviruses are selected from lentiviruses or oncoretroviruses, wherein the lentivirus is preferably selected from the group comprising: HIV-1, HIV-2, feline immunodeficiency virus (FIV), bovine immunodeficiency virus (BIV), sivian immunodeficiency viruses (SIVs), chimeras of HIV and SIV (SHIV), caprine arthritis encephalitis virus (CAEV), visna/maedi virus (VMV) or equine infectious anemia virus (EIAV), preferably HIV-1 and HIV-2, and the oncoretrovirus is preferably selected from HTLV-I, HTLV-II or bovine leukemia virus (BLV), preferably HTLV-I and HTLV-II.

The hepadnavirus is preferably selected from HBV, ground squirrel hepatitis virus (GSHV) or woodchuck hepatitis virus (WHV), preferably HBV, the herpesvirus is selected from the group comprising: Herpes simplex virus I (HSV I), herpes simplex virus II (HSV II), Epstein-Barr virus (EBV), varicella zoster virus (VZV), human cytomegalovirus (HCMV) or human herpesvirus 8 (HHV-8), preferably HCMV, and the flaviviridae is selected from HCV, West nile or Yellow Fever.

It is to be understood, that all the viruses mentioned above, also comprise drug resistant virus strains.

Examples of infective diseases are AIDS, Alveolar Hydatid Disease (AHD, Echinococcosis), Amebiasis (*Entamoeba histolytica* Infection), Angiostrongylus Infection, Anisakiasis, Anthrax, Babesiosis (*Babesia* Infection), *Balantidium* Infection (Balantidiasis), *Baylisascaris* Infection (Raccoon Roundworm), Bilharzia (Schistosomiasis), *Blastocystis hominis* Infection (Blastomycosis), Boreliosis, Botulism, Brainerd Diarrhea, Brucellosis, BSE (Bovine Spongiform Encephalopathy), Candidiasis, Capillariasis (Capillaria Infection), CFS (Chronic Fatigue Syndrome), Chagas Disease (American Trypanosomiasis), Chickenpox (Varicella-Zoster virus), *Chlamydia pneumoniae* Infection, Cholera, Chronic Fatigue Syndrome, CJD (Creutzfeldt-Jakob Disease), Clonorchiasis (Clonorchis Infection), CLM (Cutaneous Larva Migrans, Hookworm Infection), Coccidioidomycosis, Conjunctivitis, Coxsackievirus A16 (Hand, Foot and Mouth Disease), Cryptococcosis, *Cryptosporidium* Infection (Cryptosporidiosis), Culex mosquito (Vector of West Nile Virus), Cutaneous Larva Migrans (CLM), Cyclosporiasis (Cyclospora Infection), Cysticercosis (Neurocysticercosis), Cytomegalovirus Infection, Dengue/Dengue Fever, *Dipylidium* Infection (Dog and Cat Flea Tapeworm), Ebola Virus Hemorrhagic Fever, Echinococcosis (Alveolar Hydatid Disease), Encephalitis, *Entomoeba coli* Infection, *Entomoeba dispar* Infection, *Entomoeba hartmanni* Infection, *Entomoeba histolytica* Infection (Amebiasis), *Entomoeba polecki* Infection, Enterobiasis (Pinworm Infection), Enterovirus Infection (Non-Polio), Epstein-Barr Virus Infection, *Escherichia coli* Infection, Foodborne Infection, Foot and mouth Disease, Fungal Dermatitis, Gastroenteritis, Group A streptococcal Disease, Group B streptococcal Disease, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis (Isospora Infection), Lassa Fever, Leishmaniasis, Kala-azar (Kala-azar, *Leishmania* Infection), Leprosy, Lice (Body lice, Head lice, Pubic lice), Lyme Disease, Malaria, Marburg Hemorrhagic Fever, Measles, Meningitis, Mosquito-borne Diseases, *Mycobacterium avium* Complex (MAC) Infection, *Naegleria* Infection, Nosocomial Infections, Nonpathogenic Intestinal Amebae Infection, Onchocerciasis (River Blindness), Opisthorciasis (Opisthorcis Infection), Parvovirus Infection, Plague, PCP (Pneumocystis carinii Pneumonia), Polio, Q Fever, Rabies, Respiratory Syncytial Virus (RSV) Infection, Rheumatic Fever, Rift Valley Fever, River Blindness (Onchocerciasis), Rotavirus Infection, Roundworms Infection, Salmonellosis, *Salmonella Enteritidis*, Scabies, Shigellosis, Shingles, Sleeping Sickness, Smallpox, Streptococcal Infection, Tapeworm Infection (Taenia Infection), Tetanus, Toxic Shock Syndrome, Tuberculosis, Ulcers (Peptic Ulcer Disease), Valley Fever, *Vibrio parahaemolyticus* Infection, *Vibrio vulnificus* Infection, Viral Hemorrhagic Fever, Warts, Waterborne infectious Diseases, West Nile Virus Infection (West Nile Encephalitis), Whooping Cough, Yellow Fever.

Bacterial Infections

As described above, the compounds according to the general formula (I) are also useful for the preparation of a pharmaceutical composition for prophylaxis and/or treatment of bacterially induced infectious diseases, including opportunistic diseases and opportunistic infections, wherein the bacterially induced infectious diseases, including opportunistic diseases, are selected from tuberculosis, leprosy or mycobacteria-induced meningitis. One advantage of the inventive compounds disclosed herein is there use against drug resistant bacteria strains.

Prion Diseases

Another aspect of the present invention is directed to the use of at least one compound of the general formula (I) and/or pharmaceutically acceptable salts thereof for prophylaxis and/or treatment of prion diseases.

Prions are infectious agents, which do not have a nucleic acid genome. It seems that a protein alone is the infectious agent. A prion has been defined as "small proteinaceous infectious particle, which resists inactivation, by procedures that modify nucleic acids". The discovery that proteins alone can transmit an infectious disease has come as a considerable surprise to the scientific community. Prion diseases are often called "transmissible spongiform encephalopathies", because of the post mortem appearance of the brain with large vacuoles in the cortex and cerebellum. Probably most mammalian species develop these diseases. Prion diseases are a group of neurodegenerative disorders of humans and animals and the prion diseases can manifest as sporadic, genetic or infectious disorders. Examples for prion diseases acquired by exogenous infection are the Bovine spongiform encephalitis (BSE) of cattle and the new variant of Creutzfeld-Jakob disease (vCJD) caused by BSE as well as scrapie of animals. Examples of human prion diseases include kuru, sporadic Creutzfeldt-Jakob disease (sCJD), familial CJD (fCJD), iatrogenic CJD (iCJD), Gerstmann-Sträussler-Scheinker (GSS) disease, fatal familial insomnia (FFI), and especially the new variant CJD (nvCJD or vCJD).

The name "prion" is used to describe the causative agents, which underlie the transmissible spongiform encephalopathies. A prion is proposed to be a novel infectious particle that differs from viruses and viroids. It is composed solely of one unique protein that resists most inactivation procedures such as heat, radiation, and proteases. The latter characteristic has led to the term protease-resistant isoform of the prion protein. The protease-resistant isoform has been proposed to slowly catalyze the conversion of the normal prion protein into the abnormal form.

The term "isoform" in the context of prions means two proteins with exactly the same amino acid sequence, that are folded into molecules with dramatically different tertiary structures. The normal cellular isoform of the prion protein ($PrP^C$) has a high a-helix content, a low b-sheet content, and is sensitive to protease digestion. The abnormal, disease-causing isoform ($PrP^{Sc}$) has a lower a-helix content, a much higher b-sheet content, and is much more resistant to protease digestion.

As used herein the term "prion diseases" refers to transmissible spongiform encephalopathies. Examples for prion diseases comprise Scrapie (sheep, goat), TME (transmissible mink encephalopathy; mink), CWD (chronic wasting disease; muledeer, deer, elk), BSE (bovine spongiform encephalopathy; cows, cattles), CJD (Creutzfeld-Jacob Disease), vCJD, GSS (Gerstmann-Sträussler-Scheinker syndrome), FFI (Fatal familial Insomnia), Kuru, and Alpers Syndrome. Preferred are BSE, vCJD, and CJD.

Immunological Diseases

Another aspect of the present invention is directed to the use of at least one compound of the general formula (I) and/or pharmaceutically acceptable salts thereof for prophylaxis and/or treatment of immunological diseases, neuroimmunological diseases, and autoimmune diseases.

Immunological diseases are, for instance, asthma and diabetes, rheumatic and autoimmune diseases, AIDS, rejection of transplanted organs and tissues (cf. below), rhinitis, chronic obstructive pulmonary diseases, osteoporosis, ulcerative colitis, sinusitis, lupus erythematosus, recurrent infections, atopic dermatitis/eczema and occupational allergies, food allergies, drug allergies, severe anaphylactic reactions, anaphylaxis, and other manifestations of allergic disease, as well as uncommon problems such as primary immunodeficiencies, including antibody deficiency states, cell mediated immunodeficiencies (e.g., severe combined immunodeficiency, DiGeorge syndrome, Hyper-IgE syndrome, Wiskott-Aldrich syndrome, ataxia-telangiectasia), immune mediated cancers, and white cell defects.

In autoimmune diseases, such as systemic lupus erythematosus, rheumatoid arthritis (RA), multiple sclerosis (MS), immune-mediated or type 1 diabetes mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, and Hashimoto's disease, dermatomyositis, goodpastture syndrome, myasthenia gravis pseudoparalytica, ophtalmia sympatica, phakogene uveitis, chronical agressivce hepatitis, primary billiary cirrhosis, autoimmunehemolytic anemy, Werlof disease, specific cells uncontrollably attack the body's own tissues and organs (autoimmunity), producing inflammatory reactions and other serious symptoms and diseases.

Hashimoto's thyroiditis is one of the most common autoimmune diseases. "Autoimmune disease" refers to a category of more than 80 chronic illnesses, each very different in nature, that can affect everything from the endocrine glands (like the thyroid) to organs like the kidneys, as well as to the digestive system.

There are many different autoimmune diseases, and they can each affect the body in different ways. For example, the autoimmune reaction is directed against the brain in multiple sclerosis and the gut in Crohn's disease. In other autoimmune diseases such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus.

Bipolar and Clinical Disorders

Another aspect of the present invention is directed to the use of at least one compound of the general formula (I) and/or pharmaceutically acceptable salts thereof for prophylaxis and/or treatment of bipolar and clinical disorders.

The term "bipolar and clinical disorders" shall refer to adjustment disorders, anxiety disorders, delirium, dementia, amnestic and other cognitive disorders, disorders usually first diagnosed in infancy, childhood, or adolescence, dissociative disorders, eating disorders, factitious disorders, impulse-control disorders, mental disorders due to a general medical condition, mood disorders, other conditions that may be a focus of clinical attention, personality disorders, schizophrenia and other psychotic disorders, sexual and gender identity disorders, sleep disorders, somatoform disorders, substance-related disorders, generalized anxiety disorder, panic disorder, phobia, agoraphobia, obsessive-compulsive disorder, stress, acute stress disorder, anxiety neurosis, nervousness, phobia, posttraumatic stress disorder, posttraumatic stress disorder (PTSD), abuse, ADHD, obsessive-compulsive disorder (OCD), manic depressive psychosis, specific phobias, social phobia, adjustment disorder with anxious features.

Examples for anxiety disorders are: acute stress disorder, agoraphobia without history of panic disorder, anxiety disorder due to general medical condition, generalized anxiety disorder, obsessive-compulsive disorder, panic disorder with agoraphobia, panic disorder without agoraphobia, posttraumatic stress disorder, specific phobia, social phobia, substance-induced anxiety disorder.

Examples for delirium, dementia, amnestic and other cognitive disorders are: delirium due to a general medical condition, substance intoxication delirium, substance withdrawal delirium, delirium due to multiple etiologies, Alzheimer's, Creutzfeldt-Jakob disease, head trauma, Huntington's disease, HIV disease, Parkinson's disease, Pick's disease, substance-induced persisting, vascular, dementia due to other general medical conditions, dementia due to multiple etiologies, amnestic disorder due to a general medical condition, substance-induced persisting amnestic disorder.

Examples for disorders usually first diagnosed in infancy, childhood, or adolescence are: mental retardation, learning disorders, mathematics disorder, reading disorder, disorder of written expression, learning disorder, motor skills disorders, developmental coordination disorder, communication disorders, expressive language disorder, phonological disorder, mixed receptive-expressive language disorder, stuttering, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, feeding disorder of infancy or early childhood, pica, rumination disorder, tic disorders, chronic motor or vocal tic disorder, Tourette's disorder, elimination disorders, encopresis, enuresis, selective mutism, separation anxiety disorder, reactive attachment disorder of infancy or early childhood, stereotypic movement disorder.

Examples for dissociative disorders are: dissociative amnesia, depersonalization disorder, dissociative fugue and dissociative identity disorder.

Examples for eating disorders are anorexia nervosa and bulimia nervosa.

Examples for mood disorders are: mood episodes, major depressive episode, hypomanic episode, manic episode, mixed episode, depressive disorders, dysthymic disorder, major depressive disorder, single episode, recurrent, bipolar disorders, bipolar I disorder, bipolar II disorder, cyclothymic disorder, mood disorder due to a general medical condition, substance-induced mood disorder.

Examples for schizophrenia and other psychotic disorders are: schizophreniform disorder, schizoaffective disorder, delusional disorder, brief psychotic disorder, shared psychotic disorder, psychotic disorder due to a general medical condition, delusions, hallucinations, substance-induced psychotic disorder.

Examples for sexual and gender identity disorders are: female sexual arousal disorder, orgasmic disorders, premature ejaculation, sexual pain disorders, dyspareunia, vaginismus, sexual dysfunction due to a general medical condition, female dyspareunia, female hypoactive sexual desire disorder, male erectile disorder, male hypoactive sexual desire disorder, male dyspareunia, other female sexual dysfunction, other male sexual dysfunction, substance-induced sexual dysfunction, sexual dysfunction, paraphilias, exhibitionism, fetishism, frotteurism, pedophilia, masochism, sadism, transvestic fetishism, voyeurism, paraphilia, gender identity disorder.

Examples for sleep disorders are: dyssomnias, breathing-related sleep disorder, circadian rhythm sleep disorder, hypersomnia, hypersomnia related to another mental disorder, insomnia, insomnia related to another mental disorder, narcolepsy, dyssomnia, parasomnias, nightmare disorder, sleep terror disorder, sleepwalking disorder, parasomnia.

Examples for somatoform disorders are: body dysmorphic disorder, conversion disorder, hypochondriasis, pain disorder, somatization disorder, undifferentiated somatoform disorder.

Examples for substance-related disorders are: alcohol related disorders, amphetamine related disorders, caffeine related disorders, cannabis related disorders, cocaine related disorders, hallucinogen related disorders, inhalant related disorders, nicotine related disorders, opioid related disorders, psychotic disorder, psychotic disorder, phencyclidine-related disorder, abuse, persisting amnestic disorder, anxiety disorder, persisting dementia, dependence, intoxication, intoxication delirium, mood disorder, psychotic disorder, withdrawal, withdrawal delirium, sexual dysfunction, sleep disorder.

Cardiovascular Diseases

The inventive compounds are also useful for prophylaxis and/or treatment of cardiovascular diseases such as adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tabhycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

Proliferative Disease

In yet another preferred embodiment, the cell proliferative disease is cancer, which is preferably selected from the group comprising:

The proliferation disorders and cancers are preferably selected from the group comprising adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non—Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinaliomas, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

Preferred are the following cancer types: bladder, breast, central nervous system, colon, gastric, lung, kidney, melanoma, head and neck, ovarian, cervix, glioblastoma, pancreas, prostate, stomach, skin testis, leukemia, Hodgkin's lymphoma, liver and renal cancer.

Diabetes

In yet another preferred embodiment, said diabetes is selected from Type I diabetes or Type II diabetes.

Inflammation

In yet another preferred embodiment, said inflammation is mediated preferably by the cytokines TNF-α, IL-1β, GM-CSF, IL-6 and/or IL-8.

As described above, the compounds according to general formula (I) are pharmaceutically active agents for prophylaxis and/or treatment of inflammatory diseases. Thus, these compounds are used for the manufacture of a pharmaceutical formulation for prophylaxis and/or treatment of inflammations and inflammatory diseases in mammals, including humans.

Inflammatory diseases can emanate from infectious and non-infectious inflammatory conditions which may result from infection by an invading organism or from irritative, traumatic, metabolic, allergic, autoimmune, or idiopathic causes as shown in the following list.

| | | | |
|---|---|---|---|
| I. Acute infections | | | |
| | A. Viral | B. | Bacterial |
| II. Noninfectious causes | | | |
| III. Chronic (granulomatous) diseases. | | | |
| | A. Bacterial | B. | Spirochetal |
| | C. Mycotic (Fungal) | D. | Idiopathic |
| IV. Allergic, immune, and idiopathic disorders | | | |
| | A. Hypersensitivity reactions | | |
| | B. Immune and idiopathic disorders | | |
| V. Miscellaneous inflammatory conditions | | | |
| | A. Parasitic infections | | |
| | B. Inhalation causes: | Acute (thermal) injury Pollution and inhalant allergy Carcinogens | |
| | C. Radiation injury: | Radionecrosis | |

Thus, the compounds disclosed herein can be used for prophylaxis and/or treatment of inflammations caused by invading organisms such as viruses, bacteria, prions, and parasites as well as for prophylaxis and/or treatment of inflammations caused by irritative, traumatic, metabolic, allergic, autoimmune, or idiopathic reasons.

Consequently, the disclosed compounds are useful for prophylaxis and/or treatment of inflammatory diseases which are initiated or caused by viruses, parasites, and bacteria which are connected to or involved in inflammations.

The following bacteria are known to cause inflammatory diseases: *mycoplasma pulmonis* (causes e.g. chronic lung diseases (CLD), murine chronic respiratory disease), ureaplasma urealyticum (causes pneumonia in newborns), *mycoplasma pneumoniae* and *chlamydia pneumoniae* (cause chronic asthma), *C. pneumoniae* (causes atherosclerosis, pharyngitis to pneumonia with empyema, human coronary heart disease), *Helicobacter pylori* (human coronary heart disease, stomach ulcers).

The following viruses are known to cause inflammatory diseases: herpesviruses especially cytomegalovirus (causes human coronary heart disease).

The compounds disclosed herein are useful for prophylaxis and/or treatment of inflammatory diseases caused and/or induced and/or initiated and/or enhanced by the afore-mentioned bacteria or viruses.

Furthermore, the compounds of formula (I) are useful for prophylaxis and/or treatment of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx.

Examples for inflammatory diseases of the central nervous system (CNS) are algal disorders, protothecosis, bacterial disorders, abscessation, bacterial meningitis, idiopathic inflammatory disorders, eosinophilic meningoencephalitis, feline polioencephalomyelitis, granulomatous meningoencephalomyelitis, meningitis, steroid responsive meningitis-arteritis, miscellaneous meningitis/meningoencephalitis, meningoencephalitis in greyhounds, necrotizing encephalitis, pug dog encephalitis, pyogranulomatous meningoencephalomyelitis, shaker dog disease, mycotic diseases of the CNS, parasitic encephalomyelitis, prion protein induced diseases, feline spongiform encephalopathy, protozoal encephalitis-encephalomyelitis, toxoplasmosis, neosporosis, sarcocystosis, encephalitozoonosis, trypanosomiasis, acanthamebiasis, babesiosis, leishmaniasis, rickettsial disorders, rocky mountain spotted fever, canine ehrlichiosis, salmon poisoning, viral disorders, aujeszky's disease, borna disease, canine herpes virus encephalomyelitis, canine distemper encephalomyelitis, canine distemper encephalomyelitis in immature animals, multifocal distemper encephalomyelitis in mature animals, old dog encephalitis, chronic relapsing encephalomyelitis, post-vaccinal canine distemper encephalitis, feline immunodeficiency virus, feline infectious peritonitis, feline leukemia virus, infectious canine hepatitis, La Crosse virus encephalitis, parvovirus encephalitis, rabies, post-vaccinal rabies, tick-borne encephalitis in dogs.

Examples for inflammatory rheumatic diseases are rheumatoid arthritis, scleroderma, lupus, polymyositis, dermatomyositis, psoriatic arthritis, ankylosing spondylitis, Reiters's syndrome, juvenile rheumatoid arthritis, bursitis, tendinitis (tendonitis), and fibromyositis.

Examples for inflammatory diseases of blood vessels are vasculitis, autoantibodies in vasculitis, microscopic polyangiitis, giant cell arteritis, Takayasu's arteritis, vasculitis of the central nervous system, thromboangiitis obliterans (Buerger's Disease), vasculitis secondary to bacterial, fungal, and parasitic infection, vasculitis and rheumatoid arthritis, vasculitis in systemic lupus erythematosus, vasculitis in the idiopathic inflammatory myopathies, relapsing polychondritis, systemic vasculitis in sarcoidosis, vasculitis and malignancy, and drug-induced vasculitis.

Examples for inflammatory diseases of the middle ear are acute suppurative otitis media, bullous myringitis, granular myringitis, and chronic suppurative otitis media, which can manifest as mucosal disease, cholesteatoma, or both.

Examples for inflammatory bowel diseases are ulcerative colitis, Crohn's disease.

Examples for inflammatory diseases of the skin are acute inflammatory dermatoses, urticaria (hives), spongiotic dermatitis, allergic contact dermatitis, irritant contact dermatitis, atopic dermatitis, erythemal multiforme (EM minor), Stevens-Johnson syndrome (SJS, EM major), toxic epidermal necrolysis (TEN), chronic inflammatory dermatoses, psoriasis, lichen planus, discoid lupus erythematosus, and acne vulgaris Uveitis are inflammations located in and/or on the eye and may be associated with inflammation elsewhere in the body. In most circumstances, patients who have uveitis as part of a disease elsewhere in the body are aware of that illness. The majority of patients with uveitis do not have an apparent associated systemic illness. Causes of uveitis can be infectious causes, masquerade syndromes, suspected immune-mediated diseases, and/or syndromes confined primarily to the eye.

The following viruses are associated with inflammations: human immunodeficiency virus-I, herpes simplex virus, herpes zoster virus, and cytomegalovirus.

Bacterial or spirochetal caused, induced, initiated and/or enhanced inflammations are tuberculosis, leprosy, propriono-bacterium, syphilis, Whipple's disease, leptospirosis, brucellosis, and lyme disease.

Parasitic (protozoan or helminthic) caused, induced, initiated and/or enhanced inflammations are toxoplasmosis, acanthameba, toxocariasis, cysticercosis, onchocerciasis.

Examples of inflammatory diseases caused, induced, initiated and/or enhanced by fungi are histoplasmosis, coccidioidomycosis, candidiasis, aspergillosis, sporotrichosis, blastomycosis, and cryptococcosis.

Masquerade syndromes are, for instance, leukemia, lymphoma, retinitis pigmentosa, and retinoblastoma.

Suspected immune-mediated diseases can be selected from the group comprising ankylosing spondylitis, Behcet's disease, Crohn's disease, drug or hypersensitivity reaction, interstitial nephritis, juvenile rheumatoid arthritis, Kawasaki's disease, multiple sclerosis, psoriatic arthritis, Reiter's syndrome, relapsing polychondritis, sarcoidosis, Sjogren's syndrome, systemic lupus erythematosus, ulcerative colitis, vasculitis, vitiligo, Vogt Koyanagi Harada syndrome.

Syndromes confined primarily to the eye are, for instance, acute multifocal placoid pigmentary epitheliopathy, acute retinal necrosis, birdshot choroidopathy, Fuch's heterochromic cyclitis, glaucomatocyclitic crisis, lens-induced uveitis, multifocal choroiditis, pars planitis, serpiginous choroiditis, sympathetic ophthalmia, and trauma.

Examples for inflammatory diseases of the larynx are gastroesophageal (laryngopharyngeal) reflux disease, pediatric laryngitis, acute laryngeal infections of adults, chronic (granulomatous) diseases, allergic, immune, and idiopathic disorders and miscellaneous inflammatory conditions.

Pediatric laryngitis is known as acute (viral or bacterial) infection such as laryngotracheitis (croup), supraglottitis (epiglottitis), diphtheria, and noninfectious causes are for example spasmodic croup and traumatic laryngitis.

Acute laryngeal infections of adults are, for instance, viral laryngitis, common upper respiratory infection, laryngotracheitis, herpes simplex, bacterial laryngitis, supraglottitis, laryngeal abscess, and gonorrhea.

Chronic (granulomatous) diseases can be selected from the group comprising bacterial diseases, tuberculosis, leprosy, scleroma, actinomycosis, tularemia, glanders, spirochetal (syphilis) diseases, mycotic (fungal) diseases, candidiasis, blastomycosis, histoplasmosis, coccidiomycosis, aspergillosis, idiopathic diseases, sarcoidosis, and Wegener's granulomatosis.

Allergic, immune, and idiopathic disorders are, for example, hypersensitivity reactions, angioedema, Stevens-Johnson syndrome, immune and idiopathic disorders, infections of the immunocompromised host, rheuatoid arthritis, systeic lupus erythematosus, cicatricial pemphigoid, relapsing polychondritis, Sjogren's syndrome, and amyloidosis.

Miscellaneous inflammatory conditions are, for instance, parasitic infections, trichinosis, leishmaniasis, schistosomiasis, syngamus laryngeus, inhalation laryngitis, acute (thermal) injury, pollution and inhalant allergy, carcinogens, radiation injury, radiation laryngitis, radionecrosis, vocal abuse, vocal-cord hemorrhage, muscle tension dysphonias, and contact ulcer and granuloma.

Transplant Rejection

Transplant rejection is when a transplant recipient's immune system attacks a transplanted organ or tissue. No two people (except identical twins) have identical tissue antigens. Therefore, in the absence of immunosuppressive drugs, organ and tissue transplantation would almost always cause an immune response against the foreign tissue (rejection), which would result in destruction of the transplant. Though tissue typing ensures that the organ or tissue is as similar as possible to the tissues of the recipient, unless the donor is an identical twin, no match is perfect and the possibility of organ/tissue rejection remains.

The inventive compounds of general formula (I) are used as immunosuppressive drugs and/or anti-rejection drugs in order to prevent transplant rejection.

One example of transplant rejection is the graft-versus-host-disease (GVHD) that can occur following bone marrow transplant. The donor's immune cells in the transplanted marrow make antibodies against the host's (transplant patient's) tissues and attack the patient's vital organs. Transplant rejections (also known as graft rejection or tissue/organ rejection) may commonly occur when tissue or organs, which need blood supply, are transplanted. Said organs comprise especially inner organs such as heart, heart-lungs, lungs, liver, kidney, pancreas, spleen, skin, tissue, bone marrow, spinal marrow, hormone producing glands, gonads and gonadal glands.

Neurodegenerative Diseases

Another aspect of the present invention is directed to the use of at least one compound of the general formula (I) and/or pharmaceutically acceptable salts thereof for prophylaxis and/or treatment of neurodegeneration and neurodegenerative disorders.

Among the hundreds of different neurodegenerative disorders, the attention has been given only to a handful, including Alzheimer disease, Parkinson disease, Huntington disease, and amyotrophic lateral sclerosis.

It is worth to mention that the same neurodegenerative process can affect different areas of the brain, making a given disease appear very different from a symptomatic standpoint.

Neurodegenerative disorders of the central nervous system (CNS) can be grouped into diseases of the cerebral cortex (Alzheimer disease), the basal ganglia (Parkinson disease), the brain-stem and cerebellum, or the spinal cord (amyotrophic lateral sclerosis).

Examples for neurodegeneration and neurodegenerative disorders are Alzheimer disease, Parkinson disease, Huntington disease, amyotrophic lateral sclerosis, AIDS-related dementia, retinitis pigmentosa, spinal muscular atrophy and cerebrellar degeneration, fragile X-associated tremor/ataxia syndrome (FXTAS), progressive supranuclear palsy (PSP), and striatonigral degeneration (SND), which is included with olivopontocerebellear degeneration (OPCD), and Shy Drager syndrome (SDS) in a syndrome known as multiple system atrophy (MSA).

In another aspect of the present invention, the compounds according to the general formula (I) as well as pharmaceutically acceptable salts thereof are used as an inhibitor for a protein kinase, preferably as an inhibitor for a cellular protein kinase. Table 1 shows a list with all currently known cellular protein kinases.

In a preferred embodiment of this aspect said cellular protein kinase is selected from the group consisting of:
Cyclin-dependent protein kinase (CDK), protein kinase C, c-Raf, Akt, CKI, IKKβ, MAP kinases/ERKs, MAP kinases/JNKs, EGF receptor, InsR, PDGF receptor, c-Met, p70S6K, ROCK, Rsk1, Src, Abl, p56Lck, c-kit, CaMk2β, CaMk2δ, CaMk2γ, CSK or GSK-3γ and β. The cyclin-dependent protein kinase can be selected from the group comprising:
CDK1, CDK2, CDK3, CDK4, CDK5, CDK6, CDK7, CDK8, CDK9, CDK10, CDK11, CrkRS (Crk7, CDC2-related protein kinase 7), CDKL1 (cyclin-dependent kinase-like 1); KKIALRE, CDKL2 (cyclin-dependent kinase-like 2), KKIAMRE, CDKL3 (cyclin-dependent kinase-like 3), NKIAMRE, CDKL4, similar to cyclin-dependent kinase-like 1, CDC2L1 (cell division cycle 2-like 1), PITSLRE B, CDC2L1 (cell division cycle 2-like 1), PITSLRE A, CDC2L5 (cell division cycle 2-like 5), PCTK1 (PCTAIRE protein kinase 1), PCTK2 (PCTAIRE protein kinase 2), PCTK3 (PCTAIRE protein kinase 3) or PFTK1 (PFTAIRE protein kinase 1).

As used herein, a kinase "inhibitor" refers to any compound capable of downregulating, decreasing, suppressing or otherwise regulating the amount and/or activity of a kinase. Inhibition of these kinases can be achieved by any of a variety of mechanisms known in the art, including, but not limited to binding directly to the kinase polypeptide, denaturing or otherwise inactivating the kinase, or inhibiting the expression of the gene (e.g., transcription to mRNA, translation to a nascent polypeptide, and/or final polypeptide modifications to a mature protein), which encodes the kinase. Generally, kinase inhibitors may be proteins, polypeptides, nucleic acids, small molecules, or other chemical moieties. As used herein the term "inhibiting" or "inhibition" refers to the ability of an compound to downregulate, decrease, reduce, suppress, inactivate, or inhibit at least partially the activity of an enzyme, or the expression of an enzyme or protein and/or the virus replication.

In a further aspect of the present invention, a method for preventing and/or treating infectious diseases, including opportunistic diseases, in a mammal, especially in a human, is provided, which method comprises administering to the mammal an amount of at least one compound according to the general formula (I), effective to prevent and/or treat said infectious diseases, including opportunistic diseases. In a preferred embodiment of this method, the infectious diseases, including opportunistic diseases, are virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group consisting of: HTLV-I, HTLV-II or BLV. In a further preferred embodiment of this method, the hepadnavirus is selected from HBV, GSHV or WHV, preferably HBV, the herpesvirus is selected from the group comprising: HSV I, HSV II, EBV, VZV, HCMV or HHV 8, preferably HCMV and the flaviviridae is selected from HCV, West nile or Yellow Fever.

In a further aspect of the present invention, methods for preventing and/or treating infectious diseases including opportunistic diseases, prion diseases, immunological diseases, autoimmune diseases, bipolar disorders, cardiovascular diseases, cell proliferative diseases, diabetes, inflammation, transplant rejections, erectile dysfunction, neurodegenerative diseases, and stroke in a mammal, especially in a human, are provided, which methods comprise administering to the mammal an amount of at least one compound according to the general formula (I) and/or pharmaceutically acceptable salts thereof, effective to prevent and/or treat said infectious diseases including opportunistic diseases, prion diseases, immunological diseases, autoimmune diseases, bipolar disorders, cardiovascular diseases, cell proliferative diseases, diabetes, inflammation, transplant rejections, erectile dysfunction, neurodegenerative diseases, and stroke.

In further preferred embodiments, the specific diseases addressed as infectious diseases including opportunistic diseases, prion diseases, immunological diseases, autoimmune diseases, bipolar disorders, cardiovascular diseases, cell proliferative diseases, diabetes, inflammation, transplant rejections, erectile dysfunction, neurodegenerative diseases, and stroke are selected from the groups disclosed above.

The compounds shown explicitly in Table 2 are preferred to be used within the methods or indications disclosed herein. Another aspect of the present invention is that at least one compound according to the general formula (I) used as a pharmaceutically active agent may be administered in combination with further therapeutic compounds.

For the indication HIV compounds according to the general formula (I), preferably those falling under the activity range "a" for CDK9 as shown in Table 2, may be administered in combination with anti-retroviral drugs, selected from the following five classes:

1) Nucleoside reverse transcriptase inhibitors (NRTIs),
2) Non-nucleoside reverse transcriptase inhibitors (NNRTIs),
3) Protease inhibitors (PIs),
4) Fusion inhibitors or
5) Immune stimuli.

Thus, another aspect of the present invention relates to drug combinations comprising at least one inventive compound according to general formula (I) and/or pharmaceutically acceptable salts thereof together with at least one anti-retroviral drug, especially at least one of the drugs mentioned above.

The pharmaceutical compositions according to the present invention comprise at least one compound according to the present invention as an active ingredient together with at least one pharmaceutically acceptable (i.e. non-toxic) carrier, excipient and/or diluent. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95-weight % of the 4,6-disubstituted pyrimdine derivative according to the general formula (I) or analogues compound thereof or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives.

Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

Nucleotide-binding proteins play an important role in the metabolism of an organism. E.g., enzymes of the protein kinase family are essential switches of the cellular signal transduction machinery in all eucaryotic cells. They have been implicated with the control of numerous physiological and pathophysiological processes in eucaryotic organisms and therefore represent an important class of drug targets for a variety of indications such as cancer, inflammation and infectious diseases. Efficient and selective enrichment is a prerequisite for subsequent identification of protein kinase targets by a proteomics approach. Efficient pre-fractionation techniques are described in WO 04/013633.

Taking the above-mentioned necessities into account, the present invention provides a medium for separating at least one nucleotide binding protein from a pool of proteins, the medium comprises at least one compound of the general formula (II) and/or (III)

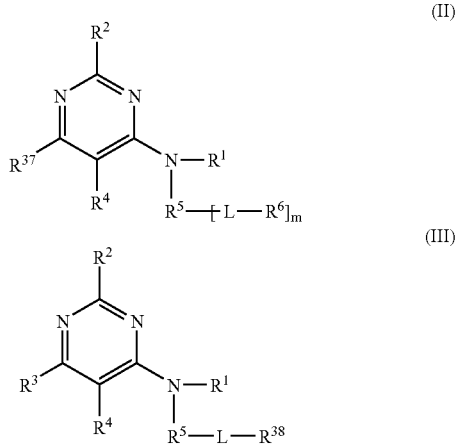

wherein
$R^1, R^2, R^3, R^4, R^5, R^6$, L and m have the meanings as defined in claim 1, $R^{37}$ and $R^{38}$ are independently of each other selected from

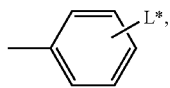

-L*, substituted or unsubstituted $C_1$-$C_6$ alkyl-L*, substituted or unsubstituted $C_3$-$C_8$ cycloalkyl-L*, substituted or unsubstituted heterocyclyl-L*, substituted or unsubstituted aryl-L*, or substituted or unsubstituted heteroaryl-L*;
L* is selected from —$X^1$—H, —$X^3$, —$X^1$—$X^3$;
$X^1$ and $X^2$ are independently of each other selected from —NH—, —S—, —O—, —N($C_1$-$C_6$ alkyl)-, —COO—, —O—CO—, —CO—NH—, —NH—CO—, —O—CO—NH—, —NH—CO—O—, —NH—CO—NH—, —O—CO—O—, —NH—C(NH)NH—, —NH—SO$_2$—, —SO$_2$—NH—;
$X^1$—H and $Y^1$—H are independently of each other selected from —NH$_2$, —SH, —OH, —N($C_1$-$C_6$ alkyl)H, —COOH, —CO—NH$_2$, —O—CO—NH$_2$, —NH—SO$_2$H, —NH—SO$_3$H, —SO$_2$—NH$_2$, —NH—C(NH)—NH$_2$,
$X^3$ is selected from —(CH$_2$)$_a$—$X^4$, —(CH$_2$)$_a$—CO—$X^4$, —(CH$_2$)$_a$—NH—SO$_2$—$X^4$, —(CH$_2$)$_a$—$Y^1$—H, —(CH$_2$)$_a$—$X^2$—(CH$_2$)$_b$—$X^4$, —(CH$_2$)$_a$—$X^2$—(CH$_2$)$_b$—$Y^1$—H;
$X^4$ is selected from —Cl, —Br, —I, —N$_3$, —OOC—$C_1$-$C_6$ alkyl, —O—SO$_2$—CH$_3$, —O—SO$_2$-p—$C_6$H$_4$—CH$_3$;
a and b are independently of each other integer from 1-10;
immobilized on a support material.

It is preferred, that the compounds according to the general formula (II) and/or (III) are covalently bound to the support material. The novel compounds according to formula (II) and (III) as well as the compounds in a form bound to a support material are subject of this invention. Thus, disclosed herewith are also the compounds according to formula (II) or (III) which are not immobilized on a support material. It is clear that to achieve such a covalent bond to the support material one radical, preferably a hydrogen must be replaced in the respective compound to form such a bond with the support material. It is furthermore preferred that these compounds are bonded to the support material via a group $Y^1$ as defined above. Therefore, all compounds according to the present invention, bearing a —NH$_2$, —SH, —OH, —N($C_1$-$C_6$ alkyl) H, —COOH, —NH—SO$_2$H, —NH—SO$_3$H, —NH—C(NH)—NH$_2$ group, can be immobilized on a support material. Especially, all compounds mentioned explicitly in Table 2, bearing a —NH$_2$, —SH, —OH, —NH($C_1$-$C_6$ alkyl), —COOH, —NH—SO$_2$H, —NH—SO$_3$H, —NH—C(NH)—NH$_2$ group, can be immobilized on a support material. Said support material comprises preferably sepharose and modified sepharose or can be any other known and common support material, preferably solid support material, which can be used for column chromatography.

In a further preferred embodiment of this medium, $R^1$, $R^2$ and $R^4$ in the compounds according to the general formula (II) and/or (III) are independently of each other selected from —H or linear or branched substituted or unsubstituted $C_1$-$C_4$ alkyl;
$R^3$ represents substituted or unsubstituted phenyl, preferably substituted phenyl, wherein the phenyl is partially or fully substituted with members of the group consisting of: linear or branched $C_1$-$C_4$ alkoxy, —OCH$_2$-Phenyl, or —NH$_2$, and wherein phenyl is preferably monosubstituted;
$R^5$ represents substituted or unsubstituted aryl, preferably substituted or unsubstituted phenyl, wherein phenyl is preferably substituted with linear or branched substituted or unsubstituted $C_1$-$C_4$ alkyl,
L is selected from the group comprising:
—NH—CO—, —NH—SO$_2$—, —SO$_2$—, —SO$_2$—NH— or —CO—NH—,
and
m is selected to be 1 and
$R^6$ is selected from the group comprising: —H. linear or branched substituted or unsubstituted $C_1$-$C_4$ alkyl, monosubstituted phenyl, substituted or unsubstituted heterocyclyl, substituted or unsubstituted heteroaryl or substituted or unsubstituted $C_3$-$C_8$ cycloalkyl, and
$R^{37}$ is selected to be

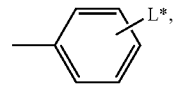

or wherein
$R^{38}$ is selected from substituted or unsubstituted $C_3$-$C_8$ cycloalkyl-L*, preferably unsubstituted $C_3$-$C_8$ cycloalkyl-L*, or from substituted or unsubstituted aryl-L*, substituted or unsubstituted $C_1$-$C_6$ alkyl-L*, substituted or unsubstituted heterocyclyl-L*, wherein the heterocyclyl is selected from pyrrolidinyl or piperidinyl.

In yet another preferred embodiment of this medium, $X^1$ in the compounds according to the general formula (II) and/or (III) is selected to be —NH— or —O—, $Y^1$—H is selected to be —NH$_2$ or —N(C$_1$-C$_6$ alkyl)H and preferably —NH$_2$, a and b are independently of each other selected to be an integer from 1 to 6, preferably from 2 to 4.

In yet another preferred embodiment of this medium, at least one compound according to the general formula (II) and/or (III) immobilized on a support material is selected from the compound list of claim 33 and preferably is 3-Amino-N-{4-[6-(2-methoxy-phenyl)-pyrimidin-4-ylamino]-phenyl}-propionamide (compound 102) and 4-Amino-N-(4-{6-[2-(3-amino-propoxy)phenyl]-pyrimidin-4-ylamino}-phenyl)-benzamide (compound 103).

In a preferred embodiment of this medium, the support material comprises or consists of sepharose, preferably modified sepharose material like epoxy-activated Sepharose 6B material, obtainable from Amersham Biosciences. Other modified sepharose material which could be used as support material are EAH-sepharose 4B and ECH sepharaose 4C, which can also be obtained by Amersham Biosciences.

According to a still further embodiment of this medium, the support material comprises or consists of ferro- or ferrimagnetic particles as e.g. known from WO 01/71732, incorporated herein by reference as far as properties of ferro- or ferrimagnetic particles are concerned. The ferro- or ferrimagnetic particles may comprise glass or plastic. The ferro- or ferrimagnetic particles that can be used with the present invention may be porous. The ferro- or ferrimagnetic glass particles may comprise about 30 to 50% by weight of $Fe_3O_4$ and about 50 to 70% by weight of $SiO_2$. The ferro- or ferrimagnetic particles used herein preferably have an average size of about 5 to 25 μm in diameter, more preferably about 6 to 15 μm, and particularly about 7 to 10 μm. The total surface area of the ferro- or ferrimagnetic particles may be 190 m$^2$/g or greater, e.g. in the range of about 190 to 270 m$^2$/g (as determined according the Brunaur Emmet Teller (BET) method).

These magnetic particles facilitate purification, separation and/or assay of biomolecules, like protein kinases. Magnetic particles (or beads) that bind a molecule of interest can be collected or retrieved by applying an external magnetic field to a container comprising the particles. Unbound molecules and supernatant liquid can be separated from the particles or discarded, and the molecules bound to the magnetic particles may be eluted in an enriched state.

In a still further preferred embodiment of this medium, compounds according to the general formula (II) and/or (III), wherein at least one of those compounds is bound to the support material, can be used to enrich nucleotide binding proteins, preferably an ATP binding protein, more preferably a kinase, and most preferably a protein kinase from a pool of different proteins, like from a proteome, a cell lysate or a tissue lysate.

According to another preferred aspect of the present invention, a method for enriching, purifying or depleting at lest one nucleotide binding protein, preferably an ATP binding protein, more preferably a kinase, and most preferably a protein kinase, from a pool of proteins containing at least one such nucleotide binding protein, wherein the method comprises the following steps:
a) Immobilizing at least one compound of the general formula (II) and/or (III)

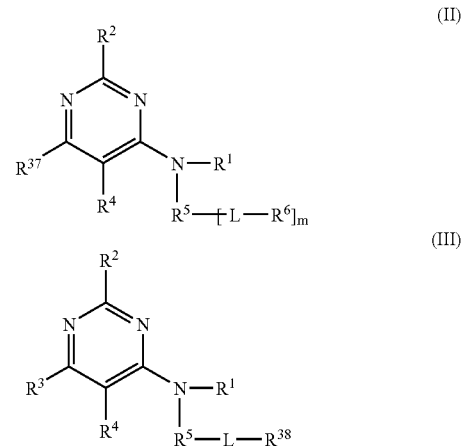

wherein
$R^1$, $R^2$, $R^3$, $R^4$, $R^5$, $R^6$, L and m have the meanings as defined in claim 1, $R^{37}$ and $R^{38}$ are independently of each other selected from

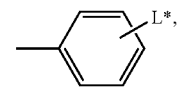

-L*, substituted or unsubstituted $C_1$-$C_6$ alkyl-L*, substituted or unsubstituted $C_3$-$C_8$ cycloalkyl-L*, substituted or unsubstituted heterocyclyl-L*, substituted or unsubstituted aryl-L*, or substituted or unsubstituted heteroaryl-L*;
L* is selected from —$X^1$—H, —$X^3$—, —$X^1$—$X^3$;
$X^1$ and $X^2$ are independently of each other selected from —NH—, —S—, —O—, —N(C$_1$-C$_6$ alkyl)-, —COO—, —O—CO—, —CO—NH—, —NH—CO—, —O—CO—NH—, —NH—CO—O—, —NH—CO—NH—, —O—CO—O—, —NH—C(NH)—NH—, —NH—SO$_2$—, —SO$_2$—NH—;
$X^1$—H and $Y^1$—H are independently of each other selected from —NH$_2$, —SH, —OH, —N(C$_1$-C$_6$ alkyl)H, —COOH, —CO—NH$_2$, —O—CO—NH$_2$, —NH—SO$_2$H, —NH—SO$_3$H, —SO$_2$—NH$_2$, —NH—C(NH)—NH$_2$,
$X^3$ is selected from —(CH$_2$)$_a$—$X^4$, —(CH$_2$)$_a$—CO—$X^4$, —(CH$_2$)$_a$—NH—SO$_2$—$X^4$, —(CH$_2$)$_a$—$Y^1$—H, —(CH$_2$)$_a$—$X^2$—(CH$_2$)$_b$—$X^4$, —(CH$_2$)$_a$—$X^2$—(CH$_2$)$_b$—$Y^1$—H;
$X^4$ is selected from —Cl, —Br, —I, —N$_3$, —OOC—C$_1$-C$_6$ alkyl, —O—SO$_2$—CH$_3$, —O—SO$_2$-p-C$_6$H$_4$—CH$_3$;
a and b are independently of each other integer from 1-10;
on a support material;
b) bringing the pool of proteins containing at least one nucleotide binding protein into contact with at least one compound according to the general formula (II) and/or according to the general formula (III) immobilized on the support material; and
c) separating the proteins not bound to the at least one compound according to the general formula (II) and/or according to the general formula (III) on the support material from the at least one nucleotide binding protein bound to the at least one said compound immobilized on the support material; and d) Releasing and collecting the at least one nucleotide binding protein bound to the at least one compound according to the general formula (II) and/or according to the general formula (III) immobilized on the support material from the at least one of said compounds.

According to a preferred embodiment of the method, in the compounds according to the general formula (II) and/or (III), $R^1$, $R^2$ and $R^4$ are independently of each other selected from —H or linear or branched substituted or unsubstituted $C_1$-$C_4$ alkyl;

$R^3$ represents substituted or unsubstituted phenyl, preferably substituted phenyl, wherein the phenyl is partially or fully substituted with members of the group consisting of: linear or branched $C_1$-$C_4$ alkoxy, —OCH$_2$-Phenyl, or —NH$_2$, and wherein phenyl is preferably monosubstituted;

$R^5$ represents substituted or unsubstituted aryl, preferably substituted or unsubstituted phenyl, wherein phenyl is preferably substituted with linear or branched substituted or unsubstituted $C_1$-$C_4$ alkyl, L is selected from the group comprising:
—NH—CO—, —NH—SO$_2$—, —SO$_2$—NH—, —CO—NH—, —NH—CO—NH—, —NH—CO—O—, —NH—CS—NH—, —NH—C(NH)—NH—, —CO—, —CO—O—, —SO—, —SO$_2$—, —SO$_3$— —NR$^{14}$—SO$_2$—, —NR$^{14}$—SO—, —NR$^{17}$—CO—, —SO$_2$—NR$^{18}$—, —CO—NR$^{19}$—, wherein $R^{14}$, $R^{17}$, $R^{18}$, and $R^{19}$ have the meanings as defined in claim 1, and m is selected to be 1 and $R^6$ is selected from the group comprising: —H, linear or branched substituted or unsubstituted $C_1$-$C_4$ alkyl, monosubstituted phenyl, substituted or unsubstituted heterocyclyl, substituted or unsubstituted heteroaryl or substituted or unsubstituted $C_3$-$C_8$ cycloalkyl, and $R^{37}$ is selected to be

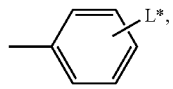

or wherein $R^{38}$ is selected from substituted or unsubstituted $C_1$-$C_8$ cycloalkyl-L*, preferably unsubstituted $C_3$-$C_8$ cycloalkyl-L*, or from substituted or unsubstituted aryl-L*, substituted or unsubstituted $C_1$-$C_6$ alkyl-L*, substituted or unsubstituted heterocyclyl-L*, wherein the heterocyclyl is selected from pyrrolidinyl or piperidinyl.

According to a further preferred embodiment of said method, in the compounds according to the general formula (II) and/or (III), $X^1$ is selected to be —NH— or —O—, $Y^1$—H is selected to be —OH, —NH$_2$ or —N(C$_1$-C$_6$ alkyl)H, preferably —NH$_2$, and a and b are independently of each other selected to be an integer from 1 to 6, preferably from 2 to 4.

Preferably, the compounds immobilized on the support material are selected from the compound list of claim 33 and especially preferred are the compounds 3-Amino-N-{4-[6-(2-methoxy-phenyl)-pyrimidin-4-ylamino]-phenyl}-propion-amide (compound 102) and 4-Amino-N-(4-{6-[2-(3-amino-propoxy)-phenyl]-pyrimidin-4-ylamino}-phenyl)-benz-amide (compound 103).

In yet another preferred embodiment of the present invention, the method further comprises the step of collecting the released at least one nucleotide binding protein, e.g. the ATP binding protein, especially the protein kinase.

The method according to the present invention can be implemented using any of the media and materials described with reference to the first aspect of the present invention.

In a further preferred aspect of the method according to the present invention in step c) the separating of the proteins not bound to the at least one compound immobilized on the support material from the at least one nucleotide binding protein, preferably a ATP binding protein, bound to the at least one compound immobilized on the support material is effected by washing with a buffer containing 5 to 500 mM Hepes pH 6.5-8.5 or 5 to 500 mM Tris-HCl pH 6.8 to 9.0, 0 to 2500 mM NaCl, 0 to 5% Triton X-100, 0 to 500 mM EDTA, and 0 to 200 mM EGTA. In another preferred embodiment the buffer contains 20 mM Hepes/NaOH pH 7.5, 100 mM NaCl, 0.15% Triton X-100, 1 mM EDTA, and 1 mM EGTA.

In yet another preferred embodiment of the method according to the present invention, in step d) the releasing of the at least one nucleotide binding protein, e.g. the protein kinase, bound to the at least one compound immobilized on the support material is effected by washing with a buffer containing 5 to 500 mM Hepes pH 6.5-8.5 or 5 to 500 mM Tris-HCl pH 6.8 to 9.0, 0 to 1000 mM NaCl, 0 to 5.0% Triton X-100, 0-5% SDS, 0 to 500 mM EDTA, 0 to 200 mM EGTA, 1 to 100 mM ATP, 1 to 200 mM MgCl$_2$ and 0.1 to 10 mM of at least one of the compounds immobilized on the support material. In another preferred embodiment the buffer contains 50 mM Hepes pH 7.5, 150 mM NaCl, 0.25% Triton X-100, 1 mM EDTA, 1 mM EGTA, 10 mM ATP, 20 mM MgCl$_2$ and 1 mM of at least one of the compounds immobilized on the support material.

In yet another preferred embodiment of the method of the present invention, the pool of proteins is a proteome, cell lysate or tissue lysate. In a further embodiment of the method according to the present invention the ATP binding protein is a protein kinase.

In a preferred embodiment of the method according to the present invention, the pool of proteins contains 0.5 to 5 M, preferably 0.5 to 3 M, and more preferably 0.75 to 2 M of a salt, and preferably is an alkali metal salt, preferably NaCl.

In a preferred embodiment of the present invention, the at least one nucleotide binding protein, preferably a ATP binding protein, is enriched at least 100-fold from the pool of proteins, preferably between 100- and 1000-fold.

In another preferred embodiment the at least one nucleotide binding protein, preferably a ATP binding protein, is enriched at least $10^4$-fold and preferably up to $10^6$ fold.

In another aspect of the present invention, the invention concerns a kit comprising a medium as outlined above. In a preferred embodiment, the kit further comprises at least one buffer as outlined above.

EXPERIMENTAL PART

Figure 1A:
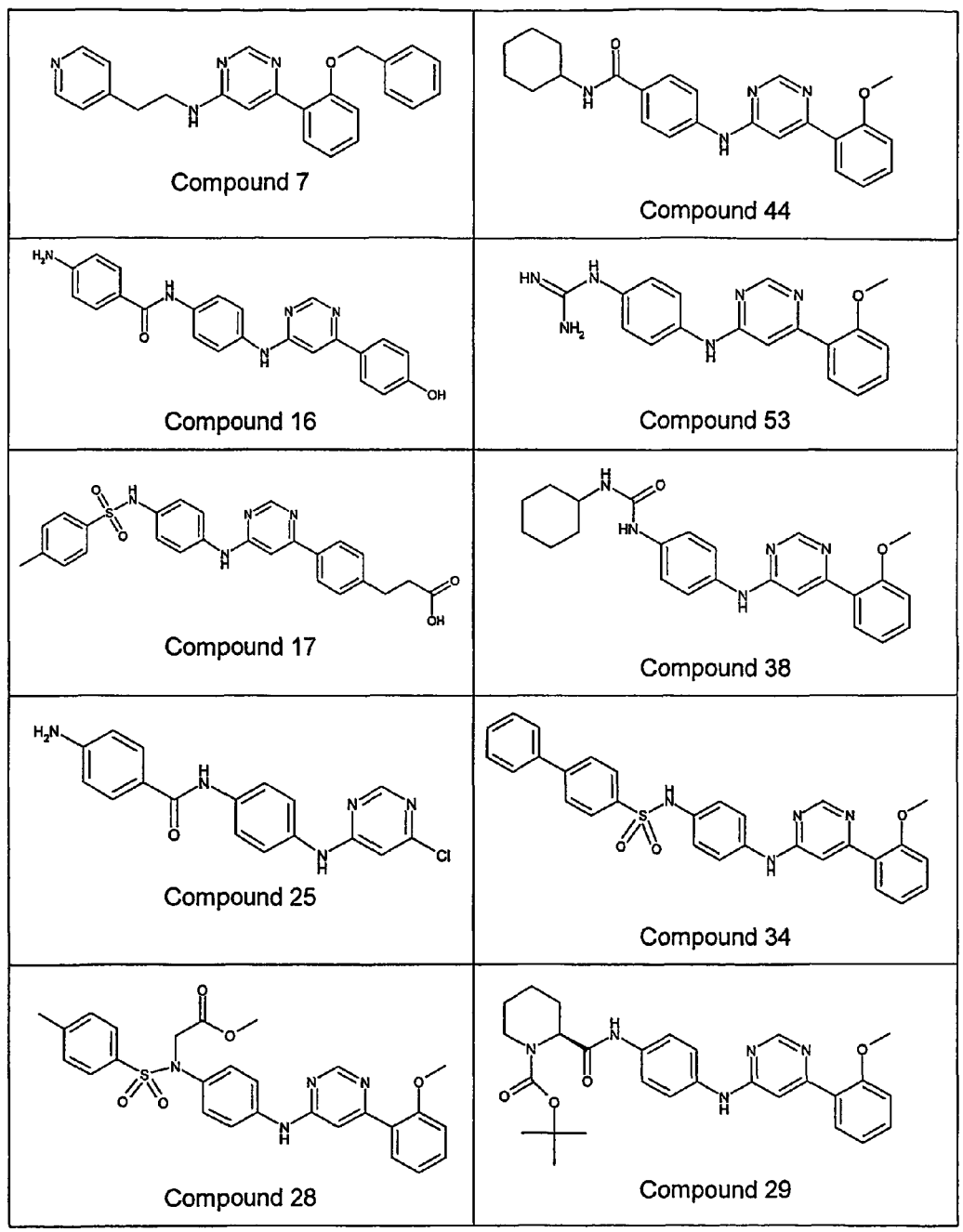
FIGS. 1*a*-1*c* show representative compounds of the general formula (I)
Figure 1B:
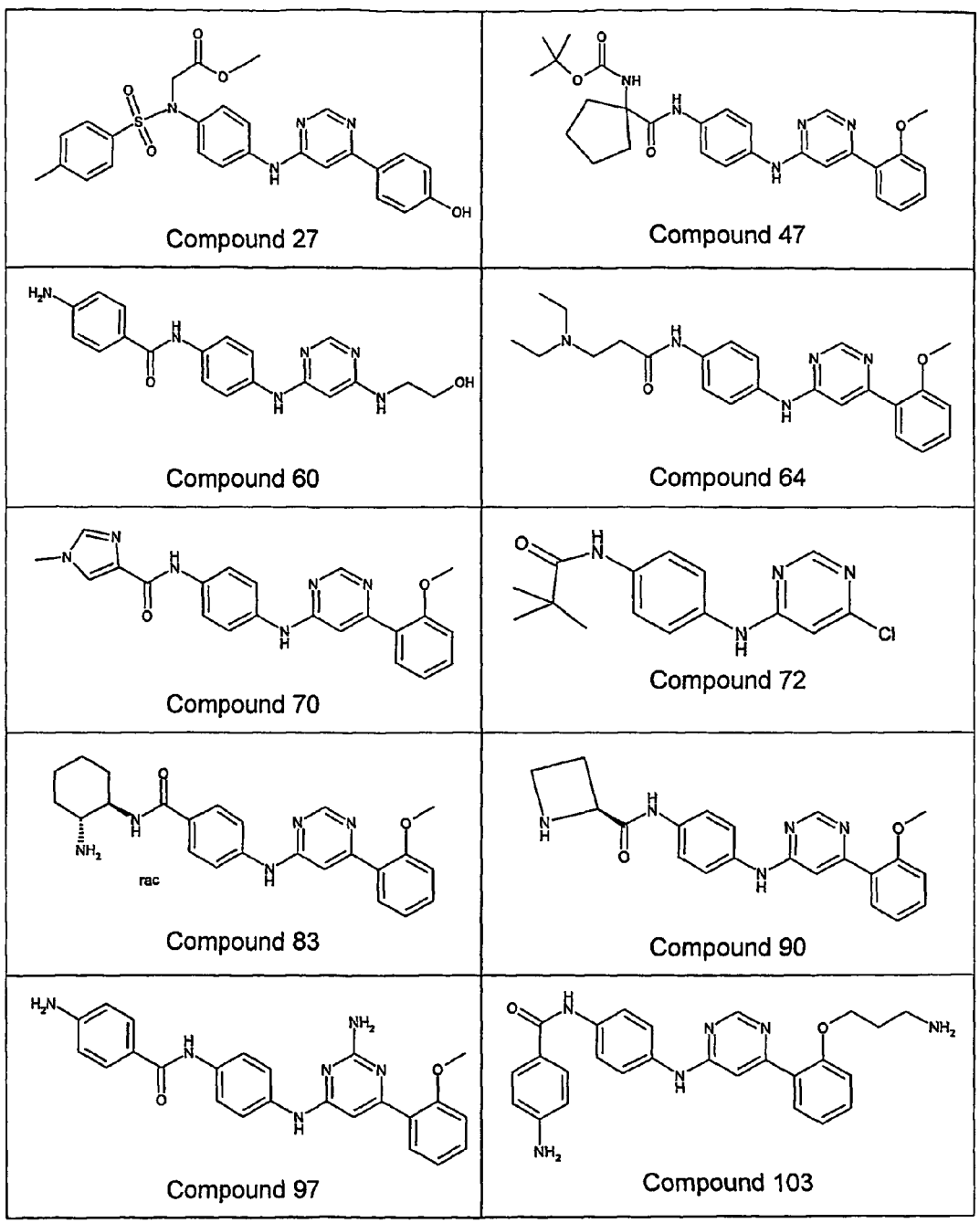
Figure 1C:
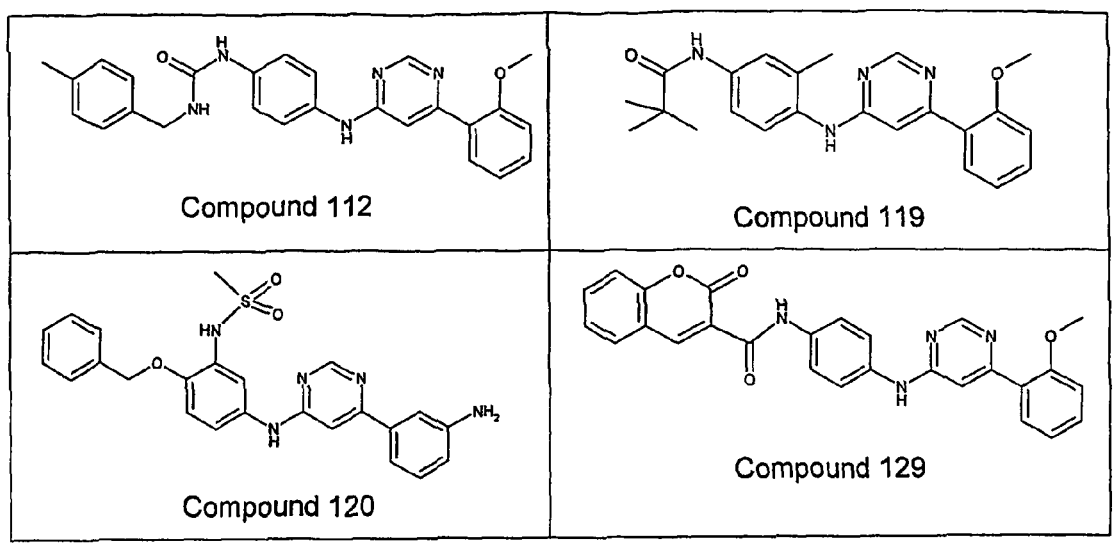

Analytical Methods:

LC/MS data were obtained using a Micromass ZQ instrument with atmospheric pressure chemical ionisation or electrospray ionisation under the conditions described below.

Standard Acidic LC-MS Conditions (Method A1)

HPLC Setup

| | |
|---|---|
| Solvents: | Acetonitrile (Far UV grade) with 0.1% (V/V) formic acid Water (High purity via Elga UHQ unit) with 0.1% formic acid |
| Column: | Phenomenex Luna 5μ C18 (2), 30 × 4.6 mm. |
| Flow Rate: | 2 ml/min |
| Gradient: | A: Water/formic acid B: MeCN/formic acid |

| Time | A % | B % |
|---|---|---|
| 0.00 | 80 | 20 |
| 2.50 | 0.00 | 100 |
| 3.50 | 0.00 | 100 |
| 3.60 | 80 | 20 |
| 4.50 | 80 | 20 |

Standard Acidic LCMS Conditions (Method A2)

HPLC Setup

| | |
|---|---|
| Solvents: | Acetonitrile (Far UV grade) with 0.1% (V/V) formic acid Water (High purity via Elga UHQ unit) with 0.1% formic acid |
| Column: | Phenomenex Luna 5μ C18 (2), 100 × 4.6 mm. |
| Flow Rate: | 2 ml/min |
| Gradient: | A: Water/formic acid B: MeCN/formic acid |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

UV Detection via HP or Waters DAD

Purity is assessed as the integral over the window 210-400 nm.

If necessary, specific wavelength traces are extracted from the DAD data.

Optional ELS detection using Polymer Labs ELS-1000.

MS Detection: Either Micromass Platform or ZQ, Both Single Quadrapole LC-MS Instruments.

Scan range for MS Data (m/z)

| | |
|---|---|
| Start (m/z) | 100 |
| End (m/z) | 650 |

With +ve/−ve switching

Ionisation is either electrospray or APCI dependent on compound types.

Standard Basic LC-MS Conditions (Method B1)

HPLC Setup

| | |
|---|---|
| Solvents: | Acetonitrile (Far UV grade) Water (High purity via Elga UHQ unit) with 10 mM ammonium bicarbonate (ammonium hydrogen carbonate) |
| Column:- | Waters Xterra MS 5μ C18, 50 × 4.6 mm. |
| Flow Rate:- | 2 ml/min |
| Gradient:- | A: Water/NH$_4$HCO$_3$ B: MeCN/NH$_4$HCO$_3$ |

| Time | A % | B % |
|---|---|---|
| 0.00 | 80 | 20 |
| 2.50 | 0 | 100 |
| 3.50 | 0 | 100 |
| 3.60 | 80 | 20 |
| 4.50 | 80 | 20 |

Standard Basic LC-MS Conditions (Method B2)

HPLC Setup

| | |
|---|---|
| Solvents: | Acetonitrile (Far UV grade) Water (High purity via Elga UHQ unit) with 10 mM ammonium bicarbonate (ammonium hydrogen carbonate) |
| Column:- | Waters Xterra MS 5μ C18, 100 × 4.6 mm. |
| Flow Rate:- | 2 ml/min |
| Gradient:- | A: Water/NH4HCO3 B: MeCN/NH4HCO3 |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

UV Detection via HP or Waters DAD

Purity is assessed as the integral over the window 210-400 nm.

If necessary, specific wavelength traces are extracted from the DAD data.

Optional ELS detection using Polymer Labs ELS-1000.

MS Detection: Either Micromass Platform or ZQ, Both Single Quadrapole LC-MS Instruments.

Scan range for MS Data (m/z)

| | |
|---|---|
| Start (m/z) | 100 |
| End (m/z) | 650 |

With +ve/−ve switching

Ionisation is either electrospray or APCI dependent on compound types.

All reagents were obtained commercially and used directly. DMF and THF were dried over 4 Å molecular sieves (Fisher Scientific). Column chromatography employed Silica Gel 60 (Fluka). TLC was carried out using pre-coated plastic sheets Polygram SIL G/UV$_{254}$ (Macherey-Nagel).

Standard Basic LC-MS Conditions (Method C1)

The conditions for the standard basic LC-MS conditions for Method C1 are the same as for Method A1, with the distinction that for method C1 no buffer like ammonium bicarbonate (ammonium hydrogen carbonate) or formic acid was used.

Standard Basic LC-MS Conditions (Method C2)

The conditions for the standard basic LC-MS conditions for Method C2 are the same as for Method A2, with the distinction that for method C2 no buffer like formic acid was used.

Standard Conditions for Flash Chromatography

Flash chromatography was done using a $SiO_2$-column and by using the following solvents:

petroleum ether (bp 40-60), ethyl acetate, methanol

Standard Neutral LC-MS Conditions (Method D1)
HPLC Setup

| Solvents: | Acetonitrile (Lichrosolv Merck) |
| --- | --- |
| | Water (Lichrosolv Merck) with 1 mM ammonium acetate pH 6.8 |
| Column:- | Waters XTerra MS $C_{18}$ 3.5 µm, 3.0 × 50 mm. |
| Flow Rate:- | 0.8 ml/min |
| Gradient:- | A: Water/$NH_4OAc$ B: MeCN |

| Time | A % | B % |
| --- | --- | --- |
| 0.00 | 98 | 2 |
| 5.00 | 5 | 95 |
| 6.50 | 5 | 95 |
| 6.60 | 98 | 2 |
| 8.00 | 98 | 2 |

Standard Neutral LC-MS Conditions (Method D2)
HPLC Setup

| Solvents: | Acetonitrile (Lichrosolv Merck) |
| --- | --- |
| | Water (Lichrosolv Merck) with 1 mM ammonium acetate pH 6.8 |
| Column:- | Waters XTerra MS $C_{18}$ 2.5 µm, 3.0 × 30 mm. |
| Flow Rate:- | 0.8 ml/min |
| Gradient:- | A: Water/$NH_4OAc$ B: MeCN |

| Time | A % | B % |
| --- | --- | --- |
| 0.00 | 100 | 0 |
| 1.50 | 100 | 0 |
| 8.50 | 30 | 70 |
| 8.60 | 5 | 95 |
| 10.60 | 5 | 95 |
| 10.70 | 100 | 0 |
| 12.00 | 100 | 0 |

Standard Neutral LC-MS Conditions (Method D3)
HPLC Setup

| Solvents: | Acetonitrite (Lichrosolv Merck) |
| --- | --- |
| | Water (Lichrosolv Merck) with 1 mM ammonium acetate pH 6.8 |
| Column:- | Bonus RP 3.5 µm, 4.6 × 75 mm. |
| Flow Rate:- | 0.8 ml/min |
| Gradient:- | A: Water/$NH_4OAc$ B: MeCN |

| Time | A % | B % |
| --- | --- | --- |
| 0.00 | 100 | 0 |
| 1.50 | 100 | 0 |
| 8.50 | 15 | 85 |
| 8.60 | 2 | 98 |
| 11.60 | 2 | 98 |
| 11.70 | 100 | 0 |
| 13.50 | 100 | 0 |

UV Detection via Waters 2996 PDA

For purity assessments the wavelengths at 215, 254 and 310 nm were extracted from the PDA data and an average purity was calculated from the peak areas.

MS Detection: Either Micromass Platform or ZQ, Both Single Quadrapole LC-MS instruments.

Scan range for MS Data (m/z)

| Start (m/z) | 100 |
| --- | --- |
| End (m/z) | 600 |

With +ve/−ve switching

Ionisation is either electrospray or APCI dependent on compound types.

Syntheses of Compounds

The synthesis of the inventive 4,6-disubstituted pyrimidines according to the present invention was preferably carried out according to the general synthetic sequence, shown in Scheme 1, involving in a first step amination of the pyrimidine ring followed by Suzuki reaction or an inverse order of the reaction steps:

Scheme 1

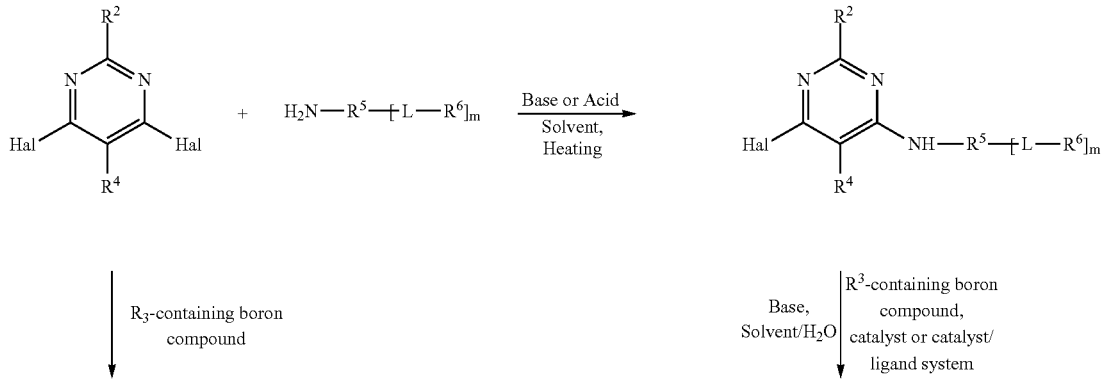

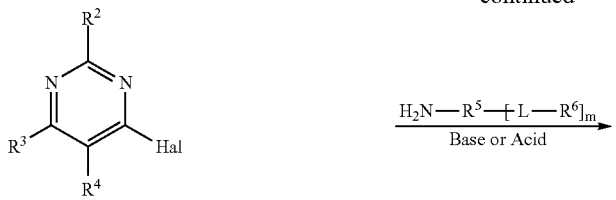 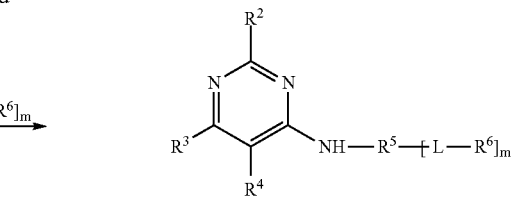

Hal represents —Cl, —Br or —I.

R² and R⁴ have independently of each other the meanings as defined in claim 1, preferably R² and R⁴ are independently of each other selected from —H, —NH₂ or —CH₃, R₃, R⁵, R⁶ and L have the meanings as defined in claim 1, and m is selected to be 0 or 1. In the case protecting groups have been used, a final deprotection step may be follow.

Introduction of the amine moiety can be performed by known methods (J. E. Arrowsmith et al., Journal of Medicinal Chemistry 1989, 32(3), 562-568, J. R. Porter et al, Bioorganic Medicinal Chemistry Letters 2002, 12(12), 1595-1598):

For example, as outlined in Scheme 1, amination is performed by reacting equimolar quantities of 4,6-dihalogenated pyrimidine and an amino compound in a polar solvent, and in the presence of an organic base or an organic or inorganic acid at temperatures in the range of 50 to 120° C. Preferably, the polar solvent is N-methyl-2-pyrrolidinone (NMP) or a lower alcohol, such as iso-propanol or butanol, the organic base is selected for instance from N,N-diisopropylethylamine (DIPEA), N-methyl-piperidine or NEt₃, the acid can be selected for instance from HCl, H₂SO₄, CH₃COOH and the reaction is carried out at a temperature in the range of 60 to 110° C., preferably in the range of 70 to 100° C. It is to be understood, that the reaction temperature depends on the reactivity of the amino compound: For less reactive amino compounds a reaction temperature in the range of 80 to 110° C. is preferred and in these cases a higher boiling solvent such as butanol or NMP affords the desired compounds in good yields.

The introduction of R³ into the pyrimidine scaffold as outlined in Scheme 1, is performed preferably via Suzuki coupling at temperatures in the range of 60 to 110° C., preferably at temperatures in the range of 70 to 100° C., more preferably between 75 to 90° C. (I. Minoru, K. Machiko, T. Masanao, Synthesis 1984, 936-938; J. P. Wolfe, R. A. Singer, B. H. Yang and S. L. Buchwald, Journal of the American Chemical Society 1999, 121, 9550-9561).

The reaction is carried out in organic solvents, such as DME, DMF, THF, Dioxane or methanol or this reaction is carried out in a mixture of an organic solvent and water, such as DMF/water, DME/water or THF/water, in the presence of a base, such as NaHCO₃, NaOH, TlOH, NaOMe, K₂CO₃, K₃PO₄, NEt₃, Cs₂CO₃ or Tl₂CO₃ and in the presence of a catalyst, such as PdCl₂(dppf) {[1,1'-bis-(diphenylphosphino)ferrocene]dichloropalladium II}, Pd(PPh₃)₄ or PdCl₂(PPh₃)₂ or a catalyst/ligand system, such as Pd(OAc)₂/PPh₃, Pd(OAc)₂/2-(Dicyclohexylphosphino)-biphenyl or Pd(OAc)₂/tris(2,4,6-trimethoxyphenyl) phosphine.

The R³ containing boron compound used for this reaction is selected from the group comprising:

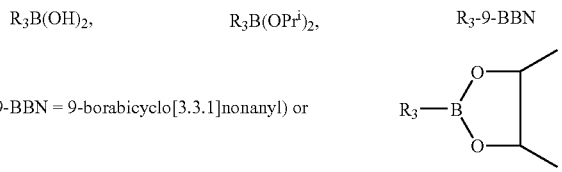

(9-BBN = 9-borabicyclo[3.3.1]nonanyl) or

The chemistry described above can be done in either order and further derivatisation can be carried out after amination and before/after subsequent Suzuki cross coupling. Other suitable methods will be apparent to the chemist skilled in the art as will be the methods for preparing the starting materials and intermediates. When protecting groups have been used, optionally a final deprotecting step can be carried out according to general deprotecting reactions known to a person skilled in the art.

For example, inventive compounds according to the present invention, such as amide derivatives, sulfonamide derivatives, urea derivatives or guanidine derivatives can be prepared from suitably functionalised anilines on reaction with the appropriate reagents. The amide and sulfonamide can be linked as shown in Scheme 2 or the reverse amide can be linked as depicted in Scheme 3.

Introduction and removal of protective groups (PG) may be necessary for several synthetic steps. This includes for example the use of t-butylcarbamate (BOC) protection for amino acids with standard conditions for introduction and removal.

Scheme 2

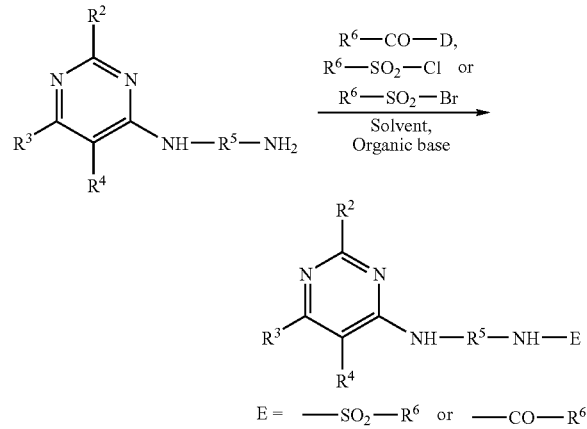

D represents —OH or —Hal.

R², R³, R⁴, R⁵ and R⁶ have the meanings as defined in claim 1, preferably R² and R⁴ represent —H.

The reaction described in Scheme 2, is carried out in the presence of an inert solvent, such as THF or CH₂Cl₂, in the presence of an organic base, such as NEt$_3$, DIPEA or 2,4,6-trimethylpyridine (TMP) and at temperatures in the range of −5° C. to 60° C., preferably at temperatures in the range of 10 to 50° C., more preferably the reaction is carried out at temperatures between 20 to 45° C. In case D represents —OH, the amine coupling is performed in the presence of a coupling agent, selected from the group comprising:
N-[(1-H-benzotriazol-1-yl)-dimethylamino)methylene]-N-methylmethanaminium hexaflorophopshate N-oxide (HBTU), O-(3,4-dihydro-4-oxo-1,2,3-benzotriazin-3-yl)1,1,3,3-tetramethyluronium hexyfluorophosphate (HDTU), O-(benzotriazol-1-yl)-1,1,3,3-bis(pentamethylene)uranium hexafluorophosphate (HBPipU) or benzotriazol-1-yl-N-oxy-tris-(pyrrolidino)phosphonium hexafluorophosphate (PyBOP). Other suitable coupling methods will be apparent to a chemist skilled in the art.

As mentioned above, the reverse amide, can be linked according to the procedure depicted in Scheme 3:

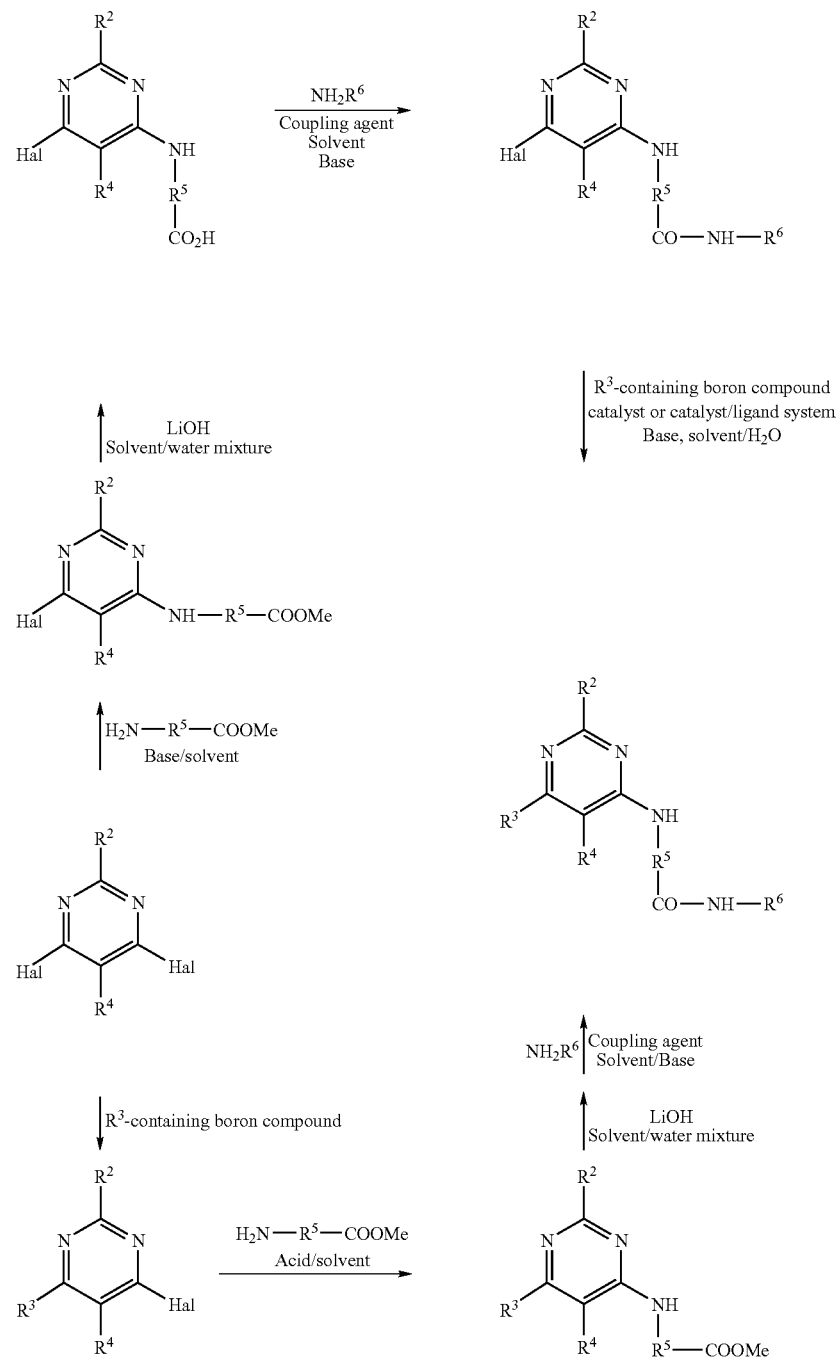

$R^2$, $R^3$, $R^4$, $R^5$ and $R^6$ have the meanings as defined in claim 1, preferably $R^2$ and $R^4$ represent —H, and Hal represents —Cl, —Br or —I.

In a first reaction step, a 4,6-dihalogenated pyrimidine is reacted with an amino alkylester compound, wherein the reaction is carried out in the presence of a base, such as DIPEA or acid such as HCl, $H_2SO_4$, in the presence of a solvent, such as NMP or DMF and at temperatures in the range of 60 to 140° C., preferably at temperatures in the range of 80 to 120° C., more preferably at temperatures in the range of 90 to 110° C.

The second reaction step is carried out in the presence of a base, such as LiOH, and in the presence of solvent/water mixture selected from the group comprising: THF/water, DME/water or DMF/water. The third reaction step, the amine coupling as shown in Scheme 3, is carried out under the same conditions as described for the correspondent reaction step in Scheme 2.

The coupling agent is selected from the group comprising: HBTU, HDTU, HBPipU or PyBOP. Other suitable coupling methods will be apparent to a chemist skilled in the art. The introduction of $R^3$ into the pyrimidine scaffold is performed as described for the correspondent reaction step in Scheme 1.

According to Scheme 3 the order of reaction steps can also be reversed.

When protecting groups have been used, optionally a final deprotecting step can be carried out according to general deprotecting reactions known to a person skilled in the art.

In Scheme 4, a reaction procedure for the synthesis of alkylated sulfonamide derivatives according to the present invention is shown:

Scheme 4

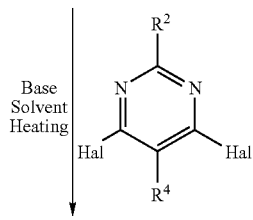

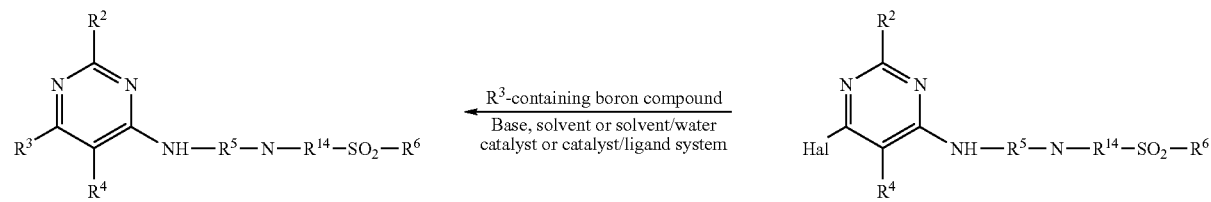

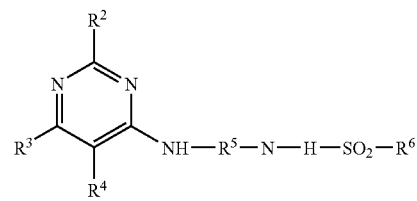

Hal represents —Cl, —Br, or —I.

$R^2$, $R^4$, $R^5$ and $R^6$ have the meanings as defined in claim 1, preferably $R^2$ and $R^4$ represent —H, and $R^{14}$ is selected to be linear or branched substituted or unsubstituted $C_1$-$C_6$ alkyl or —$(CH_2)_r$—$COOR^{16}$, wherein $R^{14}$, $R^{16}$ and r have the meanings as defined in claim 1.

Alkylated sulfonamide derivatives according to the present invention can be prepared by reaction of the corresponding sulfonamide with for example an alkyl halide or similar reagent possessing a leaving group in a polar aprotic solvent such as DMF, THF, NMP or Dioxane, in the presence of a strong base such as NaH, $NaNH_2$, $LiNH_2$ or $KO^tBu$ at temperatures in the range of −20 to 80° C., preferably at temperatures in the range of 0 to 60° C., more preferably at temperatures between 20 to 40° C. The obtained intermediates can then be transformed into the desired products as outlined in Scheme 4, whereas the correspondent reaction conditions are described in Scheme 1.

Guanidine derivatives according to the present invention can be prepared by the scheme shown below (H.-J. Musiol and L. Moroder, Organic Letters 2001, 3, 3859-3861):

$R^2$, $R^3$, $R^4$ and $R_5$ have the meanings as defined in claim 1, preferably $R^2$ and $R^4$ represent —H, and PG represents a protective group, which is defined below. X represents a leaving group such as halogen.

Guanidine derivatives can be prepared by the reaction of an amine compound with a benzotriazole derivative as shown in Scheme 5. This reaction is carried out in the presence of a base, such as $NEt_3$, DIPEA, N-Methyl-piperidine, or N-Ethyl-Morpholine and an organic solvent, selected from the group comprising: $CH_2Cl_2$, $CHCl_3$, THF, DMF, dioxane, methyltertbutylether (MTBE) or diisopropylether (DIPE). This reaction is carried out under heating, preferably at a temperature at which the used solvent refluxes.

For the protection of amino acids the protective groups known from peptide chemistry are used. Preferably, carbamate protective groups are used, more preferably a t-butyl carbamate (BOC) group is used.

The protective group can be introduced using $(BOC)_2O$, BOC—$ONH_2$, BOC—$N_3$ or BOC—O—CHCl—$CCl_3$, preferably $(BOC)_2O$. The BOC group is introduced under basic

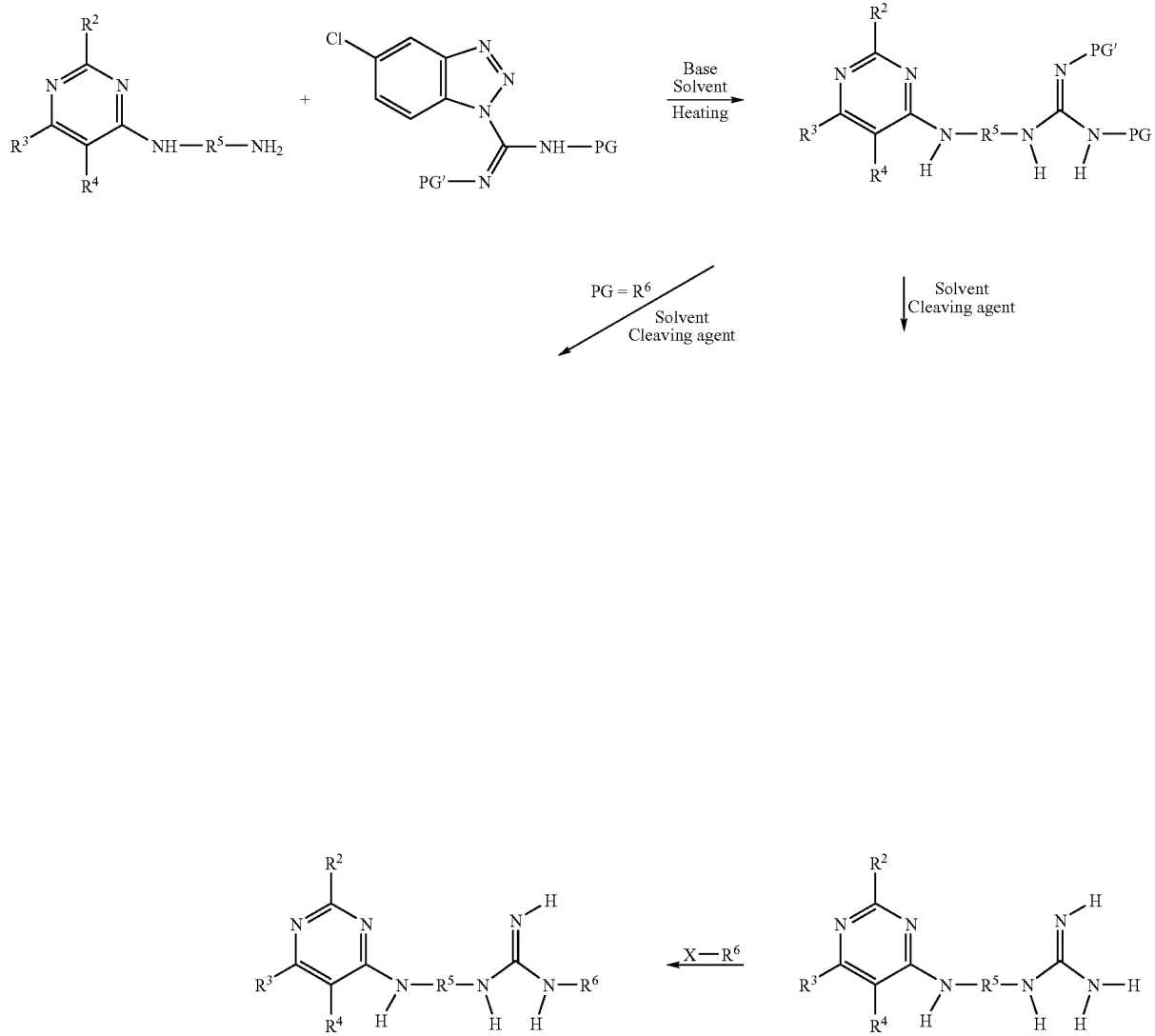

Scheme 5 conditions in a polar solvent, water or a mixture of water and solvent. Cleavage of the protective group is performed under acidic conditions, such as HCl in EtOAc, Me₃SiJ in CHCl₃, H₂SO₄ in dioxane or trifluroacetic acid in CH₂Cl₂, wherein preferably as cleaving agent/solvent mixture, trifluroacetic acid in CH₂Cl₂ is used. This reaction is carried out at temperatures in the range of 0 to 60° C., preferably at temperatures between 10 to 40° C., more preferably at temperatures between 20 to 30° C.

The synthesis of sulfonamide derivatives, wherein R³ represents aniline, is shown in Scheme 6:

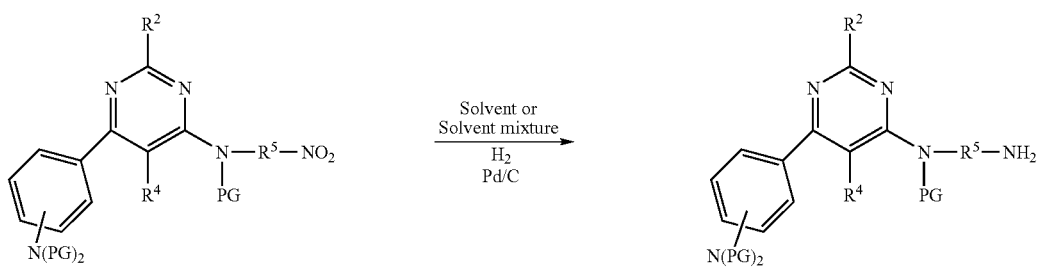

R², R⁴, R⁵ and R⁶ are defined as in claim 1, PG as a protective group is defined as above.

The N-protected nitro compound can be synthesized according to the methods described in Scheme 1 and in Scheme 5 (introduction of the protective group). The reduction of the nitro compound is carried out using a standard procedure as described by Ioffe et al, Russian Chemical Review 1966, 35, 19. The solvent can be selected from the group consisting of: MeOH, EtOH, ⁱPrOH, BuOH or MTBE, and as solvent mixture EtOH/THF can be used. The removal of the protective group is performed as described above (Scheme 5).

For compounds according to the present invention, wherein R³ represents —NH—(CH₂)ₙ—X, wherein n and X are defined as in claim 1, standard nucleophilic displacement can be carried out as shown in Scheme 1 or with the use of microwave conditions as outlined in Scheme 7 (G. Luo et al., Tetrahedron Letters, 2002, 43, 5739-5743):

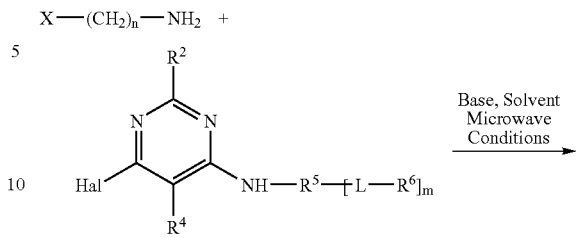

Hal represents —Cl, —Br or —I, R², R⁴, R⁵, R⁶, L and m have the meanings as defined in claim 1, preferably R² and R⁴ are —H.

For this reaction an organic base selected from NEt₃, DIPEA or N-methyl-piperidine is used, and the reaction is carried out in a polar solvent such as iso-propanol, butanol or NMP. For the microwave conditions a wattage of 100 to 300, preferably of 150 to 250 watt is used, and the reaction is carried out at temperatures in the range of 140 to 220° C., preferably at temperatures between 150 to 170° C. The preferred reaction time is between 30 min to 140 min.

Compounds according to the present inventions, wherein $R^1$ represents a linear or branched substituted or unsubstituted $C_1$-$C_6$ alkyl, can be prepared as outlined below:

In a first reaction step, deprotonation of the NH group is achieved, by using a strong inorganic base, such as NaH or an organic base such as Lithiumdiisopropylamid (LDA) or Hexamethyldisilazane (HMDS) and subsequent addition of an alkylating agent, for example an alkyl halide ($R^1$-halide), alkyl sulfate ($R^1$-sulfate) or another appropriate leaving group in organic solvents, selected from the group consisting of: DMF, THF, Dioxane, MTBE or DIPE. This reaction is carried out at temperatures in the range of −80 to 60° C., preferably at temperatures in the range of 0 to 40° C., more preferably at temperatures between 20 to 30° C. The second reaction step is performed under the conditions as described in Scheme 2.

Scheme 8

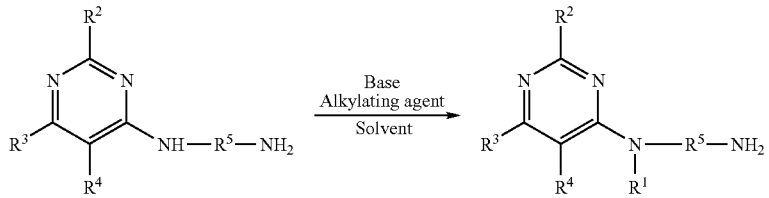

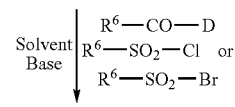

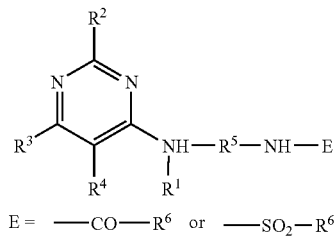

$R^2$, $R^3$, $R^4$, $R^5$ and $R^6$ as defined in claim 1, preferably and $R^2$ and $R^4$ represent ——H and D is selected to be ——OH or ——Hal.

The synthesis of urea derivatives according to the present invention, was carried out according to the two synthetical procedures, depicted in Scheme 9:

The urea derivative can be obtained by reacting an amine compound with an isocyanate using a solvent such as dioxane and using temperatures in the range of 60 to 100° C., preferably in the range of 70 to 90° C.

Scheme 9

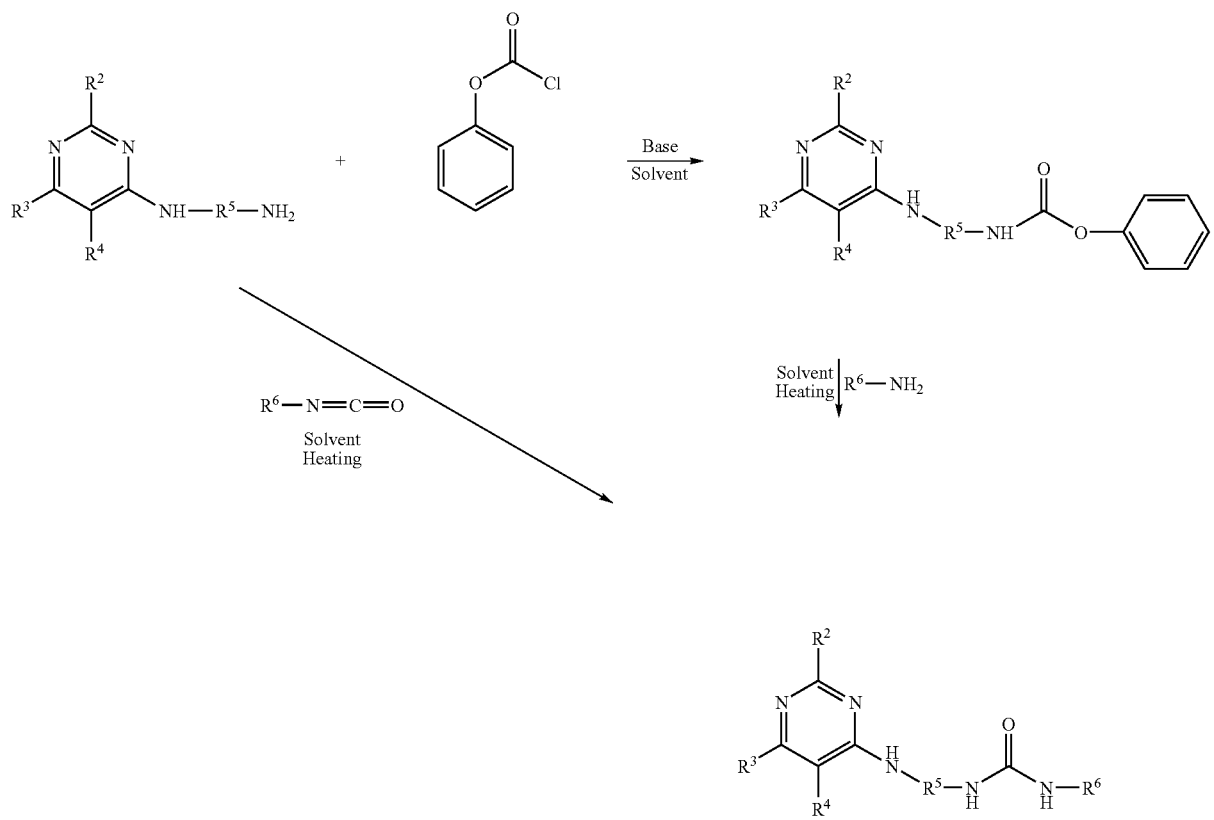

$R^2, R^3, R^4, R^5$ and $R^6$ have the meanings as defined in claim 1.

The second synthetic procedure starts by reacting an amine compound with an equimolar amount of phenyl chloroformate, whereas this reaction is carried out in the presence of a base, such as pyridine, $NEt_3$ or DIPEA, and a solvent, such as THF, DMF, Dioxane or MTBE. The reaction is performed at a temperature in the range of 0 to 60° C., preferably at a temperature in the range of 10 to 40° C., more preferably between 20 to 30° C. In a second reaction step, a $R_6$-containing amine compound is reacted with the carbamate derivative to obtain the desired product. This reaction is performed in a solvent such as THF, DMF, Dioxane or MTBE and the reaction is carried out at temperatures in the range of 20 to 100° C., preferably at temperatures in the range of 30 to 80° C., more preferably at temperatures in the range of 40 to 60° C.

Scheme 9A

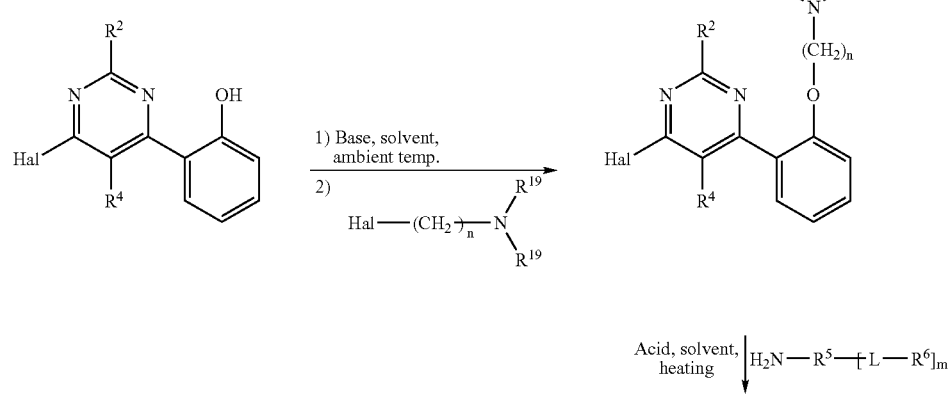

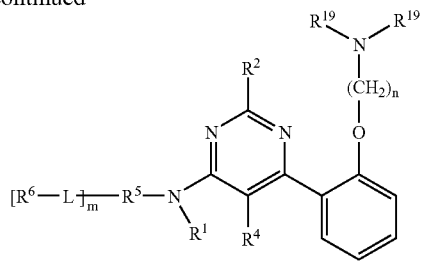

$R^2$, $R^4$, $R^5$, $R^6$, $R^{19}$, L and m have the meanings as defined in claim 1, preferably $R^2$ and $R^4$ represent —H. n is selected to be 1-8.

NaH is used as a base in organic solvents, such as THF and DMF. Amination is carried out under acid catalysts according to scheme 1.

The synthesis of amide derivatives according to the present invention, using a different method for the amination step is shown in Scheme 10.

The amination reaction is carried out in a polar solvent, using 1 equivalent of the nitro-aniline derivative and 2 equivalent of the 4,6-dihalogenated pyrimidine derivative in the presence of a base. Preferably, the polar solvent is N-methyl-2-pyrrolidinone (NMP) or a lower alcohol, such as iso-propanol or butanol, the organic base is selected from N,N-diisopropylethylamine (DIPEA), N-methyl-piperidine or NEt$_3$. This reaction is performed using the following microwave conditions as described by G. Luo et al, Tetrahedron Letters 2002, 43, 5739-5743.

As a next reaction step, a Suzuki coupling is done, under the conditions as described in Scheme 1. The following reduction step can be performed as described by Ioffe et al., Russian Chemical Review 1966, 35, 19. The last reaction step is analogue to the one depicted in Scheme 2.

Scheme 10

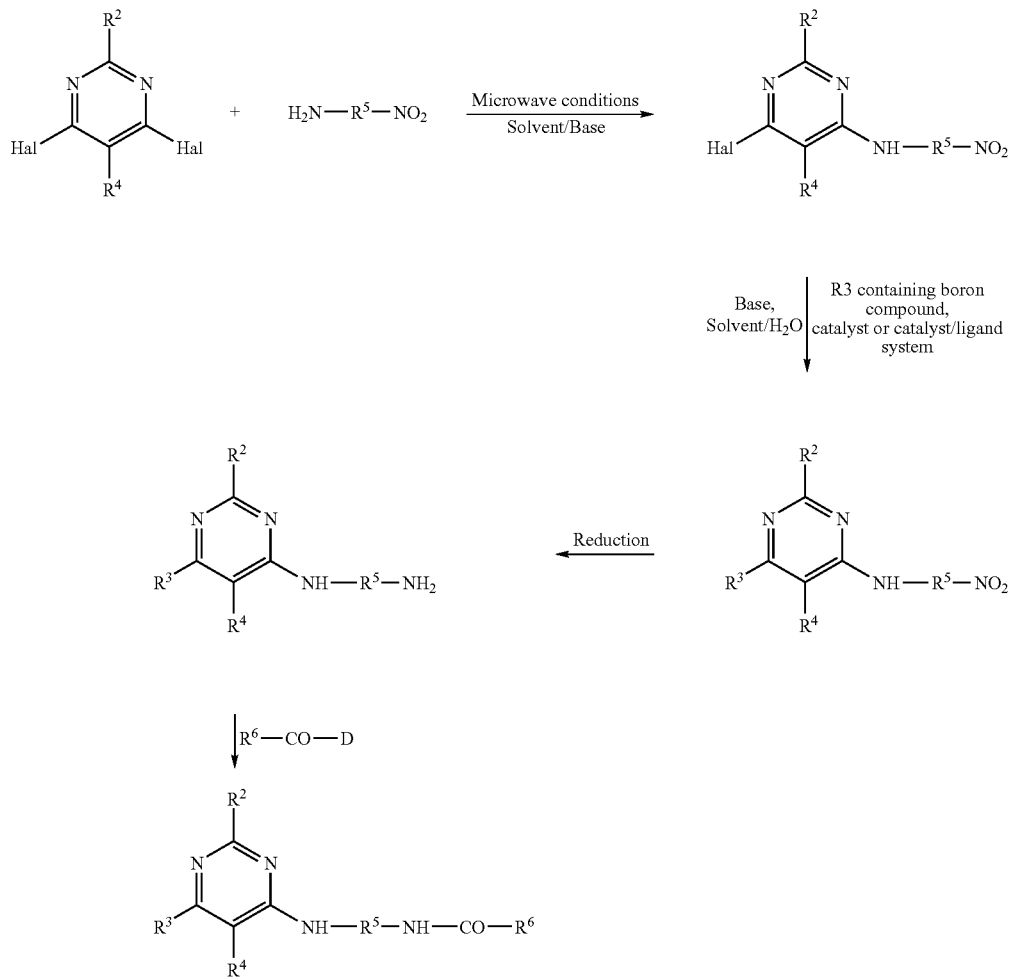

$R^2$, $R^3$, $R^4$, $R^5$ and $R_5$ have the meanings as defined in claim 1, D is defined as in Scheme 2 and Hal is defined as in Scheme 1.

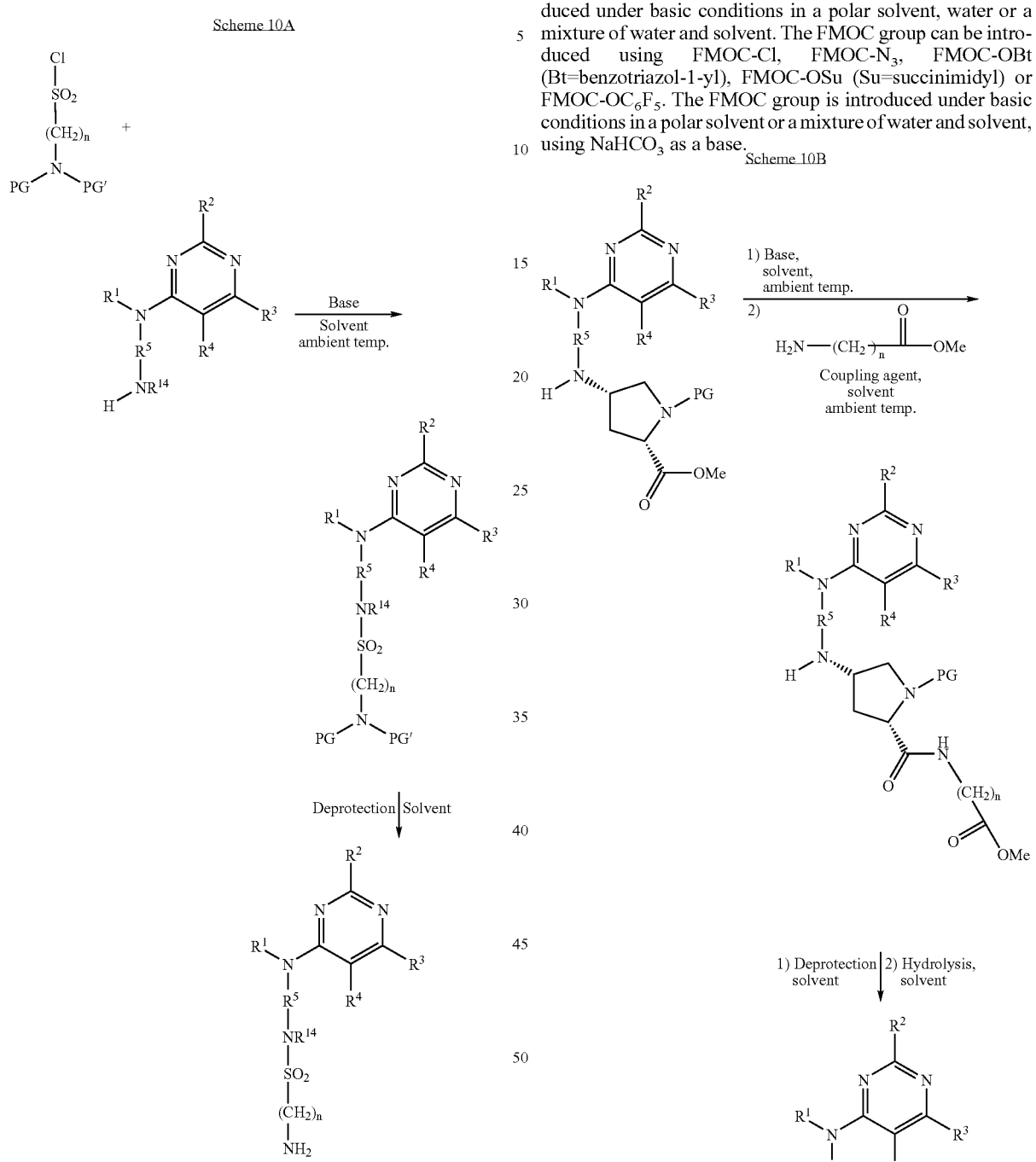

$R^1$, $R^2$, $R^3$, $R^4$, $R^5$ and $R^{14}$ have the meanings as defined in claim 1, preferably $R^2$ and $R^4$ represent —H, and PG and PG' represents protective groups, where either PG=PG' or PG'=H, which is defined below. n is selected to be a number between 1 and 8.

For the protection of the amino function, general protective groups are used. Preferably, the phthaloyl protective group is used, but also carbamates, such as a t-butyl carbamate (BOC) or a 9H-fluorenyl-9-ylmethyl carbamate (FMOC) group are used.

The phthaloyl group can be introduced using phthalic anhydride, phthalimide-NCO$_2$Et, or o-(CH$_3$OOC)C$_6$H$_4$COCl in organic solvents and at elevated temperatures, preferably using a base. The BOC group can be introduced using (BOC)$_2$O, BOC—ONH$_2$, BOC—N$_3$ or BOC—O—CHCl—CCl$_3$, preferably (BOC)$_2$O. The BOC group is introduced under basic conditions in a polar solvent, water or a mixture of water and solvent. The FMOC group can be introduced using FMOC-Cl, FMOC-N$_3$, FMOC-OBt (Bt=benzotriazol-1-yl), FMOC-OSu (Su=succinimidyl) or FMOC-OC$_6$F$_5$. The FMOC group is introduced under basic conditions in a polar solvent or a mixture of water and solvent, using NaHCO$_3$ as a base.

$R^1, R^2, R^3, R^4$ and $R^5$ have the meanings as defined in claim 1, preferably $R^2$ and $R^4$ represent —H, and PG represents a protective group, preferably a carbamate, such as a t-butyl carbamate (BOC) group. n is selected to be 1-8.

Hydrolysis of the ester groups is achieved in an organic solvent and water, such as THF/water with a base, such as LiOH. Amide coupling is carried out according to general methods, such as EDC.HCl/HOBt coupling conditions in organic solvents, such as DMF at ambient temperature.

Compounds according to the present invention, wherein L represents —NH—SO$_2$— can be synthesized as depicted in Scheme 11:

Scheme 11

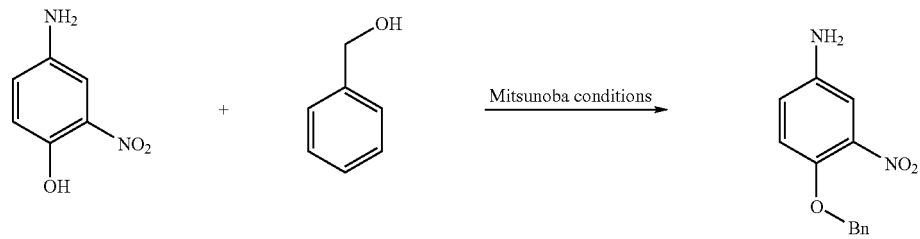

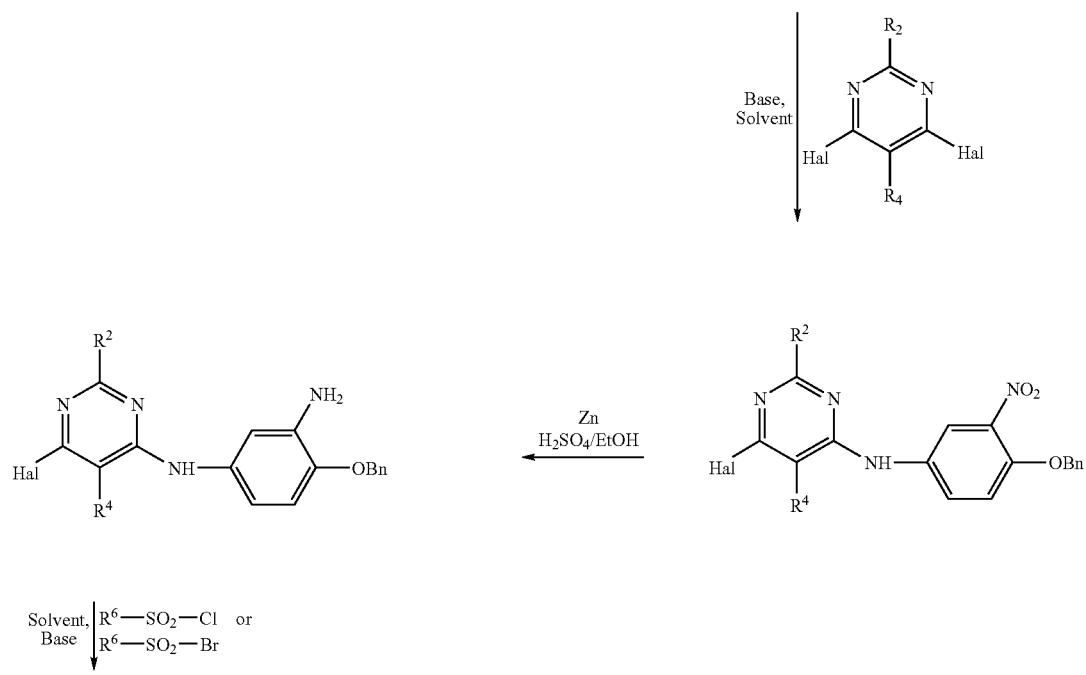

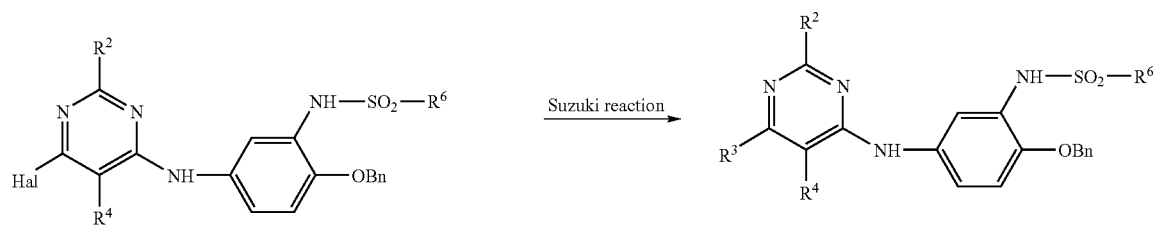

Bn=Benzyl; $R^2$, $R^3$, $R^4$ and $R^6$ have the meanings as defined in claim 1.

In a first reaction step, a benzylether compound can be synthesized using the conditions as described by O. Mitsunobu et al., Synthesis, 1981, 1-28:

Amino-nitrophenol is reacted with benzylalcohol in the presence of a trialkyl- or triarylphosphine, such as triphenylphosphine and in the presence of a dialkyl azodicarboxylate, such as diethylazo dicarboxylate (DEAD) in a solvent such as Dichloromethane to obtain a benzylether. The amination of this intermediate can be done under the conditions as described in Scheme 1. The following Zn reduction can be performed as described by Ioffe et al., Russian Chemical Review 1966, 35. 19. The last two reaction steps, shown in Scheme 11 can be performed analogously as described in Scheme 2 or in Scheme 1 (Suzuki reaction).

The synthesis of compounds of general formula (II) is depicted in Scheme 12:

$R^1$, $R^2$, $R^4$, $R^5$, $R^6$, L and m have the meanings as defined in claim 1;

$X^1$ represents —NH—, —S— or —O—, $Y^1$—H, a and b have the meanings as defined in claim 58, PG represents a protective group as defined in Scheme 6 and Hal represents —Cl, —Br or —I.

In a first reaction step, a pyrimidine derivative is reacted with an alkyl halide derivative according to the scheme below, in a polar aprotic solvent such as DMF, THF, NMP or Dioxane, in the presence of a strong base, such as NaH, $NaNH_2$, $LiNH_2$ or KO$^t$Bu, at temperatures in the range of 0 to 50° C., preferably at temperatures in the range of 10 to 40° C., more preferably at temperatures between 20 to 30° C.

The obtained intermediates can then be transformed into the desired product by cleaving off the protective group as described for the correspondent reaction step in Scheme 6.

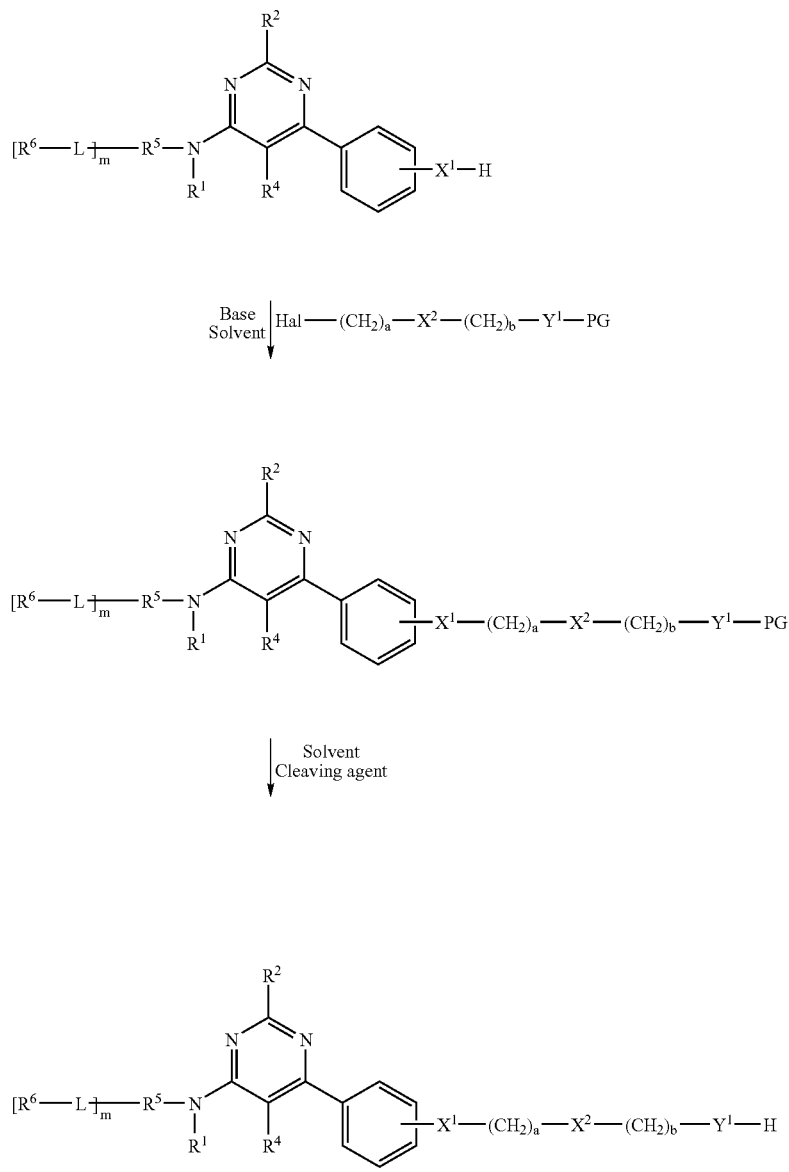

Preparation of Compounds

The LC-MS data for each compound mentioned below are shown explicitly in Table 2.

IA) Preparation of Compounds 24, 25 and 72 (According to Scheme 1)

To a solution of 4,6-Dichloropyrimidine (0.67 mmol) in $^i$PrOH (5mL), NEt$_3$ (1.3 mmol) was added at room temperature followed by the amine (0.67 mmol) and the mixture was heated at 80° C. for 18 h. The solvent was then evaporated under reduced pressure and the solid residue suspended in H$_2$O (~5 mL). The solid was separated by filtration washed with water (2×), Et$_2$O (3×) and then dried to afford the product.

IB) Preparation of Compound 309 (According to Scheme 1)

4,6-Dichloropyrimidine (1.5 mmol), methyl 4-aminobenzoate (1.5 mmol), and 3M HCl solution (4 drops) were suspended in $^i$PrOH (16 ml) and heated in a Personal Chemistry Optimizer microwave system at 100° C. for 1200 s. Upon standing at room temperature a precipitate was formed and filtrated off. The solvent of the filtrate was evaporated under reduced pressure and yielded the intermediate in 71% yield as an off-white solid. A suspension of the latter (0.38 mmol), 2-(4,4,5,5,-tetramethyl-1,3,2-dioxyborolan-2-yl)aniline (0.38 mmol), sodium carbonate (1.14 mmol), and Pd(PPh$_3$)$_2$Cl$_2$ (2 mol %) in a mixture of DME/EtOH/water (4 ml/0.5 ml/0.5 ml) was heated in a Personal Chemistry Optimizer microwave system at 100° C. for 1500 s. The reaction mixture was poured into sat. aq. NH$_4$Cl solution (20 ml) and extracted with EtOAc (3×). The combined organic layers were dried (Na$_2$SO$_4$) and the solvent evaporated under reduced pressure. The crude product was purified by prep.-HPLC (XTerra Prep. MS C$_{18}$ 5 µm, 19×150 mm, gradient from water to MeCN over 13 min) and yielded the compound 309 in 37%.

IC) Preparation of Compound 306 (According to Scheme 1)

a) Preparation of [4-(6-chloro-pyrimidin-4-ylamino)-butyl]-carbamic acid tert-butyl ester

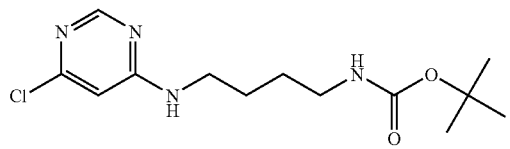

4,6-Dichloropyrimidine (4.14 mmol) and tert-butyl 4-aminobutylcarbamate (4.14 mmol) were dissolved in 13 ml of 2-propanol, and 3 drops of 3M aq. HCl were added. The mixture was heated in a Personal Chemistry Optimizer microwave system at 100° C. for 900 s. The reaction mixture was diluted with sat. aq. NH$_4$Cl-solution (50 ml) and extracted with EtOAc (2×). Drying of the organic layer (Na$_2$SO$_4$) and evaporation of the solvent under reduced pressure yielded the crude product, which was taken up in DMSO (2.5 ml) and purified via prep.-HPLC (XTerra Prep. MS C$_{18}$ 5 µm, 19×150 mm, gradient from water to MeCN over 14 min), yielding 41% of a white solid.

b) Preparation of Compound 306

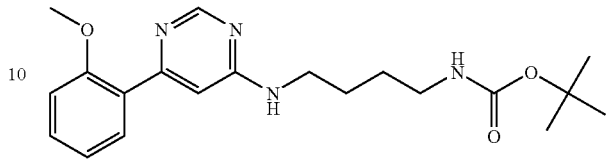

The carbamate shown above (0.65 mmol), 2-methoxyphenylboronic acid (0.67 mmol), sodium carbonate (1.95 mmol), and Pd(PPh$_3$)$_2$Cl$_2$ (5 mol %) were suspended in a mixture of DMF/EtOH/water (15 ml/2 ml/2 ml). The mixture was heated in a Personal Chemistry Optimizer microwave system at 130° C. for 720 s. The reaction mixture was diluted with sat. aq. NH$_4$Cl-solution (50 ml) and extracted with EtOAc (2×). Drying of the organic layer (Na$_2$SO$_4$) and evaporation of the solvents under reduced pressure yielded the crude product, which was taken up in DMSO (1.5 ml) and purified via prep.-HPLC (ZORBAX Bonus-RP Prep. C$_{18}$ 5 µm, 21.2×150 mm, gradient from water to MeCN over 14 min), yielding 22% of a pale yellow solid.

IIA) Preparation of Compounds 1-17, 18-22, 28, 31, 32, 35, 39, 40, 51, 52, 55-59, 62, 63, 67, 69, 73, 75-77, 85, 92-102, 104-110, 114-119, 121-146, 149-160, 162-193, 197, 200, 202-205, 214, 215, 331-376 (Suzuki Coupling According to Scheme 1)

To a solution of the intermediate obtained according to Preparation method I (0.35 mmol) in degassed DMF (5 mL), a boron compound (0.38 mmol) was added followed by NaHCO$_3$ (0.88 mmol) dissolved in degassed H$_2$O (~1 ml), PdOAc$_2$ (0.035 mmol) and PPh$_3$ (0.07 mmol). The mixture was then heated at 80-90° C. (oil bath temperature) under nitrogen atmosphere for 18 h. After being cooled to room temperature, the mixture was diluted with EtOAc (~30 mL), washed with H$_2$O (3×~5 mL) and dried (MgSO$_4$). The solvent was then evaporated under reduced pressure and the residue purified by flash chromatography.

The following alternative work up procedure can be used: Upon completion of the reaction, the solvents were evaporated under reduced pressure and the residue was partitioned between EtOAc/H$_2$O. The H$_2$O layer was separated and extracted with EtOAc (2×). The combined extracts and the organic layer were dried (MgSO$_4$), the solvent evaporated under reduced pressure and the residue purified by flash chromatography. 2-(Dicyclohexylphosphino)biphenyl was used as a ligand in place of triphenylphosphine in some cases to facilitate the purification procedure.

IIB) Preparation of Compounds 265, 293, 305, 318, 319, 322 (According to Scheme 1)

4,6-Dichloropyrimidine (0.72 mmol), 2-methoxyphenylboronic acid (0.66 mmol), sodium carbonate (1.97 mmol), and Pd(PPh$_3$)$_2$Cl$_2$ (3 mol %) were suspended in a mixture of DME/EtOH/water (2.5 ml/0.38 ml/0.38 ml). The mixture was heated in a Personal Chemistry Optimizer microwave system at 130° C. for 900 s. $^i$PrOH (5 ml) and the corresponding aniline derivative (0.66 mmol) were added, and the mixture was treated with conc. HCl under stirring to reach a pH value of 1-2. The mixture was then heated in the microwave at 150° C. for 900 s. The solvent was evaporated under reduced pressure and the residue suspended in H₂O (10 mL). With sat. NaHCO₃ solution the mixture was set to pH=6-7 and extracted with EtOAc (3×20 ml). The combined organics were washed with brine and dried over Na₂SO₄. After evaporation of the solvent the residue was taken up in DMSO and purified via prep.-HPLC (XTerra Prep. MS C₁₈ 5 µm, 19×150 mm, gradient from water to MeCN over 13 min). In the case of products with an acid group in the anilino part, the corresponding methyl esters were prepared via treatment with TMSCHN₂ (2-4 eq.) in DCM/MeOH (2 mL/1 mL) at room temperature.

IIC) Preparation of Compounds 268, 307, 313
(According to Scheme 1 & 2)

6-Nitroindoline (1.2 mmol) was dissolved in DCM (8 ml), treated with pyridine (2.4 mmol) and cooled to 0° C. MeSO₂Cl (1.3 mmol) was added dropwise and the mixture allowed to stir at room temperature overnight. 0.5 M HCl solution (10 ml) was added and the mixture extracted twice with DCM (10 ml) and twice with EtOAc (10 ml). The combined organics were washed with brine, dried over Na₂SO₄ and evaporated. The dried residue was dissolved in MeOH (5 ml) and THF (4 ml). Pd/C (100 mg) was added and the mixture stirred under an atmosphere of hydrogen at room temperature for 5 h. The mixture was filtered through a pad of Celite, which was washed with plenty of MeOH and EtOAc. The filtrate was concentrated in vacuum and the residue dried. The crude 6-amino indoline derivative and 4,6-dichloropyrimidine (1.5 mmol) were dissolved in isopropanol (6 ml) and conc. HCl (0.4 ml) and the mixture heated to reflux for 2.5 h. For precipitation of the intermediate product the mixture was stored in the fridge overnight. The precipitate (HCl salt) was filtered, washed with a small quantity of cold isopropanol and dried. The intermediate (0.17 mmol), the corresponding phenylboronic acid (0.2 mmol), Na₂CO₃ (0.58 mmol) and Pd(PPh₃)₂Cl₂ (3 mol %) were suspended in a mixture of DME/EtOH/water (1.5 ml/0.3 ml/0.2 ml). The mixture was heated in the microwave at 125° C. for 1200 s. H₂O (30 ml) was added and the mixture extracted twice with EtOAc (40 ml). Saturated NH₄Cl solution (20 ml) was added to the water phase and extracted again twice with EtOAc (40 ml). The combined organics were washed with brine and dried over Na₂SO₄. After evaporation of the solvent the residue was taken up in DMSO and purified via prep.-HPLC (XTerra Prep. MS C₁₈ 5 µm, 19×150 mm, gradient from water to MeCN over 13 min).

III) Preparation of Compounds 29, 36, 37, 41, 42, 45-50, 52, 61, 64, 65, 70, 71, 84, 87, 89 and 97
(Amide Bond Formation According to Scheme 2)

To a solution of an amine compound (0.24 mmol) in THF (4 mL) at room temperature under nitrogen atmosphere, an acid compound (0.26 mmol) was added followed by NEt₃ (0.36 mmol) and HBTU (0.25 mmol). The mixture was stirred at room temperature for 1 h and then at ~40° C. (oil bath temperature) for 18 h. After being cooled to room temperature, the mixture was diluted with water (~5 mL), extracted with EtOAc (3×) and the combined extract dried (MgSO₄). The solvent was then evaporated under reduced pressure and the residue purified by flash chromatography.

IV) Preparation of Compounds 23, 33 and 34
(Sulfonamide Bond Formation According to Scheme 2)

To a mixture of N-[6-(2-Methoxy-phenyl)-pyrimidin-4-yl]-benzene-1,4-diamine (0.229 mmol) in CH₂Cl₂ (6 mL) cooled to ~0° C. under nitrogen atmosphere, Et₃N (0.274 mmol) was added followed by the sulfonyl chloride (0.252 mmol). The mixture was allowed to warm to room temperature and then stirred for 60 h. The solvent was evaporated under reduced pressure, the residue suspended in water and extracted with EtOAc (3×). Combined extracts were dried (MgSO₄) and the solvent evaporated under reduced pressure. The residue was purified by flash chromatography to afford the product.

VA) Preparation of Compounds 44, 54, 72, 88, 147, 148, 161, 194-196, 198, 199, 201, 206-213
(According to Scheme 3)

The ester compound, 4-(6-Chloro-pyrimidin-4-yl-amino)-benzoic acid methyl ester, has been prepared according to the preparation method I. The reaction was performed in NMP as a solvent using ⁱPr₂NEt as a base at 100-110° C. (oil bath temperature) for 18 h. The product precipitated after addition of water to the reaction mixture and was separated by filtration, washed with water (2×), diethyl ether (2×) and dried. The ester compound was isolated as a pale brown solid in 77% yield.

$\delta_H$ (d₆ DMSO): 3.80 (3H, s, COOMe), 6.85 (1H, s), 7.75 (2H, d), 7.90 (2H, d), 8.55 (1H, s), 10.15 (1H, s, NH).

To a solution of 4-(6-Chloro-pyrimidin-4-yl-amino)-benzoic acid methyl ester, (0.1 g, 0.38 mmol) in THF (3 mL), LiOH×H₂O (0.017 g, 0.42 mmol) dissolved in H₂O (1 mL) was added and the mixture stirred at room temperature for 18 h. The reaction mixture was then diluted with H₂O (5 mL) and extracted with EtOAc (2×). The water layer was acidified (2.5M HCl) and extracted with EtOAc (3×). The combined organic layers were dried (MgSO₄) and the solvent evaporated under reduced pressure to afford 4-(6-Chloro-pyrimidin-4-yl-amino)-benzoic acid, as a pale yellow solid.

$\delta_H$ (d₆ DMSO): 6.95 (1H, s), 7.80 (2H, s), 7.95 (2H, s), 8.65 (1H, s) 10.30 (1H, s) 12.75 (1H, bs, COOH)

a) Starting from the above-mentioned 4-(6-Chloro-pyrimidin-4-yl-amino)-benzoic acid the following compounds were synthesized according to the preparation method III:
b) Starting from the above-mentioned 4-(6-Chloro-pyrimidin-4-yl-amino)-benzoic acid amides (compound 72 and compound 88) the following compounds 44 and 54 were synthesized according to preparation method II:

VB) Preparation of Compounds 226, 231, 330
(According to Scheme 3)

4,6-Dichloropyrimidine (1.8 mmol), 2-methoxyphenylboronic acid (1.8 mmol), sodium carbonate (5.4 mmol), and Pd(PPh₃)₂Cl₂ (2 mol %) were suspended in a mixture of DME/EtOH/water (12 ml/1.8 ml/1.8 ml). The mixture was heated in a Personal Chemistry Optimizer microwave system at 130° C. for 600 s. The solution was then poured into sat. aq. NH₄Cl solution (25 ml) and extracted with EtOAc (3×). The combined organic layers were dried (Na₂SO₄) and the solvent evaporated under reduced pressure to afford the crude product.

This material (1.8 mmol) was dissolved in ⁱPrOH (10 ml), methyl 4-aminobenzoate (2.4 mmol) and 3M HCl solution (6 drops) were added. The resulting mixture was heated in the microwave at 120° C. for 900 s, then cooled to room temperature. The precipitate was filtrated off, washed with ⁱPrOH and dried. This provided the intermediate in 49% yield (over 2 steps).

Latter compound (1.2 mmol) was subsequently dissolved in THF/water (3 ml/6 ml) and lithium hydroxide (3.58 mmol) was added. Stirring of the reaction mixture at room temperature for 16 h led to total conversion and the solution was set to pH=1 by addition of 3 M HCl solution. A precipitate was formed and filtration yielded 4-[6-(2-methoxy-phenyl)-pyrimidin-4-yl-amine]-benzoic acid in quantitative yield. This pyrimidine derivative (0.22 mmol) was subsequently reacted with different amines (0.22 mmol) in DMF (1.5 ml) with EDC.HCl (0.28 mmol) and HOBt (0.07 mmol). After stirring for 4-20 h, the reaction was poured into water (15 ml) and extracted with EtOAc (3×). The organic layer was dried ($Na_2SO_4$) and the solvent evaporated under reduced pressure. Purification by prep.-HPLC (XTerra Prep. MS $C_{18}$ 5 µm, 19×150 mm, gradient from water to MeCN over 13 min) or flash chromatography ($SiO_2$) yielded the compounds 231, 226, and 330 with up to 81% yield.

VIA) Preparation of the Compounds 26 and 27 (According to Scheme 4 & 8)

To a mixture of N-[6-(2-methoxy-phenyl)-pyrimidin-4-yl]-benzene-1,4-diamine (0.68 mmol) in DMF (4.6 ml) under nitrogen atmosphere at room temperature, NaH (0.75 mmol) was added and the mixture stirred for 30 min. MeI (0.68 mmol) was added dropwise and the reaction mixture stirred for 42 h. The mixture was then diluted with $H_2O$ (~7 mL) and extracted with EtOAc (3×). The combined extracts were dried ($MgSO_4$) and the solvent evaporated under reduced pressure. The residue was triturated with $Et_2O$ to afford the product as a brown solid.

This compound is prepared according to the procedure described for compound 26, but instead of the diamine compound N-{4-[6-(4-Hydroxy-phenyl)-pyrimidin-4-ylamino]-phenyl}4-methyl-benzenesulfonamide is used. THF was used as solvent, and 1 eq of Bromoacetic acid methyl ester as alkylating agent. The reaction was performed at 50-60° C. (oil bath temperature) for 18 h. The crude reaction mixture was purified by flash chromatography to afford the product as a pale yellow solid.

VIB) Preparation of the Compounds 234, 327, 328, 329 (According to Scheme 8A)

To a solution of the proline derivative (0.22 mmol) (prepared in analogy to compounds described in M. Tamaki, G. Han, V. J. Hruby, *J. Org. Chem.* 2001, 66, 3593-3596; J. A. Gómez-Vidal, R. B. Silverman, *Org. Lett.* 2001, 3, 2481-2484; D. J. Abraham, M. Mokotoff, L. Sheh, J. E. Simmons, *J. Med. Chem.* 1983, 26, 549-554) and 4-[6-(2-methoxy-phenyl)-pyrimidin-4-yl-amine]-benzoic acid (0.22 mmol) in DMF (1.5 ml) were added EDC.HCl (0.28 mmol) and HOBt (0.07 mmol) and the reaction stirred at room temperature for 4-18 h. The solution was then poured into water (15 ml) and extracted with EtOAc (3×). The combined organic layers were dried ($Na_2SO_4$) and the solvent evaporated under reduced pressure. The crude products were purified by flash chromatography (SiO2, c-hexane/EtOAc, 1:2) and gave compound 234 in 40% yield.

Compound 234 (0.16 mmol) was dissolved in DCM (4 ml) and treated with TFA (4 ml). After stirring at room temperature for 1 h, the solvent was evaporated under reduced pressure and the residue was purified by flash chromatography ($SiO_2$, DCM/MeOH 95:5+0.5 vol % $NEt_3$) yielding compound 327 in 76%. Subsequent reaction of compound 327 (0.11 mmol) in THF/water 1:2 with LiOH (0.44 mmol) at room temperature for 48 h gave after purification by prep.-HPLC (ZORBAX Bonus-RP Prep. $C_{18}$ 5 µm, 21.2×150 mm, gradient from water to MeCN over 15 min) compound 328.

To a solution of compound 234 (0.89 mmol) in THF (3 ml) were added water (6 ml) and lithium hydroxide (3.55 mmol) and the reaction was stirred at room temperature for 40 h. The reaction mixture was cooled to 0° C. and 3 M HCl solution was added until a precipitate was formed. Filtration and drying of the solid gave the desired intermediate in 88%. The latter (0.19 mmol) was dissolved in DMF (7 ml), methyl 6-aminobenzoate (0.24 mmol), EDC.HCl (0.24 mmol) and HOBt (0.06 mmol) were added and the reaction stirred for 4 h. Another portion of methyl 6-aminobenzoate (0.12 mmol), EDC.HCl (0.12 mmol) and HOBt (0.03 mmol) was added and the reaction stirred for another 15 h. Water (25 ml) was added and the solution extracted with EtOAc (3×). The combined organic layers were dried ($Na_2SO_4$) and the solvent evaporated under reduced pressure. Purification by flash chromatography ($SiO_2$, DCM/MeOH 95:5) yielded the product in 89%. To a solution of this compound (0.024 mmoles) in DCM (1 ml) was added TFA (1 ml) and the reaction stirred at room temperature for 30 min. After evaporation of the solvent under reduced pressure and drying of the resulting oil, the crude product was dissolved in THF (1 ml). Water (2 ml) and lithium hydroxide (1.00 mmol) were added and the reaction was stirred at room temperature for 64 h. The solvent was then evaporated under reduced pressure and the resulting mixture purified by prep.-HPLC (XTerra Prep. MS $C_{18}$ 5 µm, 19×150 mm, gradient from water to MeCN over 13 min). Compound 329 was obtained in 73%.

VII) Preparation of Compounds 30, 66, 68, 81-83, 86, 90-91 (According to Scheme 6 by Deprotection of Protected Substituents)

The BOC-protected compounds can be synthesized according to the reaction protocol as outlined in Scheme 6.

To a solution of N-Boc compound (0.07 mmol) in TFA/$CH_2Cl_2$ (1 mL, 1:1) a few drops of water were added and the mixture stirred at room temperature for 2-18 h. The reaction mixture was diluted with toluene (5 mL) and the solvents were evaporated under reduced pressure. The residue was partitioned between EtOAc/$NaHCO_3$ (saturated aqueous solution), (~15 mL, 1:1). The organic layer was separated, dried ($MgSO_4$) and the solvent evaporated under reduced pressure to afford the product.

VII) Preparation of Compounds 43, 60, 74, 78-80 (According to Scheme 7)

To a mixture of the 6-Chloro-pyrimidin-4-yl-aryl-amine (0.3 mmol) in i-PrOH (1 mL) in the microwave tube, amine (0.685 g, 0.6 mmol) was added followed by $^i$-$Pr_2NEt$ (0.6 mmol). The reaction mixture was heated under microwave conditions (200 W, t=160° C.) for 2 h and 15 min and then, after being cooled to room temperature, was diluted with EtOAc/$H_2O$ (~12 mL, 2:1). The organic layer was separated and the $H_2O$ layer extracted with EtOAc (2×). Combined organic layers were dried ($MgSO_4$), the solvent evaporated under reduced pressure and the residue purified by flash chromatography to afford the product.

IXA) Preparation of Compounds 38 and 111-113 (According to Scheme 9)

To a suspension of an amine (0.17 mmol) in dioxane (2 ml), isocyanate (0.19 mmol) was added and the mixture was heated at 80-90° C. (oil bath temperature) for 24 h. The solvent was then evaporated under reduced pressure and the residue purified by flash chromatography to afford product.

An alternative route for synthesizing urea derivatives according to the present invention is described below:

Pyridine (0.7 mMol) was added to a suspension of an amine (0.3 mMol) as outlined in Scheme 9 in dry THF (3 mL), followed by phenyl chloroformate (0.3 mMol). The mixture was stirred at room temperature for 1 hour. The solvent was evaporated and the residue partitioned in EtOAc:$H_2O$. The organic layer was dried ($MgSO_4$), solvent removed and the obtained carbamate was used in the next step without further purification. An amine compound (0.10 mMol) was added to a solution of the carbamate (0.07 mMol) in dry THF (2.5 mL) and the mixture was heated at 50° C. for 72 hours. After cooling to room temperature, a precipitate-appeared which was collected by filtration and washed with Et$_2$O to afford the desired product in 59% yield and 100% purity by LC/MS IXB) Preparation of Compounds 292, 323-326 (According to Scheme 9A)

4,6-Dichloropyrimidine (3.7 mmol), 2-hydroxyphenylboronic acid (1.2 mmol), sodium carbonate (3.7 mmol), and Pd(PPh$_3$)$_2$Cl$_2$ (2 mol %) were suspended in a mixture of DME/EtOH/water (12 ml/1.8 ml/1.8 ml), then heated in a Personal Chemistry Optimizer microwave system at 100° C. for 1500 s. The reaction mixture was poured into sat. aq. NH$_4$Cl solution (40 ml) and extracted with EtOAc (3×). The combined organic layers were dried (Na$_2$SO$_4$) and the solvent evaporated under reduced pressure to afford the crude product. Flash chromatography yielded the intermediate as light-yellow powder in 68% yield.

To as suspension of NaH (3.10 mmol) in dry DMF (1.0 ml) under nitrogen at 0° C. was added a solution of the above described intermediate (0.97 mmol) in dry DMF (1.5 ml). The resulting mixture was stirred at 0° C. for 15 min. The corresponding 2-chloro- or 2-bromoethylamines (as hydrochloride or hydrobromide salts) were then added (1.26 mmol) and the reaction stirred at 0° C. for 3 h, then the cooling bath removed and the reaction allowed to warm to room temperature. After 4 h, the reaction was diluted with EtOAc (20 ml) and water (10 ml) was carefully added. Extraction with EtOAc (3×) and drying of the combined organic layers (Na$_2$SO$_4$) gave after evaporation of the solvent under reduced pressure the crude product. This intermediate (0.18 mmol) was dissolved without further purification in $^i$PrOH (2.4 ml), methyl 4-aminobenzoate (0.23 mmol) and 3 M HCl solution (2 drops) were added and the reaction was heated in a Personal Chemistry Optimizer microwave system at 100° C. for 1200 s. The precipitate (if formed upon standing at 4° C. for 18 h, otherwise the solvent was evaporated under reduced pressure) was filtrated off and the solid was dissolved in EtOAc (20 ml) and sat. aq. NaHCO$_3$ solution (10 ml). Separation of the organic layer gave after drying (Na$_2$SO$_4$) and evaporation of the solvent the crude product. Latter was purified by flash chromatography (SiO$_2$, DCM/MeOH 14:1 with 0.5 vol % NEt$_3$) and yielded the products in 59-78% yield.

X) Preparation of Compound 53 (According to Scheme 5)

To a solution of N-[6-(2-Methoxy-phenyl)-pyrimidin-4-yl]-benzene-1,4-diamine (0.29 mmol) in CH$_2$Cl$_2$ (10 mL), NEt$_3$ (0.29 mmol) was added followed by the 5-Chloro-benzotriazole carboxamidine derivative (0.29 mmol) as shown in Scheme 5. The mixture was heated at reflux for 5 h. The solvent was then evaporated and the residue purified by flash chromatography to afford product BOC-protected compound as a white solid.

$\delta_H$ (d$_6$ DMSO): 1.50 (9H, s, Boc), 1.60 (9H, s, Boc), 4.00 (3H, s MeO), 7.15 (1H, t), 7.25 (1H, d), 7.50-7.60 (4H, m), 7.80 (2H, d), 8.05 (1H, d), 8.80 (1H, s), 9.75 (1H, s), 10.00 (1H, s) 11.55 (1H, s).

To a solution of BOC protected compound (0.11 mmol) in CH$_2$Cl$_2$ (1.5 mL), TFA (1.5 mL) was added at room temperature and the mixture stirred at room temperature for 18 h. The reaction mixture was diluted with EtOAc/H$_2$O (15 mL, 2:1 v/v) and the H$_2$O layer neutralised with solid NaHCO$_3$. The organic layer was then separated and the water layer extracted with EtOAc (3×). The combined organic layers were dried (MgSO$_4$) and the solvent evaporated under reduced pressure to afford the crude product. This material was suspended in water, separated by filtration, washed with H$_2$O (2×), Et$_2$O (3×) and dried to afford product.

XIA) Preparation of Compound 119 (According to Scheme 10)

2-Methyl-4-nitroaniline (1 mMol) was reacted with 4,6-dichloropyrimidine (1 mMol) in the presence of DIPEA (2 mMol) under microwave conditions. Suzuki coupling on this substrate was performed as previously described above. Hydrogen transfer reduction was carried out following a standard protocol (S. Hanessian et al., synthesis 1981, 396). The obtained intermediate was reacted with pivaloylchlorid using the conditions as described in Scheme 2.

XIB) Preparation of Compound 320 and (3-{6-[3-(4-Amino-butane-1-sulfonylamino)-4-methyl-phenylamino]-pyrimidin-4-yl}-phenyl)-carbamic acid 9H-fluoren-9-ylmethyl ester (According to Scheme 10A)

a) Preparation of 4-(1,3-dioxo-1,3-dihydro-isoindol-2-yl)-butane-1-sulfonic acid {5-[6-(2-methoxy-phenyl)-pyrimidin-4-ylamino]-2-methyl-phenyl}-amide and [3-(6-{3-[4-(1,3-dioxo-1,3-dihydro-isoindol-2-yl)-butane-1-sulfonylamino]4-methyl-phenylamino}-pyrimidin-4-yl)-phenyl]-carbamic acid 9H-fluoren-9-ylmethyl ester

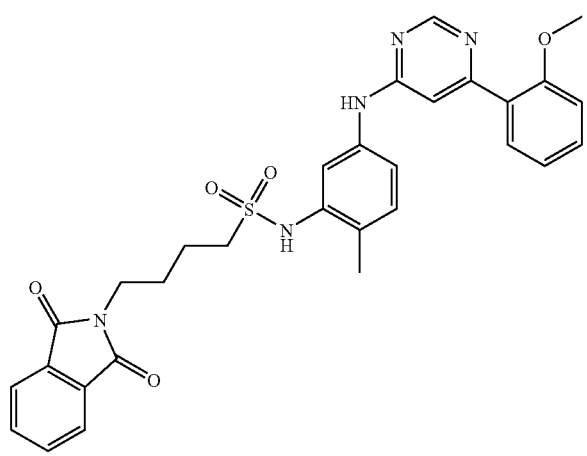

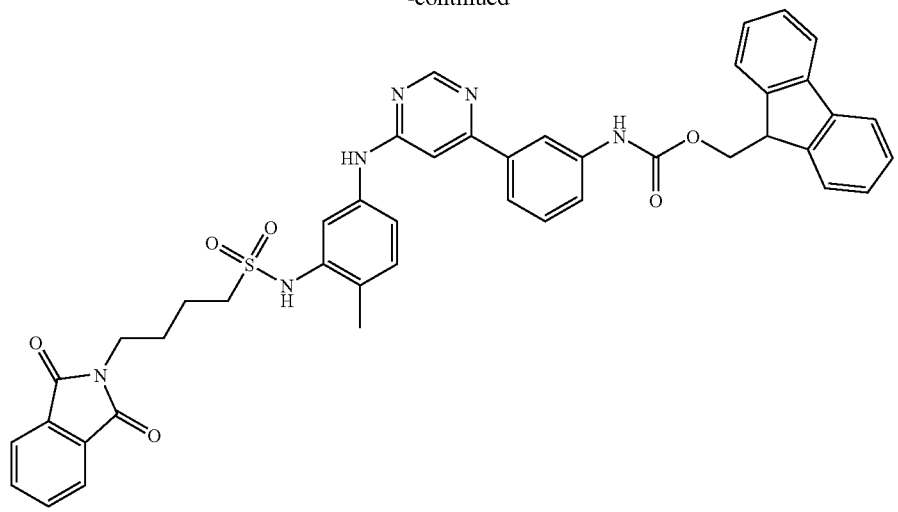

Potassium 4-(1,3-dioxo-1,3-dihydro-isoindol-2-yl)-butane-1-sulfonate (prepared according to Jiang, J., Wang, W. Sane, D. C., and Wang, B. *Bioorg. Chem.* 2001, 29, 357-379) was converted to 4-(1,3-dioxo-1,3-dihydro-isoindol-2-yl)-butane-1-sulfonyl chloride, in analogy to compounds described in the reference mentioned above. The sulfonyl chloride (0.26 mmol) and $N^1$-[6-(2-methoxy-phenyl)-pyrimidin-4-yl]-4-methyl-benzene-1,3-diamine (0.22 mmol; prepared according to scheme 1), or {3-[6-(3-amino-4-methyl-phenylamino)-pyrimidin-4-yl]-phenyl}-carbamic acid 9H-fluoren-9-ylmethyl ester (0.22 mmol; prepared according to scheme 1), were suspended in 15 ml of abs. $CH_2Cl_2$.

Pyridine (2.2 mmol) was added, and the mixture was stirred at rt for 7 d. The solvent was evaporated under reduced pressure, and the yellow residue was taken up in DMSO (2 ml) and purified via prep.-HPLC (XTerra Prep. MS $C_{18}$ 5 μm, 19×150 mm, gradient from water to MeCN over 14 min), yielding 70% of off-white powders.

b) Preparation of compound 320 and (3-{6-[3-(4-Amino-butane-1-sulfonyl-amino)-4-methyl-phenylamino]-pyrimidin-4-yl}-phenyl)-carbamic acid 9H-fluoren-9-ylmethyl ester Compound 320

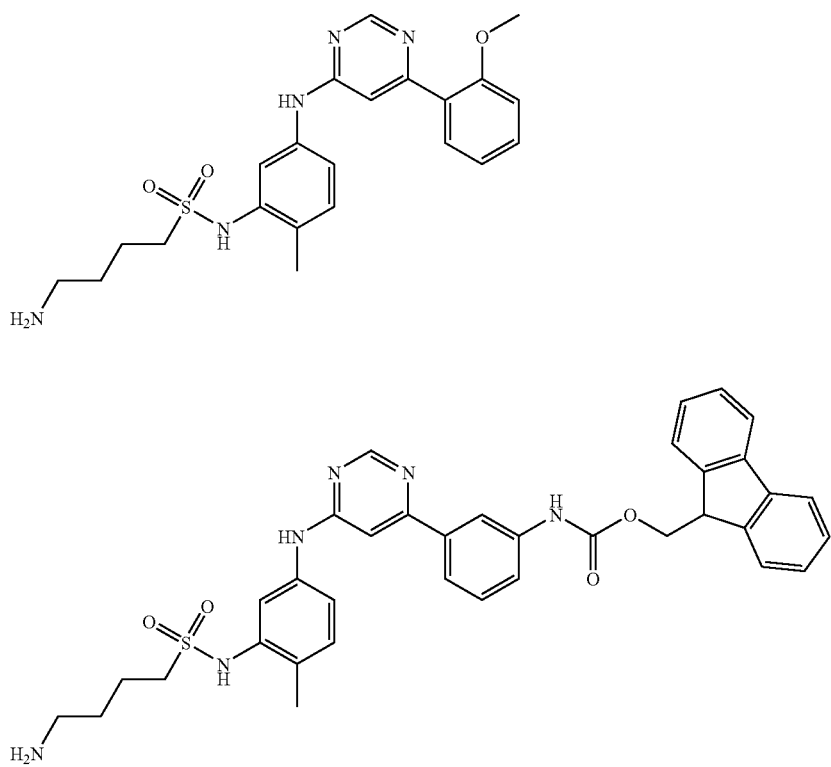

Any N-protected sulfonamide shown above (91.9 µmol) was dissolved in 10 ml of EtOH. Hydrazine monohydrate (3.7 mmol) was added, and the mixture was stirred at rt for 6 h. The solvent was evaporated under reduced pressure; the residue was re-dissolved in MeOH (3×) and the solvents evaporated. The yellow residue was taken up in DMSO (3 ml) and purified via prep.-HPLC (Zorbax Bonus-RP Prep. $C_{18}$ 5 µm, 21.2×150 mm, gradient from water to MeCN over 14 min), yielding 92% of pale yellow powders.

XII) Preparation of Compound 120 (According to Scheme 11)

To a solution of 4-amino, 2-nitrophenol (1 mmol), triphenyl phosphine (1.2 mmol) and benzyl alcohol (1.2 mmol) in dry dichloromethane (5 ml) at ambient temperature, under a nitrogen atmosphere, was added a solution of diethyl azodicarboxylate (1.2 mmol) in dry dichloromethane (2 ml). The resultant mixture was stirred at ambient temperature for 18 hr. Evaporation under reduced pressure afforded a gum that was purified by column chromatography (SiO2; diethyl ether) to give 4-benzyloxy-3-nitro-aniline, yield 85%.

$\delta_H$ ($d_6$ DMSO): 5.24 (2H, s), 5.30 (2H, s), 6.85-6.95 (1H, m, ArH) 7.10 (1H, s, ArH), 7.20 (1H, d, ArH), 7.30-7.80 (5H, m, ArH)

The reaction of 4-benzyloxy-3-nitro-aniline with 4,6-dichloropyrimidine to afford 4-(4'benzyloxy-3-nitrophenyl) amino-6-chloro-pyrimidine is performed according to Preparation method 1. $\delta_H$ ($d_6$DMSO): 5.34 (2H, s, CH$_2$Ar), 6.84, (1H, s, HetH), 7.30-7.75 (7H, m, ArH), 8.30 (1H, m, ArH), 8.55 (1H, s, Het H), 10.10 (1H, s, NH)

To a solution of 4-(4'-benzyloxy-3-nitrophenyl)amino-6-chloro-pyrimidine (4.91 g) and sulfuric acid (8 ml) in ethanol (300 ml) was added zinc dust (4.49 g). The mixture was then heated under reflux for 18 hours, cooled to room temperature then basified with sodium hydrogen carbonate. After evaporation under reduced pressure, the residue was dissolved in ethyl acetate and water. The organic phase was separated, washed with water, dried (MgSO4) and evaporated under reduced pressure. The residue was then subjected to column chromatography (SiO2; ethyl acetate:petroleum ether (40/60) 1:1) to give 4-(3'-amino-4'benzyloxyphenyl)amino-6-chloro-pyrimidine, 21% $\delta_H$ ($d_6$ DMSO): 4.84 (2H, s, NH$_2$), 5.00 (2H, s, CH$_2$Ph), 6.50-6.60 (2H, m, ArH), 6.70-6.80 (2H, m, ArH and HetH), 7.20-7.50 (5H, m, ArH), 8.30 (1H, s, HetH), 9.45 (1H, s, NH)

To a solution of 4-(3'-amino-4'benzyloxyphenyl)amino-6-chloro-pyrimidine (630 mg) in dry dichloromethane was added pyridine (8 ml) followed by methane sulfonyl chloride (0.3 ml). The mixture was stirred at room temperature overnight then evaporated under reduced pressure. The residue was dissolved in water and dichloromethane and the organic phase separated, washed with water, dried (MgSO4) and evaporated under reduced pressure. The residue was then subjected to column chromatography (SiO2;ethyl acetate: petroleum ether (40/60) 1:1) to afford N-{5-[6-chloropyrimidin-4-ylamino]-2-benzyloxy-phenyl}-methanesulfonamide (200 mg). $\delta_H$ ($d_6$ DMSO): 3.14 (3H, s, SO$_2$Me), 5.40 (2H, s, CH$_2$Ph), 6.94 (1H, s, HetH), 7.30-7.40 (1H, m, ArH), 7.50-7.85 (7H, m, ArH), 8.70 (1H, s, HetH), 9.30 (1H, s, NH), 10.00 (1H, s, NH)

The reaction of N-{5-[6-chloropyrimidin-4-ylamino]-2-benzyloxy-phenyl}-methanesulfonamide with 3 aminobenzene boronic acid was performed analogously to Preparation method 2, to give Compound 120: N-{5-[6-(3-Amino-phenyl)-pyrimidin-4-ylamino]-2-benzyloxy-phenyl}-methanesulfonamide, $\delta_H$ ($d_6$ DMSO): 2.90 (3H, s, SO$_2$Me), 5.15, (2H, s, CH$_2$Ph), 5.25 (2H, s, NH$_2$), 6.60-6.70 (1H, m, ArH), 7.00 (1H, s, HetH), 7.05-7.15 (3H, m, ArH) 7.25-7.60 (8H, m, ArH), 8.55 (1H, s, HetH) 9.00 (1H, s, NH), 9.50 (1, s, NH)

XIII) Preparation of Compound 103 (According to Scheme 12)

NaH (0.22 mMol) was added to a solution of the pyrimidine derivative as outlined in Scheme 12 (0.22 mMol) in dry DMF (2 mL) under nitrogen. The solution was stirred at room temperature for 30 minutes. N-protected chloroalkyl (0.22 mMol) was added and the mixture was heated at 80° C. for 18 hours. The solution was allowed to cool down to room temperature. Extraction was carried out in EtOAc:H$_2$O. The organic phase was dried (MgSO$_4$), solvent removed in vacuo to give a crude product which was purified by flash column chromatography to give the desired intermediate. The intermediate was dissolved in 50% TFA solution [(2 ml) in DCM plus 2 drops of H$_2$O] and the mixture was stirred for 18 hours at room temperature. The solvent was removed in vacuo and the residue was suspended in EtOAc. The organic phase was washed with NaHCO$_3$ (aq. sat.), the organic layer was dried (MgSO$_4$) and the solvent evaporated to give a residue which was dissolved in 1 mL of 2.5 M HCl. The solution was evaporated in vacuo to give a solid which was triturated with Et$_2$O and dried to give the desired compound as a hydrochloride salt in 23% overall yield.

Materials and Methods

Cloning of CDK9 and Cyclin T1:
Both cDNA fragments were cloned by PCR into pDONR201 vectors using the gateway recombination system (Invitrogen) according to the manufacturer's recommendations. The fragments were subcloned into a gateway-adapted shuttle vector (pPM7) for production of recombinant adenovirus. All plasmids were verified by restriction digests and sequencing analysis.

Expression and Purification of CDK9/Cyclin T1 Proteins:
Expression and purification was in principle performed as described by Cotten et al. (M. Cotten et al., Nucleic acids research, 2003, 31(28), 128).

Kinase Assay Using CDK9/Cyclin T1:
Kinase assays were performed in principle as described by Cotten et al. (M. Cotten et al., Nucleic acids research, 2003, 31(28), 128).

Kinase Assays Determining CDK2/CyclinA and CDK5/p35 Activity:
Kinase assays were performed as described by the manufacturers recommendations (Proqinase for CDK2/CyclinA and Upsate for CDK5/p35).

General Kinase Assay:
The inhibitory effect of compounds according to the present invention on the activity of protein kinases, depicted in Table 1, can be measured according to the following protocol:

| | |
|---|---|
| Reaction Volume: | 40 µl |
| Reaction Time: | 60 min |
| Reaction Temperature: | room temperature |
| Assay Plate: | 96 well U bottom plate (Greiner, 650161) |
| MultiScreen-PH Plate: | 96 well MAPH Filter Plates (Millipore, MAPHNOB50) |

| | |
|---|---|
| Filter Washing Solution: | 0.75% $H_3PO_4$ |
| Szintilation Liquid: | Supermix Liquid Szintillator (PerkinElmer, 1200-439) |

Controls:

| | |
|---|---|
| Negative Control (C−): | 100 mM EDTA (Ethylenediaminetetraacetic acid), no Inhibitor |
| Positive Control (C+): | no Inhibitor |
| Reaction Buffer: | |
| 20 mM Tris (Tris(hydroxymethyl)aminomethane hydrochloride), pH 7.5 | |
| 10 mM $MgCl_2$ | |
| 1 mM DTT | |

Final Assay Concentrations:

| | |
|---|---|
| Kinase: | Use kinase conc. yielding 10% ATP turn over. |
| ATP: | 1 µM |
| Adenosine 5'-[γ-$^{33}$P]triphosphate: | 12.5 µCi/ml (Amersham Biosciences, BF1000) |
| Substrate: Myelin Basic Protein | 10 µM (Invitrogen, 13228-010) |

Pipetting Sequence:
1) Add 10 µl 4 fold concentrated Substrate+4 fold concentrated ATP in 3 fold concentrated Reaction Buffer to each well of Assay Plate
2) Add 10 µl 4 fold concentrated inhibitor in 4% DMSO in $H_2O$ to each well except to C− and C+ wells
3) Add 10 µl 4% DMSO in $H_2O$ to C− and C+ wells
4) Add 10 µl 500 mM EDTA in $H_2O$ to − wells
5) Add 10 µl 50 µCi/ml Adenosine 5'-[γ-$^{33}$P]triphosphate in $H_2O$ to each well
6) Add 10 µl 4 fold concentrated kinase in Reaction Buffer to each well
7) Incubate 1 hr at room temperature
8) Add 10 µl 50 mM EDTA in $H_2O$ to each well except to C− wells
9) Prepare MAPH plates by adding 200 µl 0.75% $H_3PO_4$ to each well
10) Exhaust 0.75% $H_3PO_4$ using Millipore vacuum station
11) Add 60 µl 0.75% $H_3PO_4$ to each well of MAPH Filter Plate
12) Transfer 30 µl sample per well from Assay Plate to corresponding well of MAPH Filter Plate
13) Incubate 30 min at room temperature
14) Wash each well of MAPH Filter Plates 3× with 200 µl 0.75% $H_3PO_4$ using Millipore vacuum station.
15) Add 20 µl Scintillation Liquid to each well of MAPH Filter Plate
16) Seal MAPH Filter Plate
17) Store MAPH Filter Plate 30 min in darkness
18) Quantify radioactivity

TABLE 1

List of all protein kinases

| No. | Accession Number | Gene |
|---|---|---|
| 1 | NM_001105 | ACVR1 (activin A receptor, type I) |
| 2 | NM_004302 | ACVR1B (activin A receptor, type IB) |
| 3 | NM_145259 | ACVR1C, ALK7 |
| 4 | NM_001616 | ACVR2, activin A receptor, type II |
| 5 | NM_001106 | ACVR2B, activin A receptor, type IIB |
| 6 | NM_000020 | ACVRL1 (activin A receptor type II-like 1) |
| 7 | NM_004612 | TGFBR1 (transforming growth factor, beta receptor I (activin A receptor type II-like kinase, 53 kD)) |
| 8 | NM_003242 | TGFBR2 (transforming growth factor, beta receptor II) |
| 9 | NM_004329 | BMPR1A (bone morphogenetic protein receptor, type IA) |
| 10 | NM_001203 | BMPR1B (bone morphogenetic protein receptor, type IB) |
| 11 | NM_001204 | BMPR2 (bone morphogenetic protein receptor, type II (serine/threonine kinase)) |
| 12 | NM_006251 | PRKAA1 (protein kinase, AMP-activated, alpha 1 catalytic subunit) |
| 13 | NM_006252 | PRKAA2 (protein kinase, AMP-activated, alpha 2 catalytic subunit) |
| 14 | NM_002929 | GRK1; rhodopsin kinase |
| 15 | NM_001619 | GRK2 |
| 16 | NM_005160 | GRK3 |
| 17 | NM_005307 | GRK4 |
| 18 | NM_005308 | GRK5 |
| 19 | NM_002082 | GRK6 |
| 20 | NM_139209 | GRK7 (G protein-coupled receptor kinase 7) |
| 21 | NM_017572 | MKNK2, GPRK7 |
| 22 | NM_001654 | ARAF1 (v-raf murine sarcoma 3611 viral oncogene homolog 1) |
| 23 | NM_004333 | BRAF (v-raf murine sarcoma viral oncogene homolog B1) |
| 24 | NM_002880 | RAF1 (v-raf-1 murine leukemia viral oncogene homolog 1) |
| 25 | NM_021574 | BCR1 |
| 26 | NM_003656 | CAMK1 (calcium/calmodulin-dependent protein kinase I) |
| 27 | NM_015981 | CAMK2A (calcium/calmodulin-dependent protein kinase (CaM kinase) II alpha) |
| 28 | NM_001220 | CAMK2B (calcium/calmodulin-dependent protein kinase (CaM kinase) II beta) |
| 29 | NM_001221 | CAMK2D (calcium/calmodulin-dependent protein kinase (CaM kinase) II delta) |
| 30 | NM_020439 | CAMK1G (calcium/calmodulin-dependent protein kinase IG) |
| 31 | NM_001222 | CAMK2G (calcium/calmodulin-dependent protein kinase (CaM kinase) II gamma) |
| 32 | NM_001744 | CAMK4 (calcium/calmodulin-dependent protein kinase IV) |

TABLE 1-continued

List of all protein kinases

| No. | Accession Number | Gene |
|---|---|---|
| 33 | NM_001786 | CDC2 (cell division cycle 2) |
| 34 | NM_001798 | CDK2 (cyclin-dependent kinase 2) |
| 35 | NM_001258 | CDK3 (cyclin-dependent kinase 3) |
| 36 | NM_000075 | CDK4 (cyclin-dependent kinase 4) |
| 37 | NM_004935 | CDK5 (cyclin-dependent kinase 5) |
| 38 | NM_001259 | CDK6 (cyclin-dependent kinase 6) |
| 39 | NM_001799 | CDK7 (cyclin-dependent kinase 7) |
| 40 | NM_001260 | CDK8 (cyclin-dependent kinase 8) |
| 41 | NM_001261 | CDK9 (cyclin-dependent kinase 9 (CDC2-related kinase)) |
| 42 | NM_003674 | CDK10 (cyclin-dependent kinase (CDC2-like) 10) |
| 43 | NM_015076 | CDK11, DPK |
| 44 | NM_004196 | CDKL1 (cyclin-dependent kinase-like 1); KKIALRE |
| 45 | NM_003948 | CDKL2 (cyclin-dependent kinase-like 2); KKIAMRE |
| 46 | NM_016508 | CDKL3 (cyclin-dependent kinase-like 3); NKIAMRE |
| 47 | XM_293029 | CDKL4, similar to cyclin-dependent kinase-like 1 |
| 48 | NM_033489 | CDC2L1 (cell division cycle 2-like 1); PITSLRE B |
| 49 | NM_024011 | CDC2L1 (cell division cycle 2-like 1); PITSLRE A |
| 50 | NM_003718 | CDC2L5 (cell division cyde 2-like 5) |
| 51 | NM_006201 | PCTK1 (PCTAIRE protein kinase 1) |
| 52 | NM_002595 | PCTK2 (PCTAIRE protein kinase 2) |
| 53 | NM_002596 | PCTK3 (PCTAIRE protein kinase 3) |
| 54 | NM_012395 | PFTK1 (PFTAIRE protein kinase 1) |
| 55 | NM_001278 | IKK-alpha; CHUK |
| 56 | NM_001556 | IKK-beta; IKK2 |
| 57 | NM_001892 | CSNK1A1 (casein kinase 1, alpha 1) |
| 58 | NM_001893 | CSNK1D (casein kinase 1, delta) |
| 59 | NM_001894 | CSNK1E (casein kinase 1, epsilon) |
| 60 | NM_004384 | CSNK1G3 (casein kinase 1, gamma 3) |
| 61 | NM_001319 | CSNK1G2 (casein kinase 1, gamma 2) |
| 62 | NM_001895 | CSNK2A1 (casein kinase 2, alpha 1) |
| 63 | NM_001896 | CSNK2A2 (casein kinase 2, alpha prime) |
| 64 | NM_022048 | CSNK1G1 (casein kinase 1, gamma 1) |
| 65 | NM_004071 | CLK1 (CDC-like kinase 1) |
| 66 | NM_003993 | CLK2 (CDC-like kinase 2) |
| 67 | NM_003992 | CLK3 (CDC-like kinase 3) |
| 68 | NM_020666 | CLK4 (CDC-like kinase 4) |
| 69 | NM_004938 | DAPK1 (death-associated protein kinase 1) |
| 70 | NM_014326 | DAPK2 (death-associated protein kinase 2) |
| 71 | NM_001348 | DAPK3 (death-associated protein kinase 3) |
| 72 | NM_004954 | EMK1 (ELKL motif kinase) |
| 73 | NM_002746 | MAPK3; ERK1 |
| 74 | NM_002745 | MAPK1; ERK2 |
| 75 | NM_002748 | MAPK6; ERK3 |
| 76 | NM_002747 | MAPK4; ERK3-related |
| 77 | NM_002749 | MAPK7; ERK5 |
| 78 | NM_001315 | MAPK14; CSBP1 |
| 79 | NM_002751 | MAPK11; p38beta |
| 80 | NM_002969 | MAPK12; ERK6, p38g |
| 81 | NM_002754 | MAPK13; p38delta |
| 82 | AY065978 | ERK8 |
| 83 | NM_002750 | MAPK8; JNK1 |
| 84 | NM_002752 | MAPK9; JNK2 |
| 85 | NM_002753 | MAPK10; JNK3 |
| 86 | NM_006712 | FASTK (Fas-activated protein kinase) |
| 87 | NM_004579 | MAP4K2; GCK |
| 88 | NM_019884 | GSK3A (glycogen synthase kinase 3 alpha) |
| 89 | NM_002093 | GSK3B (glycogen synthase kinase 3 beta) |
| 90 | NM_002576 | PAK1 |
| 91 | NM_002577 | PAK2 |
| 92 | NM_002578 | PAK3 |
| 93 | NM_005884 | PAK4 |
| 94 | NM_020341 | PAK5 (PAK7) |
| 95 | NM_020168 | PAK6 |
| 96 | NM_007181 | MAP4K1; HPK1 |
| 97 | NM_004517 | ILK (integrin-linked kinase) |
| 98 | NM_001569 | IRAK1 (interleukin-1 receptor-associated kinase 1) |
| 99 | NM_001570 | IRAK2 (interleukin-1 receptor-associated kinase 2) |
| 100 | NM_007199 | IRAK-M |
| 101 | NM_016123 | IRAK4 |
| 102 | NM_006575 | MAP4K5 |
| 103 | NM_002314 | LIMK1 (LIM domain kinase 1) |
| 104 | NM_005569 | LIMK2 (LIM domain kinase 2) |
| 105 | NM_000455 | STK11; LKB1 |
| 106 | NM_005906 | MAK (male germ cell-associated kinase) |
| 107 | NM_002755 | MAP2K1; MEK1 |
| 108 | NM_030662 | MAP2K2; MEK2 |

TABLE 1-continued

List of all protein kinases

| No. | Accession Number | Gene |
|---|---|---|
| 109 | NM_002756 | MAP2K3; MEK3 |
| 110 | NM_003010 | MAP2K4; MEK4 |
| 111 | NM_002757 | MAP2K5; MEK5 |
| 112 | NM_002758 | MAP2K6; MEK6 |
| 113 | NM_005043 | MAP2K7; MKK7 |
| 114 | XM_042066 | MAP3K1; MEKK1 |
| 115 | NM_006609 | MAP3K2; MEKK2 |
| 116 | NM_002401 | MAP3K3; MEKK3 |
| 117 | NM_005922 | MAP3K4; MEKK4 |
| 118 | NM_005923 | MAP3K5; ASK1 |
| 119 | NM_004672 | MAP3K6 |
| 120 | NM_003188 | MAP3K7; TAK1 |
| 121 | NM_005204 | MAP3K8; Tpl-2 |
| 122 | XM_027237 | MAP3K9; MLK1 |
| 123 | NM_002446 | MAP3K10; MST; MLK2 |
| 124 | NM_002419 | MAP3K11; MLK3 |
| 125 | NM_006301 | MAP3K12; DLK |
| 126 | NM_004721 | MAP3K13; LZK |
| 127 | NM_003954 | MAP3K14; NIK |
| 128 | AX282911 | MAP3K7, similar to MAP/ERK kinase kinase 5; apoptosis signal regulating kinase |
| 129 | AX504239 | MAP3K8 |
| 130 | NM_015112 | MAST205 |
| 131 | NM_005965 | MYLK (myosin, light polypeptide kinase) |
| 132 | NM_033118 | MYLK2 (myosin light chain kinase 2) |
| 133 | NM_005372 | MOS (v-mos Moloney murine sarcoma viral oncogene homolog) |
| 134 | NM_006282 | STK4; MST1 |
| 135 | NM_006281 | STK3; MST2 |
| 136 | NM_003576 | STK24; MST3 |
| 137 | NM_012224 | NEK1 (NIMA (never in mitosis gene a)-related kinase 1) |
| 138 | NM_002497 | NEK2 (NIMA (never in mitosis gene a)-related kinase 2) |
| 139 | NM_002498 | NEK3 (NIMA (never in mitosis gene a)-related kinase 3) |
| 140 | AX394707 | NEK5 |
| 141 | NM_014397 | NEK6 (NIMA (never in mitosis gene a)-related kinase 6) |
| 142 | NM_133494 | NEK7 |
| 143 | NM_178170 | NEK8, NEK12A |
| 144 | NM_033116 | NEK9 |
| 145 | AX250157 | NEK10 |
| 146 | NM_024800 | NEK11 |
| 147 | NM_003157 | STK2 |
| 148 | NM_005406 | ROCK1 (Rho-associated, coiled-coil containing protein kinase 1); p160ROCK |
| 149 | NM_004850 | ROCK2 (Rho-associated, coiled-coil containing protein kinase 2) |
| 150 | NM_007271 | STK38; NDR |
| 151 | NM_015000 | STK38L, NDR2 |
| 152 | NM_004409 | DMPK1 (dystrophia myotonica-protein kinase) |
| 153 | XM_290516 | DMPK2, HSMDPKIN |
| 154 | NM_003607 | MRCKalpha (PK428) |
| 155 | NM_007174 | Citron |
| 156 | NM_002613 | PDPK1 (3-phosphoinositide dependent protein kinase-1) |
| 157 | NM_006213 | PHKG1 (phosphorylase kinase, gamma 1) |
| 158 | NM_000294 | PHKG2 (phosphorylase kinase, gamma 2) |
| 159 | NM_002648 | PIM1 |
| 160 | NM_006875 | PIM2 |
| 161 | AR208686 | PIM3 |
| 162 | NM_014791 | KIAA0175 |
| 163 | NM_002730 | PRKACA (protein kinase, cAMP-dependent, alpha) |
| 164 | NM_002731 | PRKACB (protein kinase, cAMP-dependent, beta) |
| 165 | NM_002732 | PRKACG (protein kinase, cAMP-dependent, gamma) |
| 166 | NM_002742 | PRKCM (protein kinase C, mu) |
| 167 | NM_002737 | PRKCA (protein kinase C, alpha) |
| 168 | NM_002738 | PRKCB1 (protein kinase C, beta 1) |
| 169 | NM_006254 | PRKCD (protein kinase C, delta) |
| 170 | NM_005400 | PRKCE (protein kinase C, epsilon) |
| 171 | NM_002739 | PRKCG (protein kinase C, gamma) |
| 172 | NM_006255 | PRKCH (protein kinase C, eta) |
| 173 | NM_002740 | PRKCI (protein kinase C, Iota) |
| 174 | NM_006257 | PRKCQ (protein kinase C, theta) |
| 175 | NM_002744 | PRKCZ (protein kinase C, zeta) |
| 176 | NM_002741 | PRKCL1 (protein kinase C-like 1) |
| 177 | NM_006256 | PRKCL2 (protein kinase C-like 2) |
| 178 | NM_006258 | PRKG1 (protein kinase, cGMP-dependent, type I) |
| 179 | NM_006259 | PRKG2 (protein kinase, cGMP-dependent, type II); cGKII |
| 180 | NM_002759 | PRKR (protein kinase, interferon-inducible double stranded RNA dependent) |
| 181 | NM_006852 | TLK2 (tousled-like kinase 2) |

TABLE 1-continued

List of all protein kinases

| No. | Accession Number | Gene |
|---|---|---|
| 182 | NM_012290 | TLK1 (tousled-like kinase 1) |
| 183 | NM_005044 | PRKX (protein kinase, X-linked) |
| 184 | NM_005030 | PLK (polo-like kinase) |
| 185 | NM_004073 | CNK (cytokine-inducible kinase) |
| 186 | NM_003913 | PRPF4B |
| 187 | NM_006742 | PSKH1 (protein serine kinase H1) |
| 188 | NM_005163 | AKT1 (v-akt murine thymoma viral oncogene homolog 1) |
| 189 | NM_001626 | AKT2 (v-akt murine thymoma viral oncogene homolog 2) |
| 190 | NM_005465 | AKT3 (v-akt murine thymoma viral oncogene homolog 3 (protein kinase B, gamma)) |
| 191 | NM_014264 | STK18; Sak |
| 192 | NM_005627 | SGK (serum/glucocorticoid regulated kinase) |
| 193 | NM_002376 | MARK3 (MAP/microtubule affinity-regulating kinase 3) |
| 194 | NM_006374 | STK25; YSK1 |
| 195 | NM_003137 | SRPK1 (SFRS protein kinase 1) |
| 196 | NM_182692 | SRPK2 (SFRS protein kinase 2) |
| 197 | NM_003319 | Titin |
| 198 | NM_003318 | TTK protein kinase |
| 199 | NM_003384 | VRK1 (vaccinia related kinase 1) |
| 200 | NM_006296 | VRK2 (vaccinia related kinase 2) |
| 201 | NM_003390 | WEE1 |
| 202 | NM_018650 | MARK1 (MAP/microtubule affinity-regulating kinase 1) |
| 203 | NM_003160 | STK13; (aurora/IPL1-like), AIE2, aurora kinase C |
| 204 | NM_004759 | MAPKAPK2 |
| 205 | NM_004635 | MAPKAPK3 |
| 206 | NM_003668 | MAPKAPK5 |
| 207 | NM_005734 | HIPK3 (homeodomain interacting protein kinase 3), DYRK6 |
| 208 | NM_003503 | CDC7L1 (CDC7 cell division cycle 7-like 1) |
| 209 | NM_016231 | NLK |
| 210 | NM_003565 | ULK1 (unc-51-like kinase 1) |
| 211 | NM_014683 | ULK2 (unc-51-like kinase 2) |
| 212 | AX056454 | DKFZP434C131 protein, ULK3 |
| 213 | NM_017886 | hypothetical protein FLJ20574, ULK4 |
| 214 | NM_053006 | STK22B; TSSK2 |
| 215 | NM_003684 | MKNK1 (MAP kinase-interacting serine/threonine kinase 1); MNK1 |
| 216 | NM_003804 | RIPK1 (receptor (TNFRSF)-interacting serine-threonine kinase 1); RIP |
| 217 | NM_003821 | RIPK2 (receptor-interacting serine-threonine kinase 2); RICK |
| 218 | NM_006871 | RIPK3 (receptor-interacting serine-threonine kinase 3); RIP3 |
| 219 | NM_003600 | STK6; BTAK, AIK |
| 220 | NM_004217 | STK12; IPL1, aurora kinase B |
| 221 | NM_006549 | CAMKK2 (calcium/calmodulin-dependent protein kinase kinase 2, beta) |
| 222 | NM_017719 | SNRK (SNF-1 related kinase) |
| 223 | NM_001433 | ERN1 (ER to nucleus signalling 1) |
| 224 | NM_004336 | BUB1 (BUB1 budding uninhibited by benzimidazoles 1 homolog) |
| 225 | NM_001211 | BUB1B (BUB1 budding uninhibited by benzimidazoles 1 homolog beta) |
| 226 | NM_006622 | SNK (serum-inducible kinase) |
| 227 | NM_001274 | CHEK1 (CHK1 checkpoint homolog) |
| 228 | NM_003957 | STK29; PEN11B |
| 229 | NM_013233 | STK39; SPAK |
| 230 | NM_003691 | STK16; PKL12 |
| 231 | XM_290796 | TAO1/KIAA1361 |
| 232 | NM_003159 | STK9 |
| 233 | NM_014586 | HUNK (hormonally upregulated Neu-associated kinase) |
| 234 | NM_004834 | MAP4K4; NIK; HGK |
| 235 | NM_002953 | RPS6KA1 = ribosomal protein S6 kinase, 90 kD, polypeptide 1 |
| 236 | NM_021135 | RPS6KA2 (ribosomal protein S6 kinase, 90 kD, polypeptide 2); RSK3 |
| 237 | NM_003161 | RPS6KB1 (ribosomal protein S6 kinase, 70 kD, polypeptide 1) |
| 238 | NM_004586 | RPS6KA3 = ribosomal protein S6 kinase, 90 kD, polypeptide 3; RSK2 |
| 239 | NM_004755 | RPS6KA5 (ribosomal protein S6 kinase, 90 kD, polypeptide 5); MSK1 |
| 240 | NM_003942 | RPS6KA4 (ribosomal protein S6 kinase, 90 kD, polypeptide 4); MSK2 |
| 241 | NM_003952 | RPS6KB2 (ribosomal protein S6 kinase, 70 kD, polypeptide 2) |
| 242 | NM_004760 | STK17A; DRAK1 |
| 243 | NM_014413 | HRI (heme-regulated initiation factor 2-alpha kinase) |
| 244 | NM_007194 | CHEK2 (CHK2 checkpoint homolog) |
| 245 | NM_012119 | CCRK (cell cycle related kinase) |
| 246 | NM_014370 | STK23; MSSK1 |
| 247 | NM_005990 | STK10; LOK |
| 248 | NM_004836 | EIF2AK3 (eukaryotic translation initiation factor 2-alpha kinase 3) |
| 249 | NM_003618 | MAP4K3; GLK |
| 250 | NM_014720 | SLK (SNF1 sucrose nonfermenting like kinase) |
| 251 | NM_014602 | PIK3R4 (phosphoinositide-3-kinase, regulatory subunit 4, p150) |
| 252 | NM_006285 | TESK1 (testis-specific kinase 1) |
| 253 | NM_021643 | GS3955 protein |
| 254 | NM_004203 | PKMYT1 |
| 255 | NM_015148 | PASK (PAS domain containing serine/threonine kinase) |
| 256 | NM_014002 | IKKE (IKK-related kinase epsilon; Inducible IkappaB kinase) |

TABLE 1-continued

List of all protein kinases

| No. | Accession Number | Gene |
|---|---|---|
| 257 | NM_007118 | TRIO (triple functional domain (PTPRF interacting)) |
| 258 | NM_001396 | DYRK1A (dual-specificity tyrosine-(Y)-phosphorylation regulated kinase 1A) |
| 259 | NM_004714 | DYRK1B (dual-specificity tyrosine-(Y)-phosphorylation regulated kinase 1B) |
| 260 | NM_003583 | DYRK2 (dual-specificity tyrosine-(Y)-phosphorylation regulated kinase 2) |
| 261 | NM_003582 | DYRK3 (dual-specificity tyrosine-(Y)-phosphorylation regulated kinase 3) |
| 262 | NM_003845 | DYRK4 (dual-specificity tyrosine-(Y)-phosphorylation regulated kinase 4) |
| 263 | NM_031417 | MARKL1 (MAP/microtubule affinity-regulating kinase like 1) |
| 264 | NM_014840 | KIAA0537 gene product |
| 265 | XM_039796 | TNIK (Traf2 and NCK interacting kinase) |
| 266 | XM_038150 | MAST3, KIAA0561 protein |
| 267 | XM_291141 | MAST4, KIAA0303 protein |
| 268 | NM_015375 | DustyPK |
| 269 | NM_002760 | PRKY (protein kinase, Y-linked) |
| 270 | NM_003688 | CASK (calcium/calmodulin-dependent serine protein kinase (MAGUK family)) |
| 271 | NM_004734 | DCAMKL1 (doublecortin and CaM kinase-like 1) |
| 272 | NM_152619 | hypothetical protein MGC45428, DCAMKL2 |
| 273 | AX504237 | DCAMKL3, KIAA1765 protein |
| 274 | NM_004226 | STK17B; DRAK2 |
| 275 | NM_005813 | PRKCN (protein kinase C, nu) |
| 276 | NM_005255 | GAK (cyclin G associated kinase) |
| 277 | NM_032294 | hypothetical protein DKFZp761M0423 |
| 278 | NM_014226 | RAGE1 (renal tumor antigen) |
| 279 | NM_006035 | CDC42BPB (CDC42 binding protein kinase beta (DMPK-like)) |
| 280 | NM_007170 | TESK2 (testis-specific kinase 2) |
| 281 | NM_152696 | Nbak2, KIAA0630 protein |
| 282 | NM_016151 | PSK |
| 283 | NM_173354 | SNF1LK, SIK |
| 284 | AB023190 | SAST (syntrophin associated serine/threonine kinase) |
| 285 | NM_022740 | HIPK2 (homeodomain interacting protein kinase 2) |
| 286 | AX236110 | GCN2, eIF2alpha kinase |
| 287 | NM_013355 | PKNbeta |
| 288 | NM_198465 | NRK/ZC4 (NIK-related kinase) |
| 289 | NM_013257 | SGKL (serum/glucocorticoid regulated kinase-like) |
| 290 | NM_016276 | SGK2 (serum/glucocorticoid regulated kinase 2) |
| 291 | NM_012424 | RPS6KC1 (ribosomal protein S6 kinase, 52 kD, polypeptide 1) |
| 292 | NM_014496 | RPS6KA6 (ribosomal protein S6 kinase, 90 kD, polypeptide 6); RSK4 |
| 293 | NM_013254 | TBK1 (TANK-binding kinase 1) |
| 294 | NM_016281 | JIK |
| 295 | NM_016440 | VRK3 for vaccinia related kinase 3 |
| 296 | NM_015716 | MINK (Misshapen/NIK-related kinase) |
| 297 | AX166520 | similar to Ca2+/Calmodulin-dependent protein kinase I, CAMK1b |
| 298 | NM_006410 | HTATIP2 (HIV-1 Tat interactive protein 2, 30 kD) |
| 299 | NM_016542 | MST4 |
| 300 | NM_016653 | ZAK (sterile-alpha motif and leucine zipper containing kinase AZK) |
| 301 | NM_173575 | PKE, YANK3 |
| 302 | NM_018979 | PRKWNK1 (protein kinase, lysine deficient 1); WNK1 |
| 303 | NM_006648 | PRKWNK2 (protein kinase, lysine deficient 2) |
| 304 | NM_020922 | PRKWNK3 (protein kinase, lysine deficient 3) |
| 305 | NM_032387 | PRKWNK4 (protein kinase, lysine deficient 4) |
| 306 | NM_018492 | TOPK (T-LAK cell-originated protein kinase) |
| 307 | AL359916 | (longer at STK35, CLIK1 5') |
| 308 | NM_020680 | NTKL (N-terminal kinase-like) |
| 309 | NM_032844 | MASTL, hypothetical protein FLJ14813 |
| 310 | NM_020397 | CKLIK, CamKI-like protein kinase |
| 311 | AX224725 | SCYL2 |
| 312 | NM_153335 | STLK5, LYK5 |
| 313 | NM_174944 | TSSK4 |
| 314 | NM_052841 | STK22C; TSSK3 |
| 315 | XM_166453 | TTBK1 |
| 316 | AR004796 | KSR1 (kinase suppressor of ras) |
| 317 | NM_032037 | SSTK |
| 318 | NM_016457 | PKD2 (polycystic kidney disease 2) |
| 319 | NM_025195 | C8FW, Trb1 |
| 320 | NM_033266 | ERN2 (ER to nucleus signalling 2) |
| 321 | NM_020423 | PACE-1 |
| 322 | NM_033550 | PRPK |
| 323 | NM_018401 | serine/threonine kinase HSA250839, YANK2 |
| 324 | NM_020639 | ANKRD3 (ankyrin repeat domain 3); DIK |
| 325 | NM_015690 | STK36 |
| 326 | NM_014572 | LATS2 (LATS, large tumor suppressor, homolog 2) |
| 327 | AX056397 | SPEG, KIAA1297 protein |
| 328 | AX504253 | Wee1B |

TABLE 1-continued

List of all protein kinases

| No. | Accession Number | Gene |
|---|---|---|
| 329 | AX766335 | QSK, KIAA0999 protein |
| 330 | NM_007064 | TRAD |
| 331 | NM_004690 | LATS1, (LATS, large tumor suppressor, homolog 1) |
| 332 | NM_014911 | AAK1 |
| 333 | NM_014920 | ICK, MAK-related kinase |
| 334 | NM_198892 | BMP2K, BIKE |
| 335 | NM_033126 | PSKH2 |
| 336 | NM_031464 | hypothetical protein MGC11287 similar to ribosomol protein S6 kinase |
| 337 | NM_032409 | PINK1 (PTEN induced putative protein kinase 1) |
| 338 | NM_013392 | NRBP (nuclear receptor binding protein |
| 339 | NM_016507 | CrkRS |
| 340 | NM_005109 | OSR1 (oxidative-stress responsive 1) |
| 341 | NM_139158 | ALS2CR7 |
| 342 | NM_032028 | STK22D, TSSK1 |
| 343 | NM_017771 | PXK (PX domain-containing protein kinase), Slob |
| 344 | NM_018571 | ALS2CR2 (amyotrophic lateral sclerosis 2 (juvenile) chromosome region, candidate 2), STLK6 |
| 345 | NM_031965 | GSG2, haspin |
| 346 | NM_015191 | SIK2, QIK |
| 347 | AX039412 | KIAA1639, Obscn |
| 348 | AX207388 | YANK1 |
| 349 | AX394712 | similar to MLCK, hypothetical protein LOC340156 |
| 350 | NM_178510 | ANKK1 |
| 351 | NM_021158 | C20orf97 (chromosome 20 open reading frame 97), Trb3 |
| 352 | NM_152649 | MLKL, hypothetical protein FLJ34389 |
| 353 | AX250159 | SgK223, DKFZp761P0423 |
| 354 | XM_370878 | KIAA2002 |
| 355 | NM_024652 | LRRK1 |
| 356 | NM_033115 | TBCK, hypothetical portein MGC16169 |
| 357 | AX250163 | SgK424, similar to testis expressed gene 14 (LOC126392) |
| 358 | NM_031272 | TEX14 (testis expressed sequence 14) |
| 359 | NM_024046 | hypothetical protein MGC8407, VACAMKL |
| 360 | NM_014916 | LMTK2, KIAA1079 protein, LMR2, KPI-2 |
| 361 | NM_017433 | MYO3A |
| 362 | NM_138995 | MYO3B |
| 363 | NM_030952 | SNARK |
| 364 | NM_030906 | STK33 |
| 365 | NM_182493 | similar to myosin light chain kinase (MLCK) |
| 366 | NM_032430 | BRSK1, KIAA1811 |
| 367 | XM_370948 | SBK, similar to SH3-binding kinase (LOC388228) |
| 368 | NM_032017 | SINK-homologous serine/threonine kinase, MGC4796 |
| 369 | NM_020547 | AMHR2 (anti-Mullerian hormone receptor, type II) |
| 370 | NM_031414 | STK31 |
| 371 | NM_032237 | hypothetical protein FLJ23356 |
| 372 | NM_021133 | RNASEL (ribonuclease L (2',5'-oligoisoadenylate synthetase-dependent)) |
| 373 | AX166516 | similar to protein kinase Bsk146 |
| 374 | NM_153361 | NIM1, MGC42105, similar to serine/threonine kinase (KIN1/SNF1/Nim1 subfamily) |
| 375 | NM_145203 | casein kinase 1 alpha S-like, CKIa2 |
| 376 | NM_173500 | TTBK2 |
| 377 | NM_144685 | HIPK4 |
| 378 | NM_175866 | KIS |
| 379 | AX166547 | KSR2 |
| 380 | AX056416 | NRBP2 |
| 381 | AX540378 | SgK494, hypothetical protein FLJ25006 |
| 382 | NM_152835 | CLIK1L |
| 383 | AX540373 | SgK071, similar to MGC43306 protein (LOC401568) |
| 384 | AX056460 | SgK493, hypothetical protein BC007901 (LOC91461) |
| 385 | NM_005157 | ABL1 |
| 386 | NM_005158 | ABL2, ARG |
| 387 | NM_005781 | ACK1 |
| 388 | NM_000061 | BTK |
| 389 | NM_005246 | FER |
| 390 | NM_002005 | FES |
| 391 | NM_002031 | FRK (fyn-related kinase) |
| 392 | NM_002037 | FYN |
| 393 | NM_002110 | HCK |
| 394 | NM_005248 | FGR |
| 395 | NM_005356 | LCK |
| 396 | NM_002344 | LTK |
| 397 | NM_002350 | LYN |
| 398 | NM_004383 | CSK |
| 399 | NM_005546 | ITK |
| 400 | NM_005417 | SRC |
| 401 | NM_003215 | TEC |
| 402 | NM_005433 | YES |

TABLE 1-continued

List of all protein kinases

| No. | Accession Number | Gene |
|---|---|---|
| 403 | NM_003328 | TXK |
| 404 | NM_080823 | SRMS |
| 405 | NM_001715 | BLK |
| 406 | NM_001721 | BMX |
| 407 | NM_005975 | PTK6 |
| 408 | NM_002821 | PTK7 |
| 409 | NM_002822 | PTK9 |
| 410 | NM_007284 | PTK9L |
| 411 | NM_000222 | KIT |
| 412 | NM_005211 | CSF1R |
| 413 | NM_005232 | EphA1 |
| 414 | NM_004431 | EphA2 |
| 415 | NM_005233 | EphA3 |
| 416 | NM_004438 | EphA4 |
| 417 | NM_004439 | EphA5 |
| 418 | AX250164 | EphA6 |
| 419 | NM_004440 | EphA7 |
| 420 | NM_020526 | EphA8 |
| 421 | AX166562 | EphA10 |
| 422 | NM_004441 | EphB1 |
| 423 | NM_004442 | EphB2 |
| 424 | NM_004443 | EphB3 |
| 425 | NM_004444 | EphB4 |
| 426 | NM_004445 | EphB6 |
| 427 | NM_000604 | FGFR1 |
| 428 | NM_000141 | FGFR2 |
| 429 | NM_000142 | FGFR3 |
| 430 | NM_002011 | FGFR4 |
| 431 | NM_002253 | KDR |
| 432 | NM_002019 | FLT1 |
| 433 | NM_004119 | FLT3 |
| 434 | NM_002020 | FLT4 |
| 435 | NM_005228 | EGFR |
| 436 | NM_004448 | HER2 |
| 437 | NM_001982 | HER3 |
| 438 | NM_005235 | HER4 |
| 439 | NM_002378 | MATK |
| 440 | NM_000875 | IGF1R |
| 441 | NM_000208 | INSR |
| 442 | NM_014215 | INSRR |
| 443 | NM_002227 | JAK1 |
| 444 | NM_004972 | JAK2 |
| 445 | NM_000215 | JAK3 |
| 446 | NM_003331 | TYK2 |
| 447 | NM_006343 | MER |
| 448 | NM_021913 | AXL |
| 449 | NM_006293 | TYRO3 |
| 450 | NM_000245 | MET |
| 451 | NM_002447 | MST1R, RON |
| 452 | NM_002958 | RYK |
| 453 | NM_006206 | PDGFRalpha |
| 454 | NM_002609 | PDGFRbeta |
| 455 | NM_020630 | RET |
| 456 | NM_005012 | ROR1 |
| 457 | NM_004560 | ROR2 |
| 458 | NM_002944 | ROS1 |
| 459 | NM_005607 | PTK2, FAK |
| 460 | NM_004103 | PTK2B, PYK2 |
| 461 | NM_003177 | SYK |
| 462 | NM_001079 | ZAP70 |
| 463 | NM_005424 | TIE1 |
| 464 | NM_000459 | TEK, TIE2 |
| 465 | NM_005592 | MUSK |
| 466 | NM_002529 | NTRK1 |
| 467 | NM_006180 | NTRK2 |
| 468 | NM_002530 | NTRK3 |
| 469 | NM_013994 | DDR1 |
| 470 | NM_006182 | DDR2 |
| 471 | NM_004920 | AATK/LMR1 |
| 472 | XM_055866 | LMTK3 |
| 473 | NM_003985 | TNK1 |
| 474 | L08961 | HUMSPRMTK |
| 475 | NM_004304 | ALK |
| 476 | NM_015978 | CARK |
| 477 | NM_018423 | DKFZp761P1010 |
| 478 | NM_032435 | KIAA1804, MLK4 |

TABLE 1-continued

List of all protein kinases

| No. | Accession Number | Gene |
|---|---|---|
| 479 | AJ277481 | ILK-2 |
| 480 | NM_000906 | NPR1 |
| 481 | NM_000907 | NPR2 |
| 482 | NM_004963 | GUCY2C |
| 483 | NM_000180 | GUCY2D |
| 484 | NM_001522 | GUCY2F |
| 485 | XM_058513 | DKFZp434H2111 |
| 486 | NM_006218 | PIK3CA (phosphoinositide-3-kinase, catalytic, alpha polypeptide) |
| 487 | NM_006219 | PIK3CB (phosphoinositide-3-kinase, catalytic, beta polypeptide) |
| 488 | NM_002649 | PIK3CG (phosphoinositide-3-kinase, catalytic, gamma polypeptide) |
| 489 | NM_005026 | PIK3CD (phosphoinositide-3-kinase, catalytic, delta polypeptide |
| 490 | NM_014006 | SMG1 |
| 491 | NM_000051 | ATM (ataxia telangiectasia mutated) |
| 492 | NM_001184 | ATR (ataxia telangiectasia and Rad3 related) |
| 493 | NM_014216 | ITPK1 |
| 494 | NM_004958 | FRAP1 (FK506 binding protein 12-rapamycin associated protein 1) |
| 495 | NM_002645 | PIK3C2A (phosphoinositide-3-kinase, class 2, alpha polypeptide) |
| 496 | NM_002647 | PIK3C3 (phosphoinositide-3-kinase, class 3); Vps34 |
| 497 | NM_002651 | PIK4CB (phosphatidylinositol 4-kinase, catalytic, beta polypeptide) |
| 498 | NM_002650 | PIK4CA (phosphatidylinositol 4-kinase, catalytic, alpha polypeptide) |
| 499 | NM_003496 | TRRAP (transformation/transcription domain-associated protein) |
| 500 | NM_002646 | PIK3C2B (phosphoinositide-3-kinase, class 2, beta polypeptide) |
| 501 | NM_004570 | PIK3C2G (phosphoinositide-3-kinase, class 2, gamma polypeptide) |
| 502 | NM_006904 | PRKDC (protein kinase, DNA-activated) |
| 503 | NM_013302 | elongation factor-2 kinase |
| 504 | NM_025144 | LAK (lymphocyte alpha-kinase) |
| 505 | NM_017662 | TRPM6 |
| 506 | NM_052947 | HAK |
| 507 | NM_020778 | MIDORI |
| 508 | NM_005881 | BCKDK |
| 509 | NM_002610 | PDK1 |
| 510 | NM_002611 | PDK2 |
| 511 | NM_005391 | PDK3 |
| 512 | NM_002612 | PDK4 |
| 513 | NM_018343 | RIOK2 |
| 514 | NM_031480 | RIOK1 |
| 515 | NM_003831 | RIOK3 |
| 516 | BC017459 | ADCK1 |
| 517 | NM_052853 | ADCK2 |
| 518 | NM_020247 | CABC1 |
| 519 | NM_024876 | ADCK4 |
| 520 | NM_174922 | ADCK5 |
| 521 | NM_032454 | STK19 |
| 522 | NM_001726 | BRDT |
| 523 | NM_005104 | BRD2 |
| 524 | NM_007371 | BRD3 |
| 525 | NM_058243 | BRD4, var. long |
| 526 | NM_014299 | BRD4, var. Short |
| 527 | NM_004606 | TAF1 |
| 528 | NM_153809 | TAF1L |
| 529 | NM_003852 | TIF1 |
| 530 | NM_005762 | TRIM28 |
| 531 | NM_015906 | TRIM33 |

Accession Numbers were obtained from the public data bank NCBI (http://www.ncbi.nlm.nih.gov/).

Determination of RNA Polymerase II C-terminal Domain Phosphorylation:

The phosphorylation status of RNA polymerase II C-terminal domain was determined by western blot techniques. PM1 cells were seeded in 6-well plates at a density of $5 \times 10^5$ per well. After over night incubation cells were treated with compound as indicated in the respective experiments. Cells were pelleted and lysed with 300 µL 3× Laemmli buffer followed by 30 min denaturing at 65° C. After separation of equal lysate volumes by SDS-PAGE the proteins were transferred to nitrocellulose membranes (Schleicher&Schuell) and probed with anti-SER2 (H5), anti-SER5 (H14) or RNA Poll II-antibodies purchased from Eurogentec and Santa Cruz, respectively. The amount of reactive protein was visualized by ECL detection methods (Amersham).

Growth Assay Using Alamar Blue™:

PM1 cells were seeded in 12-well plates at a density of $1.5 \times 10^5$ per well with RPMI 1640 containing 10% FCS (fetal calf serum), 1% L-Glutamine and 1% Na-Pyruvate (Sigma). Cells were incubated with compound for 2-3 days (37° C., 6% $CO_2$) followed by subsequent splitting and renewing of compound-containing medium. At each of these time points an aliquot of cells served as data point for relative growth (given in % of the DMSO control [=100%]). The cell number was determined by addition of 10 µL Alamar Blue™ (Biozol) to 100 µL cell aliquots following the manufacturer's instructions.

HIV Replication Assay in PM1 Cells:

PM1 cells were seeded in 12-well plates at a density of $1.5 \times 10^5$ per well with RPMI 1640 containing 10% FCS, 1% L-Glutamine and 1% Na-Pyruvate (Sigma). Cells were previously infected with HIV-1 BaL for 3 h at a concentration of about 5×10⁸ µg p24/cell. After addition of the respective compounds cells were incubated for 6 to 10 days. During this incubation the cells were passaged and compound-containing medium was renewed. The concentration of p24 in the cellular supernatants was determined at each of this time points using a previously described ELISA assay (Bevec et al., Proceedings of the National Academy of Sciences U.S.A. 1992, 89(20), 9870-9874).

NFκB-dependent Transcriptional Activity:

The used NIH 3T3 75E 11/300D8 cell line is described elsewhere (J. Eickhoff et al., Journal of Biological Chemistry, 2004, 279(10), 9642-9652).

HBV-replication:

To test anti—HBV-activity of compounds the HBV-producing cell line HepG2-2.2.15 (M. A. Sells, PNAS 1987, 84, 1005-1009) was used. 1.0×10⁴ cells were seeded in 96-well microtiter plates in DMEM medium supplemented with 10% FCS. After incubation at 37° C. in 5% $CO_2$ atmosphere for 24 hours the medium was replaced with fresh medium containing the appropriately diluted compound. 3 days later medium was replaced by freshly prepared inhibitor-containing medium and the cells were incubated for further 3 days. Subsequently 200 µl lysis buffer (50 mM Tris-Cl 7.5; 1 mM EDTA 8.0; 0.5% NP40) per well was added. To remove cell debris and nucleic acids, lysate was centrifuged (15000 rpm, 10 min, 4° C.). Cellular and viral RNA was removed by addition of 2 µl of RNase. 100 µl of the samples were spotted onto an uncharged nylon membrane pre-wetted with PBS (phosphate-buffered saline) using a 96 well-blotting chamber (MINIfold Dot-Blot, Schleicher&Schüll). After further washing with 200 µl PBS per well the membrane was treated twice with 0.5 M NaOH, 1.5 M NaCl (2 min) and 4 times with 0.5 M Tris 7.5, 3 M NaCl (1 min). The nucleic acids were fixed by UV-treatment and used for hybridisabon with a radioactive HBV-fragment prepared from the overgenome-length HBV-plasmid pT-HBV1.3 (L. G. Guidotti et al., Journal of Virology 1995., 69(10), 6158-6169).

The fixed membrane was pre-hybridized in a standard hybridisation buffer (50% formamide, 5×SSPE, 10×Denhards, 1% SDS, 100 µg/ml salmon sperm DNA) for at least 3 hours at 42° C. and hybridised overnight against the labelled HBV-fragment. The preparation of the HBV-fragment with the "Random primers DNA labelling system" (Invitrogen) was done according to the manufacturer's instructions. Hybridized filter were washed at room temperature with 2×SSC, at 62° C. with 2×SSC, 0.5% SDS and at 62° C. with 0.5×SSC, 0.5% SDS. Each washing step was carried out twice. The intensity of the HBV-DNA was quantified using a phosphoimager (Fuji). To test the cell viability 0.5×10⁴ HepG2-2.2.15-cells were seeded in 96-well-microtiter plates in DMEM medium supplemented with 10% fetal bovine serum. After incubation at 37° C. for 24 hours the medium was replaced by fresh compound-containing medium. 3 days later medium was replaced again by freshly prepared medium containing the inhibitor and the cells were incubated for further 3 days at 37° C. After the incubation period 1/10 volume of Alamar Blue (Serotec) solution containing a growth dependant indicator was added and the cells were incubated for 3 h at 37° C. Absorbance was monitored at 570 nm and 600 nm wavelength.

HCMV Replication:

Human foreskin fibroblasts (HFF) cell culture were grown in DMEM containing 10% FCS. For HCMV-replication assays, HFF cells were infected with HCMV strain AD169 producing EGFP (HCMV AD169-GFP; 27). 1 h post infection, medium was changed with medium containing the indicated compound concentration (0.3 µM, 1 µM and 3 µM, respectively) After incubation of 7 days cells were lysed (in 25 mM Tris, pH 7.5, 2 mM DTT, 1% Triton X-100 and 10% glycerol) and analysed for EGFP content in a Wallac Victor fluorescence detector.

HCV Relicon Assays:

Compounds were tested for activity in the HCV replicon system described by Bartenschlager and coworkers (Lohmann et al, Replication of subgenomic hepatitis C virus RNAs in a hepatoma cell line. Science 285, 110. 1999).

Affinity Chromatography Experiments:

Compound Immobilisation:

Coupling to epoxy-groups: 500 µl drained epoxy-activated Sepharose 6B (Amersham Biosciences) equilibrated to 50% DMF/0.1M $Na_2CO_3$ were resuspended in 1 ml 20 mM Compound 102 or 20 mM Compound 103, respectively, dissolved in 50% DMF (Dimethylfomamid)/0.1 M $Na_2CO_3$. 5 µl 10M NaOH was added followed by incubation overnight at 30° C. with permanent shaking in the dark. After washing three times in 1 ml 50% DMF/0.1M $Na_2CO_3$ the beads were incubated in 1 ml 1M ethanolamine for 6 h at 30° C. with permanent shaking in the dark followed by the denoted washing steps: 50% DMF/0.1M $Na_2CO_3$, then $H_2O$, then 0.1M $NaHCO_3$ pH 8.0/0.5M NaCl followed by 0.1M NaAc pH 4.0/0.1M NaCl and finally three times in chromatography buffer (see below) containing 150 mM NaCl. As control matrix epoxy-activated Sepharose 6B was incubated with 1M ethanolamine and equally treated as described above. The beads were stored in 20% ethanol at 4° C. in the dark.

Carbodiimide coupling: ECH-Sepharose 4B (Amersham Biosciences) was washed according to the manufacturer's instructions and equilibrated to 50% DMF/50% ethanol. 2.5 ml drained beads were resuspended in 5 ml 15 mM Compound 102 or Compound 103, respectively, dissolved in 50% DMF/50% ethanol followed by drop by drop addition of 750 µl 1M 1-ethyl-3-(3-dimethylaminopropyl) carbodiimide hydrochloride (EDC), dissolved in 50% DMF/50% ethanol. The suspension was incubated overnight at room temperature with permanent end-over-end rotation and washed three times with 15 ml 50% DMF/50% ethanol prior to the addition of 5 ml 33% DMF/33% ethanol/34% 1M ethanolamine pH 8.0 and 650 µl EDC. After 2 h incubation at room temperature with permanent end-over-end rotation, beads were washed three times with 15 ml 50% DMF/50% ethanol, twice with 15 ml 0.5M NaCl and once with 15 ml 20% ethanol. Control beads were incubated with 5 ml 1M ethanolamine instead of compound and treated equally as described above. The beads were stored in 20% ethanol at 4° C. in the dark.

Affinity Chromatography and Preparative Gel Electrophoresis.

1.25×10⁹ PM1 cells were lysed in 15 ml buffer containing 50 mM HEPES pH 7.5, 400 mM NaCl, 0.5% Triton X-100, 1 mM EDTA, 1 mM EGTA, 3 mM $MgCl_2$, 1 mM DTT plus additives (10 mM sodium fluoride, 1 mM orthovanadate, 10 µg/ml aprotinin, 10 µg/ml leupeptin, 1 mM PMSF), cleared by centrifugation and adjusted to 1M NaCl. The filtered lysate was loaded with a flow rate of 100 µl/min on a 25 mM×5 mM chromatography column containing 500 µl Compound 102 or Compound 103 matrix, respectively, equilibrated to chromatography buffer (20 mM HEPES pH 7.5, 0.25% Triton X-100, 1 mM EDTA, 1 mM EGTA) containing 1M NaCl. The column was washed with 25 column volumes, equilibrated to chromatography buffer containing 150 mM NaCl and bound proteins were eluted in the same buffer containing 200 µM Compound 102 or 200 µM Compound 103, respectively, 10 mM ATP and 20 mM $MgCl_2$ with a flow rate of 50 µl/min. The volume of protein containing fractions was reduced to 1/5 in a SpeedVac concentrator prior to precipitation according to Wessel & Flügge (Wessel et al., 1984). Precipitated proteins were dissolved in 16-BAC sample buffer and after reduction/alkylation separated by 2-dimensional 16-BAC/SDS-PAGE (Daub et al., Journal of Virology 2002, 76, 8214-8137). Coomassie stained spots were picked and subjected to analysis by mass spectrometry.

Results:

Expression and Kinase Activity of CDK9/CyclinT1:

CDK9/CyclinT1 complexes from HEK293 cells were completely solubilised. CDK9/CyclinT1 proteins were almost completely precipitated by and eluted from streptavidin beads (data not shown). An imagination of the enrichment can be drawn from the blots stained for protein by PonceauS. CDK9/CyclinT1 proteins can be seen in the eluate whereas they are not visible within the cells or extract. Probing nitrocellulose with antibodies against CDK2 and CDK4 revealed that those kinases do not contaminate the purifications (data not shown).

Figure 2:
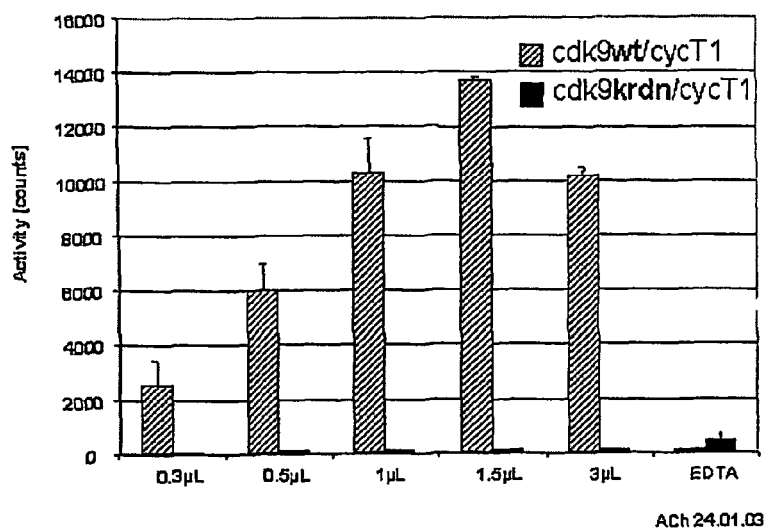
FIG. 2 shows the kinase activity of different CDK9wt and KRDN (K48R/D167N) amounts.

As shown in FIG. 2 increasing amounts of CDK9 wt proteins incubated with substrates (ATP and GST-CTDII) resulted in incorporation of radioactive phosphate. As expected, mutation of critical kinase domain residues (K48R and D167N) within CDK9 revealed no phosphate incorporation, meaning that these mutations render the kinase inactive. Additionally, EDTA pre-incubation completely inhibited activity.

These results show that purification of CDK9/CyclinT1 proteins using adenovirus leads to an active and pure enzyme. A putative contamination with other protein kinases can be ruled out because purification of mutated CDK9 resulted in negligible kinase activity.

Table 2 shows the half-maximal inhibition constant ($IC_{50}$) values of the compounds according to the present invention on CDK9 and on CDK2, respectively.

TABLE 2

Inhibitory effect on CDK9 and CDK2 of compounds according to the present invention

| | ① | ② | LCMS | ③ | ④ Nomenclature | ⑤ | ⑥ | ⑦ |
|---|---|---|---|---|---|---|---|---|
| (1) | 1 | 447 | 1.3 | A1 | N-{4-[6-(4-Methoxy-phenyl)-pyrimidin-4-ylamino]-phenyl}-4-methylbenzene-sulfonamide | c | | b |
| (2) | 1 | 447 | 1.45 | A1 | N-{4-[6-(3-Methoxy-phenyl)-pyrimidin-4-ylamino]-phenyl}-4-methyl-benzenesulfonamide | c | | c |
| (3) | 1 | 385 | 0.94 | A1 | N-{5-[6-(4-Methoxy-phenyl)-pyrimidin-4-ylamino]-2-methyl-phenyl}-methane sulfonamide | b | | a |
| (4) | 1 | 488 | 1.16 | A1 | 4-Amino-N-{4-[6-(2-benzyloxy-phenyl)-pyrimidin-4-yl-amino]-phenyl}benzamide | a | | b |
| (5) | 1 | 447 | 1.16 | A1 | N-{4-[6-(2-Methoxy-phenyl)-pyrimidin-4-ylamino]-phenyl}-4-methyl-benzene sulfonamide | a | | a |
| (6) | 1 | 412 | 0.8 | A1 | 4-Amino-N-{4-[6-(4-methoxy-phenyl)-pyrimidin-4-yl-amino]-phenyl}-benzamide | a | | b |
| (7) | 1 | 383 | 1.95 | B1 | [6-(2-Benzyloxy-phenyl)-pyrimidin-4-yl]-(2-pyridin-4-yl-ethyl)-amine | a | | b |
| (8) | 1 | 412 | 0.76 | A1 | 4-Amino-N-{4-[6-(2-methoxy-phenyl)-pyrimidin-4-yl-amino]-phenyl}-benzamide | a | | b |
| (9) | 1 | 361 | 0.78 | A1 | 1-{4-[6-(2-Methoxy-phenyl)-pyrimidin-4-ylamino]-phenyl}-pyrrolidin-2-one | a | a | a |
| (10) | 1 | 335 | 0.44 | A1 | N-{4-[6-(2-Methoxy-phenyl)-pyrimidin-4-ylamino]-phenyl}-acetamide | a | b | a |
| (11) | 1 | 433 | 1.07 | A1 | N-{4-[6-(4-Hydroxy-phenyl)-pyrimidin-4-ylamino]-phenyl}-4-methyl-benzenesulfonamide | a | | a |
| (12) | 1 | 370 | 1.57 | B1 | N-{5-[6-(3-Amino-phenyl)-pyrimidin-4-ylamino]-2-methyl-phenyl}-methane sulfonamide | a | | a |
| (13) | 1 | 292 | 1.27 | B1 | [6-(3-Amino-phenyl)-pyrimidin-4-yl]-(2-pyridin-4-yl-ethyl)-amine | b | | b |
| (14) | 1 | 321 | 1.52 | B1 | 4-[6-(2-Methoxy-phenyl)-pyrimidin-4-ylamino]-benz-amide | a | c | a |
| (15) | 1 | 336 | 2.21 | B1 | 4-[6-(2-Methoxy-phenyl)-pyrimidin-4-ylamino]-benzoic acid methyl ester | a | | a |
| (16) | 1 | 398 | 1.51 | B1 | 4-Amino-N-{4-[6-(4-hydroxy-phenyl)-pyrimidin-4-yl-amino]-phenyl}-benzamide | b | | b |
| (17) | 1 | 487 (M − H)⁻ | 1.24 | A1 | 3-(4-{6-[4-(Toluene-4-sulfonylamino)-phenylamino]-pyrimidin-4-yl}-phenyl)-propionic acid | c | | c |
| (18) | 1 | 489 | 1.6 | A1 | N-{4-[6-(2-Methoxy-phenyl)-pyrimidin-4-ylamino]-phenyl}-4-methyl-N-propyl-benzenesulfonamide | b | | c |
| (19) | 1 | 377 | 1.02 | A1 | N-{4-[6-(2-Methoxy-phenyl)-pyrimidin-4-ylamino]-phenyl}-2,2-dimethyl-propionamide | a | | b |
| (20) | 1 | 412 | 1.05 | A1 | 2-Amino-N-{4-[6-(2-methoxy-phenyl)-pyrimidin-4-ylamino]-phenyl}-benzamide | a | | b |
| (21) | 1 | 397 | 1.52 | B1 | 4-Amino-N-{4-[6-(3-amino-phenyl)-pyrimidin-4-ylamino]-phenyl}-benzamide | b | | b |
| (22) | 1 | 293 | 1.61 | B1 | N-[6-(2-Methoxy-phenyl)-pyrimidin-4-yl]-benzene-1,4-diamine | a | b | a |
| (23) | 1 + 2 | 476 | 2.38 | B1 | 4-Isopropyl-N-{4-[6-(2-methoxy-phenyl)-pyrimidin-4-ylamino]-phenyl}-benzenesulfonamide | a | | b |
| (96) | 1 | 461 | 2.24 | B1 | N-(4-{[6-(2-Methoxy-phenyl)-pyrimidin-4-yl]-methyl-amino}-phenyl)-4-methyl-benzenesulfon-amide | b | | b |
| (24) | 1 | 373 (M − H)⁻ | 2.02 | B1 | N-[4-(6-Chloro-pyrimidin-4-ylamino)-phenyl]-4-methyl-benzenesulfonamide | c | | b |
| (25) | 1 | 338 (M − H)⁻ | 1.57 | B1 | 4-Amino-N-[4-(6-chloro-pyrimidin-4-ylamino)-phenyl]-benzamide | c | | c |
| (26) | 1 + 4 + 8 | 307 | 1.79 | B1 | N-[6-(2-Methoxy-phenyl)-pyrimidin-4-yl]-N-methyl-benzene-1,4-diamine | b | | b |
| (27) | 1 + 4 + 8 | 505 | 1.28 | A1 | [{4-[6-(4-Hydroxy-phenyl)-pyrimidin-4-ylamino]-phenyl}-(toluene-4-sulfonyl)-amino]-acetic acid methyl ester | b | | a |
| (28) | 1 | 519 | 2.36 | A1 | [{4-[6-(2-Methoxy-phenyl)-pyrimidin-4-ylamino]-phenyl}-(toluene-4-sulfonyl)-amino]-acetic acid methyl ester | b | | b |
| (29) | 1 + 2 | 504 | 2.33 | B1 | (S)-2-{4-[6-(2-Methoxy-phenyl)-pyrimidin-4-ylamino]-phenyl carbamoyl}-piperidine-1-carboxylic acid tert-butyl ester | a | | b |
| (30) | 1 + 6 | 404 | 1.55 | B1 | (S)-Piperidine-2-carboxylic acid {4-[6-(2-methoxy-phenyl)-pyrimidin-4-ylamino]-phenyl}-amide | a | a | b |
| (31) | 1 | 442 | 1.78 | B1 | 4-Amino-N-{4-[6-(2,4-dimethoxy-phenyl)-pyrimidin-4-ylamino]-phenyl}-benzamide | a | | a |
| (32) | 1 | 408 | 1.91 | B1 | 4-Amino-N-{4-[6-((E)-styryl)-pyrimidin-4-ylamino]-phenyl}-benzamide | c | | c |
| (33) | 1 + 2 | 371 | 1.81 | B1 | N-{4-[6-(2-Methoxy-phenyl)-pyrimidin-4-ylamino]-phenyl}-methanesulfonamide | a | b | a |
| (34) | 1 + 2 | 509 | 2.4 | B1 | Biphenyl-4-sulfonic acid {4-[6-(2-methoxy-phenyl)-pyrimidin-4-yl-amino]-phenyl}-amide | b | | b |
| (35) | 1 | 454 | 2.12 | B1 | 4-Amino-N-{4-[6-(5-isopropyl-2-methoxy-phenyl)-pyrimidin-4-ylamino]-phenyl}-benzamide | c | | c |
| (36) | 1 + 2 | 415 | 1.21 | A1 | Bicyclo[2.2.1]heptane-2-carboxylic acid {4-[6-(2-methoxy-phenyl)-pyrimidin-4-ylamino]-phenyl}-amide | a | | c |
| (37) | 1 + 2 | 453 | 1.38 | A1 | N-{4-[6-(2-Methoxy-phenyl)-pyrimidin-4-ylamino]-phenyl}-3-methyl-2-phenyl-butyramide | b | | c |
| (38) | 1 + 9 | 418 | 1.09 | A1 | 1-Cyclohexyl-3-{4-[6-(2-methoxy-phenyl)-pyrimidin-4-ylamino]-phenyl}-urea | a | | b |

TABLE 2-continued

Inhibitory effect on CDK9 and CDK2 of compounds according to the present invention

| ① | ② | LCMS | ③ | ④ Nomenclature | ⑤ | ⑥ | ⑦ |
|---|---|---|---|---|---|---|---|
| (39) | 1 | 446 | 2.01 | B1 4-Amino-N-{4-[6-(5-chloro-2-methoxy-phenyl)-pyrimidin-4-ylamino]-phenyl}-benzamide | b | | c |
| (40) | 1 | 487 | 1.43 | B1 (E)-3-(3-{6-[4-(Toluene-4-sulfonylamino)-phenylamino]pyrimidin-4-yl}phenyl)acrylic acid | c | | c |
| (41) | 1 + 2 | 403 | 2.13 | B1 Cyclohexanecarboxylic acid {4-[6-(2-methoxy-phenyl)-pyrimidin-4-ylamino]phenyl}amide | b | | c |
| (42) | 1 + 2 | 391 | 2.07 | B1 N-{4-[6-(2-Methoxy-phenyl)-pyrimidin-4-ylamino]-phenyl}-3,3-dimethyl-butyramide | b | | b |
| (43) | 7 | 417 | 1.87 | B1 4-Amino-N-{4-[6-(cyclohexylmethyl-amino)-pyrimidin-4-ylamino]-phenyl}-benzamide | b | | c |
| (44) | 1 + 3 | 403 | 2.13 | B1 N-Cyclohexyl-4-[6-(2-methoxy-phenyl)-pyrimidin-4-ylamino]-benzamide | a | | b |
| (45) | 1 + 2 | 453 | 2.48 | B1 4-tert-Butyl-N-{4-[6-(2-methoxy-phenyl)-pyrimidin-4-ylamino]-phenyl}-benzamide | b | | c |
| (46) | 1 + 2 | 378 | 1.68 | B1 2-Dimethylamino-N-{4-[6-(2-methoxy-phenyl)-pyrimidin-4-ylamino]-phenyl}-acetamide | a | b | b |
| (47) | 1 + 2 | 504 | 2.12 | B1 (1-{4-[6-(2-Methoxy-phenyl)-pyrimidin-4-ylamino]-phenyl-carbamoyl}-cyclo-pentyl)-carbamic acid tert-butyl ester | a | | c |
| (48) | 1 + 2 | 518 | 2.18 | B1 2-({4-[6-(2-Methoxy-phenyl)-pyrimidin-4-ylamino]-phenyl-carbamoyl}-methyl)-piperidine-1-carboxylic acid tert-butyl ester | b | | b |
| (49) | 1 + 2 | 495 | 1.83 | B1 N-{4-[6-(2-Methoxy-phenyl)-pyrimidin-4-ylamino]-phenyl}-4-(4-methyl-piperazin-1-yl)-benzamide | a | | b |
| (50) | 1 + 2 | 398 | 1.66 | B1 N-{4-[6-(2-Methoxy-phenyl)-pyrimidin-4-ylamino]-phenyl}-isonicotinamide | b | | c |
| (51) | 1 | 442 | 1.58 | B1 4-Amino-N-{4-[6-(2,6-dimethoxy-phenyl)-pyrimidin-4-ylamino]-phenyl}-benzamide | b | | c |
| (52) | 1 + 2 | 397 | 2 | B1 4-[6-(2-Methoxy-phenyl)-pyrimidin-4-ylamino]-N-phenyl-benzamide | a | | c |
| (53) | 1 + 5 | 3.35 | 1.02 | A1 N-{4-[6-(2-Methoxy-phenyl)-pyrimidin-4-ylamino]-phenyl}-guanidine | b | | b |
| (54) | 1 + 3 | 377 | 2.02 | B1 N-tert-Butyl-4-[6-(2-methoxy-phenyl)-pyrimidin-4-ylamino]-benzamide | b | | b |
| (55) | 1 | 426 | 1.81 | B1 4-Amino-N-{4-[6-(2-ethoxy-phenyl)-pyrimidin-4-yl-amino]-phenyl}-benzamide | a | | b |
| (56) | 1 | 442 | 1.69 | B1 4-Amino-N-{4-[6-(2,3-dimethoxy-phenyl)-pyrimidin-4-ylamino]-phenyl}-benzamide | b | | b |
| (57) | 1 | 442 | 1.71 | B1 4-Amino-N-{4-[6-(2,5-dimethoxy-phenyl)-pyrimidin-4-ylamino]-phenyl}-benzamide | c | | c |
| (58) | 1 | 440 | 1.87 | B1 4-Amino-N-{4-[6-(2-isopropoxy-phenyl)-pyrimidin-4-yl-amino]-phenyl}-benzamide | a | | a |
| (59) | 1 | 418 | 1.45 | B1 N-{4-[6-(2-Methoxy-phenyl)-pyrimidin-4-ylamino]-phenyl}-2-piperidin-2-yl-acet-amide | a | a | b |
| (60) | 7 | 365 | 1.01 | B1 4-Amino-N-{4-[6-(2-hydroxy-ethylamino)-pyrimidin-4-ylamino]-phenyl}-benzamide | b | | c |
| (97) | 1 + 2 | 427 | 1.62 | A1 4-Amino-N-{4-[2-amino-6-(2-methoxy-phenyl)-pyrimidin-4-ylamino]-phenyl}-benzamide | b | | c |
| (61) | 1 + 2 | 455 | 2.48 | B1 Adamantane-1-carboxylic acid {4-[6-(2-methoxy-phenyl)-pyrimidin-4-ylamino]-phenyl}-amide | b | | c |
| (62) | 1 | 395 | 2.58 | B1 (4-Benzooxazol-2-yl-phenyl)-[6-(2-methoxy-phenyl)-pyrimidin-4-yl]-amine | c | | c |
| (63) | 1 | 394 | 1.88 | B1 [4-(1H-Benzoimidazol-2-yl)-phenyl]-[6-(2-methoxy-phenyl)-pyrimidin-4-yl]-amine | a | | a |
| (64) | 1 + 2 | 418 (M − H)⁻ | 1.74 | A1 3-Diethylamino-N-{4-[6-(2-methoxy-phenyl)-pyrimidin-4-ylamino]-phenyl}-propionamide | a | b | b |
| (65) | 1 + 2 | 452 | 1.98 | B1 (S)-1,2,3,4-Tetrahydro-isoquinoline-3-carboxylic acid {4-[6-(2-methoxy-phenyl)-pyrimidin-4-ylamino]-phenyl}-amide | a | c | b |
| (66) | 1 + 6 | 418 | 1.97 | B1 1-Amino-cyclohexanecarboxylic acid {4-[6-(2-methoxy-phenyl)-pyrimidin-4-ylamino]-phenyl}-amide | a | b | b |
| (67) | 1 | 383 | 1.35 | B1 4-Amino-N-[4-(6-pyridin-4-yl-pyrimidin-4-ylamino)-phenyl]-benzamide | c | | c |
| (87) | 1 + 2 | 418 | 1.59 | B1 1-Methyl-piperidine-3-carboxylic acid {4-[6-(2-methoxy-phenyl)-pyrimidin-4-ylamino]-phenyl}-amide | a | b | b |
| (98) | 1 | 448 | 2.43 | B1 Quinoline-2-carboxylic acid {4-[6-(2-methoxy-phenyl)-pyrimidin-4-ylamino]-phenyl}-amide | a | | c |
| (68) | 1 + 6 | 404 | 1.82 | B1 1-Amino-cyclopentanecarboxylic acid {4-[6-(2-methoxy-phenyl)-pyrimidin-4-ylamino]-phenyl}-amide | a | b | b |
| (69) | 1 | 404 | 1.53 | B1 (R)-Piperidine-2-carboxylic acid {4-[6-(2-methoxy-phenyl)-pyrimidin-4-ylamino]-phenyl}-amide | a | a | b |
| (70) | 1 + 2 | 401 | 1.59 | B1 1-Methyl-1H-imidazole-4-carboxylic acid {4-[6-(2-methoxy-phenyl)-pyrimidin-4-ylamino]-phenyl}-amide | a | | b |
| (71) | 1 + 2 | 411 | 1.99 | B1 N-{4-[6-(2-Methoxy-phenyl)-pyrimidin-4-ylamino]-phenyl}-2-phenyl-acetamide | a | | b |
| (72) | 1 + 3 | 305 | 1.55 | C1 N-[4-(6-Chloro-pyrimidin-4-ylamino)-phenyl]-2,2-dimethyl-propionamide | | | c |
| (73) | 1 | 348 | 1.57 | B1 2,2-Dimethyl-N-[4-(6-pyridin-3-yl-pyrimidin-4-ylamino)-phenyl]-propionamide | | | c |
| (74) | 7 | 381 (M − H)⁻ | 1.26 | B1 2,2-Dimethyl-N-{4-[6-(1-methyl-piperidin-4-ylamino)-pyrimidin-4-ylamino]-phenyl}-propionamide | c | | c |
| (75) | 1 | 389 (M − H)⁻ | 1.12 | B1 3-{6-[4-(2,2-Dimethyl-propionylamino)-phenylamino]-pyrimidin-4-yl}-benzoic acid | | | c |
| (76) | 1 | 380 (M − H)⁻ | 1.67 | B1 4-Amino-N-[4-(6-phenyl-pyrimidin-4-ylamino)-phenyl]-benzamide | b | | c |
| (77) | 1 | 386 (M − H)⁻ | 1.64 | B1 4-Amino-N-[4-(6-thiophen-2-yl-pyrimidin-4-ylamino)-phenyl]-benzamide | b | | c |
| (78) | 7 | 369 | 1.47 | B1 2,2-Dimethyl-N-{4-[6-(4-methyl-piperazin-1-yl)-pyrimidin-4-ylamino]-phenyl}-propionamide | | | c |
| (79) | 7 | 329 | 1.12 | B1 N-{4-[6-(2-Amino-ethylamino)-pyrimidin-4-ylamino]-phenyl}-2,2-dimethyl-propionamide | c | | c |
| (80) | 7 | 342 (M − H)⁻ | 1.24 | B1 N-{4-[6-(3-Hydroxy-propylamino)-pyrimidin-4-ylamino]-phenyl}-2,2-dimethyl-propionamide | c | | c |
| (81) | 1 + 6 | 426 | 1.74 | B1 (S)-2-Amino-N-{4-[6-(2-methoxy-phenyl)-pyrimidin-4-ylamino]-phenyl}-2-phenyl-acetamide | a | b | b |
| (82) | 1 + 6 | 440 | 1.86 | B1 (S)—N-{4-[6-(2-Methoxy-phenyl)-pyrimidin-4-ylamino]-phenyl}-2-methylamino-2-phenyl-acetamide | a | b | b |
| (83) | 1 + 6 | 416 (M − H)⁻ | 1.45 | B1 (R,R)/(S,S)—N-(2-Amino-cyclohexyl)-4-[6-(2-methoxy-phenyl)-pyrimidin-4-ylamino]-benzamide | a | b | b |
| (84) | 1 + 2 | 454 | 2.42 | B1 Benzothiazole-2-carboxylic acid {4-[6-(2-methoxy-phenyl)-pyrimidin-4-ylamino]-phenyl}-amide | b | | c |
| (85) | 1 | 453 | 2.31 | B1 N-{4-[6-(2-Benzyloxy-phenyl)-pyrimidin-4-ylamino]-phenyl}-2,2-dimethyl-propionamide | a | | b |
| (86) | 1 + 6 | 402 (M − H)⁻ | 1.41 | B1 4-[6-(2-Methoxy-phenyl)-pyrimidin-4-ylamino]-N-piperidin-3-yl-benzamide | a | a | a |
| (89) | 1 + 2 | 418 | 1.44 | B1 1-Methyl-piperidine-4-carboxylic acid {4-[6-(2-methoxy-phenyl)-pyrimidin-4-ylamino]-phenyl}-amide | a | b | b |

TABLE 2-continued

Inhibitory effect on CDK9 and CDK2 of compounds according to the present invention

| ① | ② | LCMS | ③ | ④ Nomenclature | ⑤ | ⑥ | ⑦ |
|---|---|---|---|---|---|---|---|
| (90) | 1 + 6 | 374 (M − H)⁻ | 1.34 | B1 (S)-Azetidine-2-carboxylic acid {4-[6-(2-methoxy-phenyl)-pyrimidin-4-ylamino]-phenyl}-amide | a | | b |
| (91) | 1 + 6 | 388 (M − H)⁻ | 1.56 | B1 (R)-Pyrrolidine-2-carboxylic acid {4-[6-(2-methoxy-phenyl)-pyrimidin-4-ylamino]-phenyl}-amide | a | b | b |
| (92) | 1 | 307 | 1.54 | B1 [6-(4-Methoxy-phenyl)-pyrimidin-4-yl]-(2-pyridin-4-yl-ethyl)-amine | c | | c |
| (93) | 1 | 307 | 1.49 | B1 [6-(2-Methoxy-phenyl)-pyrimidin-4-yl]-(2-pyridin-4-yl-ethyl)-amine | b | | c |
| (94) | 1 | 293 | 1.79 | B1 2-[6-(2-Pyridin-4-yl-ethylamino)-pyrimidin-4-yl]-phenol | b | | c |
| (95) | 1 | 397 | 1.8 | B1 4-[6-(2-Benzyloxy-phenyl)-pyrimidin-4-ylamino]-benz-amide | a | b | a |
| (99) | 1 | 335 | 1.72 | B1 [6-(2-Isopropoxy-phenyl)-pyrimidin-4-yl]-(2-pyridin-4-yl-ethyl)-amine | a | | b |
| (100) | 1 | 385 | 1.83 | B1 N-{5-[6-(3-Methoxy-phenyl)-pyrimidin-4-ylamino]-2-methyl-phenyl}-methane-sulfonamide | b | | b |
| (101) | 1 | 454 | 2.08 | B1 2-Dimethylamino-N-{4-[6-(2-methoxy-phenyl)-pyrimidin-4-ylamino]-phenyl}-2-phenyl-acetamide | a | | b |
| (102) | 1 | 364 | 1.33 | C1 3-Amino-N-{4-[6-(2-methoxy-phenyl)-pyrimidin-4-yl-amino]-phenyl}-propionamide | a | a | b |
| (103) | 1 + 12 | 455 | 1.37 | C1 4-Amino-N-(4-{6-[2-(3-amino-propoxy)-phenyl]-pyrimidin-4-ylamino}-phenyl)-benzamide | a | c | b |
| (104) | 1 | 412 | 0.76 | B1 N-{3-[6-(3-Methanesulfonylamino-4-methyl-phenylamino)-pyrimidin-4-yl]-phenyl}-acetamide | a | c | b |
| (105) | 1 | 371 | 1.54 | B1 N-{5-[6-(3-Hydroxy-phenyl)-pyrimidin-4-ylamino]-2-methyl-phenyl}-methane-sulfonamide | a | c | a |
| (106) | 1 | 355 | 1.7 | B1 N-[2-Methyl-5-(6-phenyl-pyrimidin-4-ylamino)-phenyl]-methanesulfonamide | a | c | a |
| (107) | 1 | 423 | 2.16 | B1 N-{2-Methyl-5-[6-(3-trifluoromethyl-phenyl)-pyrimidin-4-ylamino]-phenyl}-methanesulfonamide | c | c | c |
| (108) | 1 | 448 | 1.45 | B1 N-{5-[6-(3-Methanesulfonylamino-phenyl)-pyrimidin-4-ylamino]-2-methyl-phenyl}-methanesulfonamide | b | | a |
| (109) | 1 | 432 | 1.71 | B1 N-{5-[6-(3-Amino-phenyl)-pyrimidin-4-ylamino]-2-methyl-phenyl}-benzene-sulfonamide | a | | b |
| (110) | 1 | 357 | 1.26 | B1 N-[5-([4,5']Bipyrimidinyl-6-ylamino)-2-methyl-phenyl]-methanesulfonamide | b | | b |
| (111) | 1 + 9 | 456 | 1.84 | B1 1-Benzo[1,3]dioxol-5-yl-3-{4-[6-(2-methoxy-phenyl)-pyrimidin-4-ylamino]-phenyl}-urea | | | c |
| (112) | 1 + 9 | 440 | 1.93 | B1 1-{4-[6-(2-Methoxy-phenyl)-pyrimidin-4-ylamino]-phenyl}-3-(4-methyl-benzyl)-urea | a | | c |
| (113) | 1 + 9 | 392 | 1.81 | B1 1-tert-Butyl-3-{4-[6-(2-methoxy-phenyl)-pyrimidin-4-ylamino]-phenyl}-urea | a | | b |
| (114) | 1 | 415 | 2.08 | B1 2,2-Dimethyl-N-{4-[6-(2-trifluoro-methyl-phenyl)-pyrimidin-4-yl-amino]-phenyl}-propionamide | c | | c |
| (115) | 1 | 321 | 1.47 | B1 3-[6-(2-Methoxy-phenyl)-pyrimidin-4-ylamino]-benzamide | a | | a |
| (116) | 1 | 398 | 1.61 | B1 Propane-1-sulfonic acid {5-[6-(3-amino-phenyl)-pyrimidin-4-ylamino]-2-methyl-phenyl}-amide | a | | a |
| (117) | 1 | 342 | 1.07 | C1 4-[6-(3-Amino-phenyl)-pyrimidin-4-ylamino]-benzene-sulfonamide | b | | a |
| (118) | 1 | 392 | 1.66 | B1 N-{4-[6-(2-Methoxy-phenyl)-pyrimidin-4-ylamino]-phenyl}-2-methyl-2-methylamino-propionamide | a | a | b |
| (119) | 1 + 10 | 391 | 1.76 | C1 N-{4-[6-(2-Methoxy-phenyl)-pyrimidin-4-ylamino]-3-methyl-phenyl}-2,2-dimethyl-propionamide | c | | c |
| (120) | 1 + 11 | 462 | 1.68 | C1 N-{5-[6-(3-Amino-phenyl)-pyrimidin-4-ylamino]-2-benzyl-oxy-phenyl}-methane-sulfonamide | b | | b |
| (121) | 1 | 356 | 1.21 | C1 N-{3-[6-(3-Amino-phenyl)-pyrimidin-4-ylamino]-phenyl}-methanesulfonamide | a | | b |
| (122) | 1 | 377 | 1.82 | C1 N-{3-[6-(2-Methoxy-phenyl)-pyrimidin-4-ylamino]-phenyl}-2,2-dimethyl-propionamide | b | | b |
| (123) | 1 | 307 | 1.35 | C1 N*1*-[6-(2-Methoxy-phenyl)-pyrimidin-4-yl]-2-methyl-benzene-1,4-diamine | b | | b |
| (124) | 1 | 293 | 1.43 | C1 N-[6-(2-Methoxy-phenyl)-pyrimidin-4-yl]-benzene-1,3-diamine | a | b | a |
| (125) | 1 | 482 | 1.03 | B1 4-[6-(2-Methoxy-phenyl)-pyrimidin-4-ylamino]-N-(4-morpholin-4-yl-phenyl)-benzamide | a | | b |
| (126) | 1 | 373 | 2.08 | B1 2,2-Dimethyl-N-{4-[6-(2-vinyl-phenyl)-pyrimidin-4-ylamino]-phenyl}-propionamide | b | | c |
| (127) | 1 | 365 | 2.03 | B1 N-{4-[6-(2-Fluoro-phenyl)-pyrimidin-4-ylamino]-phenyl}-2,2-dimethyl-propionamide | c | | c |
| (128) | 1 | 404 | 1.92 | B1 (S)-Piperidine-2-carboxylic acid {3-[6-(2-methoxy-phenyl)-pyrimidin-4-ylamino]-phenyl}-amide | a | b | a |
| (129) | 1 | 465 | 1.26 | B1 2-Oxo-2H-chromene-3-carboxylic acid {4-[6-(2-methoxy-phenyl)-pyrimidin-4-ylamino]-phenyl}-amide | c | | |
| (130) | 1 | 441 | 1.89 | C1 Benzo[1,3]dioxole-5-carboxylic acid {4-[6-(2-methoxy-phenyl)-pyrimidin-4-ylamino]-phenyl}-amide | a | | b |
| (131) | 1 | 375 | 2.13 | C1 N-{4-[6-(2-Ethyl-phenyl)-pyrimidin-4-ylamino]-phenyl}-2,2-dimethyl-propionamide | c | | b |
| (132) | 1 | 423 | 2.19 | C1 N-[4-(6-Biphenyl-2-yl-pyrimidin-4-ylamino)-phenyl]-2,2-dimethyl-propionamide | c | | b |
| (133) | 1 | 436 | 1.07 | C1 1H-Indole-3-carboxylic acid {4-[6-(2-methoxy-phenyl)-pyrimidin-4-ylamino]-phenyl}-amide | a | | b |
| (135) | 1 | 419 | 1.7 | B1 N—((1R,2R)/(1S,2S)-2-Hydroxy-cyclohexyl)-4-[6-(2-methoxy-phenyl)-pyrimidin-4-ylamino]-benz-amide | a | | b |
| (136) | 1 | 413 | 0.91 | B1 N-(4-Hydroxy-phenyl)-4-[6-(2-methoxy-phenyl)-pyrimidin-4-ylamino]-benz-amide | a | | b |
| (137) | 1 | 439 | 1.54 | A1 N-(4-Isopropyl-phenyl)-4-[6-(2-methoxy-phenyl)-pyrimidin-4-ylamino]-benz-amide | b | | c |
| (138) | 1 | 437 | 1.34 | B1 1H-Benzoimidazole-5-carboxylic acid {4-[6-(2-methoxy-phenyl)-pyrimidin-4-ylamino]-phenyl}-amide | b | | c |
| (139) | 1 | 463 | 1.53 | A1 1-Hydroxy-naphthalene-2-carboxylic acid {4-[6-(2-methoxy-phenyl)-pyrimidin-4-ylamino]-phenyl}-amide | a | | b |
| (140) | 1 | 406 | 1.82 | B1 (2S,3S)-2-Amino-3-methyl-pentanoic acid {4-[6-(2-methoxy-phenyl)-pyrimidin-4-ylamino]-phenyl}-amide | a | b | b |
| (141) | 1 | 437 | 2.02 | B1 1H-Indazole-3-carboxylic acid {4-[6-(2-methoxy-phenyl)-pyrimidin-4-ylamino]-phenyl}-amide | b | | |
| (142) | 1 | 483 | 2.89 | B1 Quinoline-8-sulfonic acid {5-[6-(3-amino-phenyl)-pyrimidin-4-ylamino]-2-methyl-phenyl}-amide | a | | c |
| (143) | 1 | 392 | 1.69 | B1 (S)-2-Amino-N-{4-[6-(2-methoxy-phenyl)-pyrimidin-4-ylamino]-phenyl}-3-methyl-butyramide | a | b | b |
| (144) | 1 | 436 | 1.43 | A1 1-Methyl-1H-imidazole-4-sulfonic acid {5-[6-(3-amino-phenyl)-pyrimidin-4-ylamino]-2-methyl-phenyl}-amide | a | | a |
| (145) | 1 | 463 | 2.3 | B1 Hydroxy-naphthalene-2-carboxylic acid {4-[6-(2-methoxy-phenyl)-pyrimidin-4-ylamino]-phenyl}-amide | b | | |

TABLE 2-continued

Inhibitory effect on CDK9 and CDK2 of compounds according to the present invention

| ① | ② | LCMS | ③ | ④ Nomenclature | ⑤ | ⑥ | ⑦ |
|---|---|------|---|---------------|---|---|---|
| (146) | 1 | 476 | 1.81 | C1 2-Amino-N-{4-[6-(2-methoxy-phenyl)-pyrimidin-4-yl-amino]-phenyl}-2-naphthalen-2-yl-acetamide | a | | b |
| (147) | 3 | 391 | 1.63 | B1 {4-[6-(2-Methoxy-phenyl)-pyrimidin-4-ylamino]-phenyl}-morpholin-4-yl-methanone | b | b | |
| (148) | 3 | 418 | 1.76 | C1 N—((1S,2R)/(1R,2S)--2-Amino-cyclohexyl-4-[6-(2-methoxy-phenyl)-pyrimidin-4-ylamino]-benz-amide | a | | b |
| (149) | 1 | 426 | 1.69 | B1 4-Amino-N-{4-[6-(2-methoxy-phenyl)-5-methyl-pyrimidin-4-ylamino]-phenyl}-benzamide | c | | |
| (150) | 1 | 357 | 1.64 | B1 3-[6-(2-Methoxy-phenyl)-pyrimidin-4-ylamino]-benzene-sulfonamide | a | c | a |
| (151) | 1 | 398 | 1.95 | B1 4-Amino-N-{4-[6-(2-hydroxy-phenyl)-pyrimidin-4-ylamino]-phenyl}-benzamide | c | | c |
| (152) | 1 | 307 | 1.51 | B1 N-[6-(2-Methoxy-phenyl)-5-methyl-pyrimidin-4-yl]-benzene-1,4-diamine | c | | c |
| (153) | 1 | 399 | 1.61 | C1 Propane-2-sulfonic acid {4-[6-(2-methoxy-phenyl)-pyrimidin-4-yl-amino]-phenyl}-amide | a | | a |
| (154) | 1 | 399 | 1.6 | C1 Propane-1-sulfonic acid {4-[6-(2-methoxy-phenyl)-pyrimidin-4-yl-amino]-phenyl}-amide | a | | a |
| (155) | 1 | 433 | 1.79 | C1 N-{4-[6-(2-Methoxy-phenyl)-pyrimidin-4-ylamino]-phenyl}-benzenesulfonamide | a | | a |
| (156) | 1 | 461 | 2.09 | C1 N-{5-[6-(2-Benzyloxy-phenyl)-pyrimidin-4-ylamino]-2-methyl-phenyl}-methane-sulfonamide | a | | a |
| (157) | 1 | 398 | 1.7 | C1 N-{5-[6-(3-Dimethylamino-phenyl)-pyrimidin-4-ylamino]-2-methyl-phenyl}-methane-sulfonamide | a | | b |
| (158) | 1 | 413 | 1.78 | C1 N-{5-[6-(2-Isopropoxy-phenyl)-pyrimidin-4-ylamino]-2-methyl-phenyl}-methane-sulfonamide | a | | a |
| (159) | 1 | 519 | 2.31 | B1 N-Bis-propane-1-sulfonic acid-{4-[6-(2-methoxy-phenyl)-5-methyl-pyrimidin-4-yl-amino]-phenyl}-amide | c | | |
| (160) | 1 | 413 | 1.85 | B1 Propane-1-sulfonic acid {4-[6-(2-methoxy-phenyl)-5-methyl-pyrimidin-4-ylamino]-phenyl}-amide | c | | |
| (161) | 3 | 418 | 1.57 | B1 N—(1R,2R)/(1S,2S) (2-Amino-cyclo-hexyl)-4-[6-(4-methoxy-phenyl)-pyrimidin-4-ylamino]-benz-amide | a | | b |
| (162) | 1 | 385 | 1.55 | C1 N-{5-[6-(2-Methoxy-phenyl)-pyrimidin-4-ylamino]-2-methyl-phenyl}-methane sulfonamide | a | | a |
| (163) | 1 | 380 | 1.58 | C1 N-{5-[6-(3-Cyano-phenyl)-pyrimidin-4-ylamino]-2-methyl-phenyl}-methane sulfonamide | b | | b |
| (164) | 1 | 480 | 1.95 | B1 (S)-Piperidine-2-carboxylic acid {4-[6-(2-benzyloxy-phenyl)-pyrimidin-4-ylamino]-phenyl}-amide | a | | a |
| (165) | 1 | 383 | 1.49 | C1 N-{5-[6-(3-Formyl-phenyl)-pyrimidin-4-ylamino]-2-methyl-phenyl}-methane sulfonamide | b | | b |
| (166) | 1 | 385 | 1.34 | C1 N-{5-[6-(2-Hydroxymethyl-phenyl)-pyrimidin-4-ylamino]-2-methyl-phenyl}-methane sulfonamide | b | | |
| (167) | 1 | 404 | 1.61 | B1 (S)-Piperidine-2-carboxylic acid {4-[6-(4-methoxy-phenyl)-pyrimidin-4-ylamino]-phenyl}-amide | b | | |
| (168) | 1 | 402 | 1.5 | B1 (S)-Piperidine-2-carboxylic acid {4-[6-(3-formyl-phenyl)-pyrimidin-4-ylamino]-phenyl}-amide | b | b | |
| (169) | 1 | 417 | 1.72 | B1 (S)-Piperidine-2-carboxylic acid {4-[6-(3-dimethyl-amino-phenyl)-pyrimidin-4-yl-amino]-phenyl}-amide | b | | |
| (170) | 1 | 404 | 1.36 | B1 (S)-Piperidine-2-carboxylic acid {4-[6-(2-hydroxy-methyl-phenyl)-pyrimidin-4-yl-amino]-phenyl}-amide | b | | |
| (171) | 1 | 405 | 1.45 | B1 (S)-Piperidine-2-carboxylic acid {4-[6-(2-methoxy-pyridin-3-yl)-pyrimidin-4-yl-amino]-phenyl}-amide | a | b | b |
| (172) | 1 | 405 | 1.45 | B1 (S)-Piperidine-2-carboxylic acid {4-[6-(6-methoxy-pyridin-3-yl)-pyrimidin-4-ylamino]-phenyl}-amide | b | | |
| (173) | 1 | 480 | 2.1 | B1 (S)-Piperidine-2-carboxylic acid {4-[6-(4-benzyloxy-phenyl)-pyrimidin-4-ylamino]-phenyl}-amide | c | | |
| (174) | 1 | 466 | 1.94 | B1 (S)-Piperidine-2-carboxylic acid {4-[6-(4-phenoxy-phenyl)-pyrimidin-4-ylamino]-phenyl}-amide | a | | b |
| (175) | 1 | 385 | 1.16 | C1 N-{5-[6-(4-Hydroxymethyl-phenyl)-pyrimidin-4-ylamino]-2-methyl-phenyl}-methane-sulfonamide | b | | |
| (176) | 1 | 386 | 1.43 | C1 N-{5-[6-(2-Methoxy-pyridin-3-yl)-pyrimidin-4-ylamino]-2-methyl-phenyl}-methane-sulfonamide | a | | b |
| (177) | 1 | 431 | 1.3 | C1 (S)-Piperidine-2-carboxylic acid {4-[6-(4-acetylamino-phenyl)-pyrimidin-4-ylamino]-phenyl}-amide | b | | |
| (178) | 1 | 467 | 1.37 | B1 (S)-Piperidine-2-carboxylic acid {4-[6-(3-methanesulfonyl-amino-phenyl)-pyrimidin-4-ylamino]-phenyl}-amide | a | | |
| (179) | 1 | 416 | 1.43 | B1 (S)-Piperidine-2-carboxylic acid {4-[6-(3-acetyl-phenyl)-pyrimidin-4-yl-amino]-phenyl}-amide | c | | |
| (180) | 1 | 485 | 1.62 | B1 (S)-Piperidine2-carboxylic acid {4-[6-(4-cyclopentyl-carbamoyl-phenyl)-pyrimidin-4-yl-amino]-phenyl}-amide | b | | |
| (181) | 1 | 371 | 1.89 | C1 N-{5-[6-(2-Hydroxy-phenyl)-pyrimidin-4-ylamino]-2-methyl-phenyl}-methane-sulfonamide | a | | a |
| (182) | 1 | 439 | 1.85 | C1 (E)-3-{3-[6-(3-Methanesulfonylamino-4-methyl-phenyl-amino)-pyrimidin-4-yl]-phenyl}-acrylic acid methyl ester | b | | b |
| (183) | 1 | 385 | 1.34 | C1 N-{5-[6-(3-Hydroxymethyl-phenyl)-pyrimidin-4-ylamino]-2-methyl-phenyl}-methane-sulfonamide | b | | b |
| (184) | 1 | 413 | 2.22 | C1 N-Butyl-3-[6-(2-methoxy-phenyl)-pyrimidin-4-ylamino]-benzenesulfonamide | a | | b |
| (185) | 1 | 356 | 1.81 | C1 (3-Methanesulfonyl-phenyl)-[6-(2-methoxy-phenyl)-pyrimidin-4-yl]-amine | a | | a |
| (186) | 1 | 433 | 1.59 | B1 (S)-Piperidine-2-carboxylic acid {4-[6-(2,3-dimethoxy-phenyl)-pyrimidin-4-ylamino]-phenyl}-amide | b | b | c |
| (187) | 1 | 433 | 1.64 | B1 (S)-Piperidine-2-carboxylic acid {4-[6-(2,4-dimethoxy-phenyl)-pyrimidin-4-ylamino]-phenyl}-amide | a | a | b |
| (188) | 1 | 432 | 1.85 | B1 (S)-Piperidine-2-carboxylic acid {4-[6-(2-isopropoxy-phenyl)-pyrimidin-4-ylamino]-phenyl}-amide | a | a | b |
| (189) | 1 | 420 | 1.63 | B1 (S)-Piperidine-2-carboxylic acid {4-[6-(2-methylsulfanyl-phenyl)-pyrimidin-4-ylamino]-phenyl}-amide | a | a | b |
| (190) | 1 | 458 | 1.84 | B1 (S)-Piperidine-2-carboxylic acid {4-[6-(2-trifluoromethoxy-phenyl)-pyrimidin-4-ylamino]-phenyl}-amide | b | b | |

TABLE 2-continued

Inhibitory effect on CDK9 and CDK2 of compounds according to the present invention

| ① | ② | LCMS | ③ | ④ Nomenclature | ⑤ | ⑥ | ⑦ |
|---|---|---|---|---|---|---|---|
| (191) | 1 | 422 | 1.55 | B1 (S)-Piperidine-2-carboxylic acid {4-[6-(5-acetyl-thio-phen-2-yl)-pyrimidin-4-ylamino]-phenyl}-amide | b | | |
| (192) | 1 | 408 | 1.65 | B1 (S)-Piperidine-2-carboxylic acid {4-[6-(2-chloro-phenyl)-pyrimidin-4-yl-amino]-phenyl}-amide | a | | c |
| (193) | 1 | 404 | 1.31 | B1 (S)-Piperidine-2-carboxylic acid {4-[6-(3-hydroxy-methyl-phenyl)-pyrimidin-4-ylamino]-phenyl}-amide | b | | |
| (194) | 3 | 404 | 1.34 | B1 N—((1R,2R)/(1S,2S)-2-Amino-cyclo-hexyl)-4-[6-(3-hydroxy-phenyl)-pyrimidin-4-yl-amino]-benzamide | b | | |
| (195) | 3 | 481 | 1.36 | B1 N—((1R,2R)/(1S,2S)-2-Amino-cyclohex-yl)-4-[6-(3-methane sulfonylamino-phenyl)-pyrimidin-4-ylamino]-benzamide | a | | b |
| (196) | 3 | 445 | 1.44 | B1 4-[6-(2-Acetyl-amino-phenyl)-pyrimidin-4-yl-amino]-N—((1R,2R)/(1S,2S)-2-amino-cyclohexyl)-benz-amide | | | |
| (197) | 1 | 399 | 1.71 | B1 N-{5-[6-(2-Methoxymethyl-phenyl)-pyrimidin-4-ylamino]-2-methyl-phenyl}-methane-sulfonamide | b | | |
| (198) | 3 | 494 | 1.91 | B1 N—((1R,2R)/(1S,2S)-2-Amino-cyclohexyl)-4-[6-(2-benzyloxy-phenyl)-pyrimidin-4-yl-amino)-benzamide | a | a | a |
| (199) | 3 | 446 | 1.81 | B1 N—((1R,2R)/(1S,2S)-2-Amino-cyclohex-yl)-4-[6-(2-isopro-poxy-phenyl)-pyrimidin-4-ylamino]-benzamide | a | b | b |
| (200) | 1 | 426 | 1.75 | B1 4-Amino-N-{4-[6-(4-methoxy-phenyl)-5-methyl-pyrimidin-4-ylamino]-phenyl}-benzamide | c | | |
| (201) | 3 | 446 | 1.67 | B1 3-{6-[4-((1R,2R)/(1S,2S)-2-Amino-cyclohexylcarbamoyl)-phenylamino]-pyrimidin-4-yl}-benzoic acid methyl ester | b | | |
| (202) | 1 | 406 | 1.26 | B1 (S)-Piperidine-2-carboxylic acid {4-[6-(4-methoxy-phenyl)-pyrimidin-4-ylamino]-phenyl}-amide | c | | |
| (203) | 1 | 418 | 1.48 | B1 (S)-Piperidine-2-carboxylic acid {4-[6-(3-methoxymethyl-phenyl)-pyrimidin-4-ylamino]-phenyl}-amide | b | | |
| (204) | 1 | 307 | 1.59 | B1 N-[6-(2-Methoxy-phenyl)-2-methyl-pyrimidin-4-yl]-benzene-1,4-diamine | c | | |
| (205) | 1 | 307 | 1.68 | B1 N-[6-(4-Methoxy-phenyl)-2-methyl-pyrimidin-4-yl]-benzene-1,4-diamine | c | | |
| (206) | 3 | 403 | 1.27 | B1 N—((1R,2R)/(1S,2S)-2-Amino-cyclohexyl)-4-[6-(3-amino-phenyl)-pyrimidin-4-ylamino]-benzamide | b | | |
| (207) | 3 | 445 | 1.3 | B1 4-[6-(3-Acetylamino-phenyl)-pyrimidin-4-ylamino]-N—((1R,2R)/(1S,2S)-2-amino-cyclohexyl)-benzamide | b | | |
| (208) | 3 | 494 | 2.09 | B1 N—((1R,2R)/(1S,2S)-2-Amino-cyclohexyl)-4-[6-(4-benzyloxy-phenyl)-pyrimidin-4-ylamino]-benzamide | c | | |
| (209) | 3 | 413 | 1.59 | B1 N—((1R,2R)/(1S,2S)-2-Amino-cyclohexyl)-4-[6-(3-cyano-phenyl)-pyrimidin-4-ylamino]-benzamide | b | | |
| (210) | 3 | 432 | 1.49 | B1 N—((1R,2R)/(1S,2S)-2-Amino-cyclohexyl)-4-[6-(2-methoxymethyl-phenyl)-pyrimidin-4-ylamino]-benzamide | b | | |
| (211) | 3 | 431 | 1.58 | B1 (S)-Piperidine-2-carboxylic acid {4-[6-(3-dimethylaminomethyl-phenyl)-pyrimidin-4-ylamino]-phenyl}-amide | b | | |
| (212) | 3 | 439 | 1.53 | B1 N—((1R,2R)/(1S,2S)-2-Amino-cyclohexyl)-4-(6-quinolin-3-yl-pyrimidin-4-ylamino)-benzamide | c | | |
| (213) | 3 | 420 | 1.28 | B1 N—((1R,2R)/(1S,2S)-2-Amino-cyclohexyl)-4-(2'-methoxy-[4,5']bipyrimidinyl-6-ylamino)-benzamide | c | | |
| (214) | 1 | 342 | 1.31 | B1 3-[6-(3-Amino-phenyl)-pyrimidin-4-ylamino]-benzenesulfonamide | a | | b |
| (215) | 1 | 357 | 1.45 | B1 3-[6-(4-Methoxy-phenyl)-pyrimidin-4-ylamino]-benzenesulfonamide | a | | a |
| (216) | 1 | 418 | 2.43 | B2 (R,R)—N-(2-Amino-cyclohexyl)-4-[6-(2-hydroxymethyl-phenyl)-pyrimidin-4-ylamino]-benzamide | | | |
| (217) | 1 | 420 | 3.05 | B2 N-(2-Diethylamino-ethyl)-4-[6-(2-methoxy-phenyl)-pyrimidin-4-ylamino]-benzamide | b | | |
| (218) | 1 | 404 | 3.1 | B2 (R,R)—N-(2-Amino-cyclohexyl)-4-[6-(2-hydroxy-phenyl)-pyrimidin-4-ylamino]-benzamide | b | | |
| (219) | 1 | 419 | 1.46 | B1 (R,R)—N-(2-Amino-cyclohexyl)-4-[6-(2-methoxy-pyridin-3-yl)-pyrimidin-4-ylamino]-benzamide | c | | |
| (220) | 1 | 445 | 1.76 | B1 (R,R)—N-(2-Amino-cyclohexyl)-4-[6-(5-dimethylaminomethyl-pyridin-3-yl)-pyrimidin-4-ylamino]-benzamide | | | |
| (221) | 1 | 459 | 1.28 | B1 (R,R)-5-{6-[4-(2-Amino-cyclohexylcarbamoyl)-phenylamino]-pyrimidin-4-yl}-pyridine-2-carboxylic acid dimethylamide | | | |
| (222) | 1 | 434 | 1.78 | B1 (R,R)—N-(2-Amino-cyclohexyl)-4-[6-(6-methylsulfanyl-pyridin-3-yl)-pyrimidin-4-ylamino]-benzamide | | | |
| (223) | 1 | 417 | 1.41 | B1 (R,R)—N-(2-Amino-cyclohexyl)-4-[6-(5-aminomethyl-pyridin-3-yl)-pyrimidin-4-ylamino]-benzamide | | | |
| (224) | 1 | 434 | 1.59 | B1 (R,R)—N-(2-Amino-cyclohexyl)-4-[6-(4-methylsulfanyl-pyridin-3-yl)-pyrimidin-4-ylamino]-benzamide | b | | |
| (225) | 1 | 418 | 1.26 | B1 N-(2-Amino-cyclohexyl)-4-[6-(5-hydroxymethyl-pyridin-3-yl)-pyrimidin-4-ylamino]-benzamide | | | |
| (226) | 3 | 390 | 5.33 | D2 rac-4-[6-(2-Methoxy-phenyl)-pyrimidin-4-ylamino]-N-pyrrolidin-3-yl-benzamide | | | |
| (227) | 1 | 431 | 2.85 | B2 (R,R)—N-(2-Amino-cyclohexyl)-4-[6-(5-dimethyamino-pyridin-3-yl)-pyrimidin-4-ylamino]-benzamide | | | |
| (228) | 1 | 436 | 1.52 | B1 (R,R)-4-[6-(5-Acetyl-thiophen-2-yl)-pyrimidin-4-ylamino]-N-(2-amino-cyclohexyl)-benzamide | | | |
| (229) | 1 | 496 | 3.66 | B2 [6-(2-Methoxy-phenyl)-pyrimidin-4-yl]-[3-(piperidine-1-sulfonyl)-phenyl]-amine N-(2-diethylamino-ethyl)-benzamide | a | | |
| (230) | 1 | 430 | 1.43 | B1 (R,R)-4-[6-(2-Acetyl-phenyl)-pyrimidin-4-ylamino]-N-(2-amino-cyclohexyl)-benzamide | | | |
| (231) | 3 | 398 | 6.63 | D2 4-[6-(2-Methoxy-phenyl)-pyrimidin-4-ylamino]-N-pyridin-3-yl-benzamide | | | |
| (232) | 1 | 446 | 2.73 | B2 N-(1-Acetyl-piperidin-3-yl)-4-[6-(2-methoxy-phenyl)-pyrimidin-4-ylamino]-benzamide | | | |
| (233) | 1 | 431 | 2.89 | B2 (R,R)—N-(2-Amino-cyclohexyl)-4-[6-(2-dimethylamino-phenyl)-pyrimidin-4-ylamino]-benzamide | b | | |

TABLE 2-continued

Inhibitory effect on CDK9 and CDK2 of compounds according to the present invention

| ① | ② | LCMS | ③ | ④ Nomenclature | ⑤ | ⑥ | ⑦ |
|---|---|---|---|---|---|---|---|
| (234) | 8A | 548 | 7.55 | D2 4-{4-[6-(2-Methoxy-phenyl)-pyrimidin-4-ylamino]-benzoylamino}-pyrrolidine-1,2-dicarboxylic acid 1-tert-butyl ester 2-methyl ester | | | |
| (235) | 1 | 391 | 3.06 | B2 2-Chloro-5-[6-(2-methoxy-phenyl)-pyrimidin-4-ylamino]-benzenesulfonamide | | | |
| (236) | 1 | 425 | 3.75 | B2 [6-(2-Methoxy-phenyl)-pyrimidin-4-yl]-[3-(piperidine-1-sulfonyl)-phenyl]-amine | | | |
| (237) | 1 | 397 | 3.29 | B2 N-Allyl-3-[6-(2-methoxy-phenyl)-pyrimidin-4-ylamino]-benzenesulfonamide | | | |
| (238) | 1 | 447 | 3.56 | B2 N-Benzyl-3-[6-(2-methoxy-phenyl)-pyrimidin-4-ylamino]-benzenesulfonamide | | | |
| (239) | 1 | 411 | 3.8 | B2 [6-(2-Methoxy-phenyl)-pyrimidin-4-yl]-[3-(pyrrolidine-1-sulfonyl)-phenyl]-amine | | | |
| (240) | 1 | 427 | 3.31 | B2 [6-(2-Methoxy-phenyl)-pyrimidin-4-yl]-[3-(morpholine-4-sulfonyl)-phenyl]-amine | | | |
| (241) | 1 | 371 | 3.08 | B2 3-[6-(2-Methoxy-phenyl)-pyrimidin-4-ylamino]-N-methyl-benzenesulfonamide | | | |
| (242) | 1 | 399 | 2.83 | B2 N-[6-(2-Methoxy-phenyl)-pyrimidin-4-yl]-N-(3-sulfamoyl-phenyl)-acetamide | | | |
| (243) | 1 | 437 | 3.84 | B2 N,N-Diallyl-3-[6-(2-methoxy-phenyl)-pyrimidin-4-ylamino]-benzensulfonamide, | | | |
| (244) | 1 | 433 | 3.24 | B2 3-[6-(2-Benzyloxy-phenyl)-pyrimidin-4-ylamino]-benzenesulfonamide | | | |
| (245) | 1 | 465 | 3.69 | B2 [6-(2-Methoxy-phenyl)-pyrimidin-4-yl]-[4-(4-nitro-benzenesulfonyl)-phenyl]-amine | | | |
| (246) | 1 | 410 | 3.98 | B2 [6-(2-Methoxy-phenyl)-pyrimidin-4-yl]-(4-trifluoromethanesulfonyl-phenyl)-amine | | | |
| (247) | 1 | 356 | 3.07 | B2 (4-Methanesulfonyl-phenyl)-[6-(2-methoxy-phenyl)-pyrimidin-4-yl]-amine | | | |
| (248) | 1 | 452 | 2.34 | B2 N-(3,4-Dimethyl-isoxazol-5-yl)-4-[6-(2-methoxy-phenyl)-pyrimidin-4-ylamino]-benzenesulfonamide | | | |
| (249) | 1 | 399 | 3.37 | B2 4-[6-(2-Methoxy-phenyl)-pyrimidin-4-ylamino]-N-propyl-benzenesulfonamide | | | |
| (250) | 1 | 357 | 2.84 | B2 4-[6-(2-Methoxy-phenyl)-pyrimidin-4-ylamino]-benzenesulfonamide | | | |
| (251) | 1 | 385 | 3.38 | B2 4-[6-(2-Methoxy-phenyl)-pyrimidin-4-ylamino]-N,N-dimethyl-benzenesulfonamide | | | |
| (252) | 1 | 415 | 3.09 | B2 N-(2-Methoxy-ethyl)-4-[6-(2-methoxy-phenyl)-pyrimidin-4-ylamino]-benzenesulfonamide | | | |
| (253) | 1 | 432 | 3.49 | B2 [6-(2-Benzyloxy-phenyl)-pyrimidin-4-yl]-(3-methanesulfonyl-phenyl)-amine | | | |
| (254) | 1 | 342 | 3.31 | B2 2-[6-(3-Methanesulfonyl-phenylamino)-pyrimidin-4-yl]-phenol | | | |
| (255) | 1 | 341 | 2.62 | B2 [6-(3-Amino-phenyl)-pyrimidin-4-yl]-(3-methanesulfonyl-phenyl)-amine | | | |
| (256) | 1 | 372 | 2.42 | B2 5-[6-(2-Methoxy-phenyl)-pyrimidin-4-ylamino]-2-methyl-benzenesulfonic acid | | | |
| (257) | 1 | 386 | 2.77 | B2 2-{3-[6-(2-Methoxy-phenyl)-pyrimidin-4-ylamino]-benzenesulfonyl}-ethanol | | | |
| (258) | 1 | 374 | 3.1 | B2 (2-Fluoro-5-methanesulfonyl-phenyl)-[6-(2-methoxy-phenyl)-pyrimidin-4-yl]-amine | | | |
| (259) | 1 | 341 | 2.97 | B2 [6-(2-Amino-phenyl)-pyrimidin-4-yl]-(3-methanesulfonyl-phenyl)-amine | | | |
| (260) | 1 | 410 | 3.92 | B2 [6-(2-Methoxy-phenyl)-pyrimidin-4-yl]-(3-trifluoromethanesulfonyl-phenyl)-amine | | | |
| (261) | 1 | 418 | 3.54 | B2 (3-Methanesulfonyl-phenyl)-[6-(2-Phenoxy-phenyl)-pyrimidin-4-yl]-amine | | | |
| (262) | 1 | 398 | 3.55 | B2 [6-(2-Butoxy-phenyl)-pyrimidin-4-yl]-(3-methanesulfonyl-phenyl)-amine | | | |
| (263) | 1 | 368 | 3.29 | B2 (3-Ethenesulfonyl-phenyl)-[6-(2-methoxy-phenyl)-pyrimidin-4-yl]-amine | | | |
| (264) | 1 | 420 | 1.81 | B1 (S)-Piperidine-2-carboxylic acid {4-[6-(4-methylsulfanyl-phenyl)-pyrimidin-4-ylamino]-phenyl}-amide | | | |
| (265) | 1 | 370 & 372 | 4.28 | D1 2-Chloro-4-[6-(2-methoxy-phenyl)-pyrimidin-4-ylamino]-benzoic acid methyl ester | | | |
| (266) | 1 | 384 | 3.82 | B2 [6-(2-Methoxy-phenyl)-pyrimidin-4-yl]-(4-phenoxy-benzyl)-amine | | | |
| (267) | 1 | 350 | 3.98 | D1 4-[6-(2-Methoxy-phenyl)-pyrimidin-4-ylamino]-3-methyl-benzoic acid methyl ester | | | |
| (268) | 1 + 2 | 382 | 5.87 | D2 [6-(3-Amino-phenyl)-pyrimidin-4-yl]-(1-methanesulfonyl-2,3-dihydro-1H-indol-6-yl)-amine | | | |
| (269) | 1 | 385 | 3.36 | B2 3-[6-(2-Methoxy-phenyl)-pyrimidin-4-ylamino]-piperidine-1-carboxylic acid tert-butyl ester | | | |
| (270) | 1 | 336 | 2.11 | B2 {4-[6-(2-Methoxy-phenyl)-pyrimidin-4-ylamino]-phenyl}-acetic acid | | | |
| (271) | 1 | 318 | 2.87 | B2 (1H-Indazol-6-yl)-[6-(2-methoxy-phenyl)-pyrimidin-4-yl]-amine | | | |
| (272) | 1 | 348 | 3.81 | B2 1-{4-[6-(2-Methoxy-phenyl)-pyrimidin-4-ylamino]-phenyl}-butan-1-one | | | |
| (273) | 1 | 285 | 2.49 | B2 [6-(2-Methoxy-phenyl)-pyrimidin-4-yl]-piperidin-3-yl-amine | | | |
| (274) | 1 | 382 | 3.98 | B2 {4-[6-(2-Methoxy-phenyl)-pyrimidin-4-ylamino]-phenyl}-phenyl-methanone | | | |
| (275) | 1 | 369 | 3.9 | B2 N-[6-(2-Methoxy-phenyl)-pyrimidin-4-yl]-N'-phenyl-benzene-1,3-diamine | | | |
| (276) | 1 | 364 | 3.31 | B2 (3-[1,3]Dioxan-2-yl-phenyl)-[6-(2-methoxy-phenyl)-pyrimidin-4-yl]-amine | | | |
| (277) | 1 | 308 | 3.46 | B2 (3-Methoxy-phenyl)-[6-(2-methoxy-phenyl)-pyrimidin-4-yl]-amine | | | |
| (278) | 1 | 308 | 3.29 | B2 (4-Methoxy-phenyl)-[6-(2-Methoxy-phenyl)-pyrimidin-4-yl]-amine | | | |
| (279) | 1 | 369 | 3.81 | C2 N-[6-(2-Methoxy-phenyl)-pyrimidin-4-yl]-N'-phenyl-benzene-1,4-diamine | | | |
| (280) | 1 | 363 | 3.16 | B2 [6-(2-Methoxy-phenyl)-pyrimidin-4-yl]-(4-morpholin-4-yl-phenyl)-amine | b | | |
| (281) | 1 | 296 | 3.43 | B2 (2-Fluoro-phenyl)-[6-(2-methoxy-phenyl)-pyrimidin-4-yl]-amine | | | |
| (282) | 1 | 375 | 3.41 | B2 (1-Benzyl-piperidin-4-yl)-[6-(2-Methoxy-phenyl)-pyrimidin-4-yl]-amine | | | |
| (283) | 1 | 334 | 4.29 | B2 (4-Butyl-phenyl)-[6-(2-methoxy-phenyl)-pyrimidin-4-yl]-amine | | | |
| (284) | 1 | 370 | 3.98 | B2 [6-(2-Methoxy-phenyl)-pyrimidin-4-yl]-(4-phenoxy-phenyl)-amine | | | |
| (285) | 1 | 371 | 2.66 | B2 4-{[6-(2-Methoxy-phenyl)-pyrimidin-4-ylamino]-methyl}-benzenesulfonamide | | | |
| (286) | 1 | 395 | 3.17 | B2 rac-1-Dimethylamino-3-{4-[6-(2-methoxy-phenyl)-pyrimidin-4-ylamino]-phenoxy}-propan-2-ol | | | |
| (287) | 1 | 307 | 2.72 | B1 N-[6-(4-Methoxy-phenyl)-5-methyl-pyrimidin-4-yl]-benzene-1,4-amine | | | |
| (288) | 1 | 292 | 2.45 | B1 N-[6-(3-Amino-phenyl)-5-methyl-pyrimidin-4-yl]-benzene-1,4-diamine | | | |
| (289) | 1 | 285 | 2.5 | B2 [6-(2-Methoxy-phenyl)-pyrimidin-4-yl]-piperidin-4-yl-amine | | | |
| (290) | 1 | 461 | 3.98 | B2 4-[6-(2-Benzyloxy-phenyl)-pyrimidin-4-ylamino]-piperidine-1-carboxylic acid tert-butyl ester | | | |
| (291) | 1 | 284 | 3.5 | B2 Cyclohexyl-[6-(2-methoxy-phenyl)-pyrimidin-4-yl]-amine | | | |
| (292) | 9A | 433 (M − H)− | 7.05 | D2 4-{6-[2-(2-Morpholin-4-yl-ethoxy)-phenyl]-pyrimidin-4-ylamino}-benzoic acid methyl ester | | | |
| (293) | 1 | 366 | 3.75 | D1 2-Methoxy-4-[6-(2-methoxy-phenyl)-pyrimidin-4-ylamino]-benzoic acid methyl ester | | | |
| (294) | 1 | 412 | 2.42 | B2 {4-[6-(2-Benzyloxy-phenyl)-pyrimidin-4-ylamino]-phenyl}-acetic acid | b | | |
| (295) | 1 | 323 | 3.6 | B2 [6-(2-Methoxy-phenyl)-pyrimidin-4-yl]-(3-nitro-phenyl)-amine | | | |
| (296) | 1 | 308 | 2.79 | B2 {3-[6-(2-Methoxy-phenyl)-pyrimidin-4-ylamino]-phenyl}-methanol | | | |
| (297) | 1 | 354 | 3.87 | B2 [6-(2-Benzyloxy-phenyl)-pyrimidin-4-yl]-phenyl-amine | | | |
| (298) | 1 | 278 | 3.43 | B2 [6-(2-Methoxy-phenyl)-pyrimidin-4-yl]-phenyl-amine | | | |
| (299) | 1 | 296 | 3.45 | B2 (4-Fluorophenyl)-[6-(2-methoxy-phenyl)-pyrimidin-4-yl]-amine | | | |
| (300) | 1 | 370 | 4.07 | B2 [6-(2-Methoxy-phenyl)-pyrimidin-4-yl]-(3-phenoxy-phenyl)-amine | | | |
| (301) | 1 | 324 | 3.71 | B2 [6-(2-Methoxy-phenyl)-pyrimidin-4-yl]-(3-methylsulfanyl-phenyl)-amine | | | |
| (302) | 1 | 361 | 3.32 | B2 [6-(2-Benzyloxy-phenyl)-pyrimidin-4-yl]-piperidin-4-yl-amine | | | |

TABLE 2-continued

Inhibitory effect on CDK9 and CDK2 of compounds according to the present invention

| ① | ② | LCMS | ③ | ④ Nomenclature | ⑤ | ⑥ | ⑦ |
|---|---|---|---|---|---|---|---|
| (303) | 1 | 294 | 2.89 | B2 3-[6-(2-Methoxy-phenyl)-pyrimidin-4-ylamino]-phenol | | | |
| (304) | 1 | 320 | 3.31 | B2 1-{4-[6-(2-Methoxy-phenyl)-pyrimidin-4-ylamino]-phenyl}-ethanone | | | |
| (305) | 1 | 356 & 358 | 2.42 | D1 2-Chloro-4-[6-(2-methoxy-phenyl)-pyrimidin-4-ylamino]-benzoic acid | | | |
| (306) | 1 | 371 (M − H)⁻ | 4.93 | D1 {4-[6-(2-Methoxy-phenyl)-pyrimidin-4-ylamino]-butyl}-carbamic acid tert-butyl ester | | | |
| (307) | 1 + 2 | 473 | 8.87 | D3 [6-(2-Benzyloxy-phenyl)-pyrimidin-4-yl]-(1-methanesulfonyl-2,3-dihydro-1H-indol-6-yl)-amine | | | |
| (308) | 1 | 385 | 3.41 | B2 4-[6-(2-Methoxy-phenyl)-pyrimidin-4-ylamino]-piperidine-1-carboxylic acid tert-butyl ester | | | |
| (309) | 1 | 321 | 7.42 | D2 4-[6-(2-Amino-phenyl)-pyrimidin-4-ylamino]-benzoic acid methyl ester | | | |
| (310) | 1 | 324 | 3.8 | B2 [6-(2-Methoxy-phenyl)-pyrimidin-4-yl]-(4-methylsulfanyl-phenyl)-amine | | | |
| (311) | 1 | 273 | 2.2 | D1 N¹-[6-(2-Methoxy-phenyl)-pyrimidin-4-ylamino]-butane-1,4-diamine | | | |
| (312) | 1 | 471 | 3.74 | B2 1-{4-[6-(2-Benzyloxy-phenyl)-pyrimidin-4-ylamino]-phenoxy}-3-dimethylamino-propan-2-ol | | | |
| (313) | 1 + 2 | 397 | 3.6 | D1 (1-Methanesulfonyl-2,3-dihydro-1H-indol-6-yl)-[6-(2-methoxy-phenyl)-pyrimidin-4-yl]-amine | | | |
| (314) | 1 | 445 | 2.69 | B2 N-(2-Amino-cyclohexyl)-4-[6-(benzotriazol-1-yloxy)-pyrimidin-4-ylamino]-benzamide | | | |
| (315) | 1 | 545 | 2.02 | B2 (2-{4-[6-(Benzotriazol-1-yloxy)-pyrimidin-4-ylamino]-benzoylamino}-cyclohexyl)-carbamic acid tert-butyl ester | | | |
| (316) | 1 | 320 | 3.41 | C2 1-{3-[6-(2-Methoxy-phenyl)-pyrimidin-4-ylamino]-phenyl}-ethanone | | | |
| (317) | 1 | 361 | 3.96 | C2 [6-(2-Methoxy-phenyl)-pyrimidin-4-yl]-(4-piperidin-1-yl-phenyl)-amine | | | |
| (318) | 1 | 352 | 3.72 | D1 3-Hydroxy-4-[6-(2-methoxy-phenyl)-pyrimidin-4-ylamino]-benzoic acid methyl ester | | | |
| (319) | 1 | 352 | 4.25 | D1 2-Hydroxy-4-[6-(2-methoxy-phenyl)-pyrimidin-4-ylamino]-benzoic acid methyl ester | | | |
| (320) | 10A | 442 | 5.87 | D4 4-Amino-butane-1-sulfonic acid {5-[6-(2-methoxy-phenyl)-pyrimidin-4-ylamino]-2-methyl-phenyl}-amide | | | |
| (321) | 1 | | | (3-{6-[3-(4-Amino-butane-1-sulfonylamino)-4-methyl-phenylamino]-pyrimidin-4-yl}-phenyl)-carbamic acid 9H-fluoren-9-ylmethyl ester | | | |
| (322) | 1 | 366 | 4.22 | D1 3-Methoxy-4-[6-(2-methoxy-phenyl)-pyrimidin-4-ylamino]-benzoic acid methyl ester | | | |
| (323) | 9A | 434 | 5.67 | D3 4-{6-[2-(2-Piperidin-1-yl-ethoxy)-phenyl]-pyrimidin-4-ylamino}-benzoic acid methyl ester | | | |
| (324) | 9A | 393 | 5.37 | D3 4-{-6-[2-(2-Dimethylamino-ethoxy)-phenyl]-pyrimidin-4-ylamino}-benzoic acid methyl ester | | | |
| (325) | 9A | 449 | 5.2 | D3 4-{-6-[2-(2-Diisopropylamino-ethoxy)-phenyl]-pyrimidin-4-ylamino}-benzoic acid methyl ester | | | |
| (326) | 9A | 422 | 5.67 | D3 4-{-6-[2-(2-Diethylamino-ethoxy)-phenyl]-pyrimidin-4-ylamino}-benzoic acid methyl ester | | | |
| (327) | 8A | 448 | 4.03 | D2 (S,S)-4-{4-[6-(2-Methoxy-phenyl)-pyrimidin-4-ylamino]-benzoylamino}-pyrrolidine-2-carboxylic acid methyl ester | | | |
| (328) | 8A | 434 | 4.52 | D5 (S,S)-4-{4-[6-(2-Methoxy-phenyl)-pyrimidin-4-ylamino]-benzoylamino}-pyrrolidine-2-carboxylic acid | | | |
| (329) | 8A | 547 | 5.95 | D3 (S,S)-6-[(4-{4-[6-(2-Methoxy-phenyl)-pyrimidin-4-ylamino]-benzoylamino}-pyrrolidine-2-carbonyl)-amino]-hexanoic acid | | | |
| (330) | 3 | 389 | 7.32 | D2 N-Cyclopentyl-4-[6-(2-methoxy-phenyl)-pyrimidin-4-ylamino]-benzamide | | | |
| (331) | 1 | 357 | 2.82 | B2 3-[6-(2-Methoxy-phenyl)-pyrimidin-4-ylamino]-benzenesulfonamide | c | | |
| (332) | 1 | 356 | 3.70 | B2 (3-Methanesulfonyl-phenyl)-[6-(2-Methoxy-phenyl)-pyrimidin-4-yl]-amine | | | |
| (333) | 1 | 386 | 2.77 | B2 2-{3-[6-(2-Methoxy-phenyl)-pyrimidin-4-ylamino]-benzenesulfoyl}-ethanol | | | |
| (334) | 1 | 463 | 2.70 | B2 N-(4,6-Dimethyl-pyrimidin-2-yl)-4-[6-(2-methoxy-phenyl)-pyrimidin-4-ylamino]-benzenesulfonamide | | | |
| (335) | 1 | 440 | 2.54 | B2 4-[6-(2-Methoxy-phenyl)-pyrimidin-4-ylamino]-N-thiazol-2-yl-benzenesulfonamide | | | |
| (336) | 1 | 375 | 3.63 | B2 (1-Benzyl-piperidin-3-yl)-[6-(2-methoxy-phenyl)-pyrimidin-4-yl]-amine | | | |
| (337) | 1 | 313 | 2.62 | B2 3-[6-(2-Methoxy-phenyl)-pyrimidin-4-ylamino]-azepan-2-one | | | |
| (338) | 1 | 433 | 3.49 | B2 4-[6-(2-Methoxy-phenyl)-pyrimidin-4-ylamino]-N-phenyl-benzenesulfonamide | | | |
| (339) | 1 | 332 | 3.77 | B2 rac-[6-(2-Methoxy-phenyl)-pyrimidin-4-yl]-(1,2,3,4-tetrahydro-naphthalen-1-yl)-amine | | | |
| (340) | 1 | 341 | 2.89 | B2 [6-(2-Methoxy-phenyl)-pyrimidin-4-yl]-(2,2,6,6-tetramethyl-piperidin-4-yl)-amine | | | |
| (341) | 1 | 371 | 3.07 | B2 4-[6-(2-Methoxy-phenyl)-pyrimidin-4-ylamino]-N-methyl-benzenesulfonamide | b | | |
| (342) | 1 | 366 | 3.24 | B2 (1,1-Dioxo-1H-1λ⁶-benzo[b]thiophen-6-yl)-[6-(2-methoxy-phenyl)-pyrimidin-4-yl]-amine | c | | |
| (343) | 1 | 399 | 2.12 | B2 N-Acetyl-4-[6-(2-methoxy-phenyl)-pyrimidin-4-ylamino]-benzenesulfonamide | | | |
| (344) | 1 | 463 | 3.32 | B2 N-(2,6-Dimethyl-pyrimidin-4-yl)-4-[6-(2-methoxy-phenyl)-pyrimidin-4-ylamino]-benzenesulfonamide | | | |
| (345) | 1 | 425 | 3.73 | B2 [6-(2-Methoxy-phenyl)-pyrimidin-4-yl]-[4-(piperidine-1-sulfonyl)-phenyl]-amine | | | |
| (346) | 1 | 477 | 3.89 | B2 3-{3-[6-(2-Methoxy-phenyl)-pyrimidin-4-ylamino]-phenoxy}-piperidine-1-carboxylic acid tert-butyl ester | | | |
| (346) | 1 | 374 | 2.86 | B2 [6-(2-Fluoro-6-methoxy-phenyl)-pyrimidin-4-yl]-(3-methanesulfonyl-phenyl)-amine | b | | |
| (348) | 1 | 374 | 3.18 | B2 [6-(4-Fluoro-2-methoxy-phenyl)-pyrimidin-4-yl]-(3-methanesulfonyl-phenyl)-amine | | | |
| (349) | 1 | 374 | 3.20 | B2 [6-(5-Fluoro-2-methoxy-phenyl)-pyrimidin-4-yl]-(3-methanesulfonyl-phenyl)-amine | | | |
| (350) | 1 | 279 | 2.80 | B2 [6-(2-Methoxy-phenyl)-pyrimidin-4-yl]-pyridin-3-yl-amine | | | |
| (351) | 1 | 322 | 2.81 | B2 2-{4-[6-(2-Methoxy-phenyl)-pyrimidin-4-ylamino]-phenyl}-ethanol | b | | |
| (352) | 1 | 431 | 2.38 | B2 (9,9-Dioxo-9,10-dihydro-9λ⁶-thia-10-aza-phenanthren-3-yl)-[6-(2-methoxy-phenyl)-pyrimidin-4-yl]-amine | | | |
| (353) | 1 | 332 | 2.99 | B2 [6-(2-Methoxy-phenyl)-pyrimidin-4-yl]-(1-methyl-1H-indazol-6-yl)-amine | b | | |
| (354) | 1 | 336 | 3.81 | B2 Benzo[1,2,5]thiadiazol-4-yl-[6-(2-methoxy-phenyl)-pyrimidin-4-yl]-amine | | | |
| (355) | 1 | 336 | 3.62 | B2 Benzo[1,2,5]thiadiazol-5-yl-[6-(2-methoxy-phenyl)-pyrimidin-4-yl]-amine | | | |
| (356) | 1 | 377 | 3.53 | B2 rac-[6-(2-Methoxy-phenyl)-pyrimidin-4-yl]-[3-(piperidin-3-yloxy)-phenyl]-amine | | | |
| (357) | 1 | 502 | 4.24 | B2 [6-(2-Methoxy-phenyl)-pyrimidin-4-yl]-{1-[6-(2-methoxy-phenyl)-pyrimidin-4-yl]-1H-indazol-5-yl}-amine | | | |
| (358) | 1 | 317 | 3.06 | B2 (1H-Indol-5-yl)-[6-(2-methoxy-phenyl)-pyrimidin-4-yl]-amine | | | |
| (359) | 1 | 340 | 2.74 | B2 (3-Methanesulfinyl-phenyl)-[6-(2-methoxy-phenyl)-pyrimidin-4-yl]-amine | | | |
| (360) | 1 | 318 | 2.74 | B2 (1H-Indazol-5-yl)-[6-(2-methoxy-phenyl)-pyrimidin-4-yl]-amine | | | |

TABLE 2-continued

Inhibitory effect on CDK9 and CDK2 of compounds according to the present invention

| ① | ② | LCMS | ③ | ④ Nomenclature | ⑤ ⑥ ⑦ |
|---|---|---|---|---|---|
| (361) | 1 | 342 | 4.01 | B2 4-[6-(2-Methoxy-phenyl)-pyrimidin-4-ylamino]-thiophene-3-carboxylic acid methyl ester | |
| (362) | 1 | 370 | 2.80 | B2 4-Methanesulfonyl-benzyl-[6-(2-methoxy-phenyl)-pyrimidin-4-yl]-amine | |
| (363) | 1 | 352 | 3.37 | B2 (5-Chloro-1H-indazol-3-yl)-[6-(2-methoxy-phenyl)-pyrimidin-4-yl]-amine | |
| (364) | 1 | 283 | 3.19 | B2 [6-(2-Methoxy-phenyl)-pyrimidin-4-yl]-(5-methyl-isoxazol-3-yl)-amine | |
| (365) | 1 | 385 | 3.45 | B2 3-[6-(2-Methoxy-phenyl)-pyrimidin-4-ylamino]-N,N-dimethyl-benzenesulfonamide | |
| (366) | 1 | 385 | 3.27 | B2 N-Ethyl-3-[6-(2-methoxy-phenyl)-pyrimidin-4-ylamino]-benzenesulfonamide | |
| (367) | 1 | 399 | 3.46 | B2 3-[6-(2-Methoxy-phenyl)-pyrimidin-4-ylamino]-N-propyl-benzenesulfonamide | |
| (368) | 1 | 331 | 3.24 | B2 [6-(2-Methoxy-phenyl)-pyrimidin-4-yl]-(2-methyl-1H-indol-5-yl)-amine | |
| (369) | 1 | 413 (M − H)⁻ | 3.12 | B2 N-(2-Methoxy-ethyl)-3-[6-(2-methoxy-phenyl)-pyrimidin-4-ylamino]-benzenesulfonamide | |
| (370) | 1 | 413 | 3.5 | B2 N-tert-Butyl-3-[6-(2-methoxy-phenyl)-pyrimidin-4-ylamino]-benzenesulfonamide | |
| (371) | 1 | 293 | 2.71 | B2 [6-(2-Methoxy-phenyl)-pyrimidin-4-yl]-pyridin-2-ylmethyl-amine | |
| (372) | 1 | 293 | 2.61 | B2 [6-(2-Methoxy-phenyl)-pyrimidin-4-yl]-pyridin-3-ylmethyl-amine | |
| (373) | 1 | 293 | 2.59 | B2 [6-(2-Methoxy-phenyl)-pyrimidin-4-yl]-pyridin-4-ylmethyl-amine | |
| (374) | 1 | 371 | 3.15 | B2 5-[6-(2-Methoxy-phenyl)-pyrimidin-4-ylamino]-2-methyl-benzenesulfonamide | |
| (375) | 1 | 429 | 3.45 | B2 N-(2-Methoxy-ethyl)-5-[6-(2-methoxy-phenyl)-pyrimidin-4-ylamino]-2-methyl-benzenesulfonamide | |
| (376) | 1 | 415 | 3.03 | B2 N-(2-Hydroxy-ethyl)-5-[6-(2-methoxy-phenyl)-pyrimidin-4-ylamino]-2-methyl-benzenesulfonamide | |
| (377) | 1 | 348 | 2.17 | A2 N,N-Diethyl-N'-[6-(2-methoxy-phenyl)-pyrimidin-4-yl]-benzene-1,4-diamine | |
| (378) | 1 | 528 | 3.78 | A2 1-(4-Chloro-3-trifluoromethyl-phenyl)-3-{5-[6-(2-methoxy-phenyl)-pyrimidin-4-ylamino]-2-methyl-phenyl}-urea | |
| (379) | 1 | 431 | 3.27 | A2 1-Cyclohexyl-3-{5-[6-(2-methoxy-phenyl)-pyrimidin-4-ylamino]-2-methyl-phenyl}-urea | |
| (380) | 1 | 346 | 3.14 | A2 [6-(2-Methoxy-phenyl)-pyrimidin-4-yl]-(4-pyrrolidin-1-yl-phenyl)-amine | |
| (381) | 1 | 326 | 2.74 | A2 4-Chloro-N-1-[6-(2-methoxy-phenyl)-pyrimidin-4-yl]-benzene-1,3-diamine | |
| (382) | 1 | 391 | 3.35 | A2 1-Isopropyl-3-{5-[6-(2-methoxy-phenyl)-pyrimidin-4-ylamino]-2-methyl-phenyl}-urea | |
| (383) | 1 | 462 | 2.80 | A2 1-{5-[6-(2-Methoxy-phenyl)-pyrimidin-4-ylamino]-2-methyl-phenyl}-3-(2-morpholin-4-yl-ethyl)-urea | |
| (384) | 1 | | 2.79 | A2 1-(2-Dimethylamino-ethyl)-3-{5-[6-(2-methoxy-phenyl)-pyrimidin-4-ylamino]-2-methyl-phenyl}-urea | |
| (385) | 1 | 356 | 3.81 | A2 (4-Chloro-3-nitro-phenyl)-[6-(2-methoxy-phenyl)-pyrimidin-4-yl]-amine | |

Activity range "a" means, that the compounds do have an $IC_{50}$ between 1–1000 nM, activity range "b" means, that the compounds do have an $IC_{50}$ between 1000–10000 nM and activity range "c" means that the compounds do have an $IC_{50}$ between 10000 and 250000 nM. All LCMS values relate to $(M + H)^+$ if not explicitly indicated as $(M − H)^-$ ①: Compound Number
②: Method of synthesis according to scheme 1–12
③: Retention time (minutes)
④: LC Method
⑤: CDK9 (activity range)
⑥: CDK4 (activity range)
⑦: CDK2 (activity range)

RNA-Polymerase II Phosphorylation:

In order to see, if the compounds according to the general formula (I) do have the intrinsic capacity to penetrate cells and act against cellular target proteins, especially CDK9, the effect of Compound 30 on CDK9-dependent phosphorylation of RNA-polymerase II was investigated. Probing blots with antibodies against the phosphorylated forms of RNA polymerase II showed, that specifically serine 2 phosphorylation was decreased, whereas antibodies recognizing serine 5 phosphorylation did not show any differences. These results indicate, that kinases being responsible for the phosphorylation of this site, for example CDK7 are not touched. Additionally, a reduction in the molecular weight of RNA polymerase II was observed indicating that phosphorylation is decreased (data not shown).

Growth of PM1 Cells:

The growth of PM1 cells is not generally affected by compounds according to the present invention as shown by the results, summarized in Table 3. Indeed, only a small proportion of the compounds seem to affect severely the growth of PM1 cells. Those compounds, Compound 9 and Compound 28, had a tendency to inhibit potently CDK2. Therefore the observed effect on growth might be a cell cycle arrest more than toxicity towards the cells.

Additionally, no correlation between CDK9 inhibition and toxicity is observed.

TABLE 3

Growth inhibition by described compounds (the numbers are growth rates compared to rates of DMSO treated cells given in %).

| Compound No | Growth after 7 days [% at 1 µM] |
|---|---|
| Compound 9, 28 | ≦50 |
| Compound 1, 2, 3, 4, 5, 6, 8, 10, 11, 15, 18, 19, 20, 22, 25, 30 | 51-100 |
| Compound 7, 17, 21, 29 | 101-150 |

HIV Replication in PM1 Cells:

Compounds according to the general formula (I) are potent inhibitors of HIV replication. Table 4 shows the inhibition of HIV replication (% of DMSO control [=0%]) in cell culture of Compound 4, Compound 12, Compound 13, Compound 14, Compound 16, Compound 27, Compound 31, Compound 32, Compound 38, Compound 58, Compound 59, Compound 82, Compound 83, Compound 86, Compound 91, Compound 95, Compound 109, Compound 112, and Compound 116.

As is evident from Table 4 representative examples for the most effective compounds of those tested in inhibiting the HIV replication are compound 4, compound 12, compound 14, compound 27, compound 58, compound 82, compound 83, compound 86, compound 95, compound 112 and compound 116 reducing HIV replication by over 60%. With compound 13, compound 16, compound 31, compound 32, compound 38, compound 59, compound 91 and compound 109 satisfactory results regarding inhibition of HIV replication were obtained (between 20 and 60% inhibition).

TABLE 4

Relative inhibition of HIV replication

| Compound | [%] Inhibition of HIV Replication |
|---|---|
| Compound 13, 16, 31, 32, 38, 59, 91, 109 | 20-60 |
| Compound 4, 12, 14, 27, 58, 82, 83, 86, 95, 112, 116 | 61-95 |

Selectivity Panel Data:

Table 5 shows the inhibitory effect of selected compounds according to the present invention on the activity of certain protein kinases. The activity of these protein kinases is depicted as % inhibition in the presence of 10 μM of compound in comparison to DMSO (0% inhibition).

TABLE 5

Selectivity panel data (% inhibition) of selected compounds according to the present invention

| Cpd. No. | Abl | CDK1 | CDK5 | EGFR | GSK-3β | PDGFR | c-Kit | p56 Lck | c-Src | RSK1 | cMet |
|---|---|---|---|---|---|---|---|---|---|---|---|
| 4 | | a | | c | a | | | a | | | |
| 6 | | a | | | b | c | b | c | | | |
| 8 | | a | | | | | b | b | | | |
| 9 | | a | | b | b | c | c | b | | c | |
| 10 | | a | | b | b | c | b | b | | | |
| 12 | | a | a | a | | c | b | b | | | |
| 22 | | a | a | | c | c | b | b | | | |
| 30 | b | a | a | | c | c | b | b | b | | c |
| 33 | | a | | b | b | b | b | b | | c | |
| 38 | | b | | c | c | b | b | b | | | |
| 49 | b | a | | b | b | c | b | b | | | |
| 58 | | a | | b | a | | | a | | | |
| 59 | b | a | | a | | b | b | b | | | |
| 64 | b | a | | a | c | b | b | b | | | |
| 65 | b | b | | a | | b | b | b | | | |
| 66 | b | b | | a | | b | b | b | | | |
| 68 | b | b | | a | | b | b | b | | | |
| 69 | b | b | | a | | b | b | a | | | |
| 70 | c | a | | b | b | b | b | b | | b | |
| 71 | | a | | c | c | b | b | | | | |
| 81 | b | a | a | b | b | b | | | | | |
| 82 | c | b | b | a | c | c | | | | | |
| 83 | c | a | | b | c | b | b | b | b | | b |
| 86 | c | a | | a | b | b | | b | | | |
| 87 | b | a | | a | | b | b | b | | b | c |
| 91 | b | b | | a | c | b | | b | | | |
| 95 | | a | | b | a | c | | b | b | | |
| 102 | c | b | a | a | | b | | | | | |
| 103 | | b | b | a | b | c | | | | | |
| 109 | | a | a | b | a | c | | | | | |
| 116 | | a | | a | a | c | | b | | | |
| 118 | c | b | b | a | | b | | | | | |

(Cpd. = Compound, n.a. = not available; inhibition greater than 80%: a; inhibition between 80 and 50%: b; inhibition between 50 and 30%: c;).

These data show, that compounds according to the present invention, do have an inhibitory effect on the protein kinase activity of various protein kinases, such as Abl, CDK1, CDK5, EGFR, GSK-3β, PDGFR, c-kit and p56Lck. Additionally c-Src, RSK1 and cMet were affected by some cpds in their activity (Table 5).

Figure 3:
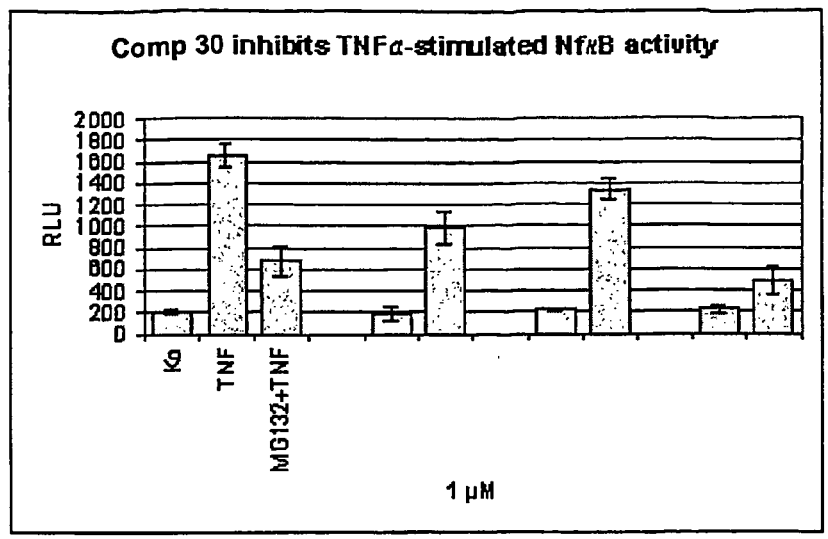
FIG. 3 shows the effect of selected compounds on the dependent Nfκb-transcriptional activity.

Impact on NFκB-dependent Transcriptional Activity:

It is known, that CDK9 regulates the NFκB-dependent transitional activity. With Compound 4, Compound 7 and Compound 30 studies were done, to evaluate their effect on NFκB-dependent transcriptional activity. Compound 30 was able, to affect TNF-α stimulated NFκB-dependent promoter activity at 1 μM final concentration as shown in FIG. 3. Interestingly under non-stimulated conditions no inhibition was observed. Compound 4 and Compound 7 inhibited NFκB less effectively, closely reflecting the $IC_{50}$ values of these compounds on CDK9/Cyclin T1. A titration of these three compounds showed $EC_{50}$ values of about 2 μM for compound 4 and 1 μM for Compound 30.

HBV Replication

Figure 4:
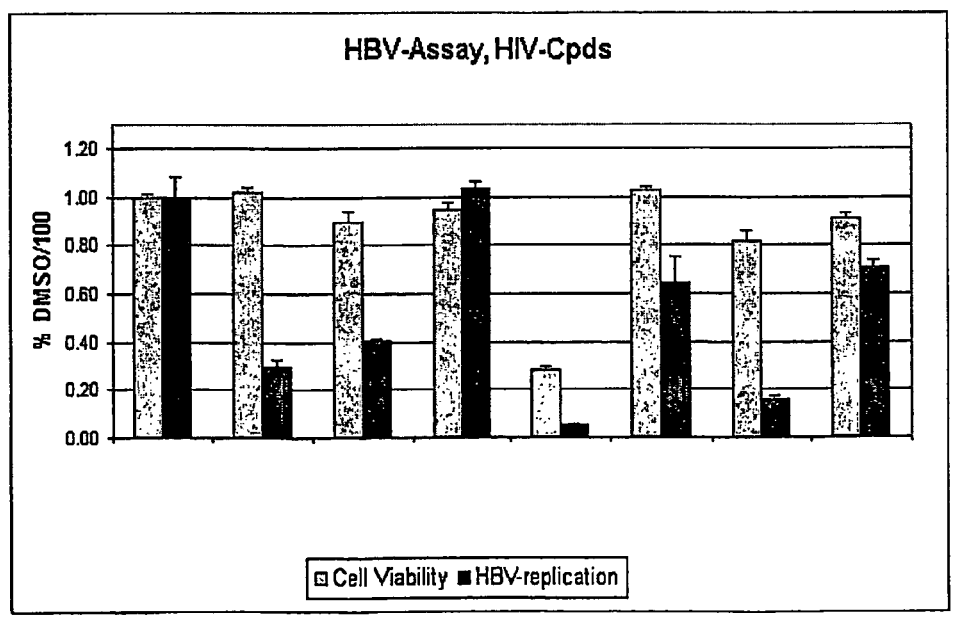
FIG. 4 shows the effect of selected compounds on HBV replication.

Selected compounds according to the present invention were tested in a HBV replication assay. As the results, depicted in FIG. 4 show, only Compound 7 inhibited replication without affecting viability in those cells. Compound 30 was inactive in those assays indicating that other protein kinase targets than CDK9 (especially further CDKs) might be important for HBV replication. This is underlined by flavopiridol, which inhibits replication, but is known to be a more or less unspecific inhibitor of CDKs.

Figure 5:
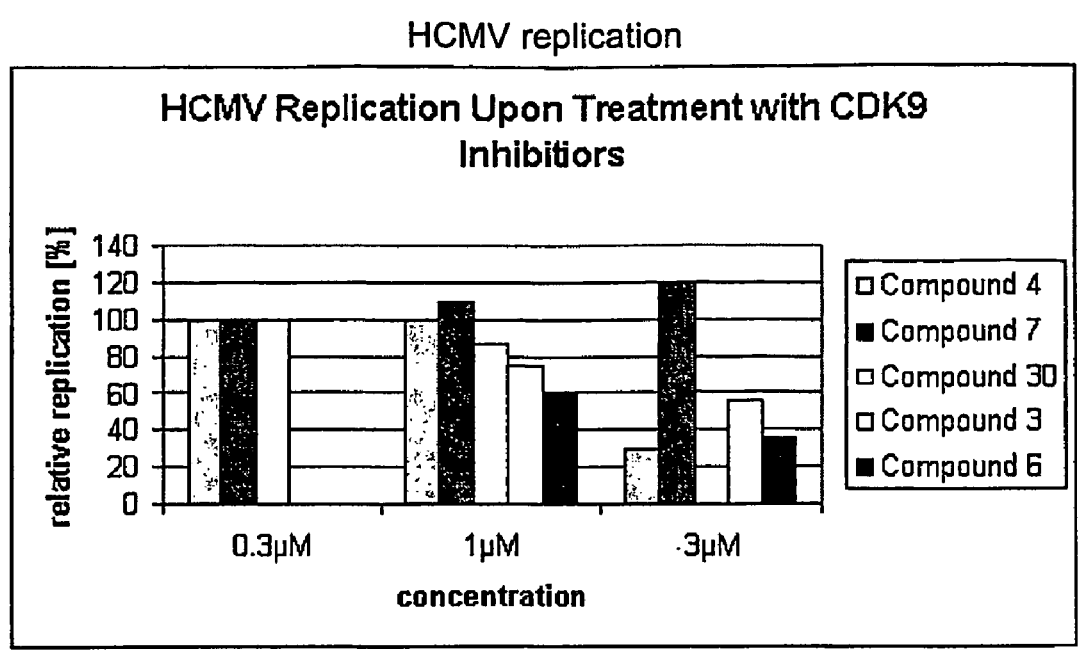
FIG. 5 shows the effect of selected compounds on HCMV replication.

HCMV Replication:

Compounds according to the present invention were identified as potent inhibitors of HCMV replication in cell culture (see FIG. 5):

Compound 4, Compound 6 and Compound 30 showed inhibition of HCMV replication (using strain AD 169 in HFF cells).

Affinity Chromatography and Preparative Gel Electrophoresis:

Compound 102 or Compound 103, known as Cyclin-dependent kinase 9 (CDK9) inhibitors were covalently coupled to ECH-Sepharose and used as media for affinity chromatography as described above.

Results from analysis by mass spectrometry revealed that both affinity media were able to isolate CDK9 out of crude PM1 cell lysates. Furthermore, both affinity media described here were able to identify additional targets for these compound molecules known to inhibit Cyclin-dependent kinase 9 (CDK9). In particular $Ca^{2+}$/Calmodulin-dependent protein kinase II γ (CaMK2γ), $Ca^{2+}$/Calmodulin-dependent protein kinase II δ (CaMK2δ), Cyclin-dependent kinase 2 (CDK2) and mixed lineage kinase-related kinase (MRK-beta, ZAK) were specifically bound by compound 102. In contrast, Glycogen synthase kinase 3 beta (GSK3β) and c-Src tyrosine kinase (CSK) were specifically bound by compound 103.

LCMS analysis of eluates reproduced those results. Furthermore, within this last set of experiments the following protein kinases were identified: For Compound 102 $Ca^{2+}$/Calmodulin-dependent protein kinase II β (CaMK2β), mixed lineage kinase (MLK, MRK-alpha), the src-like kinase yes, human cdc2-like protein kinase (similar to CDC2L5), CrkRS (Crk7, CDC2-related protein kinase 7), and Male germ cell-associated kinase (MAK) were identified.

For Compound 103 $Ca^{2+}$/Calmodulin-dependent protein kinase II β (CaMK2β), Glycogen synthase kinase 3α (GSK3α), Cyclin-dependent kinase 2 (CDK2), CrkRS (Crk7, CDC2-related protein kinase 7), and a growth factor receptor similar to fibroblast growth factor receptor 3 (FGFR-3) sequences were detected.

REFERENCES

Prenzel N, Fischer O M, Streit S, Hart S, Ullrich A.
The epidermal growth factor receptor family as a central element for cellular signal transduction and diversification. Endocr Relat Cancer. 2001 March; 8(1):11-31. Review.
Manning G, Whyte D B, Martinez R, Hunter T, Sudarsanam S.
The protein kinase complement of the human genome. Science. 2002 Dec. 6; 298(5600): 1912-34. Review.
Blume-Jensen P, Hunter T.
Oncogenic kinase signalling. Nature. 2001 May 17; 411(6835):355-65. Review.
Flores O, Lee G, Kessler J, Miller M, Schlief W, Tomassini J, Hazuda D.
Host-cell positive transcription elongation factor b kinase activity is essential and limiting for HIV type 1 replication. Proc Natl Acad Sci USA. 1999 Jun. 22; 96(13):7208-13.
Mancebo H S, Lee G, Flygare J, Tomassini J, Luu P, Zhu Y, Peng J, Blau C, Hazuda D, Price D, Flores O.
P-TEFb kinase is required for HIV Tat transcriptional activation in vivo and in vitro. Genes Dev. 1997 Oct. 15; 11 (20):2633-44.
Zhu Y, Pe'ery T, Peng J, Ramanathan Y, Marshall N, Marshall T, Amendt B, Mathews M B, Price D H.
Transcription elongation factor P-TEFb is required for HIV-1 tat transactivation in vitro. Genes Dev. 1997 Oct. 15; 11(20):2622-32.
Shim E Y, Walker A K, Shi Y, Blackwell T K.
CDK-9/cyclin T (P-TEFb) is required in two postinitiation pathways for transcription in the C. elegans embryo. Genes Dev. 2002 Aug. 15; 16(16):2135-46.
Hampsey M, Reinberg D.
Tails of intrigue: phosphorylation of RNA polymerase II mediates histone methylation. Cell. 2003 May 16; 113(4):429-32. Review
Bieniasz P D, Grdina T A, Bogerd H P, Cullen B R.
Recruitment of cyclin T1/P-TEFb to an HIV type 1 long terminal repeat promoter proximal RNA target is both necessary and sufficient for full activation of transcription. Proc Natl Acad Sci USA. 1999 Jul. 6; 96(14):7791-6
Bevec D, Dobrovnik M, Hauber J, Bohnlein E.
Inhibition of human immunodeficiency virus type 1 replication in human T cells by retroviral-mediated gene transfer of a dominant-negative Rev trans-activator. Proc Natl Acad Sci USA. 1992 Oct. 15; 89(20):98704.
Sells M A, Zelent A Z, Shvartsman M, Acs G.
Replicative intermediates of hepatitis B virus in HepG2 cells that produce infectious virions. J Virol. 1988 August; 62(8):2836-44.
Sells M A, Chen M L, Acs G (1987): Production of hepatitis B virus particles in HepG2 cells transfected with the cloned hepatitis B virus DNA, PNAS, 84, p. 1005-1009.
Guidotti L G, Matzke B, Schaller H, Chisari F V.
High-level hepatitis B virus replication in transgenic mice. J Virol. 1995 October; 69(10):6158-69.
Brignola P S, Lackey K, Kadwell S H, Hoffman C, Horne E, Carter H L, Stuart J D, Blackburn K, Mover M B, Alligood K J, Knight W B, Wood E R.
Comparison of the biochemical and kinetic properties of the type 1 receptor tyrosine kinase intracellular domains. Demonstration of differential sensitivity to kinase inhibitors. J Biol Chem. 2002 Jan. 11; 277(2):1576-85. Epub 2001 Nov. 5.
Huwe A, Mazitschek R, Giannis A.
Small molecules as inhibitors of cyclin-dependent kinases. Angew Chem Int Ed Engl. 2003 May 16; 42(19):2122-38.

The invention claimed is:
1. A compound having the general formula (I)

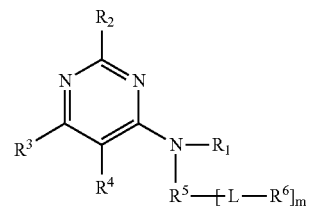

wherein
$R^1$, $R^2$, and $R^4$ are each hydrogen;
$R^3$ is a phenyl substituted with between one and four $R^S$ each independently selected from, Sub, —$OR^{S1}$, or —$N(R^{S1})_2$, wherein each $R^{S1}$ is independently selected from linear or branched $C_5$-$C_6$ alkyl;
$R^5$ is a phenyl substituted with between zero and four $R^A$ each independently selected from Sub, —$OR^{A1}$, or —$N(R^{A1})_2$, wherein each $R^{A1}$ is independently selected from linear or branched $C_5$-$C_6$ alkyl;
$R^6$ is hydrogen or is selected from the group consisting of: linear or branched $C_1$-$C_8$ alkyl, aryl, HA, HC, pyrrolidinyl, $C_3$-$C_8$ cycloalkyl, cyclohexyl, cyclopentyl, $C_5$-$C_{12}$ bicycloalkyl, adamantyl, in each case optionally substituted with Sub, or $R^6$ is selected from —$(CH_2)_q$-group, wherein q is an integer from 1 to 3, under the proviso, if $R^6$ is selected to be a methylene chain —$(CH_2)_q$-group, $R^{17}$ or $R^{19}$ are selected to be a methylene chain —$(CH_2)_s$-group, wherein s is an integer from 1 to 3 or a —$(CH_2)_t$ A-group, t is an integer from 1 to 3 and A is selected from O or N, respectively, and $R^6$ and $R^{17}$ or $R^6$ and $R^{19}$ form together a 5 to 8 membered ring system,
or $R^6$ represents —$(CH_2)_p$—Z, wherein p is an integer from 0 to 6 and Z is selected from the group comprising:

aryl, HA, HC, linear or branched $C_1$-$C_6$ alkyl, in each case optionally substituted with Sub, and —N($R^7R^8$), wherein $R^7$ and $R^8$ represent independently from each other —H, or linear or branched $C_1$-$C_6$ alkyl, or Z is selected from —($CR^9R^{10}R^{11}$), wherein $R^9$, $R^{10}$ and $R^{11}$ are independently of each other hydrogen or selected from the group consisting of:

linear or branched $C_1$-$C_8$ alkyl, aryl in each case optionally substituted with Sub or —N($R^{12}R^{13}$),
wherein $R^{12}$ and $R^{13}$ represent independently of each other —H or linear or branched $C_1$-$C_6$ alkyl optionally substituted with Sub, under the proviso, if Z represents —($CR^9R^{10}R^{11}$) as defined above, p is selected to be an integer from 0 to 6, and if Z is selected from aryl, HA, HC, or —N($R^7R^8$) as defined above, p is selected to be an integer from 1 to 6;

L is in the meta- or para-position of the phenyl represented by $R^5$ and selected from the group comprising:
—$NR^{14}$—$SO_2$—, $NR^{14}$—SO—,
  wherein $R^{14}$ is selected from —H, linear or branched $C_1$-$C_6$ alkyl, —$SO_2$—$R^{15}$, wherein $R^{15}$ is selected from linear or branched $C_1$-$C_6$ alkyl or $C_1$-$C_6$ alkylene, or $R^{14}$ represents —$(CH_2)_r$—$COOR^{16}$, wherein r is an integer from 0 to 6 and $R^{16}$ is selected from —H or linear or branched $C_1$-$C_6$ alkyl,
—$NR^{17}$—CO—,
  wherein $R^{17}$ is selected from —H, linear or branched $C_1$-$C_6$ alkyl, or a —$(CH_2)_s$-group,
  wherein s is an integer from 1 to 3, and
  wherein if $R^6$ and $R^{17}$ both represent a methylene chain group, $R^6$ and $R^{17}$ may form together a 5 to 8 membered ring system:

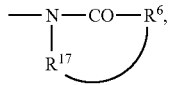

—$SO_2$—$NR^{18}$—,
wherein $R^{18}$ is selected from —H, or linear or branched $C_1$-$C_6$ alkyl,
—CO—$NR^{19}$—,
wherein $R^{19}$ is selected from —H, linear or branched $C_1$-$C_6$ alkyl, or a —$(CH_2)_t$-A- group, wherein t is an integer from 1 to 3 and A is selected from N or O, and wherein if $R_6$ represents a —$(CH_2)_q$-group and $R^{19}$ represents a —$(CH_2)_r$-A- group, $R^6$ and $R^{19}$ may form together a 5 to 8 membered ring system

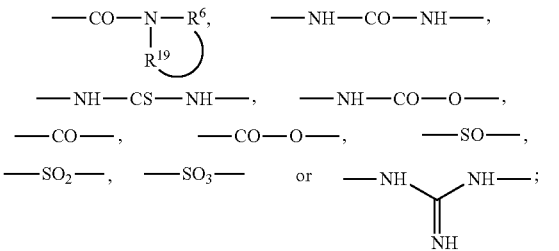

and m is 1,
Sub is independently selected from —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —OPh, —$OCH_2Ph$, —$OCPh_3$, —SH, —$SCH_3$, —$SC_2H_5$, —$SC_3H_7$, —S-cyclo-$C_3H_5$, —$SCH(CH_3)_2$, —$SC(CH_3)_3$, —$NO_2$, —F, —Cl, —Br, —I, —$N_3$, —CN, —OCN, —NCO, —SCN, —NCS, —CHO, —$COCH_3$, —$COC_2H_5$, —$COC_3H_7$, —CO-cyclo-$C_3H_5$, —$COCH(CH_3)_2$, —$COC(CH_3)_3$, —COOH, —COCN, —$COOCH_3$, —$COOC_2H_5$, —$COOC_3H_7$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC-cyclo-$C_3H_5$, —OOC—$CH(CH_3)_2$, —OOC—$C(CH_3)_3$, —$CONH_2$, —$CONHCH_3$, —$CONHC_2H_5$, —$CONHC_3H_7$, —CONH-cyclo-$C_3H_5$, —$CONH[CH(CH_3)_2]$, —$CONH[C(CH_3)_3]$, —$CON(CH_3)_2$, —$CON(C_2H_5)_2$, —$CON(C_3H_7)_2$, —CON(cyclo-$C_3H_5)_2$, —$CON[CH(CH_3)_2]_2$, —$CON[C(CH_3)_3]_2$, —$NH_2$, —$NHCH_3$, —$NHC_2H_5$, —$NHC_3H_7$, —NH-cyclo-$C_3H_5$, —$NHCH(CH_3)_2$, —$NHC(CH_3)_3$, —$N(CH_3)_2$, —$N(C_2H_5)_2$, —$N(C_3H_7)_2$, —N(cyclo-$C_3H_5)_2$, —$N[CH(CH_3)_2]_2$, —$N[C(CH_3)_3]_2$, —$SOCH_3$, —$SOC_2H_5$, —$SOC_3H_7$, —SO-cyclo-$C_3H_5$, —$SOCH(CH_3)_2$, —$SOC(CH_3)_3$, —$SO_2CH_3$, —$SO_2C_2H_5$, —$SO_2C_3H_7$, —SO2-cyclo-$C_3H_5$, —$SO_2CH(CH_3)_2$, —$SO_2C(CH_3)_3$, —$SO_3H$, —$SO_3CH_3$, —$SO_3C_2H_5$, —$SO_3C_3H_7$, —$SO_3$-cyclo-$C_3H_5$, —$SO_3CH(CH_3)_2$, —$SO_3C(CH_3)_3$, —$OCF_3$, —$OC_2F_5$, —O—$COOCH_3$, —O—$COOC_2H_5$, —O—$COOC_3H_7$, —O—COO-cyclo-$C_3H_5$, —O—$COOCH(CH_3)_2$, —O—$COOC(CH_3)_3$, —NH—CO—$NH_2$, —NH—CO—$NHCH_3$, —NH—$CONHC_2H_5$, —NH—CO—$NHC_3H_7$, —NH—CO—NH-cyclo-$C_3H_5$, —NH—CO—$NH[CH(CH_3)_2]$, —NH—CO—$NH[C(CH_3)_3]$, —NH—CO—$N(CH_3)_2$, —NH—CO—$N(C_2H_5)_2$, —NH—CO—$N(C_3H_7)_2$, —NH—CO—N(cyclo-$C_3H_5)_2$, —NH—CO—$N[CH(CH_3)_2]_2$, —NH—CO—$N[C(CH_3)_3]_2$, —NH—CS—$NH_2$, —NH—CS—$NHCH_3$, —NH—CS—$NHC_2H_5$, —NH—CS—$NHC_3H_7$, —NH—CS—NH-cyclo-$C_3H_5$, —NH—CS—$NH[CH(CH_3)_2]$, —NH—CS—$NH[C(CH_3)_3]$, —NH—CS—$N(CH_3)_2$, —NH—CS—$N(C_2H_5)_2$, —NH—CS—$N(C_3H_7)_2$, —NH—CS—N(cyclo-$C_3H_5)_2$, —NH—CS—$N[CH(CH_3)_2]_2$, —NH—CS—$N[C(CH_3)_3]_2$, —NH—C(=NH)—$NH_2$, —NH—C(=NH)$NHCH_3$, —NH—C(=NH)—$NHC_2H_5$, —NH—C(=NH)—$NHC_3H_7$, —NH—C(=NH)—NH-cyclo-$C_3H_5$, —NH—C(=NH)—$NH[CH(CH_3)_2]$, —NH—C(=NH)—$NH[C(CH_3)_3]$, —NH—C(=NH)—$N(CH_3)_2$, —NH—C(=NH)—$N(C_2H_5)_2$, —NH—C(=NH)—$N(C_3H_7)_2$, —NH—C(=NH)—N(cyclo-$C_3H_5)_2$, —NH—C(=NH)—$N[CH(CH_3)_2]_2$, —NH—C(=NH)—$N[C(CH_3)_3]_2$, —O—CO—$NH_2$, —O—CO—$NHCH_3$, —O—CO—$NHC_2H_5$, —O—CO—$NHC_3H_7$, —O—CO—NH-cyclo-$C_3H_5$, —O—CO—$NH[CH(CH_3)_2]$, —O—CO—$NH[C(CH_3)_3]$, —O—CO—$N(CH_3)_2$, —O—CO—$N(C_2H_5)_2$, —O—CO—$N(C_3H_7)_2$, —O—CO—N(cyclo-$C_3H_5)_2$, —O—CO—$N[CH(CH_3)_2]_2$, —O—CO—$N[C(CH_3)_3]_2$, —O—CO—$OCH_3$, —O—CO—$OC_2H_5$, —O—CO—$OC_3H_7$, —O—CO—O-cyclo-$C_3H_5$, —O—CO—$OCH(CH_3)_2$, —O—CO—$OC(CH_3)_3$, —$CH_2F$—$CHF_2$, —$CF_3$, —$CH_2Cl$, —$CHCl_2$, —$CCl_3$, —$CH_2Br$—$CHBr_2$, —$CBr_3$, —$CH_2I$—$CHI_2$, —$Cl_3$, —$CH_2$—$CH_2F$, —$CH_2$—$CHF_2$, —$CH_2$—$CF_3$, —$CH_2$—$CH_2Cl$, —$CH_2$—$CHCl_2$, —$CH_2$—$CCl_3$, —$CH_2$—$CH_2Br$ —$CH_2$—$CHBr_2$, —$CH_2$—$CBr_3$, —$CH_2$—$CH_2I$—$CH_2$—$CHI_2$, —$CH_2$—$Cl_3$, —$CH_3$, —$C_2H_5$, —$C_3H_7$, -cyclo-$C_3H_5$, —$CH(CH_3)_2$, —$C(CH_3)_3$, —$C_4H_9$, —$CH_2$—$CH(CH_3)_2$, —$CH(CH_3)$—$C_2H_5$, —$C(CH_3)_3$, -Ph, —$CH_2$-Ph, —$CPh_3$, —CH=CH$_2$, —CH$_2$CH=CH$_2$, —C(CH$_3$)=CH$_2$, —CH=CHCH$_3$, —C$_2$H$_4$—CH=CH$_2$, —CH=C(CH$_3$)$_2$, —CCCH$_3$, or —CH$_2$—CCH, HA is a partially or fully unsaturated 5 to 10 membered mono- or bicyclic ring system, containing one to three heteroatoms independently selected from oxygen, sulfur or nitrogen independently;

HC is a 5 to 10 membered mono- or bicyclic ring system, containing one to three heteroatoms independently selected from oxygen, sulfur or nitrogen; or a stereoisomeric form thereof; or a pharmaceutically acceptable salt thereof.

2. The compound according to claim 1, wherein each RS is independently selected from —F, —Cl, —Br, I, —OR$^{S2}$, or N(R$^{S2}$)$_2$, wherein each R$^{S2}$ is independently selected from hydrogen or linear or branched C$_1$-C$_6$ alkyl or benzyl.

3. The compound according to claim 1, wherein the phenyl of R$^3$ is substituted with one R$^S$ selected from —OCH$_3$, —OC$_2$H$_5$, —OC$_3$H$_7$, —O-cyclo-C$_3$H$_5$, —OCH(CH$_3$)$_2$, —OC(CH$_3$)$_3$, or —OC$_4$H$_9$.

4. The compound according to claim 1, wherein the phenyl of R$^3$ is substituted with one R$^S$ selected from —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, or —N[C(CH$_3$)$_3$]$_2$.

5. The compound according to claim 1, wherein the phenyl of R$^5$ is substituted with one R$^A$ selected from —F, —Cl, —Br, I, —OR$^{A2}$, or N(R$^{A2}$)$_2$, wherein each R$^{A2}$ is independently selected from hydrogen or linear or branched C$_1$-C$_6$ alkyl.

6. The compound according to claim 1, wherein the phenyl of R$^5$ is not substituted with R$^A$.

7. The compound according to claim 1, wherein R$^6$ is hydrogen, or linear or branched C$_1$-C$_6$ alkyl.

8. The compound according to claim 1, wherein R$^6$ is selected from —H, —CH$_3$, —C$_2$H$_5$, —C$_3$H$_7$, —CH(CH$_3$)$_2$, —C(CH$_3$)$_3$ or —CH$_2$C(CH$_3$)$_3$.

9. The compound according to claim 1, wherein R$^6$ is selected from H, CH$_3$, or C(CH$_3$)$_3$.

10. The compound according to claim 1, wherein R$^6$ is aryl, optionally substituted with Sub.

11. The compound according to claim 1, wherein R$^6$ is phenyl, optionally substituted with Sub.

12. The compound according to claim 1, wherein R$^6$ is a C$_3$-C$_8$ cycloalkyl, optionally substituted with Sub.

13. The compound according to claim 1, wherein R$^6$ is cyclopentyl or cyclohexyl, optionally substituted with between one and three linear or branched C$_1$-C$_6$ alkyl, —OH, —NH$_2$ or —NHCOOR$^3$$_5$, wherein R$^3$$_5$ represents —H or linear or branched C$_1$-C$_6$ alkyl.

14. The compound according to claim 1, wherein R$^6$ is cyclopentyl or cyclohexyl, substituted with one —NH$_2$.

15. The compound according to claim 1, wherein R$^6$ is selected from thiazolyl, oxazolyl, isothioazolyl, isoxazolyl, piperidinyl, piperazinyl or morpholinyl.

16. The compound according to claim 1, wherein L is —NR$^{14}$—SO$_2$—, R$^{14}$ is selected from H, linear or branched C$_1$-C$_4$ alkyl, —SO$_2$—R$^{15}$—, wherein R$^{15}$ is selected from linear or branched C$_1$-C$_4$ alkyl or C$_1$-C$_4$ alkylene, or R$^{14}$ represents —(CH$_2$)$_r$—COOR$^{16}$—, wherein r is an integer from 0 to 4 and R$^{16}$ is selected from —H or linear or branched C$_1$-C$_4$ alkyl.

17. The compound according to claim 1, wherein L is —NR$^{17}$—CO—, R$^{17}$ is selected from —H, linear or branched C$_1$-C$_4$ alkyl, or a —(CH$_2$)$_s$— group, wherein s is an integer from 1 to 3, and wherein if R$^6$ represents a —(CH$_2$)$_q$ group, wherein q is an integer from 1 to 3, and R$^{17}$ represents a methylene chain —(CH$_2$)$_s$— group, R$^6$ and R$^{17}$ may form together a 5 to 8 membered ring system.

18. The compound according to claim 1, wherein L is —SO$_2$—NR$^{18}$—, R$^{18}$ is selected from —H or linear or branched C$_1$-C$_4$ alkyl.

19. The compound according to claim 1, wherein L is —CO—NR$^{19}$—, wherein R$^{19}$ is selected from —H, linear or branched C$_1$-C$_4$ alkyl, or a —(CH$_2$)$_t$-A- group, wherein t is an integer from 1 to 3 and A is selected from N or O, and wherein if R$^6$ represents a —(CH$_2$)$_q$— group wherein q is an integer from 1 to 3, and R$^{19}$ represents a —(CH$_2$)$_t$-A- group, wherein t is selected to be 2 and A represents O, R$^6$ and R$^{19}$ may form together a 6-membered ring system

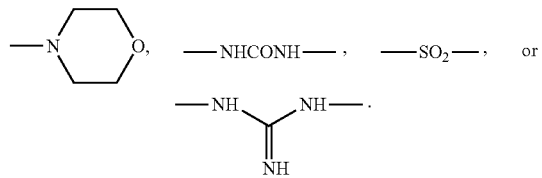

20. The compound according to claim 1, wherein L is —NR$^{14}$—SO$_2$—, wherein R$^{14}$ is selected from —H, —(CH$_2$)$_2$CH$_3$, —SO$_2$R$^{15}$, wherein R$^{15}$ represents —(CH$_2$)$_2$CH$^3$, or —(CH$_2$), COOR$^{16}$, wherein r is selected to be an integer from 0 to 2, and R$^{16}$ represents —CH$_3$.

21. The compound according to claim 20, wherein r is 1.

22. The compound according to claim 1, wherein L is selected from the group: —NHSO$_2$—, —NHCO—, —CONH—, —SO$_2$NH—, —NHCONH— or —SO$_2$—.

23. A pharmaceutical composition comprising at least one compound according to claim 1 as an active ingredient, together with at least one pharmaceutically acceptable carrier, excipient and/or diluent.

24. The compound of claim 1 wherein HA is selected from the group: pyrrolyl, furanyl, thiophenyl, thienyl, imidazolyl, pyrazolyl, thiazolyl, oxazolyl, isothiazolyl, isoxazolyl, pyridinyl, pyridyl, pyrimidinyl, pyrimidyl, pyrazinyl, pyrazyl, pyradizinyl, pyradizyl, 3-methylpyridyl, benzothienyl, 4-ethylbenzothienyl, 3,4-diethylfuranyl, pyrrolyl, tetrahydroquinolyl, quinolyl, tetrahydroisoquinolinyl, isoquinolinyl, benzoimidazolyl, benzothiazolyl, benzooxyzolyl, benzo[1,3]dioxolyl, indolyl, benzofuranyl, benzothiophenyl, indazolyl and chrom-2-onyl.

25. The compound of claim 24 wherein HC is independently selected from the group: aziridinyl, azetidinyl, pyrrolidinyl, tetrahydrofuranyl, tetrahydrothiophenyl, piperidinyl, piperadizinyl, piperazinyl, tetrahydropyranyl, tetrahydrothiopyranyl and morpholinyl.

* * * * *